US012807735B2

(12) United States Patent
Darowski et al.

(10) Patent No.: US 12,807,735 B2
(45) **Date of Patent: *Nov. 24, 2026**

(54) ANTIGEN BINDING RECEPTORS

(71) Applicant: Hoffmann-La Roche Inc., Little Falls, NJ (US)

(72) Inventors: Diana Darowski, Wuestenrot (DE); Anne Freimoser-Grundschober, Zurich (CH); Christian Klein, Bonstetten (CH); Ekkehard Moessner, Kreuzlingen (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 788 days.

This patent is subject to a terminal disclaimer.

(21) Appl. No.: 18/162,508

(22) Filed: Jan. 31, 2023

(65) Prior Publication Data

US 2023/0322950 A1 Oct. 12, 2023

Related U.S. Application Data

(63) Continuation of application No. PCT/EP2021/071515, filed on Aug. 2, 2021.

(30) Foreign Application Priority Data

Aug. 3, 2020 (EP) .................................... 20189196
Feb. 23, 2021 (EP) .................................... 21158659

(51) Int. Cl.

| | |
|---|---|
| ***C07K 16/42*** | (2006.01) |
| ***A61K 38/00*** | (2006.01) |
| ***A61K 40/11*** | (2025.01) |
| ***A61K 40/31*** | (2025.01) |
| ***A61K 40/33*** | (2025.01) |
| ***A61K 40/41*** | (2025.01) |
| ***A61K 40/42*** | (2025.01) |
| ***C07K 14/705*** | (2006.01) |

(52) U.S. Cl.

CPC .............. *C07K 16/42* (2013.01); *A61K 40/11* (2025.01); *A61K 40/31* (2025.01); *A61K 40/33* (2025.01); *A61K 40/41* (2025.01); *A61K 40/4221* (2025.01); *C07K 14/7051* (2013.01); *C07K 14/70521* (2013.01); *C07K 14/70578* (2013.01); *A61K 38/00* (2013.01); *A61K 2239/13* (2023.05); *A61K 2239/21* (2023.05); *A61K 2239/22* (2023.05); *C07K 2317/24* (2013.01); *C07K 2317/52* (2013.01); *C07K 2317/565* (2013.01); *C07K 2317/92* (2013.01); *C07K 2319/02* (2013.01); *C07K 2319/03* (2013.01); *C07K 2319/33* (2013.01)

(58) Field of Classification Search

CPC ................ C07K 16/42; C07K 14/7051; C07K 14/70521; C07K 14/70578; C07K 2317/24; C07K 2317/52; C07K 2317/565; C07K 2317/92; C07K 2319/02; C07K 2319/03; C07K 2319/33; C07K 2317/21; C07K 2317/515; C07K 2317/622; A61K 40/11; A61K 40/31; A61K 40/33; A61K 40/41; A61K 40/4221; A61K 38/00; A61K 2239/13; A61K 2239/21; A61K 2239/22; A61K 2121/00; A61K 2300/00; A61K 40/42; A61P 35/00; C12N 2510/00

See application file for complete search history.

(56) References Cited

U.S. PATENT DOCUMENTS

| | | | | |
|---|---|---|---|---|
| 6,737,056 | B1 | 5/2004 | Presta et al. | |
| 7,332,581 | B2 | 2/2008 | Presta et al. | |
| 2020/0093860 | A1* | 3/2020 | Stubenrauch | C07K 14/70521 |
| 2023/0357431 | A1* | 11/2023 | Darowski | C07K 16/3015 |
| 2024/0043535 | A1* | 2/2024 | Amann | C07K 16/2818 |
| 2024/0269176 | A1* | 8/2024 | Darowski | A61P 35/00 |
| 2024/0424095 | A1* | 12/2024 | Chen | A61K 40/32 |

FOREIGN PATENT DOCUMENTS

| | | | |
|---|---|---|---|
| CL | 201902717 | | 9/2019 |
| MX | 320492 | B | 5/2026 |
| RU | 2515108 | C2 | 5/2014 |
| WO | 2007/024715 | | 3/2007 |
| WO | 2012/130831 | A1 | 10/2012 |
| WO | 2018/177966 | A1 | 10/2018 |
| WO | 2019/122046 | A1 | 6/2019 |
| WO | 2022/090181 | A1 | 5/2022 |

OTHER PUBLICATIONS

U.S. Appl. No. 19/272,092, filed Jan. 18, 2024, Darowski; Diana.*
U.S. Appl. No. 19/412,397, filed May 27, 2024, Gasser; Stephan.*
Van Regenmortel. Mapping Epitope Structure and Activity: From One-Dimensional Prediction to Four-Dimensional Description of Antigenic Specificity. Methods. Jun. 1996;9(3):465-72. doi: 10.1006/meth.1996.0054. PMID: 8812702. (Year: 1996).*
Darowski D, et al. P329G-CAR-J: a novel Jurkat-NFAT-based CAR-T reporter system recognizing the P329G Fc mutation. Protein Eng Des Sel. Dec. 31, 2019;32(5):207-218. doi: 10.1093/protein/gzz027. PMID: 31504896. (Year: 2019).*
Zhang et al., "Comprehensive optimization of a single-chain variable domain antibody fragment as a targeting ligand for a cytotoxic nanoparticle" mAbs 7(1):42-52 ( 2015).

(Continued)

*Primary Examiner* — Misook Yu
*Assistant Examiner* — Alec Jon Peters
(74) *Attorney, Agent, or Firm* — Roberto K. Rodriguez

(57) ABSTRACT

Provided herein are antigen binding receptors capable of specific binding to an Fc domain comprising the amino acid mutation P329G according to EU numbering, as well as nucleic acid molecules and vectors encoding such antigen binding receptors. T cells, transduced with an antigen binding receptor which is recruited by specifically binding to/interacting with the mutated Fc domain of therapeutic antibodies, and kits comprising such transduced T cells, are also provided. Further provided herein are tumor targeting antibodies comprising a mutated Fc domain.

12 Claims, 11 Drawing Sheets

Figure 1A:
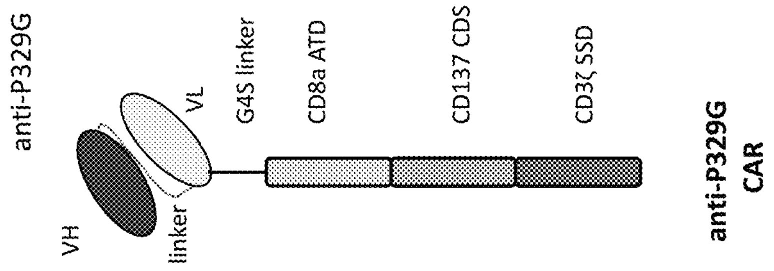

Specification includes a Sequence Listing.

(56) References Cited

OTHER PUBLICATIONS

Badri, H., et al., "Optimization of radiation dosing schedules for proneural glioblastoma" J Math Biol 72(5):1301-1336 (Apr. 1, 2016).
Baylot et al., "TCTP Has a Crucial Role in the Different Stages of Prostate Cancer Malignant Progression" Results Probl. Cell. Differ. 64:255-261 ( 2017).
Mariuzza et al., "The Structural Basis of Antigen-Antibody Recognition" Annu. Rev. Biophys. Biophs. Chem. 16:139-159 ( 1987).
Luu et al., "B7-H7 Is Inducible on T Cells to Regulate Their Immune Response and Serves as a Marker for Exhaustion" Frontiers in Immunology ((11 pages)), 12 ( 2021).
Tang et al., "CD137 Co-Stimulation Improves The Antitumor Effect Of LMP1-Specific Chimeric Antigen Receptor T Cells In Vitro And In Vivo" OncoTargets and Therapy 12:9341-9350 ( 2019).
Teschner et al., "In Vitro Stimulation and Expansion of Human Tumour-Reactive CD8+ Cytotoxic T Lymphocytes by Anti-CD3/CD28/CD137 Magnetic Beads" Scandinavian Journal of Immunology 74:155-164 ( 2011).
Blanco, I., et al., "Anti-idiotypic response against murine monoclonal antibodies reactive with tumor-associated antigen TAG-72" J Clin Immunol 17(1):96-109 (Jan. 1, 1997).
Cao, Y., et al., "Design of Switchable Chimeric Antigen Receptor T Cells Targeting Breast Cancer" Angew Chem Int Ed Engl 55(26):7520-7524 (Jun. 20, 2016).
Carter, P., et al., "Humanization of an anti-p185 HER2 antibody for human cancer therapy" PNAS USA 89(10):4285-4289 (May 15, 1992).
Chothia, C., et al., "Canonical structures for the hypervariable regions of immunoglobulins" J Mol Biol 196(4):901-917 (Aug. 20, 1987).
Chothia, C., et al., "Conformations of immunoglobulin hypervariable regions" Nature 342(6252):877-883 (Dec. 28, 1989).
Darowski, D., et al., "Anti-P329G-CAR-T cells as a novel universal CAR-T cell platform" Cancer Res (Abstract 4229), 80(SUPPL 16):1-4 (Aug. 15, 2020).
Darowski, D., et al., "Combining the best of two worlds: highly flexible chimeric antigen receptor adaptor molecules (CAR-adaptors) for the recruitment of chimeric antigen receptor T cells" MABS 11(4):621-631 (Jun. 1, 2019).
Darowski, D., et al., "P329G-CAR-J: a novel Jurkat-NFAT-based CAR-T reporter system recognizing the P329G Fc mutation" Protein Eng Design Sel 32(5):207-218 (Dec. 31, 2019).
Darowski, D.,, "Entwicklung einer modularen adoptiven T-Zell-Plattform, basierend auf einem anti-P329G chimären Antigenrezeptor, für das Screening von Antikörpern im IgG1 Format und zur Anwendung für die adoptive T-Zell-Therapie" (PhD Thesis—Ludwig-Maximilians Universitat-Munchen),:1-67 (Oct. 14, 2020) https://edoc.ub.uni-muenchen.de/26846/1/Darowski_Diana.pdf.
Dudley, M., et al., "Adoptive Cell Therapy for Patients With Metastatic Melanoma: Evaluation of Intensive Myeloablative Chemoradiation Preparative Regimens" J Clin Oncol 26(32):5233-5239 (Nov. 10, 2008).
Dudley, M., et al., "Generation of Tumor-Infiltrating Lymphocyte Cultures for Use in Adoptive Transfer Therapy for Melanoma Patients" J Immunol 26(4):332-342 (Jul. 1, 2003).
Duewell, P., et al., "RIG-I-like helicases induce immunogenic cell death of pancreatic cancer cells and sensitize tumors toward killing by CD8+ T cells" Cell Death Differ 21(12):1825-1837 (Jul. 11, 2014).
Ekkens, M., et al., "Th1 and Th2 Cells Help CD8 T-Cell Responses" Infect Immun 75(5):2291-2296 (May 1, 2007).
Ge, Q., et al., "Homeostatic T cell proliferation in a T cell-dendritic cell coculture system" PNAS 99(5):2983-2988 (Mar. 5, 2002).
Grupp, S., et al., "Chimeric Antigen Receptor-Modified T Cells for Acute Lymphoid Leukemia" New Engl J Med 368(16):1509-1518 (Apr. 18, 2013).
Holliger, P., et al., "Engineered antibody fragments and the rise of single domains" Nat Biotechnol 23(9):1126-1136 (Sep. 1, 2005).
"International Preliminary Report on Patentability—PCT/EP2021/071515" (Report Issuance Date: Feb. 7, 2023, Chapter I), pp. 1-9 (Feb. 16, 2023).
"International Search Report—PCT/EP2021/071515" (w/Written Opinion), pp. 1-18 (Jan. 13, 2022).
Kabat, E. et al. Sequences of Proteins of Immunological Interest 5th edition, Bethesda, MD:NIH, vol. 1:669, 671, 687, 696 (1991).
Kim, M., et al., "Redirection of Genetically Engineered CAR-T Cells Using Bifunctional Small Molecules" J Am Chem Soc 137(8):2832-2835 (Feb. 18, 2015).
Kochenderfer, JN et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor" J Clin Oncol 33(6):540-549 (Feb. 20, 2015).
Krutzik, P., et al. Methods in Molecular Biology "Chapter 9: Phospho Flow Cytometry Methods for the Analysis of Kinase Signaling in Cell Lines and Primary Human Blood Samples" Hawley, T.S., eds., New Jersey: Springer-Humana Press, vol. 699:179-202 (Jan. 1, 2011).
Ma, J., et al., "Versatile strategy for controlling the specificity and activity of engineered T cells" PNAS USA 113(4):E450-E458 (Jan. 12, 2016).
Maccallum, R., et al., "Antibody-antigen Interactions: Contact Analysis and Binding Site Topography" J Mol Biol 262:732-745 (Oct. 11, 1996).
Maude, S., et al., "Chimeric Antigen Receptor T Cells for Sustained Remissions in Leukemia" New Engl J Med 371(16):1507-1517 (Oct. 16, 2014).
Maus, M., et al., "T cells expressing chimeric antigen receptors can cause anaphylaxis in humans" Cancer Immunol Res 1:26-31 (Jul. 1, 2013).
Rodgers, D., et al., "Switch-mediated activation and retargeting of CAR-T cells for B-cell malignancies" PNAS USA 113(4):E459-E468 (Jan. 12, 2016).
Rosenberg, S., et al., "Adoptive cell transfer as personalized immunotherapy for human cancer" Science 348(6230):62-68 (Apr. 3, 2015).
Tamada, K., et al., "Redirecting Gene-Modified T Cells toward Various Cancer Types Using Tagged Antibodies" Clin Cancer Res 18(23):6436-6445 (Dec. 1, 2012).
Thakur, M., et al., "Real time monitoring of the cell viability during treatment with tumor-targeted toxins and saponins using impedance measurement" Biosensors 35(1):503-506 (Mar. 21, 2012).
Cheng, Y et al., "A VL-linker-VH Orientation Dependent Single Chain Variable Antibody Fragment Against Rabies Virus G Protein with Enhanced Neutralizing Potency in vivo" Protein Pept Lett. 23(1):pp. 24-32 (2016) DOI: 10.2174/0929866522666151026122752.

* cited by examiner

CMV = Cytomegalovirus promotor
SP= Signal peptide
VH = variable heavy chain
VL = variable light chain
TM = transmembrane domain
IRES= internal ribosomal entry site anti_P329G_CAR_selection
_WSUDLCL2 (5:1)

| | EC50 |
|---|---|
| original Binder | ~ 1.907e+050 |
| VH1 x VL1 | ~ 0.002187 |
| VH3 x VL1 | ~ 0.08500 |
| VL1 x VH 3 | ~ 0.07828 |
| VH2 x VL1 | 1.187e-007 |

anti_P329G_CAR_selection
_WSUDLCL2 (5:1)

| | EC50 |
|---|---|
| original Binder | 0.006995 |
| VH1 x VL1 | 0.008099 |
| VH3 x VL1 | 0.007570 |
| VL1 x VH 3 | ~ 0.006577 |
| VH2 x VL1 | ~ 0.006932 |

anti_P329G_CAR selection
without target cells

| | EC50 |
|---|---|
| original Binder | |
| VH1 x VL1 | 0.009863 |
| VH3 x VL1 | |
| VL1 x VH 3 | 0.0002879 |
| VH2 x VL1 | |

anti_P329G_CAR_selection WSUDLCL2 (5:1)

| | EC50 |
|---|---|
| original Binder | ~ 6.320 |
| VH1 x VL1 | ~ 4.847e-005 |
| VH3 x VL1 | ~ 1608804828772 |
| VL1 x VH 3 | ~ 2.339e-007 |
| VH2 x VL1 | ~ 0.000 |

anti_P329G_CAR_selection WSUDLCL2 (5:1)

| | EC50 |
|---|---|
| original Binder | 0.004193 |
| VH1 x VL1 | 0.008139 |
| VH3 x VL1 | 0.005823 |
| VL1 x VH 3 | 0.006188 |
| VH2 x VL1 | 0.01042 |

anti_P329G_CAR_selection WSUDLCL2 (5:1)

| | EC50 |
|---|---|
| original Binder | 0.1829 |
| VH1 x VL1 | ~ 327243519 |
| VH3 x VL1 | 43.24 |
| VL1 x VH 3 | 7.424 |
| VH2 x VL1 | 0.2932 |

| | EC50 |
|---|---|
| **original Binder** | ~ 0.05551 |
| **VH1 x VL1** | 0.04639 |
| **VH3 x VL1** | 0.03461 |
| **VL1 x VH 3** | 0.08399 |
| **VH2 x VL1** | 0.01673 |

| | EC50 |
|---|---|
| **original Binder** | 0.09999 |
| **VH1 x VL1** | 0.08469 |
| **VH3 x VL1** | 0.1168 |
| **VL1 x VH 3** | 0.2034 |
| **VH2 x VL1** | ~ 0.07242 |

| | EC50 |
|---|---|
| **original Binder** | 0.1925 |
| **VH1 x VL1** | 0.2221 |
| **VH3 x VL1** | 0.1535 |
| **VL1 x VH 3** | 0.5814 |
| **VH2 x VL1** | 0.3039 |

| | EC50 |
|---|---|
| original Binder | ~ 0.07453 |
| VH1 x VL1 | ~ 0.07597 |
| VH3 x VL1 | 0.1056 |
| VL1 x VH 3 | ~ 0.07672 |
| VH2 x VL1 | 0.1048 |

| | EC50 |
|---|---|
| original Binder | ~ 0.6653 |
| VH1 x VL1 | 0.4107 |
| VH3 x VL1 | 0.3086 |
| VL1 x VH 3 | 1.374 |
| VH2 x VL1 | 0.5968 |

| | EC50 |
|---|---|
| original Binder | 2.156 |
| VH1 x VL1 | 1.204 |
| VH3 x VL1 | 2.356 |
| VL1 x VH 3 | 0.7996 |
| VH2 x VL1 | 0.9668 |

anti_P329G_CAR_selection
HT29 (FolR1 low)

| | EC50 |
|---|---|
| original Binder | ~ 0.7553 |
| VH1 x VL1 | 1.681 |
| VH3 x VL1 | ~ 0.6597 |
| VL1 x VH 3 | 4.124 |
| VH2 x VL1 | 0.007609 |

anti_P329G_CAR_selection
HT29 (FolR1 low)

| | EC50 |
|---|---|
| original Binder | ~ 1883859 |
| VH1 x VL1 | ~ 0.6734 |
| VH3 x VL1 | 0.2125 |
| VL1 x VH 3 | |
| VH2 x VL1 | |

anti_P329G_CAR_selection
HT29 (FolR1 low)

| | EC50 |
|---|---|
| original Binder | ~ 6.169e+017 |
| VH1 x VL1 | ~ 0.006323 |
| VH3 x VL1 | ~ 0.02181 |
| VL1 x VH 3 | ~ 1.592 |
| VH2 x VL1 | ~ 4.466e+018 |

| | EC50 |
|---|---|
| original Binder | 0.04284 |
| VH3 x VL1 | 0.03942 |
| VH2 x VL1 | 0.03319 |
| VH1 x VL1 | 0.04236 |
| VL1 x VH3 | 0.07668 |

| | EC50 |
|---|---|
| original Binder | ~ 0.006906 |
| VH3 x VL1 | ~ 0.008634 |
| VH2 x VL1 | ~ 0.008091 |
| VH1 x VL1 | ~ 0.008236 |
| VL1 x VH3 | ~ 0.007126 |

ANTIGEN BINDING RECEPTORS

CROSS-REFERENCE TO RELATED APPLICATIONS

This application is a Continuation Application of International Patent Application No. PCT/EP2021/071515, filed Aug. 2, 2021, which claims benefit of priority to European Patent Application No. 20189196.7, filed Aug. 3, 2020 and European Patent Application No. 21158659.9, filed Feb. 23, 2021, each of which is incorporated herein by reference in its entirety.

SEQUENCE LISTING

This application contains a Sequence Listing which has been submitted electronically in XML format and is hereby incorporated by reference in its entirety. Said XML copy, created on Jan. 23, 2023, is named P36277-US.xml and is 185,206 bytes in size.

Entry of the amendments to the specification is respectfully requested.

The present invention generally relates to antigen binding receptors capable of specific binding to an Fc domain comprising the amino acid mutation P329G according to EU numbering. The present invention also relates to T cells, transduced with a antigen binding receptor which is recruited by specifically binding to/interacting with the mutated Fc domain of therapeutic antibodies. Furthermore, the invention relates to a kit comprising the transduced T cells of the invention and/or nucleic acid molecules, vectors encoding the antigen binding receptors of the present invention and tumor targeting antibodies comprising a mutated Fc domain.

BACKGROUND

Adoptive T cell therapy (ACT) is a powerful treatment approach using cancer-specific T cells (Rosenberg and Restifo, Science 348(6230) (2015), 62-68). ACT may use naturally occurring tumor-specific cells or T cells rendered specific by genetic engineering using T cell or chimeric antigen receptors (Rosenberg and Restifo, Science 348 (6230) (2015), 62-68). ACT can successfully treat and induce remission in patients suffering even from advanced and otherwise treatment refractory diseases such as acute lymphatic leukemia, non-hodgkins lymphoma or melanoma (Dudley et al., J Clin Oncol 26(32) (2008), 5233-5239; Grupp et al., N Engl J Med 368 (16) (2013), 1509-1518; Kochenderfer et al., J Clin Oncol. (2015) 33(6):540-549, doi: 10.1200/JCO.2014.56.2025. Epub 2014 Aug. 25).

However, despite impressive clinical efficacy, ACT is limited by treatment-related toxicities. The specificity, and resulting on-target and off-target effects, of engineered T cells used in ACT is mainly driven by the tumor targeting antigen binding moiety implemented in the antigen binding receptors. Non-exclusive expression of the tumor antigen or temporal difference in the expression level can result with serious side effects or even abortion of ACT due to non-tolerable toxicity of the treatment.

Additionally, the availability of tumor-specific T cells for efficient tumor cells lysis is dependent on the long-term survival and proliferation capacity of engineered T cells in vivo. On the other hand, in vivo survival and proliferation of T cells may also result in unwanted long-term effects due to the persistence of an uncontrolled T cell response which can result in damage of healthy tissue (Grupp et al. 2013 N Engl J Med 368(16):1509-18, Maude et al. 2014 2014 N Engl J Med 371(16):1507-17).

One approach for limiting serious treatment-related toxicities and to improve safety of ACT is to restrict the activation and proliferation of T cells by introducing adaptor molecules in the immunological synapse. Such adaptor molecules comprise small molecular bimodular switches as e.g. recently described folate-FITC switch (Kim et al. J Am Chem Soc 2015; 137:2832-2835). A further approach included artificially modified antibodies comprising a tag to guide and direct the specificity of the T cells to target tumor cells (Ma et al. PNAS 2016; 113(4):E450-458, Cao et al. Angew Chem 2016; 128:1-6, Rogers et al. PNAS 2016; 113(4):E459-468, Tamada et al. Clin Cancer Res 2012; 18(23):6436-6445).

However, existing approaches have several limitations. Immunological synapses relying on molecular switches require introduction of additional elements that might elicit an immune response or result with non-specific off-target effects. Furthermore, the complexity of such multicomponent systems may limit treatment efficacy and tolerability. On the other hand, the introduction of tag structure in existing therapeutic monoclonal antibodies may affect the efficacy and safety profile of these constructs. Further, adding tags require additional modification and purification steps making the production of such antibodies more complex and further require additional safety testing.

Furthermore, the in vivo use of non-human or partially human antibodies can lead to the formation of anti-drug antibodies (ADAs), including anti-idiotypic or human anti-mouse antibody (HAMA) (Blanco et al Clin Immunol 17, 96-106 (1997)). These ADAs can affect the pharmacokinetic properties, the safety and functionality of the administered antibodies and humanization has been applied to tackle this (Carter et al PNAS 89, 4285-4289 (1992)). Similarly, ADAs have been observed for mouse based CAR-T cells: Although human anti-mouse IgG antibodies have been known to develop with CAR-transduced T cells, they have been thought to have no adverse clinical consequences. Maus et al described for the first time anaphylaxis resulting from CAR-modified T cells, most likely through IgE antibodies specific to the CAR. These results indicate that the potential immunogenicity of antigen binding receptors derived from murine antibodies may be a safety issue, especially when administered using an intermittent dosing schedule (Maus et al Cancer Immunol Res 1, 26-31 (2013)). Accordingly, the targeted tumor therapy, particularly the adoptive T cell therapy needs to be improved in order to suffice the needs of the cancer patients. Thus, there is still a need to provide improved means having the potential to improve safety and efficacy of ACT and overcome the above disadvantages.

SUMMARY OF THE INVENTION

The present invention provides antigen binding receptors with improved properties, in particular humanized antigen binding receptors which are stable and highly expressed in transduced cells.

Herein provided is an antigen binding receptor comprising an anchoring transmembrane domain and an extracellular domain, wherein the extracellular domain comprises an antigen binding moiety comprising (i) a heavy chain variable domain (VH) comprising a heavy chain complementary determining region (HCDR) 1 of SEQ ID NO:1, a HCDR 2 of SEQ ID NO:2 or SEQ ID NO:40, and a HCDR 3 of SEQ ID NO:3, and (ii) a light chain variable domain (VL) comprising a light chain complementarity determining region (LCDR) 1 of SEQ ID NO:4, a LCDR 2 of SEQ ID NO:5 and a LCDR 3 of SEQ ID NO:6.

In one embodiment, the VH domain comprises an amino acid sequence that is at least about 95%, 96%, 97%, 98%, 99% or 100% identical to an amino acid sequence selected from the group consisting of SEQ ID NO:8, SEQ ID NO:41, SEQ ID NO:44 and SEQ ID NO:126.

In one embodiment, the VL domain comprises an amino acid sequence that is at least about 95%, 96%, 97%, 98%, 99% or 100% identical to the amino acid sequence of SEQ ID NO:9.

In one embodiment, the VL domain comprises an amino acid sequence that is at least about 95%, 96%, 97%, 98%, 99% or 100% identical to the amino acid sequence of SEQ ID NO:127.

In one embodiment, the anchoring transmembrane domain is a transmembrane domain selected from the group consisting of the CD8, the CD4, the CD3z, the FCGR3A, the NKG2D, the CD27, the CD28, the CD137, the OX40, the ICOS, the DAP10 or the DAP12 transmembrane domain or a fragment thereof, in particular wherein the anchoring transmembrane domain is the CD8 transmembrane domain or a fragment thereof.

In one embodiment, the antigen binding receptor comprises at least one stimulatory signaling domain and/or at least one co-stimulatory signaling domain.

In one embodiment, the at least one stimulatory signaling domain is individually selected from the group consisting of the intracellular domain of CD3z, of FCGR3A and of NKG2D, or fragments thereof that retains stimulatory signaling activity, in particular wherein the at least one stimulatory signaling domain is the CD3z intracellular domain or a fragment thereof that retains CD3z stimulatory signaling activity.

In one embodiment, the at least one co-stimulatory signaling domain is individually selected from the group consisting of the intracellular domain of CD27, of CD28, of CD137, of OX40, of ICOS, of DAP10 and of DAP12, or fragments thereof that retain co-stimulatory signaling activity.

In one embodiment, the antigen binding receptor, comprises at least one CD28 costimulatory domain or a fragment thereof, and/or at least one CD137 costimulatory domain or a fragment thereof that retains CD28 co-stimulatory activity.

In one embodiment, the antigen binding receptor comprises a stimulatory signaling domain comprising the intracellular domain of CD3z, or a fragment thereof that retains CD3z stimulatory signaling activity, and wherein the antigen binding receptor comprises a co-stimulatory signaling domain comprising the intracellular domain of CD28, or a fragment thereof that retains CD28 co-stimulatory signaling activity.

In one embodiment, the antigen binding receptor comprises one stimulatory signaling domain comprising the intracellular domain of CD3z, or a fragment thereof that retains CD3z stimulatory signaling activity, and wherein the antigen binding receptor comprises one co-stimulatory signaling domain comprising the intracellular domain of CD137, or a fragment thereof that retains CD137 co-stimulatory signaling activity.

In one embodiment, the antigen binding moiety is connected at the C-terminus to the N-terminus of the anchoring transmembrane domain, optionally through a peptide linker.

In one embodiment, the light chain variable domain (VL) of the antigen binding moiety is connected at the C-terminus to the N-terminus of the anchoring transmembrane domain, optionally through a peptide linker, and/or wherein the heavy chain variable domain (VH) is connected at the C-terminus to the N-terminus of the light chain variable domain (VL), optionally through a peptide linker.

In one embodiment, provided is a T cell capable of expressing the antigen binding receptor as herein described.

In one embodiment, provided is an isolated polynucleotide encoding the antigen binding receptor as herein described.

In one embodiment, provides is a vector, particularly an expression vector, comprising the polynucleotide as herein described.

In one embodiment, provided is a kit comprising (A) a transduced T cell capable of expressing the antigen binding receptor as herein described; and (B) an antibody that binds to a target cell antigen and that comprises an Fc domain comprising the amino acid mutation P329G according to EU numbering.

In one embodiment, provided is a kit comprising (A) an isolated polynucleotide encoding the antigen binding receptor as herein described; and (B) an antibody that binds to a target cell antigen and that comprises an Fc domain comprising the amino acid mutation P329G according to EU numbering.

In one embodiment, the target cell antigen is selected from the group consisting of fibroblast activation protein (FAP), carcinoembryonic antigen (CEA), mesothelin (MSLN), CD20, folate receptor 1 (FOLR1), and tenascin (TNC).

In one embodiment, provided is the kit as herein described for use as a medicament.

In one embodiment, provided is the kit as herein described for use in the treatment of a disease, in particular for use in the treatment of cancer.

In one embodiment, provided is the transduced T cell as herein described for use as a medicament, wherein the transduced T cell is administered before, simultaneously with or after administration of an antibody that binds to a target cell antigen and comprises an Fc domain comprising the amino acid mutation P329G according to EU numbering In one embodiment, the treatment comprises administration of the transduced T cell before, simultaneously with or after administration of an antibody that binds to a target cell antigen and that comprises an Fc domain comprising the amino acid mutation P329G according to EU numbering.

In one embodiment, provided is a method of treating a disease in a subject, comprising administering to the subject a transduced T cell capable of expressing the antigen binding receptor as herein described and administering before, simultaneously with or after administration of the transduced T cell a therapeutically effective amount of an antibody that binds to a target cell antigen and that comprises an Fc domain comprising the amino acid mutation P329G according to EU numbering.

In one embodiment, provided is a method for inducing lysis of a target cell, comprising contacting the target cell with a transduced T cell capable of expressing the antigen binding receptor as herein described in the presence of an antibody that binds to a target cell antigen and that comprises an Fc domain comprising the amino acid mutation P329G according to EU numbering.

In one embodiment, provided is the use of the antigen binding receptor as herein described, the polynucleotide as herein described or the transduced T cell as herein described for the manufacture of a medicament for the treatment of cancer.

SHORT DESCRIPTION OF THE FIGURES

Figure 1B:
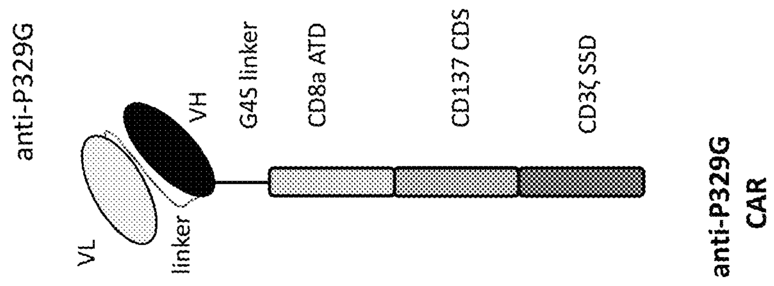
Figure 1C:
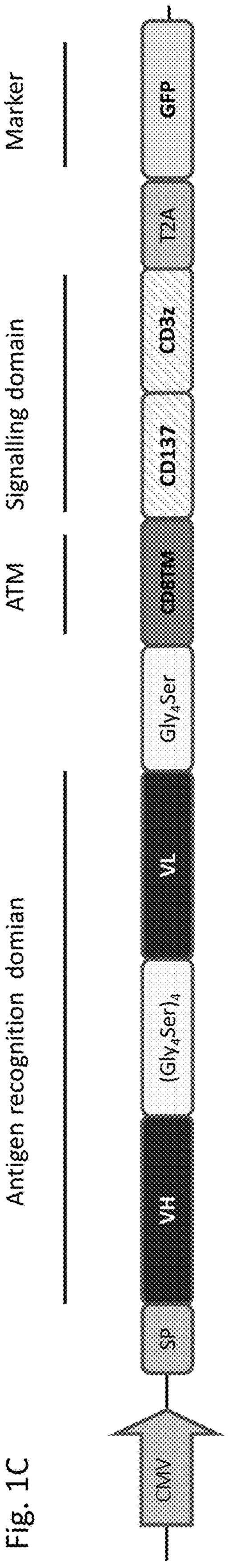
Figure 1D:
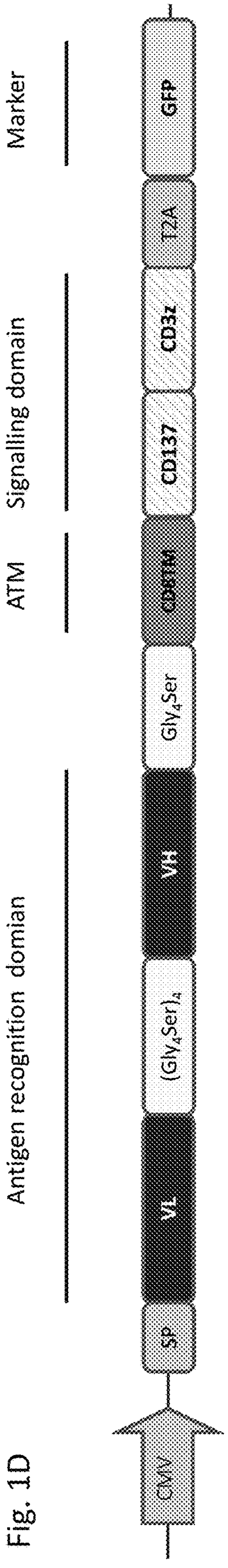

FIGS. 1A-1D: Schematic representation of second generation chimeric antigen binding receptor with anti-P329G binding moiety in the scFv format. In VH×VL scFv (FIG. 1A) orientation and VL×VH (FIG. 1B) orientation. FIGS. 1C and 1D show DNA constructs encoding the antigen binding receptors depicted in FIGS. 1A and 1B, respectively.

Figure 2B:
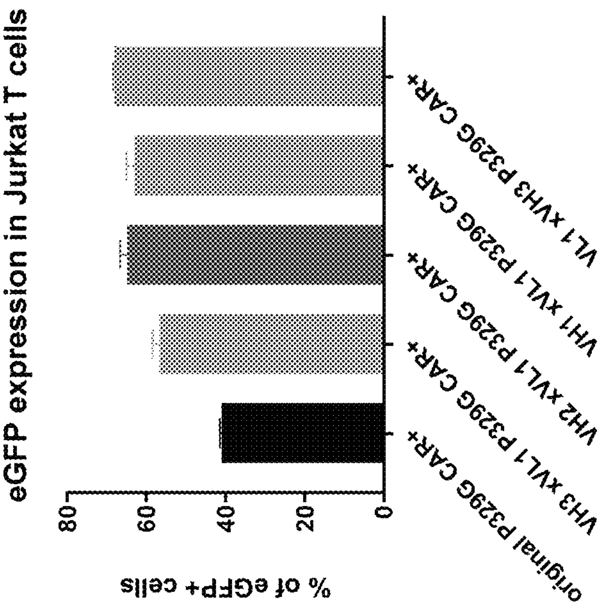
Figure 2A:
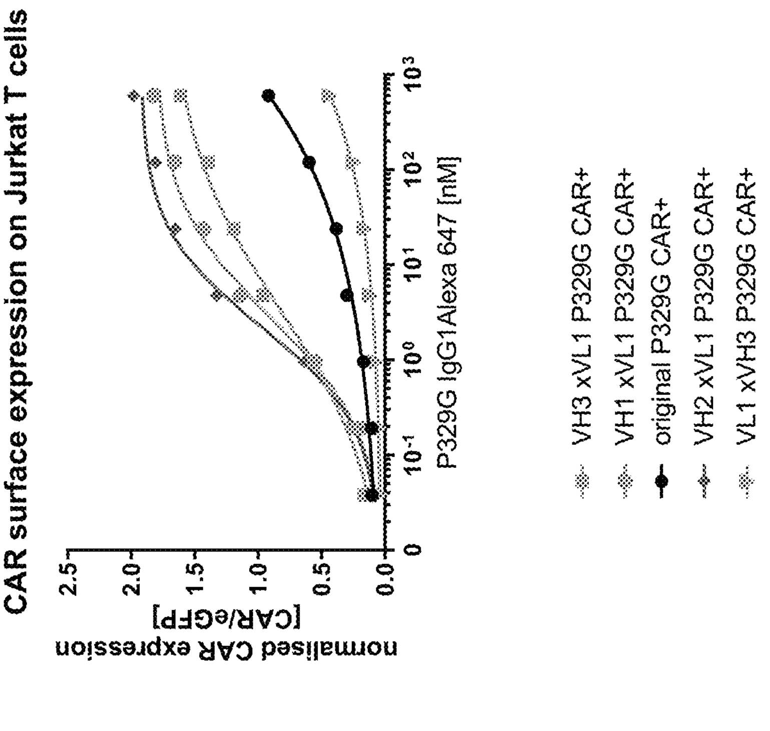
Figure 3A:
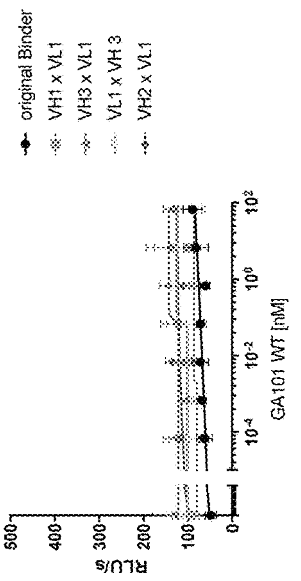
Figure 3B:
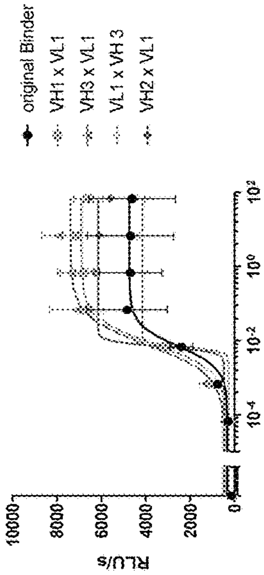
Figure 3C:
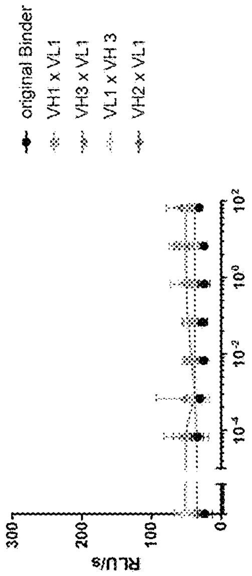
Figure 3D:
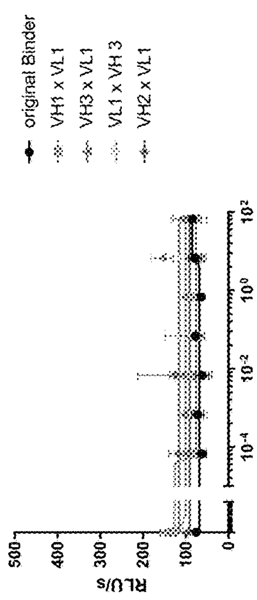
Figure 3E:
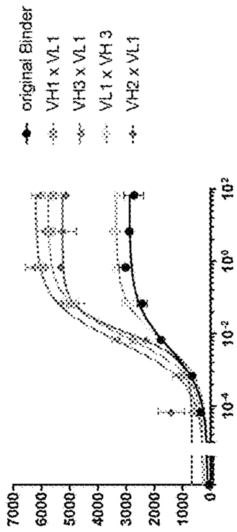
Figure 3F:
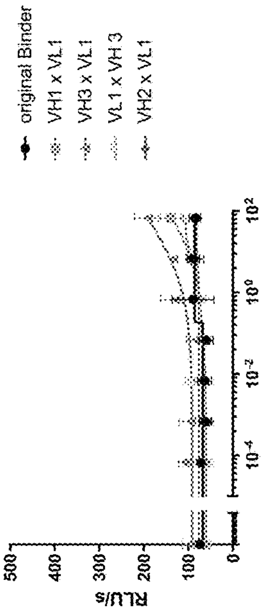
Figure 4A:
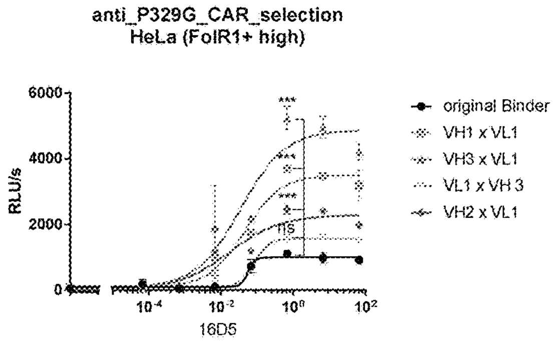
Figure 4B:
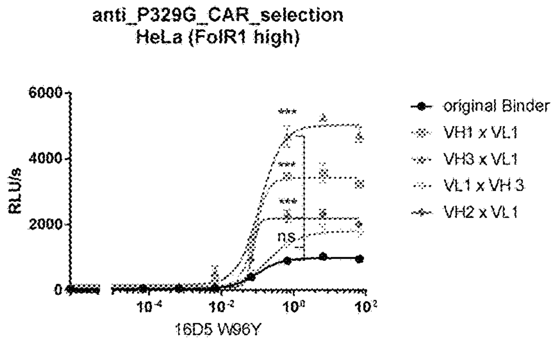
Figure 4C:
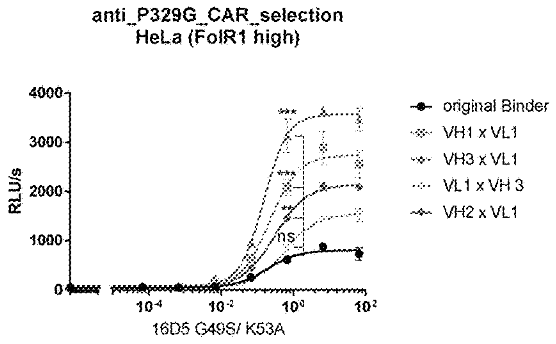
Figure 4D:
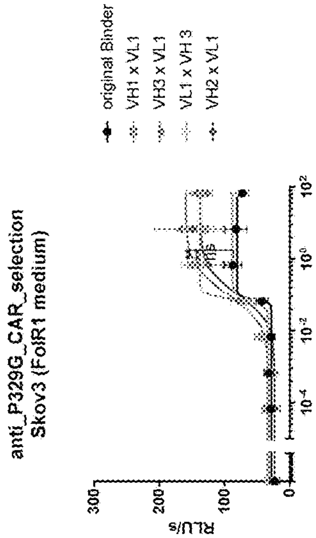
Figure 4E:
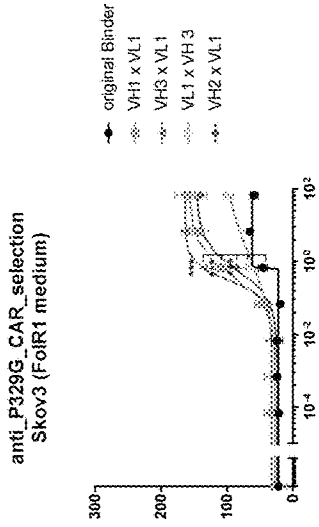
Figure 4F:
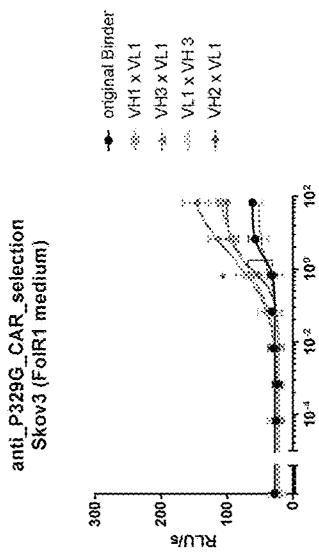
Figure 4G:
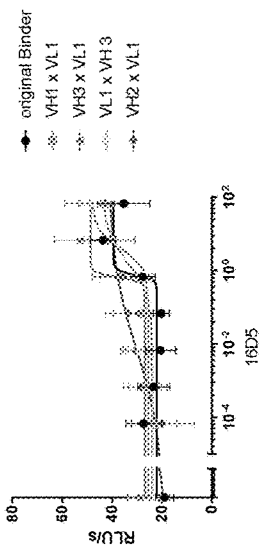
Figure 4H:
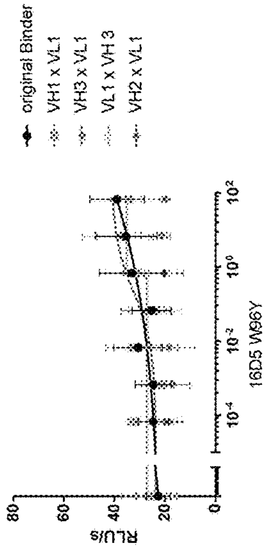
Figure 4I:
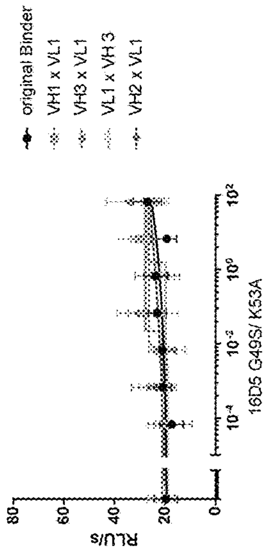

FIGS. 2A-2B: depicted is the CAR surface expression of different humanized scFv variants (FIG. 2A) and the correlating GFP expression serving as transduction control (FIG. 2B)

FIGS. 3A-3F: Evaluation of unspecific signaling of anti-P329G CAR Jurkat reporter T cells employing different humanized versions of the P329G binder as binding moiety. Activation was assessed by quantification of the intensity of CD3 downstream signaling using anti-P329G CAR Jurkat-NFAT reporter assay either in the presence of antibodies possessing different Fc variants or with P329G Fc variants but without target cells. Depicted are technical average values from triplicates, error bars indicate SD.

FIGS. 4A-4I: Activation of anti-P329G CAR Jurkat reporter T cells employing different humanized versions of the P329G binder in the presence of $FolR1^+$ target cells with high (HeLa-FolR1), medium (Skov3) and low (HT29) target expression levels in combination with antibodies that possess high (16D5), medium (16D5 W96Y) or low (16D5 G49S/K53A) affinities towards FolR1. Activation was assessed by quantification of the intensity of CD3 downstream signaling using anti-P329G CAR Jurkat-NFAT reporter assay. Depicted are technical average values from triplicates, error bars indicate SD.

Figure 5A:
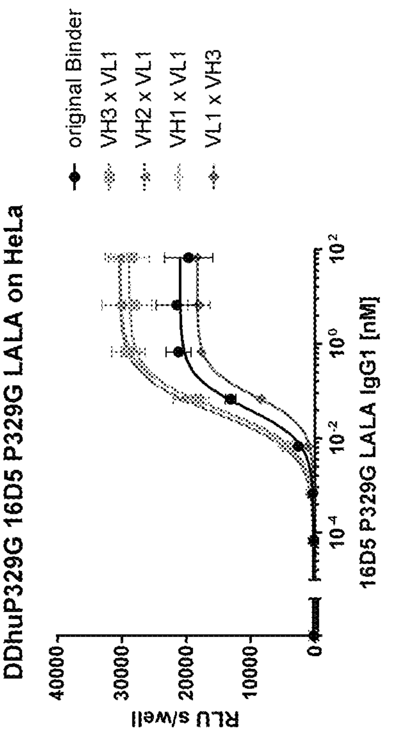
Figure 5B:
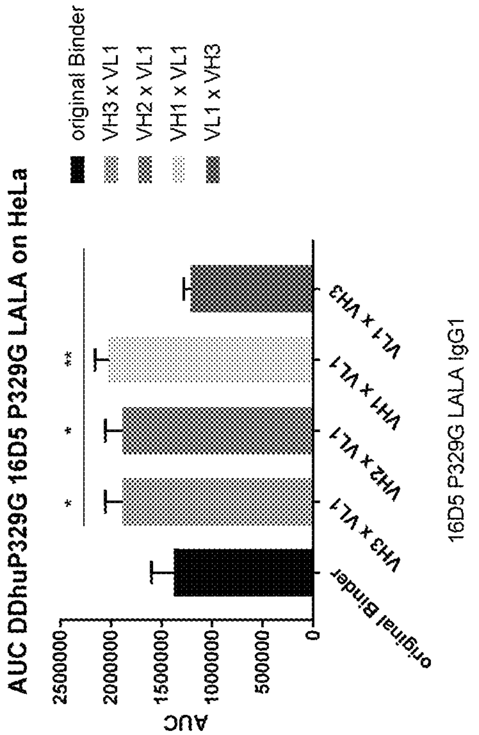

FIGS. 5A-5B: Activation of anti-P329G CAR Jurkat NFAT reporter T cells employing different humanized versions of the P329G binder as binding moiety. Activity of the reporter cells was evaluated in the presence of anti-FolR1 (16D5) P329G IgG1 targeting IgG and HeLa ($FolR1^+$) target cells (FIG. 5A). Antibody does-dependent activation was assessed by quantification of the intensity of CD3 downstream signaling using anti-P329G CAR Jurkat-NFAT reporter assay and the area under the curve was calculated (FIG. 5B). Depicted are technical average values from triplicates, error bars indicate SD.

Figure 6A:
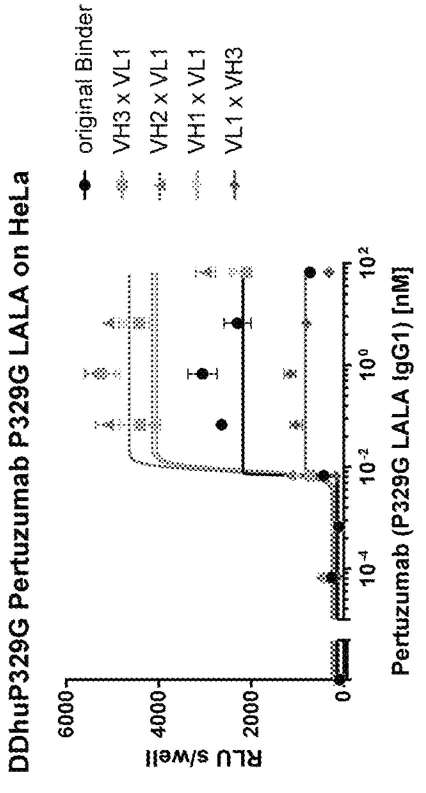
Figure 6B:
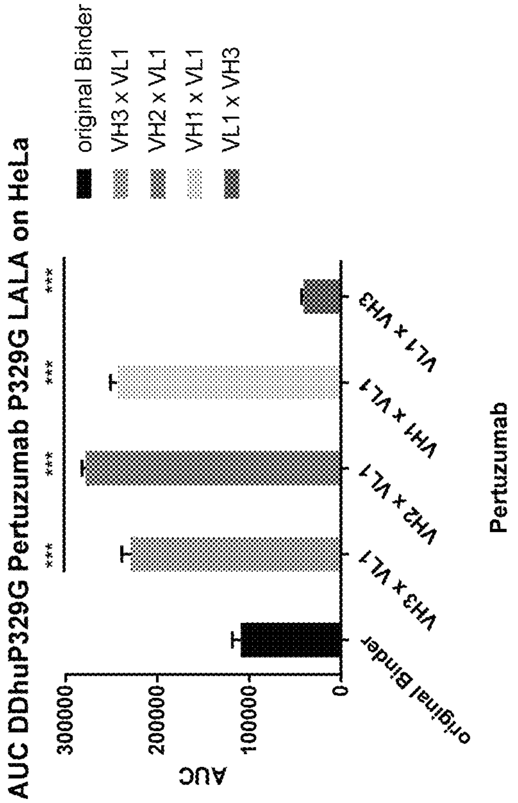

FIGS. 6A-6B: Activation of anti-P329G CAR Jurkat NFAT reporter T cells employing different humanised versions of the P329G binder as binding moiety. Activity of the reporter cells was evaluated in the presence of anti-HER2 (Pertuzumab) P329G IgG1 targeting IgG and HeLa ($HER2^+$) target cells (FIG. 6A). Antibody does-dependent activation was assessed by quantification of the intensity of CD3 downstream signaling using anti-P329G CAR Jurkat-NFAT reporter assay and the area under the curve was calculated (FIG. 6B). Depicted are technical average values from triplicates, error bars indicate SD.

Figure 7:
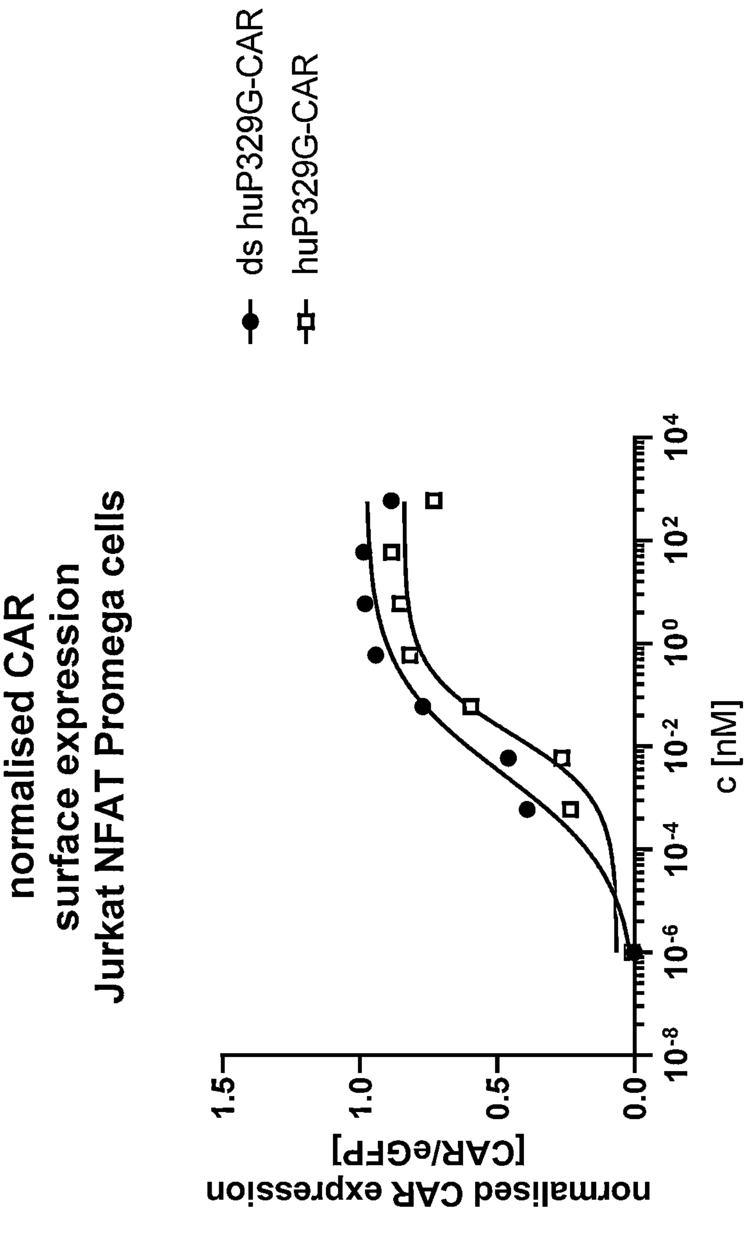

FIG. 7: depicted is the CAR surface expression of the disulfide stabilized VH×VL1 scFv variant.

DETAILED DESCRIPTION

Definitions

Terms are used herein as generally used in the art, unless otherwise defined in the following.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes are 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

"Antibody-dependent cell-mediated cytotoxicity" ("ADCC") is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent, e.g., a pharmaceutical composition, refers to an amount effective, at dosages and for periods of time necessary, to achieve the desired therapeutic or prophylactic result. "Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are described in the following.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g. hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

As used herein, the term "antigen binding molecule" refers in its broadest sense to a molecule that specifically binds an antigenic determinant. Examples of antigen binding molecules are immunoglobulins and derivatives, e.g., fragments, thereof as well as antigen binding receptors and derivatives thereof.

As used herein, the term "antigen binding moiety" refers to a polypeptide molecule that specifically binds to an antigenic determinant. In one embodiment, an antigen binding moiety is able to direct the entity to which it is attached (e.g. a cell expressing an antigen binding receptor comprising the antigen binding moiety) to a target site, for example to a specific type of tumor cell or tumor stroma bearing the antigenic determinant. Antigen binding moieties include antibodies and fragments thereof as further defined herein. Particular antigen binding moieties include an antigen binding domain of an antibody, comprising an antibody heavy chain variable region and an antibody light chain variable region (e.g. a scFv fragment). In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

In the context of the present invention the term "antigen binding receptor" relates to an antigen binding molecule comprising an anchoring transmembrane domain and an extracellular domain comprising at least one antigen binding moiety. An antigen binding receptor can be made of polypeptide parts from different sources. Accordingly, it may be also understood as a "fusion protein" and/or a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. Further details to the antigen binding receptors of the present invention are described herein below. In the context of the present invention a CAR (chimeric antigen receptor) is understood to be an antigen binding receptor comprising an extracellular portion comprising an antigen binding moiety fused by a spacer sequence to an anchoring transmembrane domain which is itself fused to intracellular signaling domains.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

The term "antigen binding domain" refers to the part of an antibody or an antigen binding receptor that comprises the area which specifically binds to and is complementary to part or all of an antigen. An antigen binding domain may be provided by, for example, one or more immunoglobuling variable domains (also called variable regions). Particularly, an antigen binding domain comprises an immunoglobulin light chain variable domain (VL) and an immunoglobulin heavy chain variable domain (VH).

As used herein, the term "antigenic determinant" is synonymous with "antigen" and "epitope" and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

"Antibodies comprising a mutated Fc domain" according to the present invention, i.e. therapeutic antibodies may have one, two, three or more binding domains and may be monospecific, bispecific or multispecific. The antibodies can be full length from a single species, or be chimerized or humanized. For an antibody with more than two antigen binding domains, some binding domains may be identical and/or have the same specificity.

The term "ATD" as used herein refers to "anchoring transmembrane domain" which defines a polypeptide stretch capable of integrating in (the) cellular membrane(s) of a cell. The ATM can be fused to extracellular and/or intracellular polypeptide domains wherein these extracellular and/or intracellular polypeptide domains will be confined to the cell membrane. In the context of the antigen binding receptors of the present invention the ATM confers membrane attachment and confinement of the antigen binding receptor of the present invention. The antigen binding receptors of the present invention comprise at least one ATM and an extracellular domain comprising an antigen binding moiety. Additionally, the ATM may be fused to intracellular signaling domains.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore™ instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "CDR" as employed herein relates to "complementary determining region", which is well known in the art. The CDRs are parts of immunoglobulins or antigen binding receptors that determine the specificity of said molecules and make contact with a specific ligand. The CDRs are the most variable part of the molecule and contribute to the antigen binding diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in "Kabat" (Sequences of Proteins of Immunological Interest", 5th edit. NIH Publication no. 91-3242 U.S. Department of Health and Human Services (1991); Chothia J. Mol. Biol. 196 (1987), 901-917) or "Chothia" (Nature 342 (1989), 877-883).

The term "CD3z" refers to T-cell surface glycoprotein CD3 zeta chain, also known as "T-cell receptor T3 zeta chain" and "CD247".

The term "chimeric antigen receptor" or "chimeric receptor" or "CAR" refers to an antigen binding receptor constituted of an extracellular portion of an antigen binding moiety (e.g. a single chain antibody domain) fused by a spacer sequence to intracellular signaling/co-signaling domains (such as e.g. of CD3z and CD28).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, IgG4, $IgA_1$, and $IgA_2$. In certain aspects, the antibody is of the $IgG_1$ isotype. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

The terms "constant region derived from human origin" or "human constant region" as used in the current application denotes a constant heavy chain region of a human antibody of the subclass IgG1, IgG2, IgG3, or IgG4 and/or a constant light chain kappa or lambda region. Such constant regions can be used in human or humanized antibodies and are well known in the state of the art and e.g. described by Kabat, E. A., et al., Sequences of Proteins of Immunological Interest, 5th ed., Public Health Service, National Institutes of Health, Bethesda, MD (1991) (see also e.g. Johnson, G., and Wu, T. T., Nucleic Acids Res. 28 (2000) 214-218; Kabat, E. A., et al., Proc. Natl. Acad. Sci. USA 72 (1975) 2785-2788). Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

By a "crossover" Fab molecule (also termed "Crossfab") is meant a Fab molecule wherein the variable domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the crossover Fab molecule.

The term "CSD" as used herein refers to co-stimulatory signaling domain.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

A "Fab molecule" refers to a protein consisting of the VH and CH1 domain of the heavy chain (the "Fab heavy chain") and the VL and CL domain of the light chain (the "Fab light chain") of an immunoglobulin.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprises an additional C-terminal glycine-lysine dipeptide (G446 and K447, numbering according to EU index of Kabat). In one embodiment of the invention, a heavy chain including a subunit of an Fc domain as specified herein, comprises an additional C-terminal glycine residue (G446, numbering according to EU index of Kabat). Compositions of the invention, such as the pharmaceutical compositions described herein, comprise a population of antigen binding molecules of the invention. The population of antigen binding molecule may comprise molecules having a full-length heavy chain and molecules having a cleaved variant heavy chain. The population of antigen binding molecules may consist of a mixture of molecules having a full-length heavy chain and molecules having a cleaved variant heavy chain, wherein at least 50%, at least 60%, at least 70%, at least 80% or at least 90% of the antigen binding molecules have a cleaved variant heavy chain. In one embodiment of the invention a composition comprising a population of antigen binding molecules of the invention comprises an antigen binding molecule comprising a heavy chain including a subunit of an Fc domain as specified herein with an additional C-terminal glycine-lysine dipeptide (G446 and K447, numbering according to EU index of Kabat). In one embodiment of the invention a composition comprising a population of antigen binding molecules of the invention comprises an immune activating Fc domain binding molecule comprising a heavy chain including a subunit of an Fc domain as specified herein with an additional C-terminal glycine residue (G446, numbering according to EU index of Kabat). In one embodiment of the invention such a composition comprises a population of antigen binding molecules comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

By "fused" is meant that the components (e.g., a Fab and a transmembrane domain) are linked by peptide bonds, either directly or via one or more peptide linkers.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one aspect, for the VL, the subgroup is subgroup kappa I as in Kabat et al., supra. In one aspect, for the VH, the subgroup is subgroup III as in Kabat et al., supra.

A "humanized" antibody (e.g. a humanized scFv fragment) refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the individual or subject is a human.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

By "isolated nucleic acid" molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed below for polypeptides (e.g., ALIGN-2).

By an "isolated polypeptide" or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or http://www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header. The term "nucleic acid molecule" relates to the sequence of bases comprising purine- and pyrimidine bases which are comprised by polynucleotides, whereby said bases represent the primary structure of a nucleic acid molecule. Herein, the term nucleic acid molecule includes DNA, cDNA, genomic DNA, RNA, synthetic forms of DNA and mixed polymers comprising two or more of these molecules. In addition, the term nucleic acid molecule includes both, sense and antisense strands. Moreover, the herein described nucleic acid molecule may contain non-natural or derivatized nucleotide bases, as will be readily appreciated by those skilled in the art.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical composition" refers to a preparation which is in such form as to permit the biological activity of an active ingredient contained therein to be effective, and which contains no additional components which are unacceptably toxic to a subject to which the formulation would be administered. A pharmaceutical composition usually comprises one or more pharmaceutically acceptable carrier(s).

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative. As used herein, term "polypeptide" refers to a molecule composed of monomers (amino acids) linearly linked by amide bonds (also known as peptide bonds).

The term "polypeptide" refers to any chain of two or more amino acids, and does not refer to a specific length of the product. Thus, peptides, dipeptides, tripeptides, oligopeptides, "protein", "amino acid chain", or any other term used to refer to a chain of two or more amino acids, are included within the definition of "polypeptide", and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term nucleic acid molecule refers to any one or more nucleic acid segments, e.g., DNA or RNA fragments, present in a polynucleotide.

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule. In a preferred embodiment, the antigen binding moiety is a scFv fragment.

The term "SSD" as used herein refers to "stimulatory signaling domain".

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The immune activating Fc domain binding molecules of the invention are capable of inducing T cell activation. Suitable assays to measure T cell activation are known in the art described herein.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. *Kuby Immunology, 6th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

Antigen Binding Receptors Capable of Specific Binding to a Mutated Fc Domain

The present invention relates to antigen binding receptors capable of specific binding to the mutated Fc domain of an antibody, e.g. a therapeutic antibody targeting a cancer cell. In a preferred aspect, the present invention relates to antigen binding receptors capable of specific binding to a mutated Fc domain comprising the amino acid mutation P329G according to EU numbering. The antigen binding receptors of the present invention comprise an extracellular domain comprising at least one antigen binding moiety capable of specific binding to the mutated Fc domain but not capable of specific binding to the parent non-mutated Fc domain. In preferred embodiments, the antigen binding moiety of the antigen binding receptor is a humanized or human antigen binding moiety, e.g. a humanized or human scFv. In one preferred embodiment, the amino acid mutation is P329G and specific binding to a mutated Fc domain comprising the amino acid mutation P329G according to EU numbering is measured by SPR at 25° C.

The present invention further relates to the transduction of T cells, such as CD8+ T cells, CD4+ T cells, CD3+ T cells, γδ T cells or natural killer (NK) T cells, preferably CD8+ T cells, with an antigen binding receptor as described herein and their targeted recruitment, e.g., to a tumor, by an antibody molecule, e.g. a therapeutic antibody, comprising a mutated Fc domain (e.g. an Fc domain comprising the amino acid mutation P329G according to EU numbering). In one embodiment, the antibody is capable of specific binding to a tumor-specific antigen that is naturally occurring on the surface of a tumor cell.

As shown in the appended Examples, as a proof of concept, the antigen binding receptor comprising an anchoring transmembrane domain and a humanized extracellular domain according to the invention (SEQ ID NO:7 as encoded by the DNA sequence shown in SEQ ID NO:20) was constructed which is capable of specific binding to a therapeutic antibody (represented by the anti-CD20 antibody comprising a heavy chain of SEQ ID NO ID: 102 and a light chain of SEQ ID NO:103) comprising the P329G mutation. Transduced T cells (Jurkat NFAT T cells) expressing the VH3VL1-CD8ATD-CD137CSD-CD3zSSD fusion protein (SEQ ID NO:7 as encoded by the DNA sequence shown in SEQ ID NO:20) could be strongly activated by co-incubation with the anti-CD20 antibody comprising the P329G mutation in the Fc domain together with CD20 positive tumor cells.

The treatment of tumor cells by the combination of an antibody directed against a tumor antigen wherein the antibody comprises the P329G mutation together with transduced T cells expressing the VH3VL1-CD8ATD-CD137CSD-CD3zSSD fusion protein (SEQ ID NO:7 as encoded by the DNA sequence shown in SEQ ID NO:20) surprisingly leads to stronger activation of the transduced T cell compared to the transduced T cells expressing the VL1VH3-CD8ATD-CD137CSD-CD3zSSD (SEQ ID NO:31 as encoded by the DNA sequence shown in SEQ ID NO:33).

In the VH3VL1-CD8ATD-CD137CSD-CD3zSSD fusion protein, the VH domain (VH3) is fused at its C-terminus to the N-terminus of the VL domain (VL1) through a peptide linker to form a scFv. The scFv is fused at its C-terminus (the C-terminus of the VL domain) through a peptide linker to the anchoring transmembrane domain (ATD). On the other hand, the VL1VH3-CD8ATD-CD137CSD-CD3zSSD fusion protein, the VL domain (VL1) is fused at its C-terminus to the N-terminus of the VH domain (VH3) through a peptide linker to form a scFv. The scFv is fused at its C-terminus (the C-terminus of the VH domain) through a peptide linker to the anchoring transmembrane domain (ATD). Without being bound to theory, the observation that the VH3VL1-CD8ATD-CD137CSD-CD3zSSD fusion protein leads to stronger activation of the transduced T cell compared to the VL1VH3-CD28ATD-CD137CSD-CD3zSSD suggests that fusion of the VL domain to the anchoring domain (through a peptide linker) leads to a more potent antigen binding receptor. This is unexpected and surprising.

Combination of the VH domain VH3 with the VL domain VLT, both identified by the present inventors is especially favorable since these variable domains are humanized antibody domains. Without being bound to theory humanized antibody domains are preferable since less side effect can be expected when applying antigen binding moieties comprising such humanized antibody domains to human patients (such as e.g. less formation of anti-drug antibodies (ADA)). However, humanization can result in loss of binding of an antigen binding moiety (e.g. one deriving from a non-human source). As shown in the appended Examples, the humanized VH3 and VLT domains retain binding to an Fc domain comprising the comprising the amino acid mutation P329G according to EU numbering. This result is unexpected as shown for example by the failure of other humanized VH and VL domains to retain comparable binding to an Fc domain comprising the amino acid mutation P329G according to EU numbering.

Hence, in a preferred embodiment of the present invention provided is an antigen binding receptor comprising a humanized antigen binding moiety capable of specific binding to an Fc domain comprising the amino acid mutation P329G according to EU numbering. The concept of the present invention and its components (humanized antigen binding receptor and therapeutic antibody) are further described in detail herein below.

According to the present invention, pairing of a tumor-specific antibody, i.e. a therapeutic antibody, comprising a mutated Fc domain (e.g. comprising the amino acid mutation P329G according to EU numbering with T cells transduced with an antigen binding receptor which comprise/consist of an extracellular domain comprising an antigen binding moiety capable of specific binding to the mutated Fc domain results in a specific activation of the T cells and subsequent lysis of the tumor cell. This approach bears significant safety advantages over conventional T cell based approaches, as the T cell would be inert in the absence of the antibody comprising the mutated Fc domain. Accordingly, the invention provides a versatile therapeutic platform wherein IgG type antibodies are used to mark or label tumor cells as a guidance for T cell and wherein transduced T cells are specifically targeted toward the tumor cells by providing specificity for a mutated Fc domain of the IgG type antibody. After binding to the mutated Fc domain of the antibody on the surface of a tumor cell, the transduced T cell as described herein becomes activated and the tumor cell will subsequently be lysed. The platform is flexible and specific by allowing the use of diverse (existing or newly developed) target antibodies or co-application of multiple antibodies with different antigen specificity but comprising the same mutation in the Fc domain (such as e.g. the P329G mutation). The degree of T cell activation can further be adjusted by adjusting the dosage of the co-applied therapeutic antibody or by switching to different antibody specificities or formats. Transduced T cell according to the invention are inert without co-application of a targeting antibody comprising a mutated Fc domain because mutations to the Fc domain as described herein do not occur in natural or non-mutated immunoglobulins. Accordingly, in one embodiment, the mutated Fc domain does not naturally occur in (human) immunoglobulins.

Accordingly, the present invention relates to an antigen binding receptor comprising an extracellular domain comprising at least one antigen binding moiety capable of specific binding to a mutated Fc domain, wherein the at least one antigen binding moiety is not capable of specific binding to the parent non-mutated Fc domain. It may be particularly desirable to use therapeutic antibodies with reduced effector function in cancer therapy since effector function may lead to severe side effects of antibody-based tumor therapies as further described herein. In the context of the present invention, the antigen binding receptor comprises an extracellular domain that does not naturally occur in or on T cells. Thus, the antigen binding receptor is capable of providing tailored binding specificity to cells expressing the antigen binding receptor according to the invention. Cells, e.g. T cells, transduced with (an) antigen binding receptor(s) of the invention become capable of specific binding to a mutated Fc domain but not to the non-mutated parent Fc domain. Specificity is provided by the antigen binding moiety of the extracellular domain of the antigen binding receptor. In the context of the present invention and as explained herein, the antigen binding moiety capable of specific binding to a mutated Fc domain bind to/interact with the mutated Fc domain but not to/with the non-mutated parent Fc domain.

Antigen Binding Moieties

In an illustrative embodiment of the present invention, as a proof of concept, provided are humanized antigen binding receptors capable of specific binding to a mutated Fc domain comprising the amino acid mutation P329G and effector cells expressing said antigen binding receptors. The P329G mutation reduces binding to Fcγ receptors and associated effector function. Accordingly, the mutated Fc domain comprising the P329G mutation binds to Fcγ receptors with reduced or abolished affinity compared to the non-mutated Fc domain.

In one embodiment the antigen binding moiety is capable of specific binding to a mutated Fc domain composed of a first and a second subunit capable of stable association. In one embodiment the Fc domain is an IgG, specifically an $IgG_1$ or $IgG_4$, Fc domain. In one embodiment the Fc domain is a human Fc domain. In one embodiment the mutated Fc domain exhibits reduced binding affinity to an Fc receptor and/or reduced effector function, as compared to a native $IgG_1$ Fc domain. In one embodiment the Fc domain comprises one or more amino acid mutations that reduce binding to an Fc receptor and/or effector function.

In a preferred embodiment, the mutated Fc domain comprises the P329G mutation. Accordingly, the mutated Fc domain comprising the P329G mutation binds to Fey receptors with reduced or abolished affinity compared to the non-mutated Fc domain.

In one embodiment, the antigen binding receptor comprises an extracellular domain comprising an antigen binding moiety. In one embodiment, the antigen binding moiety is capable of specific binding to an Fc domain comprising the amino acid mutation P329G according to EU numbering In one embodiment, the antigen binding moiety comprises a heavy chain variable domain (VH) comprising at least one of:

(a) a heavy chain complementarity determining region (CDR H) 1 amino acid sequence of RYWMN (SEQ ID NO:1);
(b) a CDR H2 amino acid sequence of EITPDSSTINYAPSLKG (SEQ ID NO:2) or of EITPDSSTINYTPSLKG (SEQ ID NO:40); and
(c) a CDR H3 amino acid sequence of PYDYGAWFAS (SEQ ID NO:3).

In one embodiment the antigen binding moiety comprises a light chain variable domain (VL) comprising at least one of:

(d) a light chain (CDR L)1 amino acid sequence of RSSTGAVTTSNYAN (SEQ ID NO:4);
(e) a CDR L2 amino acid sequence of GTNKRAP (SEQ ID NO:5); and
(f) a CDR L3 amino acid sequence of ALWYSNHWV (SEQ ID NO:6).

In a preferred embodiment the antigen binding moiety comprises a heavy chain variable domain (VH) comprising:

(a) a heavy chain complementarity determining region (CDR H) 1 amino acid sequence of RYWMN (SEQ ID NO:1);
(b) a CDR H2 amino acid sequence of EITPDSSTINYAPSLKG (SEQ ID NO:2) or of EITPDSSTINYTPSLKG (SEQ ID NO:40);

(c) a CDR H3 amino acid sequence of PYDYGAWFAS (SEQ ID NO:3);

and a light chain variable domain (VL) comprising:

(d) a light chain (CDR L)1 amino acid sequence of RSSTGAVTTSNYAN (SEQ ID NO:4);

(e) a CDR L2 amino acid sequence of GTNKRAP (SEQ ID NO:5); and (f) a CDR L3 amino acid sequence of ALWYSNHWV (SEQ ID NO:6).

In one particular embodiment the antigen binding moiety comprises a heavy chain variable domain (VH) comprising:

(a) a heavy chain complementarity determining region (CDR H) 1 amino acid sequence of RYWMN (SEQ ID NO:1);

(b) a CDR H2 amino acid sequence of EITPDSSTINYAPSLKG (SEQ ID NO:2);

(c) a CDR H3 amino acid sequence of PYDYGAWFAS (SEQ ID NO:3);

and a light chain variable domain (VL) comprising:

(d) a light chain (CDR L)1 amino acid sequence of RSSTGAVTTSNYAN (SEQ ID NO:4);

(e) a CDR L2 amino acid sequence of GTNKRAP (SEQ ID NO:5); and (f) a CDR L3 amino acid sequence of ALWYSNHWV (SEQ ID NO:6).

In another particular embodiment the antigen binding moiety comprises a heavy chain variable domain (VH) comprising:

(a) a heavy chain complementarity determining region (CDR H) 1 amino acid sequence of RYWMN (SEQ ID NO:1);

(b) a CDR H2 amino acid sequence of EITPDSSTINYTPSLKG (SEQ ID NO:40);

(c) a CDR H3 amino acid sequence of PYDYGAWFAS (SEQ ID NO:3);

and a light chain variable domain (VL) comprising:

(d) a light chain (CDR L)1 amino acid sequence of RSSTGAVTTSNYAN (SEQ ID NO:4);

(e) a CDR L2 amino acid sequence of GTNKRAP (SEQ ID NO:5); and (f) a CDR L3 amino acid sequence of ALWYSNHWV (SEQ ID NO:6).

In one embodiment the antigen binding moiety comprises a heavy chain variable domain (VH) comprising an amino acid sequence that is at least about 95%, 96%, 97%, 98%, 99% or 100% identical to an amino acid sequence selected from the group consisting of SEQ ID NO:8, SEQ ID NO:41 and SEQ ID NO:44.

In one embodiment the antigen binding moiety comprises a heavy chain variable domain (VH) comprising an amino acid sequence that is at least about 95%, 96%, 97%, 98%, 99% or 100% identical to the amino acid sequence of SEQ ID NO:8.

In one embodiment the antigen binding moiety comprises a heavy chain variable domain (VH) comprising an amino acid sequence that is at least about 95%, 96%, 97%, 98%, 99% or 100% identical to the amino acid sequence of SEQ ID NO:41.

In one embodiment the antigen binding moiety comprises a heavy chain variable domain (VH) comprising an amino acid sequence that is at least about 95%, 96%, 97%, 98%, 99% or 100% identical to the amino acid sequence of SEQ ID NO:44.

In one embodiment the antigen binding moiety comprises a heavy chain variable domain (VH) comprising an amino acid sequence that is at least about 95%, 96%, 97%, 98%, 99% or 100% identical to the amino acid sequence of SEQ ID NO:126.

In one embodiment the antigen binding moiety comprises a light chain variable domain (VL) comprising an amino acid sequence that is at least about 95%, 96%, 97%, 98%, 99% or 100% identical to the amino acid sequence of SEQ ID NO:9.

In one embodiment the antigen binding moiety comprises a light chain variable domain (VL) comprising an amino acid sequence that is at least about 95%, 96%, 97%, 98%, 99% or 100% identical to the amino acid sequence of SEQ ID NO:127.

In one embodiment, the antigen binding moiety comprises a heavy chain variable domain (VH) comprising an amino acid sequence that is at least about 95%, 96%, 97%, 98%, 99% or 100% identical to the amino acid sequence of SEQ ID NO:8 and a light chain variable domain (VL) comprising an amino acid sequence that is at least about 95%, 96%, 97%, 98%, 99% or 100% identical to the amino acid sequence of SEQ ID NO:9.

In one embodiment, the antigen binding moiety comprises a heavy chain variable domain (VH) comprising an amino acid sequence that is at least about 95%, 96%, 97%, 98%, 99% or 100% identical to the amino acid sequence of SEQ ID NO:41 and a light chain variable domain (VL) comprising an amino acid sequence that is at least about 95%, 96%, 97%, 98%, 99% or 100% identical to the amino acid sequence of SEQ ID NO:9.

In one embodiment, the antigen binding moiety comprises a heavy chain variable domain (VH) comprising an amino acid sequence that is at least about 95%, 96%, 97%, 98%, 99% or 100% identical to the amino acid sequence of SEQ ID NO:44 and a light chain variable domain (VL) comprising an amino acid sequence that is at least about 95%, 96%, 97%, 98%, 99% or 100% identical to the amino acid sequence of SEQ ID NO:9.

In another embodiment, the antigen binding moiety comprises a heavy chain variable domain (VH) comprising an amino acid sequence that is at least about 95%, 96%, 97%, 98%, 99% or 100% identical to the amino acid sequence of SEQ ID NO:126 and a light chain variable domain (VL) comprising an amino acid sequence that is at least about 95%, 96%, 97%, 98%, 99% or 100% identical to the amino acid sequence of SEQ ID NO:127.

In a preferred embodiment the antigen binding moiety comprises a heavy chain variable domain (VH) comprising the amino acid sequence of SEQ ID NO:8, and a light chain variable domain (VL) comprising the amino acid sequence of SEQ ID NO:9.

In another preferred embodiment the antigen binding moiety comprises a heavy chain variable domain (VH) comprising the amino acid sequence of SEQ ID NO:126, and a light chain variable domain (VL) comprising the amino acid sequence of SEQ ID NO:127.

In one embodiment, the antigen binding moiety is a scFv, or a scFab. In a preferred embodiment, the antigen binding moiety is a scFv.

In one embodiment, the antigen binding moiety comprises a heavy chain variable domain (VH) and a light chain variable domain (VL), wherein the VH domain is connected to the VL domain, in particular through a peptide linker. In one embodiment, the C-terminus of the VL domain is connected to the N-terminus of the VH domain, in particular through a peptide linker. In a preferred embodiment, the C-terminus of the VH domain is connected to the N-terminus of the VL domain, in particular through a peptide linker.

In one embodiment, the peptide linker comprises the amino acid sequence GGGGSGGGGSGGGGSGGGGS (SEQ ID NO:16).

In one embodiment the antigen binding moiety is a scFv which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv has the configuration VH-linker-VL.

In one embodiment, the antigen binding moiety comprises an amino acid sequence that is at least about 95%, 96%, 97%, 98%, 99% or 100% identical to an amino acid sequence selected from the group consisting of SEQ ID NO:10, SEQ ID NO:122 and SEQ ID NO:124.

In one embodiment, the antigen binding moiety comprises an amino acid sequence that is at least about 95%, 96%, 97%, 98%, 99% or 100% identical to the amino acid sequence of SEQ ID NO:10. In one embodiment, the antigen binding moiety comprises the amino acid sequence of SEQ ID NO:10.

In one embodiment, the antigen binding moiety comprises an amino acid sequence that is at least about 95%, 96%, 97%, 98%, 99% or 100% identical to the amino acid sequence of SEQ ID NO:122. In one embodiment, the antigen binding moiety comprises the amino acid sequence of SEQ ID NO:122.

In one embodiment, the antigen binding moiety comprises an amino acid sequence that is at least about 95%, 96%, 97%, 98%, 99% or 100% identical to the amino acid sequence of SEQ ID NO:124. In one embodiment, the antigen binding moiety comprises the amino acid sequence of SEQ ID NO:124.

Antigen binding moieties comprising a heavy chain variable domain (VH) and a light chain variable domain (VL), such as the scFv and scFab fragments as described herein may be further stabilized by introducing interchain disulfide bridges between the VH and the VL domain. Accordingly, in one embodiment, the scFv fragment(s) and/or the scFab fragment(s) comprised in the antigen binding receptors according to the invention are further stabilized by generation of interchain disulfide bonds via insertion of cysteine residues (e.g., position 44 in the variable heavy chain and position 100 in the variable light chain according to Kabat numbering). In one embodiment, provided is any one of the above provided VH and/or VL sequences comprising at least one substitution of an amino acid with cysteine (in particular at position 44 in the variable heavy chain and/or position 100 in the variable light chain according to Kabat numbering).

In one embodiment, the antigen binding moiety comprises an amino acid sequence that is at least about 95%, 96%, 97%, 98%, 99% or 100% identical to the amino acid sequence of SEQ ID NO:128. In one embodiment, the antigen binding moiety comprises the amino acid sequence of SEQ ID NO:128.

Anchoring Transmembrane Domain (ATD)

In the context of the present invention, the anchoring transmembrane domain of the antigen binding receptors of the present invention may be characterized by not having a cleavage site for mammalian proteases. In the context of the present invention, proteases refer to proteolytic enzymes that are able to hydrolyze the amino acid sequence of a transmembrane domain comprising a cleavage site for the protease. The term proteases include both endopeptidases and exopeptidases. In the context of the present invention any anchoring transmembrane domain of a transmembrane protein as laid down among others by the CD-nomenclature may be used to generate the antigen binding receptors of the invention.

Accordingly, in the context of the present invention, the anchoring transmembrane domain may comprise part of a murine/mouse or preferably of a human transmembrane domain. An example for such an anchoring transmembrane domain is a transmembrane domain of CD8, for example, having the amino acid sequence as shown herein in SEQ ID NO:11 (as encoded by the DNA sequence shown in SEQ ID NO:24). In the context of the present invention, the anchoring transmembrane domain of the antigen binding receptor of the present invention may comprise/consist of an amino acid sequence as shown in SEQ ID NO:11 (as encoded by the DNA sequence shown in SEQ ID NO:24).

In another embodiment, the herein provided antigen binding receptor may comprise the transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO:61 (as encoded by the cDNA shown in SEQ ID NO:70).

Alternatively, any protein having a transmembrane domain, as provided among others by the CD nomenclature, may be used as an anchoring transmembrane domain of the antigen binding receptor protein of the invention.

In some embodiments, the anchoring transmembrane domain comprises the transmembrane domain of any one of the group consisting of CD27 (SEQ ID NO:59 as encoded by SEQ ID NO:58), CD137 (SEQ ID NO:67 as encoded by SEQ ID NO:66), OX40 (SEQ ID NO:71, as encoded by SEQ ID NO:70), ICOS (SEQ ID NO:75 as encoded by SEQ ID NO:74), DAP10 (SEQ ID NO:80 as encoded by SEQ ID NO:79), DAP12 (SEQ ID NO:83 as encoded by SEQ ID NO:82), CD3z (SEQ ID NO:88 as encoded by SEQ ID NO:87), FCGR3A (SEQ ID NO:90 as encoded by SEQ ID NO:91), NKG2D (SEQ ID NO:94 as encoded by SEQ ID NO:95), CD8 (SEQ ID NO:119 as encoded by SEQ ID NO:120), or a fragment of the transmembrane thereof that retains the capability to anchor the antigen binding receptor to the membrane.

Human sequences might be beneficial in the context of the common invention, for example because (parts) of the anchoring transmembrane domain might be accessible from the extracellular space and hence to the immune system of a patient. In a preferred embodiment, the anchoring transmembrane domain comprises a human sequence. In such embodiments, the anchoring transmembrane domain comprises the transmembrane domain of any one of the group consisting of human CD27 (SEQ ID NO:57 as encoded by SEQ ID NO:56), human CD137 (SEQ ID NO:65 as encoded by SEQ ID NO:64), human OX40 (SEQ ID NO:69, as encoded by SEQ ID NO:68), human ICOS (SEQ ID NO:73 as encoded by SEQ ID NO:72), human DAP10 (SEQ ID NO:78 as encoded by SEQ ID NO:77), human DAP12 (SEQ ID NO:81 as encoded by SEQ ID NO:80), human CD3z (SEQ ID NO:86 as encoded by SEQ ID NO:85), human FCGR3A (SEQ ID NO:88 as encoded by SEQ ID NO:89), human NKG2D (SEQ ID NO:92 as encoded by SEQ ID NO:93), human CD8 (SEQ ID NO:117 as encoded by SEQ ID NO:118), or a fragment of the transmembrane thereof that retains the capability to anchor the antigen binding receptor to the membrane.

Stimulatory Signaling Domain (SSD) and Co-Stimulatory Signaling Domain (CSD)

Preferably, the antigen binding receptor of the present invention comprises at least one stimulatory signaling domain and/or at least one co-stimulatory signaling domain. Accordingly, the herein provided antigen binding receptor preferably comprises a stimulatory signaling domain, which provides T cell activation. The herein provided antigen binding receptor may comprise a stimulatory signaling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is 054709 (version number 132 with sequence number 2)).

Thus, the stimulatory signaling domain which is comprised in the herein provided antigen binding receptor may be a fragment/polypeptide part of the full length of CD3z, FCGR3A or NKG2D. The amino acid sequences of the murine/mouse full length of CD3z, or NKG2D are shown herein as SEQ ID NOs: 86 (CD3z), 90 (FCGR3A) or 94 (NKG2D) (murine/mouse as encoded by the DNA sequences shown in SEQ ID NOs:87 (CD3z), 91 (FCGR3A) or 95 (NKG2D). The amino acid sequences of the human full length CD3z, FCGR3A or NKG2D are shown herein as SEQ ID NOs:84 (CD3z), 88 (FCGR3A) or 92 (NKG2D) (human as encoded by the DNA sequences shown in SEQ ID NOs:85 (CD3z), 89 (FCGR3A) or 93 (NKG2D)). The antigen binding receptor of the present invention may comprise fragments of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the antigen binding receptor of the present invention comprises polypeptides which are derived from human origin. Thus, more preferably, the herein provided antigen binding receptor comprises the amino acid sequences as shown herein as SEQ ID NOs:84 (CD3z), 88 (FCGR3A) or 92 (NKG2D) (human as encoded by the DNA sequences shown in SEQ ID NOs:85 (CD3z), 89 (FCGR3A) or 93 (NKG2D)). In one embodiment, the antigen binding receptor of the present invention may comprise or consist of the amino acid sequence shown in SEQ ID NO:13 (as encoded by the DNA sequence shown in SEQ ID NO:26). In further embodiments the antigen binding receptor comprises the sequence as shown in SEQ ID NO:13 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO:13 and which is characterized by having a stimulatory signaling activity. Specific configurations of antigen binding receptors comprising a stimulatory signaling domain (SSD) are provided herein below and in the Examples and Figures. The stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

Furthermore, the herein provided antigen binding receptor preferably comprises at least one co-stimulatory signaling domain which provides additional activity to the T cell. The herein provided antigen binding receptor may comprise a co-stimulatory signaling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the Uniprot Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)), DAP10 (the UniProt Entry of the human DAP10 is Q9UBJ5 (version number 25 with sequence number 1); the UniProt entry of the murine/mouse DAP10 is Q9QUJ0 (primary citable accession number) or Q9R1E7 (secondary citable accession number) with the version number 101 and the sequence number 1)) or DAP12 (the UniProt Entry of the human DAP12 is O43914 (version number 146 and the sequence number 1); the UniProt entry of the murine/mouse DAP12 is 0054885 (primary citable accession number) or Q9R1E7 (secondary citable accession number) with the version number 123 and the sequence number 1). In certain embodiments of the present invention the antigen binding receptor of the present invention may comprise one or more, i.e. 1, 2, 3, 4, 5, 6 or 7 of the herein defined co-stimulatory signaling domains. Accordingly, in the context of the present invention, the antigen binding receptor of the present invention may comprise a fragment/polypeptide part of a murine/mouse or preferably of a human CD137 as first co-stimulatory signaling domain and the second co-stimulatory signaling domain is selected from the group consisting of the murine/mouse or preferably of the human CD27, CD28, CD137, OX40, ICOS, DAP10 and DAP12, or fragments thereof. Preferably, the antigen binding receptor of the present invention comprises a co-stimulatory signaling domain which is derived from a human origin. Thus, more preferably, the co-stimulatory signaling domain(s) which is (are) comprised in the antigen binding receptor of the present invention may comprise or consist of the amino acid sequence as shown in SEQ ID NO:12 (as encoded by the DNA sequence shown in SEQ ID NO:25).

Thus, the co-stimulatory signaling domain which may be optionally comprised in the herein provided antigen binding receptor is a fragment/polypeptide part of the full length CD27, CD28, CD137, OX40, ICOS, DAP10 or DAP12. The amino acid sequences of the murine/mouse full length CD27, CD28, CD137, OX40, ICOS, CD27, DAP10 and DAP12 are shown herein as SEQ ID NOs:59 (CD27), 63 (CD28), 67 (CD137), 71 (OX40), 75 (ICOS), 79 (DAP10) or 83 (DAP12) (murine/mouse as encoded by the DNA sequences shown in SEQ ID NOs:58 (CD27), 62 (CD28), 66 (CD137), 70 (OX40), 74 (ICOS), 78 (DAP10) or 82 (DAP12)). However, because human sequences are most preferred in the context of the present invention, the co-stimulatory signaling domain which may be optionally comprised in the herein provided antigen binding receptor protein is a fragment/polypeptide part of the human full length CD27, CD28, CD137, OX40, ICOS, DAP10 or DAP12. The amino acid sequences of the human full length CD27, CD28, CD137, OX40, ICOS, DAP10 or DAP12 are shown herein as SEQ ID NOs: 57, (CD27), 61 (CD28), 65 (CD137), 69 (OX40), 73 (ICOS), 77 (DAP10) or 81 (DAP12) (human as encoded by the DNA sequences shown in SEQ ID NOs: 56 (CD27), 60 (CD28), 64 (CD137), 68 (OX40), 72 (ICOS), 76 (DAP10) or 80 (DAP12)).

In one preferred embodiment, the antigen binding receptor comprises CD28 or a fragment thereof as co-stimulatory signaling domain. The herein provided antigen binding receptor may comprise a fragment of CD28 as co-stimulatory signaling domain, provided that at least one signaling domain of CD28 is comprised. In particular, any part/fragment of CD28 is suitable for the antigen binding receptor of the invention as long as at least one of the signaling motives of CD28 is comprised. The co-stimulatory signaling domains PYAP (AA 208 to 211 of CD28) and YMNM (AA 191 to 194 of CD28) are beneficial for the function of the CD28 polypeptide and the functional effects enumerated above. The amino acid sequence of the YMNM domain is shown in SEQ ID NO:96; the amino acid sequence of the PYAP domain is shown in SEQ ID NO:97. Accordingly, in the antigen binding receptor of the present invention, the CD28 polypeptide preferably comprises a sequence derived from intracellular domain of a CD28 polypeptide having the sequences YMNM (SEQ ID NO:96) and/or PYAP (SEQ ID NO:97). In other embodiments, in the antigen binding receptor of the present invention, one or both of these domains are mutated to FMNM (SEQ ID NO:98) and/or AYAA (SEQ ID NO:99), respectively. Either of these mutations reduces the ability of a transduced cell comprising the antigen binding receptor to release cytokines without affecting its ability to proliferate and can advantageously be used to prolong the viability and thus the therapeutic potential of the transduced cells. Or, in other words, such a non-functional mutation preferably enhances the persistence of the cells which are transduced with the herein provided antigen binding receptor in vivo. These signaling motives may, however, be present at any site within the intracellular domain of the herein provided antigen binding receptor.

In another preferred embodiment, the antigen binding receptor comprises CD137 or a fragment thereof as co-stimulatory signaling domain. The herein provided antigen binding receptor may comprise a fragment of CD137 as co-stimulatory signaling domain, provided that at least one signaling domain of CD137 is comprised. In particular, any part/fragment of CD137 is suitable for the antigen binding receptor of the invention as long as at least one of the signaling motives of CD137 is comprised. In a preferred embodiment, the CD137 polypeptide which is comprised in the antigen binding receptor protein of the present invention comprises or consists of the amino acid sequence shown in SEQ ID NO:12 (as encoded by the DNA sequence shown in SEQ ID NO:25).

Specific configurations of antigen binding receptors comprising a co-stimulatory signaling domain (CSD) are provided herein below and in the Examples and Figures. The co-stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays. As mentioned above, in an embodiment of the present invention, the co-stimulatory signaling domain of the antigen binding receptor may be derived from the human CD28 and/or CD137 gene T cell activity, defined as cytokine production, proliferation and lytic activity of the transduced cell described herein, like a transduced T cell. CD28 and/or CD137 activity can be measured by release of cytokines by ELISA or flow cytometry of cytokines such as interferon-gamma (IFN-γ) or interleukin 2 (IL-2), proliferation of T cells measured e.g. by ki67-measurement, cell quantification by flow cytometry, or lytic activity as assessed by real time impedence measurement of the target cell (by using e.g. an ICELLligence instrument as described e.g. in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Duwell et al., Cell Death Differ. 21(12) (2014), 1825-1837, Erratum in: Cell Death Differ. 21(12) (2014), 161).

Linker and Signal Peptides

Moreover, the herein provided antigen binding receptor may comprise at least one linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein provided antigen binding receptor may comprise a linker between the extracellular domain comprising at least one antigen binding moiety capable of specific binding to a mutated Fc domain, the anchoring transmembrane domain, the co-stimulatory signaling domain and/or the stimulatory signaling domain. Furthermore, the herein provided antigen binding receptor may comprise a linker in the antigen binding moiety, in particular between immunoglobulin domains of the antigen binding moiety (such as between VH and VL domains of a scFv). Such linkers have the advantage that they increase the probability that the different polypeptides of the antigen binding receptor (i.e. the extracellular domain comprising at least one antigen binding moiety, the anchoring transmembrane domain, the co-stimulatory signaling domain and/or the stimulatory signaling domain) fold independently and behave as expected. Thus, in the context of the present invention, the extracellular domain comprising at least one antigen binding moiety, the anchoring transmembrane domain, the co-stimulatory signaling domain and the stimulatory signaling domain may be comprised in a single-chain multi-functional polypeptide. A single-chain fusion construct e.g. may consist of (a) polypeptide(s) comprising (an) extracellular domain(s) comprising at least one antigen binding moiety, (an) anchoring transmembrane domain(s), (a) co-stimulatory signaling domain(s) and/or (a) stimulatory signaling domain(s). Accordingly, the antigen binding moiety, the anchoring transmembrane domain, the co-stimulatory signaling domain and the stimulatory signaling domain may be connected by one or more identical or different peptide linker as described herein. For example, in the herein provided antigen binding receptor the linker between the extracellular domain comprising at least one antigen binding moiety and the anchoring transmembrane domain may comprise or consist of the amino and amino acid sequence as shown in SEQ ID NO:17. In another embodiment, the linker between the antigen binding moiety and the anchoring transmembrane domain comprises or consists of the amino and amino acid sequence as shown in SEQ ID NO:19. Accordingly, the anchoring transmembrane domain, the co-stimulatory signaling domain and/or the stimulatory domain may be connected to each other by peptide linkers or alternatively, by direct fusion of the domains.

In preferred embodiments according to the invention the antigen binding moiety comprised in the extracellular domain is a single-chain variable fragment (scFv) which is a fusion protein of the variable domains of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. In a preferred embodiment, the linker connects the N-terminus of the VL domain with the C-terminus of the VH domain. For example, in the herein provided antigen binding receptor the linker may have the amino and amino acid sequence as shown in SEQ ID NO:16. scFv antibodies are, e.g. described in Houston, J. S., Methods in Enzymol. 203 (1991) 46-96).

In some embodiments according to the invention the antigen binding moiety comprised in the extracellular domain is a single chain Fab fragment or scFab which is a polypeptide consisting of an heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CHT-linker-VL-CL, b) VL-CL-linker-VH-CHT, c) VH-CL-linker-VL-CH1 or d) VL-CHT-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain.

The herein provided antigen binding receptor or parts thereof may comprise a signal peptide. Such a signal peptide will bring the protein to the surface of the T cell membrane. For example, in the herein provided antigen binding receptor the signal peptide may have the amino and amino acid sequence as shown in SEQ ID NO:100 (as encoded by the DNA sequence shown in SEQ ID NO:101).

T Cell Activating Antigen Binding Receptors Capable of Specific Binding to Mutated Fc Domains The components of the antigen binding receptors as described herein can be fused to each other in a variety of configurations to generate T cell activating antigen binding receptors.

In some embodiments, the antigen binding receptor comprises an extracellular domain composed of a heavy chain variable domain (VH) and a light chain variable domain (VL) connected to an anchoring transmembrane domain. In preferred embodiments, the VH domain is fused at the C-terminus to the N-terminus of the VL domain, optionally through a peptide linker. In other embodiments, the antigen binding receptor further comprises a stimulatory signaling domain and/or a co-stimulatory signaling domain. In a specific such embodiment, the antigen binding receptor essentially consists of a VH domain and a VL domain, an anchoring transmembrane domain, and optionally a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain. Optionally, the antigen binding receptor further comprises a co-stimulatory signaling domain. In one such specific embodiment, the antigen binding receptor essentially consists of a VH domain and a VL domain, an anchoring transmembrane domain, a stimulatory signaling domain and a co-stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain, wherein the stimulatory signaling domain is fused at the C-terminus to the N-terminus of the co-stimulatory signaling domain. In an alternative embodiment, the co-stimulatory signaling domain is connected to the anchoring transmembrane domain instead of the stimulatory signaling domain. In a preferred embodiment, the antigen binding receptor essentially consists of a VH domain and a VL domain, an anchoring transmembrane domain, a co-stimulatory signaling domain and a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the co-stimulatory signaling domain, wherein the co-stimulatory signaling domain is fused at the C-terminus to the N-terminus of the stimulatory signaling domain.

The antigen binding moiety, the anchoring transmembrane domain and the stimulatory signaling and/or co-stimulatory signaling domains may be fused to each other directly or through one or more peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers, wherein "n" is generally a number between 1 and 10, typically between 2 and 4. A preferred peptide linker for connecting the antigen binding moiety and the anchoring transmembrane moiety is GGGGS ($G_4S$) according to SEQ ID NO 17. Another preferred peptide linker for connecting the antigen binding moiety and the anchoring transmembrane moiety is KPTTTPAPRPPTPAPTIASQPLSLRPEACRPAAGGAVHTRGLDFACD (CD8stalk) according to SEQ ID NO 19. An exemplary peptide linker suitable for connecting variable heavy chain domain (VH) and the variable light chain domain (VL) is GGGSGGGSGGGSGGGS $(G_4S)_4$ according to SEQ ID NO 16.

Additionally, linkers may comprise (a portion of) an immunoglobulin hinge region. Particularly where an antigen binding moiety is fused to the N-terminus of an anchoring transmembrane domain, it may be fused via an immunoglobulin hinge region or a portion thereof, with or without an additional peptide linker.

As described herein, the antigen binding receptors of the present invention comprise an extracellular domain comprising at least one antigen binding moiety. An antigen binding receptor with a single antigen binding moiety capable of specific binding to a target cell antigen is useful and preferred, particularly in cases where high expression of the antigen binding receptor is needed. In such cases, the presence of more than one antigen binding moiety specific for the target cell antigen may limit the expression efficiency of the antigen binding receptor. In other cases, however, it will be advantageous to have an antigen binding receptor comprising two or more antigen binding moieties specific for a target cell antigen, for example to optimize targeting to the target site or to allow crosslinking of target cell antigens.

In one particular embodiment, the antigen binding receptor comprises one antigen binding moiety capable of specific binding to a mutated Fc domain, in particular an IgG1 Fc domain, comprising the P329G mutation (according to EU numbering). In one embodiment, the antigen binding moiety capable of specific binding to a mutated Fc domain but not capable of specific binding to the non-mutated parent Fc domain is a scFv.

In one embodiment, the antigen binding moiety is fused at the C-terminus of the scFv fragment to the N-terminus of an anchoring transmembrane domain, optionally through a peptide linker. In one embodiment the peptide linker comprises the amino acid sequence KPTTTPAPRPPTPAPTIASQPLSLRPEACRPAAGGAVHTRGLDFACD (SEQ ID NO:19). In one embodiment, the anchoring transmembrane domain is a transmembrane domain selected from the group consisting of the CD8, the CD4, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD8 transmembrane domain or a fragment thereof. In a particular embodiment, the anchoring transmembrane domain comprises or consist of the amino acid sequence of IYIWAPLAGTCGVLLLSLVIT (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, of CD28, of CD137, of OX40, of ICOS, of DAP10 and of DAP12, or fragments thereof as described herein before. In a preferred embodiment, the co-stimulatory signaling domain is the intracellular domain of CD28 or a fragment thereof. In one preferred embodiment, the co-stimulatory signaling domain comprises the intracellular domain of CD28 or a fragment thereof that retains CD28 signaling. In another preferred embodiment, the co-stimulatory signaling domain comprises the intracellular domain of CD137 or a fragment thereof that retains CD137 signaling. In a particular embodiment the co-stimulatory signaling domain comprises or consists of SEQ ID NO:12. In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof that retains CD3z signaling. In a particular embodiment the co-stimulatory signaling domain comprises or consists of SEQ ID NO:13.

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGDVEENPGP (T2A) according to SEQ ID NO:18.

In a particular embodiment, the antigen binding receptor comprises an anchoring transmembrane domain and an extracellular domain comprising at least one antigen binding moiety, wherein the at least one antigen binding moiety is a scFv capable of specific binding to a mutated Fc domain but not capable of specific binding to the non-mutated parent Fc domain, wherein the mutated Fc domain comprises the P329G mutation (according to EU numbering). The P329G mutation reduces Fcγ receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration scFv-ATD-CSD-SSD. In a preferred embodiment, the antigen binding receptor has the configuration VH-VL-ATD-CSD-SSD. In a more specific such embodiment, the antigen binding receptor has the configuration VH-linker-VL-linker-ATD-CSD-SSD.

In a particular embodiment, the antigen binding moiety is a scFv capable of specific binding to a mutated Fc domain comprising the P329G mutation, wherein the antigen binding moiety comprises at least one heavy chain complementarity determining region (CDR) selected from the group consisting of SEQ ID NO:1, SEQ ID NO:2 and SEQ ID NO:3 and at least one light chain CDR selected from the group of SEQ ID NO:4, SEQ ID NO:5, SEQ ID NO:6.

In another particular embodiment, the antigen binding moiety is a scFv capable of specific binding to a mutated Fc domain comprising the P329G mutation, wherein the antigen binding moiety comprises at least one heavy chain complementarity determining region (CDR) selected from the group consisting of SEQ ID NO:1, SEQ ID NO:40 and SEQ ID NO:3 and at least one light chain CDR selected from the group of SEQ ID NO:4, SEQ ID NO:5, SEQ ID NO:6.

In a preferred embodiment, the antigen binding moiety is a scFv capable of specific binding to a mutated Fc domain comprising the P329G mutation, wherein the antigen binding moiety comprises the complementarity determining region (CDR H) 1 amino acid sequence RYWMN (SEQ ID NO:1), the CDR H2 amino acid sequence EITPDSSTINYAPSLKG (SEQ ID NO:2), the CDR H3 amino acid sequence PYDYGAWFAS (SEQ ID NO:3), the light chain complementary-determining region (CDR L) 1 amino acid sequence RSSTGAVTTSNYAN (SEQ ID NO:4), the CDR L2 amino acid sequence GTNKRAP (SEQ ID NO:5) and the CDR L3 amino acid sequence ALWYSNHWV (SEQ ID NO:6).

In one embodiment the present invention provides an antigen binding receptor comprising in order from the N-terminus to the C-terminus:

(i) a heavy chain variable domain (VH) comprising the heavy chain complementarity determining region (CDR) 1 of SEQ ID NO:1, the heavy chain CDR 2 of SEQ ID NO:2, the heavy chain CDR 3 of SEQ ID NO:3, (ii) a peptide linker, in particular the peptide linker of SEQ ID NO:16, (iii) a light chain variable domain (VL) comprising the light chain CDR 1 of SEQ ID NO:4, the light chain CDR 2 of SEQ ID NO:5 and the light chain CDR 3 of SEQ ID NO:6, (iv) a peptide linker, in particular the peptide linker of SEQ ID NO:19, (v) an anchoring transmembrane domain, in particular the anchoring transmembrane domain of SEQ ID NO:11, (vi) a co-stimulatory signaling domain, in particular the co-stimulatory signaling domain of SEQ ID NO:12, and (vii) a stimulatory signaling domain, in particular the stimulatory signaling domain of SEQ ID NO:13.

In one embodiment the present invention provides an antigen binding receptor comprising in order from the N-terminus to the C-terminus:

(i) a heavy chain variable domain (VH) comprising the heavy chain complementarity determining region (CDR) 1 of SEQ ID NO:1, the heavy chain CDR 2 of SEQ ID NO:40, the heavy chain CDR 3 of SEQ ID NO:3, (ii) a peptide linker, in particular the peptide linker of SEQ ID NO:16, (iii) a light chain variable domain (VL) comprising the light chain CDR 1 of SEQ ID NO:4, the light chain CDR 2 of SEQ ID NO:5 and the light chain CDR 3 of SEQ ID NO:6, (iv) a peptide linker, in particular the peptide linker of SEQ ID NO:19, (v) an anchoring transmembrane domain, in particular the anchoring transmembrane domain of SEQ ID NO:11, (vi) a co-stimulatory signaling domain, in particular the co-stimulatory signaling domain of SEQ ID NO:12, and (vii) a stimulatory signaling domain, in particular the stimulatory signaling domain of SEQ ID NO:13.

In one embodiment, the present invention provides an antigen binding receptor comprising in order from the N-terminus to the C-terminus (i) a heavy chain variable domain (VH), (ii) a peptide linker, in particular the peptide linker of SEQ ID NO:16, (iii) a light chain variable domain (VL) that is at least about 95%, 96%, 97%, 98%, 99% or 100% identical to the amino acid sequence of SEQ ID NO:9, wherein the VH and VL domains are capable of forming an antigen binding moiety that binds to an Fc domain comprising the amino acid mutation P329G according to EU numbering, (iv) a peptide linker, in particular the peptide linker of SEQ ID NO:19, (v) an anchoring transmembrane domain, in particular an anchoring transmembrane domain that is at least about 95%, 96%, 97%, 98%, 99% or 100% identical to the amino acid sequence of SEQ ID NO:11, (vi) a co-stimulatory signaling domain, in particular a co-stimulatory signaling domain that is at least about 95%, 96%, 97%, 98%, 99% or 100% identical to the amino acid sequence of SEQ ID NO:12, and (vii) a stimulatory signaling domain, in particular a stimulatory signaling domain that is at least about 95%, 96%, 97%, 98%, 99% or 100% identical to the amino acid sequence of SEQ ID NO:13.

In one embodiment, the present invention provides an antigen binding receptor comprising in order from the N-terminus to the C-terminus (i) a heavy chain variable domain (VH) that is at least about 95%, 96%, 97%, 98%, 99% or 100% identical to the amino acid sequence of SEQ ID NO:8, (ii) a peptide linker, in particular the peptide linker of SEQ ID NO:16, (iii) a light chain variable domain (VL) that is at least about 95%, 96%, 97%, 98%, 99% or 100% identical to the amino acid sequence of SEQ ID NO:9, (iv) a peptide linker, in particular the peptide linker of SEQ ID NO:19, (v) an anchoring transmembrane domain, in particular an anchoring transmembrane domain that is at least about 95%, 96%, 97%, 98%, 99% or 100% identical to the amino acid sequence of SEQ ID NO:11, (vi) a co-stimulatory signaling domain, in particular a co-stimulatory signaling domain that is at least about 95%, 96%, 97%, 98%, 99% or 100% identical to the amino acid sequence of SEQ ID NO:12, and (vii) a stimulatory signaling domain, in particular a stimulatory signaling domain that is at least about 95%, 96%, 97%, 98%, 99% or 100% identical to the amino acid sequence of SEQ ID NO:13.

In one embodiment, the present invention provides an antigen binding receptor comprising in order from the N-terminus to the C-terminus (i) a heavy chain variable domain (VH) that is at least about 95%, 96%, 97%, 98%, 99% or 100% identical to the amino acid sequence of SEQ ID NO:41, (ii) a peptide linker, in particular the peptide linker of SEQ ID NO:16, (iii) a light chain variable domain (VL) that is at least about 95%, 96%, 97%, 98%, 99% or 100% identical to the amino acid sequence of SEQ ID NO:9, (iv) a peptide linker, in particular the peptide linker of SEQ ID NO:19, (v) an anchoring transmembrane domain, in particular an anchoring transmembrane domain that is at least about 95%, 96%, 97%, 98%, 99% or 100% identical to the amino acid sequence of SEQ ID NO:11, (vi) a co-stimulatory signaling domain, in particular a co-stimulatory signaling domain that is at least about 95%, 96%, 97%, 98%, 99% or 100% identical to the amino acid sequence of SEQ ID NO:12, and (vii) a stimulatory signaling domain, in particular a stimulatory signaling domain that is at least about 95%, 96%, 97%, 98%, 99% or 100% identical to the amino acid sequence of SEQ ID NO:13.

In one embodiment, the present invention provides an antigen binding receptor comprising in order from the N-terminus to the C-terminus (i) a heavy chain variable domain (VH) that is at least about 95%, 96%, 97%, 98%, 99% or 100% identical to the amino acid sequence of SEQ ID NO:44, (ii) a peptide linker, in particular the peptide linker of SEQ ID NO:16, (iii) a light chain variable domain (VL) that is at least about 95%, 96%, 97%, 98%, 99% or 100% identical to the amino acid sequence of SEQ ID NO:9, (iv) a peptide linker, in particular the peptide linker of SEQ ID NO:19, (v) an anchoring transmembrane domain, in particular an anchoring transmembrane domain that is at least about 95%, 96%, 97%, 98%, 99% or 100% identical to the amino acid sequence of SEQ ID NO:11, (vi) a co-stimulatory signaling domain, in particular a co-stimulatory signaling domain that is at least about 95%, 96%, 97%, 98%, 99% or 100% identical to the amino acid sequence of SEQ ID NO:12, and (vii) a stimulatory signaling domain, in particular a stimulatory signaling domain that is at least about 95%, 96%, 97%, 98%, 99% or 100% identical to the amino acid sequence of SEQ ID NO:13.

In one embodiment, the present invention provides an antigen binding receptor comprising in order from the N-terminus to the C-terminus (i) a heavy chain variable domain (VH) that is at least about 95%, 96%, 97%, 98%, 99% or 100% identical to the amino acid sequence of SEQ ID NO:126, (ii) a peptide linker, in particular the peptide linker of SEQ ID NO:16, (iii) a light chain variable domain (VL) that is at least about 95%, 96%, 97%, 98%, 99% or 100% identical to the amino acid sequence of SEQ ID NO:127, (iv) a peptide linker, in particular the peptide linker of SEQ ID NO:19, (v) an anchoring transmembrane domain, in particular an anchoring transmembrane domain that is at least about 95%, 96%, 97%, 98%, 99% or 100% identical to the amino acid sequence of SEQ ID NO:11, (vi) a co-stimulatory signaling domain, in particular a co-stimulatory signaling domain that is at least about 95%, 96%, 97%, 98%, 99% or 100% identical to the amino acid sequence of SEQ ID NO:12, and (vii) a stimulatory signaling domain, in particular a stimulatory signaling domain that is at least about 95%, 96%, 97%, 98%, 99% or 100% identical to the amino acid sequence of SEQ ID NO:13.

In one embodiment, provided is an antigen binding receptor comprising an amino acid sequence that is at least about 95%, 96%, 97%, 98%, 99% or 100% identical to the amino acid sequence of: SEQ ID NO:7. In one embodiment, provided is an antigen binding receptor comprising the amino acid sequence of: SEQ ID NO:7.

In one embodiment, provided is an antigen binding receptor comprising an amino acid sequence that is at least about 95%, 96%, 97%, 98%, 99% or 100% identical to the amino acid sequence of: SEQ ID NO:121. In one embodiment, provided is an antigen binding receptor comprising the amino acid sequence of: SEQ ID NO:121.

In one embodiment, provided is an antigen binding receptor comprising an amino acid sequence that is at least about 95%, 96%, 97%, 98%, 99% or 100% identical to the amino acid sequence of: SEQ ID NO:123. In one embodiment, provided is an antigen binding receptor comprising the amino acid sequence of: SEQ ID NO:123.

In one embodiment, provided is an antigen binding receptor comprising an amino acid sequence that is at least about 95%, 96%, 97%, 98%, 99% or 100% identical to the amino acid sequence of: SEQ ID NO:125. In one embodiment, provided is an antigen binding receptor comprising the amino acid sequence of: SEQ ID NO:125.

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) of SEQ ID NO:18.

Transduced Cells Capable of Expressing Antigen Binding Receptors of the Invention A further aspect of the present invention are transduced T cells capable of expressing an antigen binding receptor of the present invention. The antigen binding receptors as described herein relate to molecules which are naturally not comprised in and/or on the surface of T cells and which are not (endogenously) expressed in or on normal (non-transduced) T cells. Thus, the antigen binding receptor of the invention in and/or on T cells is artificially introduced into T cells. In the context of the present invention said T cells, preferably CD8+ T cells, may be isolated/obtained from a subject to be treated as defined herein. Accordingly, the antigen binding receptors as described herein which are artificially introduced and subsequently presented in and/or on the surface of said T cells comprise domains comprising one or more antigen binding moiety accessible (in vitro or in vivo) to (Ig-derived) immunoglobulins, preferably antibodies, in particular to the Fc domain of the antibodies. In the context of the present invention, these artificially introduced molecules are presented in and/or on the surface of said T cells after (retroviral, lentiviral or non-viral) transduction as described herein below. Accordingly, after transduction, T cells according to the invention can be activated by immunoglobulins, preferably (therapeutic) antibodies comprising specific mutations in the Fc domain as described herein and in the presence of target cells.

The invention also relates to transduced T cells expressing an antigen binding receptor encoded by (a) nucleic acid molecule(s) encoding the antigen binding receptor of the present invention. Accordingly, in the context of the present invention, the transduced cell may comprise a nucleic acid molecule encoding the antigen binding receptor of the present invention or a vector of the present invention which expresses an antigen binding receptor of the present invention.

In the context of the present invention, the term "transduced T cell" relates to a genetically modified T cell (i.e. a T cell wherein a nucleic acid molecule has been introduced deliberately). The herein provided transduced T cell may comprise the vector of the present invention. Preferably, the herein provided transduced T cell comprises the nucleic acid molecule encoding the antigen binding receptor of the present invention and/or the vector of the present invention. The transduced T cell of the invention may be a T cell which transiently or stably expresses the foreign DNA (i.e. the nucleic acid molecule which has been introduced into the T cell). In particular, the nucleic acid molecule encoding the antigen binding receptor of the present invention can be stably integrated into the genome of the T cell by using a retroviral or lentiviral transduction. By using mRNA transfection, the nucleic acid molecule encoding the antigen binding receptor of the present invention may be expressed transiently. Preferably, the herein provided transduced T cell has been genetically modified by introducing a nucleic acid molecule in the T cell via a viral vector (e.g. a retroviral vector or a lentiviral vector). Accordingly, the expression of the antigen binding receptors may be constitutive and the extracellular domain of the antigen binding receptor may be detectable on the cell surface. This extracellular domain of the antigen binding receptor may comprise the complete extracellular domain of an antigen binding receptor as defined herein but also parts thereof. The minimal size required being the antigen binding site of the antigen binding moiety in the antigen binding receptor.

The expression may also be conditional or inducible in the case that the antigen binding receptor is introduced into T cells under the control of an inducible or repressible promoter. Examples for such inducible or repressible promoters can be a transcriptional system containing the alcohol dehydrogenase I (alcA) gene promoter and the transactivator protein AlcR. Different agricultural alcohol-based formulations are used to control the expression of a gene of interest linked to the alcA promoter. Furthermore, tetracycline-responsive promoter systems can function either to activate or repress gene expression system in the presence of tetracycline. Some of the elements of the systems include a tetracycline repressor protein (TetR), a tetracycline operator sequence (tetO) and a tetracycline transactivator fusion protein (tTA), which is the fusion of TetR and a herpes simplex virus protein 16 (VP16) activation sequence. Further, steroid-responsive promoters, metal-regulated or pathogenesis-related (PR) protein related promoters can be used.

The expression can be constitutive or constitutional, depending on the system used. The antigen binding receptors of the present invention can be expressed on the surface of the herein provided transduced T cell. The extracellular portion of the antigen binding receptor (i.e. the extracellular domain of the antigen binding receptor can be detected on the cell surface, while the intracellular portion (i.e. the co-stimulatory signaling domain(s) and the stimulatory signaling domain) are not detectable on the cell surface. The detection of the extracellular domain of the antigen binding receptor can be carried out by using an antibody which specifically binds to this extracellular domain or by the mutated Fc domain which the extracellular domain is capable to bind. The extracellular domain can be detected using these antibodies or Fc domains by flow cytometry or microscopy.

Other cells can also be transduced with the antigen binding receptors of the invention and therby be directed against target cells. These further cells include but are not limited to B-cells, Natural Killer (NK) cells, innate lymphoid cells, macrophages, monocytes, dendritic cells, or neutrophils. Preferentially, said immune cell would be a lymphocyte. Triggering of the antigen binding receptor of the present invention on the surface of the leukocyte will render the cell cytotoxic against a target cell in conjunction with a therapeutic antibody comprising a mutated Fc domain irrespective of the lineage the cell originated from. Cytotoxicity will happen irrespective of the stimulatory signaling domain or co-stimulatory signaling domain chosen for the antigen binding receptor and is not dependent on the exogenous supply of additional cytokines. Accordingly, the transduced cell of the present invention may be, e.g., a CD4+ T cell, a CD8+− T cell, a γδ T cell, a Natural Killer (NK) T cell, a Natural Killer (NK) cell, a tumor-infiltrating lymphocyte (TIL) cell, a myeloid cell, or a mesenchymal stem cell. Preferably, the herein provided transduced cell is a T cell (e.g. an autologous T cell), more preferably, the transduced cell is a CD8+ T cell. Accordingly, in the context of the present invention, the transduced cell is a CD8+ T cell. Further, in the context of the present invention, the transduced cell is an autologous T cell. Accordingly, in the context of the present invention, the transduced cell is preferably an autologous CD8+ T cell. In addition to the use of autologous cells (e.g. T cells) isolated from the subject, the present invention also comprehends the use of allogeneic cells. Accordingly, in the context of the present invention the transduced cell may also be an allogeneic cell, such as an allogeneic CD8+ T cell. The term allogeneic refers to cells coming from an unrelated donor individual/subject which is human leukocyte antigen (HLA) compatible to the individual/subject which will be treated by e.g. the herein described antigen binding receptor expressing transduced cell. Autologous cells refer to cells which are isolated/obtained as described herein above from the subject to be treated with the transduced cell described herein.

The transduced cell of the invention may be co-transduced with further nucleic acid molecules, e.g. with a nucleic acid molecule encoding a cytokine.

The present invention also relates to a method for the production of a transduced T cell expressing an antigen binding receptor of the invention, comprising the steps of transducing a T cell with a vector of the present invention, culturing the transduced T cell under conditions allowing the expressing of the antigen binding receptor in or on said transduced cell and recovering said transduced T cell.

In the context of the present invention, the transduced cell of the present invention is preferably produced by isolating cells (e.g., T cells, preferably CD8+ T cells) from a subject (preferably a human patient). Methods for isolating/obtaining cells (e.g. T cells, preferably CD8+ T cells) from patients or from donors are well known in the art and in the context of the present cells (e.g. T cells, preferably CD8+ T cells) from patients or from donors, e.g. cells may be isolated by blood draw or removal of bone marrow. After isolating/obtaining cells as a sample of the patient, the cells (e.g. T cells) are separated from the other ingredients of the sample. Several methods for separating cells (e.g. T cells) from the sample are known and include, without being limiting, e.g. leukapheresis for obtaining cells from the peripheral blood sample from a patient or from a donor, isolating/obtaining cells by using a FACS cell sorting apparatus. The isolated/obtained cells T cells, are subsequently cultivated and expanded, e.g., by using an anti-CD3 antibody, by using anti-CD3 and anti-CD28 monoclonal antibodies and/or by using an anti-CD3 antibody, an anti-CD28 antibody and interleukin-2 (IL-2) (see, e.g., Dudley, Immunother. 26 (2003), 332-342 or Dudley, Clin. Oncol. 26 (2008), 5233-5239).

In a subsequent step the cells (e.g. T cells) are artificially/genetically modified/transduced by methods known in the art (see, e.g., Lemoine, J Gene Med 6 (2004), 374-386). Methods for transducing cells (e.g. T cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector which is not a viral vector In the context of the present invention, the methods for transducing cells (e.g. T cells) include retroviral or lentiviral T cell transduction, non-viral vectors (e.g., sleeping beauty minicircle vector) as well as mRNA transfection. "mRNA transfection" refers to a method well known to those skilled in the art to transiently express a protein of interest, like in the present case the antigen binding receptor of the present invention, in a cell to be transduced. In brief cells may be electroporated with the mRNA coding for the antigen binding receptor of the present by using an electroporation system (such as e.g. Gene Pulser, Bio-Rad) and thereafter cultured by standard cell (e.g. T cell) culture protocol as described above (see Zhao et al., Mol Ther. 13(1) (2006), 151-159.) The transduced cell of the invention can be generated by lentiviral, or most preferably retroviral transduction.

In this context, suitable retroviral vectors for transducing cells are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87

(1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), and LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In the context of the present invention, suitable lentiviral vector for transducing cells (e.g. T cells) are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rsl3), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Marr et al., J Mol Neurosci. 22(1-2) (2004), 5-11), or pLEX (Addgene Catalogue No.: 27976).

The transduced cells of the present invention is/are preferably grown under controlled conditions, outside of their natural environment. In particular, the term "culturing" means that cells (e.g. the transduced cell(s) of the invention) which are derived from multi-cellular eukaryotes (preferably from a human patient) are grown in vitro. Culturing cells is a laboratory technique of keeping cells alive which are separated from their original tissue source. Herein, the transduced cell of the present invention is cultured under conditions allowing the expression of the antigen binding receptor of the present invention in or on said transduced cells. Conditions which allow the expression or a transgene (i.e. of the antigen binding receptor of the present invention) are commonly known in the art and include, e.g., agonistic anti-CD3- and anti-CD28 antibodies and the addition of cytokines such as interleukin 2 (IL-2), interleukin 7 (IL-7), interleukin 12 (IL-12) and/or interleukin 15 (IL-15). After expression of the antigen binding receptor of the present invention in the cultured transduced cell (e.g., a CD8+T), the transduced cell is recovered (i.e. re-extracted) from the culture (i.e. from the culture medium). Accordingly, also encompassed by the invention is a transduced cell, preferably a T cell, in particular a CD8+ T expressing an antigen binding receptor encoded by a nucleic acid molecule of the invention obtainable by the method of the present invention.

Nucleic Acid Molecules

A further aspect of the present invention are nucleic acids and vectors encoding one or several antigen binding receptors of the present invention. An exemplary nucleic acid molecules encoding the antigen binding receptors of the present invention is shown in SEQ ID NOs:20. The nucleic acid molecules of the invention may be under the control of regulatory sequences. For example, promoters, transcriptional enhancers and/or sequences which allow for induced expression of the antigen binding receptor of the invention may be employed. In the context of the present invention, the nucleic acid molecules are expressed under the control of constitutive or inducible promoter. Suitable promoters are e.g. the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24). The present invention therefore also relates to (a) vector(s) comprising the nucleic acid molecule(s) described in the present invention. Herein the term vector relates to a circular or linear nucleic acid molecule which can autonomously replicate in a cell into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT.

The invention also relates to (a) vector(s) comprising (a) nucleic acid molecule(s) which is (are) a regulatory sequence operably linked to said nucleic acid molecule(s) encoding an antigen binding receptor as defined herein. In the context of the present invention the vector can be polycistronic. Such regulatory sequences (control elements) are known to the skilled person and may include a promoter, a splice cassette, translation initiation codon, translation and insertion site for introducing an insert into the vector(s). In the context of the present invention, said nucleic acid molecule(s) is (are) operatively linked to said expression control sequences allowing expression in eukaryotic or prokaryotic cells. It is envisaged that said vector(s) is (are) (an) expression vector(s) comprising the nucleic acid molecule(s) encoding the antigen binding receptor as defined herein. Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector(s) is (are) an expression vector(s). An expression vector is a construct that can be used to transform a selected cell and provides for expression of a coding sequence in the selected cell. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in *E. coli*, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences encoding signal peptides capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode an antigen binding receptor including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogene), pEF-DHFR, pEF-ADA or pEF-neo (Raum et al. Cancer Immunol Immunother 50 (2001), 141-150) or pSPORT1 (GIBCO BRL).

In the context of the present invention, the expression control sequences will be eukaryotic promoter systems in vectors capable of transforming or transfecting eukaryotic cells, but control sequences for prokaryotic cells may also be used. Once the vector has been incorporated into the appropriate cell, the cell is maintained under conditions suitable for high level expression of the nucleotide sequences, and as desired. Additional regulatory elements may include transcriptional as well as translational enhancers. Advantageously, the above-described vectors of the invention comprise a selectable and/or scorable marker. Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (omithine decarboxylase) which confers resistance to the ornithine decarboxylase inhibitor, 2-(difluoromethyl)-DL-omithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or 8-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule(s) can be used alone or as part of (a) vector(s) to express the antigen binding receptors of the invention in cells, for, e.g., adoptive T cell therapy but also for gene therapy purposes. The nucleic acid molecules or vector(s) containing the DNA sequence(s) encoding any one of the herein described antigen binding receptors is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957; U.S. Pat. Nos. 5,580,859; 5,589,466; or Schaper, Current Opinion in Biotechnology 7 (1996), 635-640. The recited nucleic acid molecule(s) and vector(s) may be designed for direct introduction or for introduction via liposomes, or viral vectors (e.g., adenoviral, retroviral) into the cell. In the context of the present invention, said cell is a T cells, such as CD8+ T cells, CD4+ T cells, CD3+ T cells, γδ T cells or natural killer (NK) T cells, preferably CD8+ T cells.

In accordance with the above, the present invention relates to methods to derive vectors, particularly plasmids, cosmids and bacteriophages used conventionally in genetic engineering that comprise a nucleic acid molecule encoding the polypeptide sequence of an antigen binding receptor defined herein. In the context of the present invention, said vector is an expression vector and/or a gene transfer or targeting vector. Expression vectors derived from viruses such as retroviruses, vaccinia virus, adeno-associated virus, herpes virus, or bovine papilloma virus, may be used for delivery of the recited polynucleotides or vector into targeted cell populations. Methods which are well known to those skilled in the art can be used to construct (a) recombinant vector(s); see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra. The recited vector may, inter alia, be the pEF-DHFR, pEF-ADA or pEF-neo. The vectors pEF-DHFR, pEF-ADA and pEF-neo have been described in the art, e.g. in Mack et al. Proc. Natl. Acad. Sci. USA 92 (1995), 7021-7025 and Raum et al. Cancer Immunol Immunother 50 (2001), 141-150.

The invention also provides for a T cell transduced with a vector as described herein. Said T cell may be produced by introducing at least one of the above described vector or at least one of the above described nucleic acid molecules into the T cell or its precursor cell. The presence of said at least one vector or at least one nucleic acid molecule in the T cell mediates the expression of a gene encoding the above described antigen binding receptor comprising an extracellular domain comprising an antigen binding moiety capable of specific binding to a mutated Fc domain. The vector of the present invention can be polycistronic.

The described nucleic acid molecule(s) or vector(s) which is (are) introduced in the T cell or its precursor cell may either integrate into the genome of the cell or it may be maintained extrachromosomally.

Target Cell Antigens

As mentioned above, the (Ig-derived) domain(s) of the herein-described antibody comprising a mutated Fc domain, in particular an Fc domain comprising the amino acid mutation P329G (according to EU numbering), comprise an antigen-interaction-site with specificity for a target cell surface molecule, e.g. a tumor-specific antigen that naturally occurs on the surface of a tumor cell. In the context of the present invention, such antibodies will bring transduced T cells as described herein comprising the antigen binding receptor of the invention in physical contact with a target cell (e.g. a tumor cell), wherein the transduced T cell becomes activated. Activation of transduced T cells of the present invention preferentially results in lysis of the target cell as described herein.

Examples of target cell antigens (e.g., tumor markers) that naturally occur on the surface of target (e.g. tumor) cells are given herein below and comprise, but are not limited to FAP (fibroblast activation protein), CEA (carcinoembryonic antigen), p95 (p95HER2), BCMA (B-cell maturation antigen), EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD19, CD20, CD22, CD33, CD38, CD52Flt3, folate receptor 1 (FOLR1), human trophoblast cell-surface antigen 2 (Trop-2) cancer antigen 12-5 (CA-12-5), human leukocyte antigen-antigen D related (HLA-DR), MUC-1 (Mucin-1), A33-antigen, PSMA (prostate-specific membrane antigen), FMS-like tyrosine kinase 3 (FLT-3), PSMA (prostate specific membrane antigen), PSCA (prostate stem cell antigen), transferrin-receptor, TNC (tenascin), carbon anhydrase IX (CA-IX), and/or peptides bound to a molecule of the human major histocompatibility complex (MHC).

Accordingly, in the context of the present invention, the antigen binding receptor as described herein binds to an Fc domain comprising the amino acid mutation P329G (according to EU numbering), i.e. a therapeutic antibody capable of specific binding to an antigen/marker that naturally occurs on the surface of tumor cells selected from the group consisting of FAP (fibroblast activation protein), CEA (carcinoembryonic antigen), p95 (p95HER2), BCMA (B-cell maturation antigen), EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD19, CD20, CD22, CD33, CD38, CD52Flt3, folate receptor 1 (FOLR1), human trophoblast cell-surface antigen 2 (Trop-2) cancer antigen 12-5 (CA-12-5), human leukocyte antigen-antigen D related (HLA-DR), MUC-1 (Mucin-1), A33-antigen, PSMA (prostate-specific membrane antigen), FMS-like tyrosine kinase 3 (FLT-3), PSMA (prostate specific membrane antigen), PSCA (prostate stem cell antigen), transferrin-receptor, TNC (tenascin), carbon anhydrase IX (CA-IX), and/or peptides bound to a molecule of the human major histocompatibility complex (MHC).

The sequence(s) of the (human) members of the A33-antigen, BCMA (B-cell maturation antigen), cancer antigen 12-5 (CA-12-5), carbon anhydrase IX (CA-IX), CD19, CD20, CD22, CD33, CD38, CEA (carcinoembryonic antigen), EpCAM (epithelial cell adhesion molecule), FAP (fibroblast activation protein), FMS-like tyrosine kinase 3 (FLT-3), folate receptor 1 (FOLR1), HER-1 (human epidermal growth factor 1), HER-2 (human epidermal growth factor 2), HER-3 (human epidermal growth factor 3), human leukocyte antigen-antigen D related (HLA-DR), MSLN (mesothelin), MCSP (melanoma chondroitin sulfate proteoglycan), MUC-1 (Mucin-1), PSMA (prostate specific membrane antigen), PSMA (prostate-specific membrane antigen), PSCA (prostate stem cell antigen), p95 (p95HER2), transferrin-receptor, TNC (tenascin), human trophoblast cell-surface antigen 2 (Trop-2) are available in the UniProtKB/Swiss-Prot database and can be retrieved from http://www.uniprot.org/uniprot/?query=reviewed %3Ayes. These (protein) sequences also relate to annotated modified sequences. The present invention also provides techniques and methods wherein homologous sequences, and also genetic allelic variants and the like of the concise sequences provided herein are used. Preferably such variants and the like of the concise sequences herein are used. Preferably, such variants are genetic variants. The skilled person may easily deduce the relevant coding region of these (protein) sequences in these databank entries, which may also comprise the entry of genomic DNA as well as mRNA/cDNA. The sequence(s) of the (human) FAP (fibroblast activation protein) can be obtained from the Swiss-Prot database entry Q12884 (entry version 168, sequence version 5); The sequence(s) of the (human) CEA (carcinoembryonic antigen) can be obtained from the Swiss-Prot database entry P06731 (entry version 171, sequence version 3); the sequence(s) of the (human) EpCAM (Epithelial cell adhesion molecule) can be obtained from the Swiss-Prot database entry P16422 (entry version 117, sequence version 2); the sequence(s) of the (human) MSLN (mesothelin) can be obtained from the UniProt Entry number Q13421 (version number 132; sequence version 2); the sequence(s) of the (human) FMS-like tyrosine kinase 3 (FLT-3) can be obtained from the Swiss-Prot database entry P36888 (primary citable accession number) or Q13414 (secondary accession number) with the version number 165 and the sequence version 2; the sequences of (human) MCSP (melanoma chondroitin sulfate proteoglycan) can be obtained from the UniProt Entry number Q6UVK1 (version number 118; sequence version 2); the sequence(s) of the (human) folate receptor 1 (FOLR1) can be obtained from the UniProt Entry number P15328 (primary citable accession number) or Q53EW2 (secondary accession number) with the version number 153 and the sequence version 3; the sequence(s) of the (human) trophoblast cell-surface antigen 2 (Trop-2) can be obtained from the UniProt Entry number P09758 (primary citable accession number) or Q15658 (secondary accession number) with the version number 172 and the sequence version 3; the sequence(s) of the (human) PSCA (prostate stem cell antigen) can be obtained from the UniProt Entry number 043653 (primary citable accession number) or Q6UW92 (secondary accession number) with the version number 134 and the sequence version 1; the sequence(s) of the (human) HER-1 (Epidermal growth factor receptor) can be obtained from the Swiss-Prot database entry P00533 (entry version 177, sequence version 2); the sequence(s) of the (human) HER-2 (Receptor tyrosine-protein kinase erbB-2) can be obtained from the Swiss-Prot database entry P04626 (entry version 161, sequence version 1); the sequence(s) of the (human) HER-3 (Receptor tyrosine-protein kinase erbB-3) can be otained from the Swiss-Prot database entry P21860 (entry version 140, sequence version 1); the sequence(s) of the (human) CD20 (B-lymphocyte antigen CD20) can be obtained from the Swiss-Prot database entry P11836 (entry version 117, sequence version 1); the sequence(s) of the (human) CD22 (B-lymphocyte antigen CD22) can be obtained from the Swiss-Prot database entry P20273 (entry version 135, sequence version 2); the sequence(s) of the (human) CD33 (B-lymphocyte antigen CD33) can be obtained from the Swiss-Prot database entry P20138 (entry version 129, sequence version 2); the sequence(s) of the (human) CA-12-5 (Mucin 16) can be obtained from the Swiss-Prot database entry Q8WX17 (entry version 66, sequence version 2); the sequence(s) of the (human) HLA-DR can be obtained from the Swiss-Prot database entry Q29900 (entry version 59, sequence version 1); the sequence(s) of the (human) MUC-1 (Mucin-1) can be obtained from the Swiss-Prot database entry P15941 (entry version 135, sequence version 3); the sequence(s) of the (human) A33 (cell surface A33 antigen) can be obtained from the Swiss-Prot database entry Q99795 (entry version 104, sequence version 1); the sequence(s) of the (human) PSMA (Glutamate carboxypeptidase 2) can be obtained from the Swiss-Prot database entry Q04609 (entry version 133, sequence version 1), the sequence(s) of the (human) transferrin receptor can be obtained from the Swiss-Prot database entries Q9UP52 (entry version 99, sequence version 1) and P02786 (entry version 152, sequence version 2); the sequence of the (human) TNC (tenascin) can be obtained from the Swiss-Prot database entry P24821 (entry version 141, sequence version 3); or the sequence(s) of the (human) CA-IX (carbonic anhydrase IX) can be obtained from the Swiss-Prot database entry Q16790 (entry version 115, sequence version 2).

In a preferred embodiment, the target cell antigen is selected from the group consisting of fibroblast activation protein (FAP), carcinoembryonic antigen (CEA), mesothelin (MSLN), CD20, folate receptor 1 (FOLR1), and tenascin (TNC).

Antibodies capable of specific binding to any of the above mentioned target cell antigens can be generated using methods well known in the art such as immunizing a mammalian immune system and/or phage display using recombinant libraries.

The antibodies used according to the present invention comprise an Fc domain comprising the P329G mutation (according to EU numbering). The P329G mutation reduced Fc receptor binding and/or effector function and can be used in combination with further Fc mutations that affect binding and/or effector function. Accordingly, in further embodiments the mutated Fc domain of the antibodies exhibits reduced binding affinity to an Fc receptor and/or reduced effector function, as compared to a native $IgG_1$ Fc domain. In one such embodiment the mutated Fc domain (or the antibody comprising said Fc mutated domain) exhibits less than 50%, preferably less than 20%, more preferably less than 10% and most preferably less than 5% of the binding affinity to an Fc receptor, as compared to a native $IgG_1$ Fc domain (or an antibody comprising a native $IgG_1$ Fc domain), and/or less than 50%, preferably less than 20%, more preferably less than 10% and most preferably less than 5% of the effector function, as compared to a native $IgG_1$ Fc domain (or an antibody comprising a native $IgG_1$ Fc domain). In one embodiment, the mutated Fc domain (or the antibody comprising said mutated Fc domain) does not substantially bind to an Fc receptor and/or induce effector function. In a particular embodiment the Fc receptor is an Fey receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the mutated Fc domain exhibits substantially altered binding affinity to neonatal Fc receptor (FcRn), as compared to a native $IgG_1$ Fc domain. In one embodiment the antibody comprising mutated Fc domain exhibits less than 20%, particularly less than 10%, more particularly less than 5% of the binding affinity to an Fc receptor as compared to a antibody comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced.

In certain embodiments the Fc domain of the antibody is mutated to have reduced effector function, as compared to a non-mutated Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or an antibody comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297 and P331. In a more specific embodiment the Fc domain comprises an amino acid substitution at the positions L234 and/or L235. In some embodiments the Fc domain comprises the amino acid substitutions L234A and L235A. In one such embodiment, the Fc domain is an $IgG_1$ Fc domain, particularly a human $IgG_1$ Fc domain. In a more specific embodiment the further amino acid substitution is E233P, L234A, L235A, L235E, N297A, N297D or P331S. In a preferred embodiment the Fc domain comprises the amino acid mutations L234A, L235A and P329G ("P329G LALA") according to EU numbering. In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

In certain embodiments N-glycosylation of the Fc domain has been eliminated. In one such embodiment the Fc domain comprises an amino acid mutation at position N297, particularly an amino acid mutation replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with mutation of one or more of Fc domain residues 238, 265, 269, 270, 297, 327 and 329 (U.S. Pat. No. 6,737,056). Such Fc mutants include Fc mutants with mutations at two or more of amino acid positions 265, 269, 270 and 297, including the so-called "DANA" Fc mutant with mutation of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIAcore™ instrument (GE Healthcare), and Fc receptors such as may be obtained by recombinant expression.

Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor. Effector function of an Fc domain, or an antibody comprising an Fc domain, can be measured by methods known in the art. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the antibody is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Kits

A further aspect of the present invention are kits comprising or consisting of a nucleic acid encoding an antigen binding receptor of the invention and/or cells, preferably T cells for transduction/transduced with antigen binding receptors of the invention and, optionally, (an) antibody/antibodies comprising a mutated Fc domain, wherein the antigen binding receptor is capable of specific binding to the mutated Fc domain.

Accordingly, provided is a kit comprising (A) a transduced T cell capable of expressing an antigen binding receptor of the invention; and (B) an antibody that binds to a target cell antigen and that comprises an Fc domain comprising the amino acid mutation P329G according to EU numbering.

Further provided is a kit comprising (A) an isolated polynucleotide and/or a vector encoding an antigen binding receptor of the invention; and (B) an antibody that binds to a target cell antigen and that comprises an Fc domain comprising the amino acid mutation P329G according to EU numbering.

The kits of the present invention may comprise transduced T cells, isolated polynucleotides and/or vectors and one or more antibodies comprising an Fc domain comprising the amino acid mutation P329G according to EU numbering. In particular embodiments, the antibody is a therapeutic antibody, e.g. a tumor specific antibody as hereinbefore described. Tumor specific antigens are known in the art and hereinbefore described. In the context of the present invention, the antibody is administered before, simultaneously with or after administration of transduced T cell expressing an antigen binding receptor of the invention. The kits according to the present invention comprise transduced T cells or polynucleotides/vectors to generate transduced T cells. In this context, the transduced T cells are universal T cells since they are not specific to a given tumor but can be targeted to any tumor by use of a therapeutic antibody comprising the mutated Fc domain. Herein provided are examples of antibodies comprising an Fc domain comprising the amino acid mutation P329G according to EU numbering (for example SEQ ID Nos: 102-115), however, any antibody comprising an Fc domain comprising the amino acid mutation P329G according to EU numbering may be used according to the invention and included in the herein provided kits.

In a specific embodiment, the antibody comprising the mutated Fc region is capable of specific binding to CD20 and comprises the heavy chain sequence of SEQ ID NO:102, and the light chain sequence of SEQ ID NO:103. In one embodiment, the antibody comprising the mutated Fc region is capable of specific binding to FAP and comprises the heavy chain sequence of SEQ ID NO:104, and the light chain sequence of SEQ ID NO:105. In one embodiment, the antibody comprising the mutated Fc region is capable of specific binding to CEA and comprises the heavy chain sequence of SEQ ID NO:106 and the light chain sequence of SEQ ID NO:107, the heavy chain sequence of SEQ ID NO:108 and the light chain sequence of SEQ ID NO:109, the heavy chain sequence of SEQ ID NO:110 and the light chain sequence of SEQ ID NO:111, or the heavy chain sequence of SEQ ID NO: 112 and the light chain sequence of SEQ ID NO:113. In further embodiments, the antibody comprising the mutated Fc region is capable of specific binding to tenascin (TNC) and comprises the heavy chain sequence of SEQ ID NO:114, and the light chain sequence of SEQ ID NO:115.

In one embodiment of the present invention, provided is a kit comprising a transduced T cell capable of expressing the amino acid sequence of SEQ ID NO:7 ("VH3VL1-CD8ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:102 and a light chain of SEQ ID NO:103. This kit can be used for the treatment of CD20 positive cancer.

In another embodiment of the present invention, provided is a kit comprising a transduced T cell capable of expressing the amino acid sequence of SEQ ID NO:7 ("VH3VL1-CD8ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:104 and a light chain of SEQ ID NO:105. This kit can be used for the treatment of FAP positive cancer.

In another embodiment of the present invention, provided is a kit comprising a transduced T cell capable of expressing the amino acid sequence of SEQ ID NO:7 ("VH3VL1-CD8ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:106 and a light chain of SEQ ID NO:107. Alternatively, provided is a kit comprising a transduced T cell capable of expressing the amino acid sequence of SEQ ID NO:7 ("VH3VL1-CD28ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:108 and a light chain of SEQ ID NO:109.

This kit can be used for the treatment of FAP positive cancer. Alternatively, provided is a kit comprising a transduced T cell capable of expressing the amino acid sequence of SEQ ID NO:7 ("VH3VL1-CD28ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:110 and a light chain of SEQ ID NO:111. In another embodiment, provided is a kit comprising a transduced T cell capable of expressing the amino acid sequence of SEQ ID NO:7 ("VH3VL1-CD8ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:112 and a light chain of SEQ ID NO: 113. These kits can be used for the treatment of CEA positive cancer.

In another embodiment of the present invention, provided is a kit comprising a transduced T cell capable of expressing the amino acid sequence of SEQ ID NO:7 ("VH3VL1-CD8ATD-CD137CSD-CD3zSSD", or alternatively, the kit comprises a polynucleotide encoding the amino acid sequence of SEQ ID NO:7 (for example the kit comprises a polynucleotide comprising the sequence of SEQ ID NO:20), combined with an antibody comprising a heavy chain of SEQ ID NO:114 and a light chain of SEQ ID NO:115. This kit can be used for the treatment of TNC positive cancer.

Furthermore, parts of the kit of the invention can be packaged individually in vials or bottles or in combination in containers or multicontainer units. Additionally, the kit of the present invention may comprise a (closed) bag cell incubation system where patient cells, preferably T cells as described herein, can be transduced with (an) antigen binding receptor(s) of the invention and incubated under GMP (good manufacturing practice, as described in the guidelines for good manufacturating practice published by the European Commission under http://ec.europa.eu/health/documents/eudralex/index_en.htm) conditions. Furthermore, the kit of the present invention comprises a (closed) bag cell incubation system where isolated/obtained patients T cells can be transduced with (an) antigen binding receptor(s) of the invention and incubated under GMP. Furthermore, in the context of the present invention, the kit may also comprise a vector encoding (the) antigen binding receptor(s) as described herein. The kit of the present invention may be advantageously used, inter alia, for carrying out the method of the invention and could be employed in a variety of applications referred herein, e.g., as research tools or medical tools. The manufacture of the kits preferably follows standard procedures which are known to the person skilled in the art.

In this context, patient derived cells, preferably T cells, can be transduced with an antigen binding receptor of the invention capable of specific binding to a mutated Fc domain as described herein using the kit as described above. The extracellular domain comprising an antigen binding moiety capable of specific binding to a mutated Fc domain does not naturally occur in or on T cells. Accordingly, the patient derived cells transduced with the kits of the invention will acquire the capability of specific binding to a mutated Fc domain of an antibody, e.g. a therapeutic antibody and will become capable of inducing elimination/lysis of target cells via interaction with a therapeutic antibody comprising the mutated Fc domain, wherein the therapeutic antibody is able to bind to a tumor-specific antigen naturally occurring (that is endogenously expressed) on the surface of a tumor cell. Binding of the extracellular domain of the antigen binding receptor as described herein activates that T cell and brings it into physical contact with the tumor cell through the therapeutic antibody comprising the mutated Fc domain. Non-transduced or endogenous T cells (e.g. CD8+ T cells) are unable to bind to the mutated Fc domain of the therapeutic antibody comprising the mutated Fc domain. The transduced T cells expressing the antigen binding receptor comprising the extracellular domain capable of specific binding to a mutated Fc domain remain unaffected by a therapeutic antibody not comprising the mutations in the Fc domain as described herein. Accordingly, T cells expressing the inventive antigen binding receptor molecule have the ability to lyse target cells in the presence of an antibody comprising the mutations in the Fc domain as described herein in vivo and/or in vitro. Corresponding target cells comprise cells expressing a surface molecule, i.e. a tumor-specific antigen naturally occurring on the surface of a tumor cell, which is recognized by at least one, preferably two, binding domains of the therapeutic antibody as described herein. Such surface molecules are characterized herein below.

Lysis of the target cell can be detected by methods known in the art. Accordingly, such methods comprise, inter alia, physiological in vitro assays. Such physiological assays may monitor cell death, for example by loss of cell membrane integrity (e.g. FACS based propidium Iodide assay, trypan blue influx assay, photometric enzyme release assays (LDH), radiometric 51Cr release assay, fluorometric Europium release and CalceinAM release assays). Further assays comprise monitoring of cell viability, for example by photometric MTT, XTT, WST-1 and alamarBlue assays, radiometric 3H-Thd incorporation assay, clonogenic assay measuring cell division activity, and fluorometric Rhodamine123 assay measuring mitochondrial transmembrane gradient. In addition, apoptosis may be monitored for example by FACS-based phosphatidylserin exposure assay, ELISA-based TUNEL test, caspase activity assay (photometric, fluorometric or ELISA-based) or analyzing changed cell morphology (shrinking, membrane blebbing).

Therapeutic Use and Methods of Treatment

The molecules or constructs (e.g., antigen binding receptors, transduced T cells and kits) provided herein are particularly useful in medical settings, in particular for treatment of cancer. For example a tumor may be treated with a transduced T cell expressing an antigen binding receptor of the present invention in conjunction with a therapeutic antibody that binds to a target antigen on the tumor cell and comprising a mutated Fc domain (i.e. an Fc domain comprising the P329G mutation according to EU numbering). Accordingly, in certain embodiments, the antigen binding receptor, the transduced T cell or the kit are used in the treatment of cancer, in particular cancer of epithelial, endothelial or mesothelial origin and cancer of the blood.

The tumor specificity of the treatment is provided by the therapeutic antibody that binds to a target cell antigen, wherein the antibody is administered before, simultaneously with or after administration of transduced T cell expressing an antigen binding receptor of the invention. In this context, the transduced T cells are universal T cells since they are not specific for a given tumor but can target any tumor depending on the specificity of the therapeutic antibody used according to the invention.

The cancer may be a cancer/carcinoma of epithelial, endothelial or mesothelial origin or a cancer of the blood. In one embodiment the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitourinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

For example, tumorous diseases and/or lymphomas may be treated with a specific construct directed against these medical indication(s). For example, gastrointestinal cancer, pancreatic cancer, cholangiocellular cancer, lung cancer, breast cancer, ovarian cancer, skin cancer and/or oral cancer may be treated with an antibody directed against (human) EpCAM (as the tumor-specific antigen naturally occurring on the surface of a tumor cell).

Gastrointestinal cancer, pancreatic cancer, cholangiocellular cancer, lung cancer, breast cancer, ovarian cancer, skin cancer and/or oral cancer may be treated with a transduced T cell of the present invention administered before, simultaneously with or after administration of a therapeutic antibody directed against HER1, preferably human HER1. Furthermore, gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody directed against MCSP, preferably human MCSP. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody directed against FOLR1, preferably human FOLR1. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody directed against Trop-2, preferably human Trop-2. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody directed against PSCA, preferably human PSCA. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody directed against EGFRvIII, preferably human EGFRvIII. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody directed against MSLN, preferably human MSLN. Gastric cancer, breast cancer and/or cervical cancer may be treated with a transduced T cell of the present invention administered before, simultaneously with or after administration of a therapeutic antibody directed against HER2, preferably human HER2. Gastric cancer and/or lung cancer may be treated with a transduced T cell of the present invention administered before, simultaneously with or after administration of a therapeutic antibody directed against HER3, preferably human HER3. B-cell lymphoma and/or T cell lymphoma may be treated with a transduced T cell of the present invention administered before, simultaneously with or after administration of a therapeutic antibody directed against CD20, preferably human CD20. B-cell lymphoma and/or T cell lymphoma may be treated with a transduced T cell of the present invention administered before, simultaneously with or after administration of a therapeutic antibody directed against CD22, preferably human CD22. Myeloid leukemia may be treated with a transduced T cell of the present invention administered before, simultaneously with or after administration of a therapeutic antibody directed against CD33, preferably human CD33. Ovarian cancer, lung cancer, breast cancer and/or gastrointestinal cancer may be treated with a transduced T cell of the present invention administered before, simultaneously with or after administration of a therapeutic antibody directed against CA12-5, preferably human CA12-5. Gastrointestinal cancer, leukemia and/or nasopharyngeal carcinoma may be treated with a transduced T cell of the present invention administered before, simultaneously with or after administration of a therapeutic antibody directed against HLA-DR, preferably human HLA-DR. Colon cancer, breast cancer, ovarian cancer, lung cancer and/or pancreatic cancer may be with a transduced T cell of the present invention administered before, simultaneously with or after administration of a therapeutic antibody directed against MUC-1, preferably human MUC-1. Colon cancer may be treated with a transduced T cell of the present invention administered before, simultaneously with or after administration of a therapeutic antibody directed against A33, preferably human A33. Prostate cancer may be treated with a transduced T cell of the present invention administered before, simultaneously with or after administration of a therapeutic antibody directed against PSMA, preferably human PSMA. Gastrointestinal cancer, pancreatic cancer, cholangiocellular cancer, lung cancer, breast cancer, ovarian cancer, skin cancer and/or oral cancer may be treated with a transduced T cell of the present invention administered before, simultaneously with or after administration of a therapeutic directed against the transferrin receptor, preferably the human transferring receptor. Pancreatic cancer, lunger cancer and/or breast cancer may be treated with a transduced T cell of the present invention administered before, simultaneously with or after administration of a therapeutic antibody directed against the transferrin receptor, preferably the human transferring receptor. Renal cancer may be with a transduced T cell of the present invention administered before, simultaneously with or after administration of a therapeutic antibody directed against CA-IX, preferably human CA-IX.

The invention also relates to a method for the treatment of a disease, a malignant disease such as cancer of epithelial, endothelial or mesothelial origin and/or cancer of blood. In the context of the present invention, said subject is a human.

In the context of the present invention a particular method for the treatment of a disease comprises the steps of (a) isolating T cells, preferably CD8+ T cells, from a subject;
(b) transducing said isolated T cells, preferably CD8+ T cells, with an antigen binding receptor as described herein; and
(c) administering the transduced T cells, preferably CD8+ T cells, to said subject.

In the context of the present invention, said transduced T cells, preferably CD8+ T cells, and/or therapeutic antibody/antibodies are co-administered to said subject by intravenous infusion.

Moreover, in the context of the present invention the present invention, provides a method for the treatment of a disease comprising the steps of (a) isolating T cells, preferably CD8+ T cells, from a subject;
(b) transducing said isolated T cells, preferably CD8+ T cells, with an antigen binding receptor as described herein;
(c) optionally co-transducing said isolated T cells, preferably CD8+ T cells, with a T cell receptor;
(d) expanding the T cells, preferably CD8+ T cells, by anti-CD3 and anti-CD28 antibodies; and
(e) administering the transduced T cells, preferably CD8+ T cells, to said subject.

The above mentioned step (d) (referring to the expanding step of the T cells such as TIL by anti-CD3 and/or anti-CD28 antibodies) may also be performed in the presence of (stimulating) cytokines such as interleukin-2 and/or interleukin-15 (IL-15). In the context of the present invention, the above mentioned step (d) (referring to the expanding step of the T cells such as TIL by anti-CD3 and/or anti-CD28 antibodies) may also be performed in the presence of interleukin-12 (IL-12), interleukin-7 (IL-7) and/or interleukin-21 (IL-21).

The method for the treatment, in addition, comprise the administration of the antibody used according to the present invention. Said antibody may be administered before, simultaneously with or after the transduced T cells are to be administered. In the context of the present invention the administration of the transduced T cells will be performed by intravenous infusion. In the context of the present invention that transduced T cells are isolated/obtained from the subject to be treated.

The invention further envisages the co-administration protocols with other compounds, e.g., molecules capable of providing an activation signal for immune effector cells, for cell proliferation or for cell stimulation. Said molecule may be, e.g., a further primary activation signal for T cells (e.g. a further costimulatory molecule: molecules of B7 family, Ox40L, 4.1 BBL, CD40L, anti-CTLA-4, anti-PD-1), or a further cytokine interleukin (e.g., IL-2).

The composition of the invention as described above may also be a diagnostic composition further comprising, optionally, means and methods for detection.

Compositions

Furthermore, the invention provides compositions (medicaments) comprising (an) antibody molecule(s) with (a) mutated Fc domain(s), and/or (a) transduced T cell(s) comprising an antigen binding receptor of the invention, and/or (a) nucleic acid molecule(s) and (a) vector(s) encoding the antigen binding receptors according to the invention. Furthermore, the invention provides kits comprising one or more of said compositions. In the context of the present invention, the composition is a pharmaceutical composition further comprising, optionally, suitable formulations of carrier, stabilizers and/or excipients. Accordingly, in the context of the present invention a pharmaceutical composition (medicament) is provided that comprises an antibody molecule comprising a mutated Fc domain as defined herein which is to be administered in combination with a transduced T cell comprising an antigen binding receptor as described herein and/or a composition comprising said transduced T cell, wherein said antibody molecule is to be administered before, simultaneously with or after administration of transduced T cells comprising an antigen binding receptor of the invention.

The use of the term "in combination" does not restrict the order in which the components of the treatment regimen are to be administered to the subject. Accordingly, the pharmaceutical composition/medicament described herein encompass the administration of an antibody as defined herein before, simultaneously with or after administration of transduced T cells comprising an antigen binding receptor of the present invention. "In combination" as used herein also does not restrict the timing between the administration of an antibody as defined herein before and the transduced T cells comprising an antigen binding receptor as defined herein. Thus, when the two components are not administered simultaneously with/concurrently, the administrations may be separated by 1 minute, 5 minutes, 15 minutes, 30 minutes, 45 minutes, 1 hour, 2 hours, 4 hours, 6 hours, 12 hours, 24 hours, 48 hours or 72 hours or by any suitable time differential readily determined by one of skill in art and/or described herein.

In the context of the present invention the term "in combination" also encompasses the situation where the antibody as defined herein and the transduced T cells comprising an antigen binding receptor according to the invention are pre-incubated together before administration to the subject. Thus, the two components may be pre-incubated before administration, for example, for 1 minute, 5 minutes, 10 minutes, 15 minutes, 30 minutes, 45 minutes or 1 hour or for any suitable time readily determined by one skilled in the art. The invention, in another preferred embodiment, relates to a treatment regimen, in which the antibody as defined herein and the transduced T cells comprising an antigen binding receptor as defined herein, are to be administered simultaneously with/concurrently. In the context of the present invention, the antibody as defined herein may be administered after the transduced T cells comprising an antigen binding receptor has been administered.

Further, "in combination" as used herein does not restrict the disclosed treatment regimens to the administration of an antibody as defined herein and transduced T cells, preferably CD8+ T cells, comprising an antigen binding receptor of the invention in immediate sequence (i.e., the administration of one of the two components, followed (after a certain time interval) by the administration of the other without the administration and/or practice of any other treatment protocol in between. Therefore, the present treatment regimens also encompass the separate administration of an antibody molecule as defined herein and transduced T cells, preferably CD8+ T cells, comprising an antigen binding receptor according to the invention, wherein the administrations are separated by one or more treatment protocols necessary and/or suitable for the treatment or prevention of the disease, or a symptom thereof. Examples of such intervening treatment protocols include but are not limited to, administration of pain medications; administration of chemotherapeutics, surgical handling of the disease or a symptom thereof. Accordingly, the treatment regimens as disclosed herein encompass the administration of an antibody as defined herein and transduced T cells, preferably CD8+ T cells, comprising an antigen binding receptor as defined herein together with none, one, or more than one treatment protocol suitable for the treatment or prevention of a disease, or a symptom thereof, as described herein or as known in the art.

It is particular envisaged, that said pharmaceutical composition(s)/medicament(s) is (are) to be administered to a patient via infusion or injection. In the context of the present invention the transduced T cells comprising an antigen binding receptor as described herein is to be administered to a patient via infusion or injection. Administration of the suitable compositions/medicaments may be effected by different ways, intravenous, intraperitoneal, subcutaneous, intramuscular, topical or intradermal administration.

The pharmaceutical composition/medicament of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 μg to 5 g units per day. However, a more preferred dosage for continuous infusion might be in the range of 0.01 μg to 2 mg, preferably 0.01 μg to 1 mg, more preferably 0.01 μg to 100 μg, even more preferably 0.01 μg to 50 μg and most preferably 0.01 μg to 10 μg units per kilogram of body weight per hour. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule.

The compositions of the invention may be administered locally or systematically. Administration will generally be parenterally, e.g., intravenously; transduced T cells may also be administered directed to the target site, e.g., by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous antibody constructs or nucleic acid molecules or vectors encoding the same (as described in this invention), and/or cells, further biologically active agents, depending on the intended use of the pharmaceutical composition. Such agents might be drugs acting on the gastro-intestinal system, drugs acting as cytostatica, drugs preventing hyperurikemia, drugs inhibiting immunereactions (e.g. corticosteroids), drugs acting on the circulatory system and/or agents such as T cell co-stimulatory molecules or cytokines known in the art.

EXEMPLARY EMBODIMENTS

1. An antigen binding receptor comprising an anchoring transmembrane domain and an extracellular domain, wherein the extracellular domain comprises an antigen binding moiety comprising
   - (i) a heavy chain variable domain (VH) comprising a heavy chain complementary determining region (HCDR) 1 of SEQ ID NO:1, a HCDR 2 of SEQ ID NO:2 or SEQ ID NO:40, and a HCDR 3 of SEQ ID NO:3, and
   - (ii) a light chain variable domain (VL) comprising a light chain complementarity determining region (LCDR) 1 of SEQ ID NO:4, a LCDR 2 of SEQ ID NO:5 and a LCDR 3 of SEQ ID NO:6.

2. The antigen binding receptor of embodiment 1, wherein the VH domain comprises an amino acid sequence that is at least about 95%, 96%, 97%, 98%, 99% or 100% identical to an amino acid sequence selected from the group consisting of SEQ ID NO:8, SEQ ID NO:41, SEQ ID NO:44 and SEQ ID NO:126.

3. The antigen binding receptor of embodiment 1 or 2, wherein the VL domain comprises an amino acid sequence that is at least about 95%, 96%, 97%, 98%, 99% or 100% identical to the amino acid sequence of SEQ ID NO:9 or SEQ ID NO:127.

4. An antigen binding receptor comprising an anchoring transmembrane domain and an extracellular domain, wherein the extracellular domain comprises an antigen binding moiety comprising a heavy chain variable domain (VH) of SEQ ID NO:8 and a light chain variable domain (VL) of SEQ ID NO:9; or an antigen binding receptor comprising an anchoring transmembrane domain and an extracellular domain, wherein the extracellular domain comprises an antigen binding moiety comprising a heavy chain variable domain (VH) of SEQ ID NO:126 and a light chain variable domain (VL) of SEQ ID NO:127.

5. An antigen binding receptor comprising an anchoring transmembrane domain and an extracellular domain, wherein the extracellular domain comprises an antigen binding moiety comprising a heavy chain variable domain (VH) of SEQ ID NO:41 and a light chain variable domain (VL) of SEQ ID NO:9.

6. An antigen binding receptor comprising an anchoring transmembrane domain and an extracellular domain, wherein the extracellular domain comprises an antigen binding moiety comprising a heavy chain variable domain (VH) of SEQ ID NO:44 and a light chain variable domain (VL) of SEQ ID NO:9.

7. The antigen binding receptor of any one of embodiments 1-6, wherein the antigen binding moiety is a scFv.

8. The antigen binding receptor of any one of embodiments 1-7, wherein the antigen binding moiety comprises an amino acid sequence that is at least about 95%, 96%, 97%, 98%, 99% or 100% identical to the an amino acid sequence selected from the group consisting of SEQ ID NO:10, SEQ ID NO:122, SEQ ID NO:124 or SEQ ID NO:128.

9. An antigen binding receptor comprising an anchoring transmembrane domain and an extracellular domain, wherein the extracellular domain comprises an antigen binding moiety, wherein the antigen binding moiety comprises the amino acid sequence of SEQ ID NO:10, or an antigen binding receptor comprising an anchoring transmembrane domain and an extracellular domain, wherein the extracellular domain comprises an antigen binding moiety, wherein the antigen binding moiety comprises the amino acid sequence of SEQ ID NO:128.

10. An antigen binding receptor comprising an anchoring transmembrane domain and an extracellular domain, wherein the extracellular domain comprises an antigen binding moiety, wherein the antigen binding moiety comprises the amino acid sequence of SEQ ID NO:122.

11. An antigen binding receptor comprising an anchoring transmembrane domain and an extracellular domain, wherein the extracellular domain comprises an antigen binding moiety, wherein the antigen binding moiety comprises the amino acid sequence of SEQ ID NO:124.

12. The antigen binding receptor of any one of embodiments 1-11, wherein the anchoring transmembrane domain is a transmembrane domain selected from the group consisting of the CD8, the CD4, the CD3z, the FCGR3A, the NKG2D, the CD27, the CD28, the CD137, the OX40, the ICOS, the DAP10 or the DAP12 transmembrane domain or a fragment thereof.

13. The antigen binding receptor of any one of embodiments 1-12, wherein the anchoring transmembrane domain is the CD8 transmembrane domain, in particular wherein the anchoring transmembrane domain comprises the amino acid sequence of SEQ ID NO:11.

14. The antigen binding receptor of any one of embodiments 1-13 further comprising at least one stimulatory signaling domain and/or at least one co-stimulatory signaling domain.

15. The antigen binding receptor of any one of embodiments 1-14, wherein the at least one stimulatory signaling domain is individually selected from the group consisting of the intracellular domain of CD3z, of FCGR3A and of NKG2D, or fragments thereof that retain stimulatory signaling activity.

16. The antigen binding receptor of any one of embodiments 1-15, wherein the at least one stimulatory signaling domain is the intracellular domain of CD3z or a fragment thereof that retains stimulatory signaling activity, in particular wherein the at least one stimulatory signaling domain comprises the amino acid sequence of SEQ ID NO:13.

17. The antigen binding receptor of any one of embodiments 1-16, wherein the at least one co-stimulatory signaling domain is individually selected from the group consisting of the intracellular domain of CD27, of CD28, of CD137, of OX40, of ICOS, of DAP10 and of DAP12, or fragments thereof that retain co-stimulatory signaling activity.

18. The antigen binding receptor of any one of embodiments 1-17, comprising a CD137 co-stimulatory domain or a fragment thereof that retains CD137 co-stimulatory activity, in particular wherein the antigen binding receptor comprises a co-stimulatory signaling domain comprising the amino acid sequence of SEQ ID NO:12.

19. The antigen binding receptor of any one of embodiments 1-18, wherein the at least one co-stimulatory signaling domain is the CD28 intracellular domain or a fragment thereof that retains CD28 co-stimulatory activity.

20. The antigen binding receptor of any one of embodiments 1-19, wherein the antigen binding receptor comprises a stimulatory signaling domain comprising the intracellular domain of CD3z, or a fragment thereof that retains CD3z stimulatory signaling activity, and wherein the antigen binding receptor comprises a co-stimulatory signaling domain comprising the intracellular domain of CD28, or a fragment thereof that retains CD28 co-stimulatory signaling activity.

21. The antigen binding receptor of embodiment 20, wherein the stimulatory signaling domain comprises the amino acid sequence of SEQ ID NO:13.

22. The antigen binding receptor of any one of embodiments 1-18, wherein the antigen binding receptor comprises one stimulatory signaling domain comprising the intracellular domain of CD3z, or a fragment thereof that retains CD3z stimulatory signaling activity, and wherein the antigen binding receptor comprises one co-stimulatory signaling domain comprising the intracellular domain of CD137, or a fragment thereof that retains CD137 co-stimulatory signaling activity.

23. The antigen binding receptor of embodiment 22, wherein the stimulatory signaling domain comprises the amino acid sequence of SEQ ID NO:13 and the co-stimulatory signaling domain comprises the amino acid sequence of SEQ ID NO:12.

24. The antigen binding receptor of any one of embodiments 1-23, wherein the extracellular domain is connected to the anchoring transmembrane domain, optionally through a peptide linker.

25. The antigen binding receptor of embodiment 24, wherein the peptide linker comprises the amino acid sequence of SEQ ID NO:19.

26. The antigen binding receptor of any one of embodiments 14-25, wherein the anchoring transmembrane domain is connected to the co-signaling domain or to the stimulatory signaling domain, optionally through a peptide linker.

27. The antigen binding receptor of any one of embodiments 1-26, wherein the signaling and/or co-signaling domains are connected, optionally through at least one peptide linker.

28. The antigen binding receptor of any one of embodiments 1-27, wherein the antigen binding moiety is connected at the C-terminus to the N-terminus of the anchoring transmembrane domain, optionally through a peptide linker.

29. The antigen binding receptor of any one of embodiments 1-28, wherein the light chain variable domain (VL) is connected at the C-terminus to the N-terminus of the anchoring transmembrane, optionally through a peptide linker.

30. The antigen binding receptor of any one of embodiments 1-29, wherein the heavy chain variable domain (VH) is connected at the C-terminus to the N-terminus of the light chain variable domain (VL), optionally through a peptide linker.

31. The antigen binding receptor of any one of embodiments 14-30, wherein the antigen binding receptor comprises one co-signaling domain, wherein the co-signaling domain is connected at the N-terminus to the C-terminus of the anchoring transmembrane domain.

32. The antigen binding receptor of embodiment 31, wherein the antigen binding receptor additionally comprises one stimulatory signaling domain, wherein the stimulatory signaling domain is connected at the N-terminus to the C-terminus of the co-stimulatory signaling domain.

33. The antigen binding receptor of any one of embodiments 1-32, wherein the antigen binding receptor comprises an amino acid sequence that is at least about 95%, 96%, 97%, 98%, 99% or 100% identical to the amino acid sequence of SEQ ID NO:7 or SEQ ID NO:125.

34. An antigen binding receptor comprising the amino acid sequence of SEQ ID NO:7; or an antigen binding receptor comprising the amino acid sequence of SEQ ID NO:125.

35. An isolated polynucleotide encoding the antigen binding receptor of any one of embodiments 1 to 34.

36. A polypeptide encoded by the isolated polynucleotide of embodiments 35.

37. A vector, particularly an expression vector, comprising the polynucleotide of embodiment 35.

38. A transduced T cell comprising the polynucleotide of embodiment 35 or the vector of embodiment 37.

39. A transduced T cell capable of expressing the antigen binding receptor of any one of embodiments 1 to 34.

40. A kit comprising (A) a transduced T cell capable of expressing the antigen binding receptor of any one of embodiments 1 to 34; and (B) an antibody that binds to a target cell antigen and that comprises an Fc domain comprising the amino acid mutation P329G according to EU numbering.

41. A kit comprising (A) an isolated polynucleotide encoding the antigen binding receptor of any one of embodiments 1 to 34; and (B) an antibody that binds to a target cell antigen and that comprises an Fc domain comprising the amino acid mutation P329G according to EU numbering.

42. A kit comprising (A) the isolated polynucleotide of embodiment 35 or the vector of embodiment 37; and (B) an antibody that binds to a target cell antigen and that comprises an Fc domain comprising the amino acid mutation P329G according to EU numbering.

43. The kit of any one of embodiments 40 to 42, wherein the Fc domain is an IgG1 or an IgG4 Fc domain, particularly a human IgG1 Fc domain.

44. The kit of any one of embodiments 40 to 43, wherein the target cell antigen selected from the group consisting of fibroblast activation protein (FAP), carcinoembryonic antigen (CEA), mesothelin (MSLN), CD20, folate receptor 1 (FOLR1) and tenascin (TNC).

45. The kit of any one of embodiments 40 to 44 for use as a medicament.

46. The antigen binding receptor of any one of embodiments 1 to 34 or the transduced T cell of any one of embodiments 38 to 39 for use as a medicament, wherein a transduced T cell expressing the antigen binding receptor is administered before, simultaneously with or after administration of an antibody that binds to a target cell antigen, in particular a cancer cell antigen, and that comprises an Fc domain comprising the amino acid mutation P329G according to EU numbering.

47. The kit of any one of embodiments 40 to 45 for use in the treatment of a disease, in particular for use in the treatment of a cancer.

48. The antigen binding receptor of any one of embodiments 1 to 34 or the transduced T cell of any one of embodiments 38 to 39 for use in the treatment of cancer, wherein the treatment comprises administration of a transduced T cell expressing the antigen binding receptor before, simultaneously with or after administration of an antibody that binds to a cancer cell antigen and that comprises an Fc domain comprising the amino acid mutation P329G according to EU numbering.

49. The antigen binding receptor, the transduced T cell or the kit for use according to embodiment 47 or 48 wherein said caner is selected from cancer of epithelial, endothelial or mesothelial origin and cancer of the blood.

50. The antigen binding receptor, the transduced T cell or the kit for use according to embodiment 49, wherein the cancer antigen selected from the group consisting of fibroblast activation protein (FAP), carcinoembryonic antigen (CEA), mesothelin (MSLN), CD20, folate receptor 1 (FOLR1) and tenascin (TNC).

51. The antigen binding receptor, the transduced T cell or the kit for use according to any one of embodiments 48 to 50, wherein the transduced T cell is derived from a cell isolated from the subject to be treated.

52. The antigen binding receptor, the transduced T cell or the kit for use according to any one of embodiments 48 to 51, wherein the transduced T cell is not derived from a cell isolated from the subject to be treated.

53. A method of treating a disease in a subject, comprising administering to the subject a transduced T cell capable of expressing the antigen binding receptor of any one of embodiments 1 to 34 and administering before, simultaneously with or after administration of the transduced T cell a therapeutically effective amount of an antibody that binds to a target cell antigen and that comprises an Fc domain comprising the amino acid mutation P329G according to EU numbering.

54. The method of embodiment 48, additionally comprising isolating a T cell from the subject and generating the transduced T cell by transducing the isolated T cell with the polynucleotide of embodiment 35, or the vector of embodiment 37.

55. The method of embodiment 54, wherein the T cell is transduced with a retroviral or lentiviral vector construct, or with a non-viral vector construct.

56. The method of any one of embodiments 53 to 55, wherein the transduced T cell is administered to the subject by intravenous infusion.

57. The method of any one of embodiments 53 to 56, wherein the transduced T cell is contacted with anti-CD3 and/or anti-CD28 antibodies prior to administration to the subject.

58. The method of any one of embodiments 53 to 57, wherein the transduced T cell is contacted with at least one cytokine prior to administration to the subject, preferably with interleukin-2 (IL-2), interleukin-7 (IL-7), interleukin-15 (IL-15), and/or interleukin-21, or variants thereof.

59. The method of any one of embodiments 53 to 58, wherein the disease is cancer.

60. The method of embodiment 59, wherein the cancer is selected from cancer of epithelial, endothelial or mesothelial origin and cancer of the blood.

61. A method for inducing lysis of a target cell, comprising contacting the target cell with a transduced T cell capable of expressing the antigen binding receptor of any one of embodiments 1 to 34 in the presence of an antibody that binds to a target cell antigen and that comprises an Fc domain comprising the amino acid mutation P329G according to EU numbering.

62. The method of embodiment 61, wherein the target cell is a cancer cell.

63. The method of of embodimens 61 or 62, wherein the target cell expresses an antigen selected from the group consisting of fibroblast activation protein (FAP), carcinoembryonic antigen (CEA), mesothelin (MSLN), CD20, folate receptor 1 (FOLR1), and tenascin (TNC).

64. Use of the antigen binding receptor of any one of embodiments 1 to 34, the polynucleotide of embodiments 35 or the transduced T cell of embodiment 38 or 39 for the manufacture of a medicament.

65. The use of embodiment 64, wherein the medicament is for treatment of cancer.

66. The use of embodiment 65, characterized in that said cancer is selected from cancer of epithelial, endothelial or mesothelial origin and cancer of the blood.

67. The invention as hereinbefore described.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com.

Exemplary Sequences

TABLE 2

Exemplary VH3VL1 P329G-CAR amino acid sequences: CDR definition according to Kabat

| Construct | Amino acid sequence | SEQ ID NO |
|---|---|---|
| VH3 CDR H1 | RYWMN | 1 |
| VH3 CDR H2 | EITPDSSTINYAPSLKG | 2 |
| VH3 CDR H3 | PYDYGAWFAS | 3 |
| VL1 CDR L1 | RSSTGAVTTSNYAN | 4 |
| VL1 CDR L2 | GTNKRAP | 5 |
| VL1 CDR L3 | ALWYSNHWV | 6 |
| VH3VL1-CD8ATD-CD137CSD-CD3zSSD fusion | EVQLVESGGGLVQPGGSLRLSCAASGFTFSRYWMNWV RQAPGKGLEWVGEITPDSSTINYAPSLKGRFTISRDNAKN SLYLQMNSLRAEDTAVYYCARPYDYGAWFASWGQGTL VTVSSGGGGSGGGGSGGGGSGGGGSQAVVTQEPSLTVS PGGTVTLTCRSSTGAVTTSNYANWVQEKPDHLFTGLIGG TNKRAPGTPARFSGSLLGGKAALTLSGAQPEDEAEYYC ALWYSNHWVFGGGTKLTVLGGGGSLKPTTTPAPRPPTP APTIASQPLSLRPEACRPAAGGAVHTRGLDFACDIYIWAP LAGTCGVLLLSLVITKRGRKKLLYIFKQPFMRPVQTTQE | 7 |

TABLE 2-continued

Exemplary VH3VL1 P329G-CAR amino acid sequences: CDR definition according to Kabat

| Construct | Amino acid sequence | SEQ ID NO |
|---|---|---|
| | EDGCSCRFPEEEEGGCELRVKFSRSADAPAYQQGQNQL YNELNLGRREEYDVLDKRRGRDPEMGGKPRRKNPQEG LYNELQKDKMAEAYSEIGMKGERRRGKGHDGLYQGLS TATKDTYDALHMQALPPR | |
| VH3 VH | EVQLVESGGGLVQPGGSLRLSCAASGFTFSRYWMNWV RQAPGKGLEWVGEITPDSSTINYAPSLKGRFTISRDNAKN SLYLQMNSLRAEDTAVYYCARPYDYGAWFASWGQGTL VTVSS | 8 |
| VL1 VL | QAVVTQEPSLTVSPGGTVTLTCRSSTGAVTTSNYANWV QEKPDHLFTGLIGGTNKRAPGTPARFSGSLLGGKAALTL SGAQPEDEAEYYCALWYSNHWVFGGGTKLTVL | 9 |
| VH3VL1 scFv | EVQLVESGGGLVQPGGSLRLSCAASGFTFSRYWMNWV RQAPGKGLEWVGEITPDSSTINYAPSLKGRFTISRDNAKN SLYLQMNSLRAEDTAVYYCARPYDYGAWFASWGQGTL VTVSSGGGGSGGGGSGGGGSGGGGSQAVVTQEPSLTVS PGGTVTLTCRSSTGAVTTSNYANWVQEKPDHLFTGLIGG TNKRAPGTPARFSGSLLGGKAALTLSGAQPEDEAEYYC ALWYSNHWVFGGGTKLTVL | 10 |
| CD8ATD | IYIWAPLAGTCGVLLLSLVIT | 11 |
| CD137CSD | KRGRKKLLYIFKQPFMRPVQTTQEEDGCSCRFPEEEEGG CEL | 12 |
| CD3zSSD | RVKFSRSADAPAYQQGQNQLYNELNLGRREEYDVLDK RRGRDPEMGGKPRRKNPQEGLYNELQKDKMAEAYSEIG MKGERRRGKGHDGLYQGLSTATKDTYDALHMQALPPR | 13 |
| CD28ATD-CD137CSD-CD3zSSD | KPTTTPAPRPPTPAPTIASQPLSLRPEACRPAAGGAVHTR GLDFACDIYIWAPLAGTCGVLLLSLVITKRGRKKLLYIFK QPFMRPVQTTQEEDGCSCRFPEEEEGGCELRVKFSRSAD APAYQQGQNQLYNELNLGRREEYDVLDKRRGRDPEMG GKPRRKNPQEGLYNELQKDKMAEAYSEIGMKGERRRG KGHDGLYQGLSTATKDTYDALHMQALPPR | 14 |
| eGFP | VSKGEELFTGVVPILVELDGDVNGHKFSVSGEGEGDATY GKLTLKFICTTGKLPVPWPTLVTTLTYGVQCFSRYPDHM KQHDFFKSAMPEGYVQERTIFFKDDGNYKTRAEVKFEG DTLVNRIELKGIDFKEDGNILGHKLEYNYNSHNVYIMAD KQKNGIKVNFKIRHNIEDGSVQLADHYQQNTPIGDGPVL LPDNHYLSTQSALSKDPNEKRDHMVLLEFVTAAGITLG MDELYK | 15 |
| (G4S)4 linker | GGGGSGGGGSGGGGSGGGGS | 16 |
| G4S linker | GGGGS | 17 |
| T2A linker | GEGRGSLLTCGDVEENPGP | 18 |
| CD8stalk | KPTTTPAPRPPTPAPTIASQPLSLRPEACRPAAGGAVHTR GLDFACD | 19 |

TABLE 3

Exemplary VH3 x VL1 P329G-CAR DNA sequences:

| Construct | DNA sequence | SEQ ID NO |
|---|---|---|
| VH3VL1-CD28ATD-CD137CSD-CD3zSSD fusion | GAGGTGCAGCTGGTGGAGAGCGGCGGCGGCCTGGTGC AGCCCGGCGGCAGCCTGAGGCTGAGCTGCGCCGCCAG CGGCTTCACCTTCAGCAGGTACTGGATGAACTGGGTGA GGCAGGCCCCCGGCAAGGGCCTGGAGTGGGTGGGCGA GATCACCCCCGACAGCAGCACCATCAACTACGCCCCCA GCCTGAAGGGCAGGTTCACCATCAGCAGGGACAACGC CAAGAACAGCCTGTACCTGCAGATGAACAGCCTGAGG GCCGAGGACACCGCCGTGTACTACTGCGCCAGGCCCTA CGACTACGGCGCCTGGTTCGCCAGCTGGGGCCAGGGCA | 20 |

TABLE 3-continued

Exemplary VH3 x VL1 P329G-CAR DNA sequences:

| Construct | DNA sequence | SEQ ID NO |
|---|---|---|
| | CCCTGGTGACCGTGAGCAGCGGAGGGGGCGGAAGTGG<br>TGGCGGGGGAAGCGGCGGGGGTGGCAGCGGAGGGGGC<br>GGATCTCAGGCCGTGGTGACCCAGGAGCCCAGCCTGAC<br>CGTGAGCCCCGGCGGCACCGTGACCCTGACCTGCAGGA<br>GCAGCACCGGCGCCGTGACCACCAGCAACTACGCCAA<br>CTGGGTGCAGGAGAAGCCCGACCACCTGTTCACCGGCC<br>TGATCGGCGGCACCAACAAGAGGGCCCCCGGCACCCC<br>CGCCAGGTTCAGCGGCAGCCTGCTGGGCGGCAAGGCC<br>GCCCTGACCCTGAGCGGCGCCCAGCCCGAGGACGAGG<br>CCGAGTACTACTGCGCCCTGTGGTACAGCAACCACTGG<br>GTGTTCGGCGGCGGCACCAAGCTGACCGTCCTAGGAGG<br>GGGCGGATCCTTGAAGCCCACCACGACGCCAGCGCCGC<br>GACCACCAACACCGGCGCCCACCATCGCGTCGCAGCCC<br>CTGTCCCTGCGCCCAGAGGCGTGCCGGCCAGCGGCGGG<br>GGGCGCAGTGCACACGAGGGGGCTGGACTTCGCCTGTG<br>ATATCTACATCTGGGCGCCCCTGGCCGGGACTTGTGGG<br>GTCCTTCTCCTGTCACTGGTTATCACCAAACGGGGCAG<br>AAAGAAACTCCTGTATATATTCAAACAACCATTTATGA<br>GACCAGTACAAACTACTCAAGAGGAAGATGGCTGTAG<br>CTGCCGATTTCCAGAAGAAGAAGAAGGAGGATGTGAA<br>CTGAGAGTGAAGTTCAGCAGGAGCGCAGACGCCCCCG<br>CGTACCAGCAGGGCCAGAACCAGCTCTATAACGAGCTC<br>AATCTAGGACGAAGAGAGGAGTACGATGTTTTGGACA<br>AGAGACGTGGCCGGGACCCTGAGATGGGGGGAAAGCC<br>GAGAAGGAAGAACCCTCAGGAAGGCCTGTACAATGAA<br>CTGCAGAAAGATAAGATGGCGGAGGCCTACAGTGAGA<br>TTGGGATGAAAGGCGAGCGCCGGAGGGGCAAGGGGCA<br>CGATGGCCTTTACCAGGGTCTCAGTACAGCCACCAAGG<br>ACACCTACGACGCCCTTCACATGCAGGCCCTGCCCCCT<br>CGC | |
| VH3 | GAGGTGCAGCTGGTGGAGAGCGGCGGCGGCCTGGTGC<br>AGCCCGGCGGCAGCCTGAGGCTGAGCTGCGCCGCCAG<br>CGGCTTCACCTTCAGCAGGTACTGGATGAACTGGGTGA<br>GGCAGGCCCCCGGCAAGGGCCTGGAGTGGGTGGGCGA<br>GATCACCCCCGACAGCAGCACCATCAACTACGCCCCCA<br>GCCTGAAGGGCAGGTTCACCATCAGCAGGGACAACGC<br>CAAGAACAGCCTGTACCTGCAGATGAACAGCCTGAGG<br>GCCGAGGACACCGCCGTGTACTACTGCGCCAGGCCCTA<br>CGACTACGGCGCCTGGTTCGCCAGCTGGGGCCAGGGCA<br>CCCTGGTGACCGTGAGCAGC | 21 |
| VL1 | CAGGCCGTGGTGACCCAGGAGCCCAGCCTGACCGTGA<br>GCCCCGGCGGCACCGTGACCCTGACCTGCAGGAGCAGC<br>ACCGGCGCCGTGACCACCAGCAACTACGCCAACTGGGT<br>GCAGGAGAAGCCCGACCACCTGTTCACCGGCCTGATCG<br>GCGGCACCAACAAGAGGGCCCCCGGCACCCCCGCCAG<br>GTTCAGCGGCAGCCTGCTGGGCGGCAAGGCCGCCCTGA<br>CCCTGAGCGGCGCCCAGCCCGAGGACGAGGCCGAGTA<br>CTACTGCGCCCTGTGGTACAGCAACCACTGGGTGTTCG<br>GCGGCGGCACCAAGCTGACCGTCCTA | 22 |
| VH3VL1<br>scFv | GAGGTGCAGCTGGTGGAGAGCGGCGGCGGCCTGGTGC<br>AGCCCGGCGGCAGCCTGAGGCTGAGCTGCGCCGCCAG<br>CGGCTTCACCTTCAGCAGGTACTGGATGAACTGGGTGA<br>GGCAGGCCCCCGGCAAGGGCCTGGAGTGGGTGGGCGA<br>GATCACCCCCGACAGCAGCACCATCAACTACGCCCCCA<br>GCCTGAAGGGCAGGTTCACCATCAGCAGGGACAACGC<br>CAAGAACAGCCTGTACCTGCAGATGAACAGCCTGAGG<br>GCCGAGGACACCGCCGTGTACTACTGCGCCAGGCCCTA<br>CGACTACGGCGCCTGGTTCGCCAGCTGGGGCCAGGGCA<br>CCCTGGTGACCGTGAGCAGCGGAGGGGGCGGAAGTGG<br>TGGCGGGGGAAGCGGCGGGGGTGGCAGCGGAGGGGGC<br>GGATCTCAGGCCGTGGTGACCCAGGAGCCCAGCCTGAC<br>CGTGAGCCCCGGCGGCACCGTGACCCTGACCTGCAGGA<br>GCAGCACCGGCGCCGTGACCACCAGCAACTACGCCAA<br>CTGGGTGCAGGAGAAGCCCGACCACCTGTTCACCGGCC<br>TGATCGGCGGCACCAACAAGAGGGCCCCCGGCACCCC<br>CGCCAGGTTCAGCGGCAGCCTGCTGGGCGGCAAGGCC<br>GCCCTGACCCTGAGCGGCGCCCAGCCCGAGGACGAGG<br>CCGAGTACTACTGCGCCCTGTGGTACAGCAACCACTGG<br>GTGTTCGGCGGCGGCACCAAGCTGACCGTCCTA | 23 |
| CD8ATD | ATCTACATCTGGGCGCCCCTGGCCGGGACTTGTGGGGT<br>CCTTCTCCTGTCACTGGTTATCACC | 24 |

TABLE 3-continued

| Exemplary VH3 x VL1 P329G-CAR DNA sequences: | | |
|---|---|---|
| Construct | DNA sequence | SEQ ID NO |
| CD137CSD | AAACGGGGCAGAAAGAAACTCCTGTATATATTCAAAC AACCATTTATGAGACCAGTACAAACTACTCAAGAGGAA GATGGCTGTAGCTGCCGATTTCCAGAAGAAGAAGAAG GAGGATGTGAACTG | 25 |
| CD3ZSSD | AGAGTGAAGTTCAGCAGGAGCGCAGACGCCCCCGCGT ACCAGCAGGGCCAGAACCAGCTCTATAACGAGCTCAAT CTAGGACGAAGAGAGGAGTACGATGTTTTGGACAAGA GACGTGGCCGGGACCCTGAGATGGGGGGAAAGCCGAG AAGGAAGAACCCTCAGGAAGGCCTGTACAATGAACTG CAGAAAGATAAGATGGCGGAGGCCTACAGTGAGATTG GGATGAAAGGCGAGCGCCGGAGGGGCAAGGGGCACGA TGGCCTTTACCAGGGTCTCAGTACAGCCACCAAGGACA CCTACGACGCCCTTCACATGCAGGCCCTGCCCCCTCGC | 26 |
| CD28ATD-CD137CSD-CD3zSSD | ATCTACATCTGGGCGCCCCTGGCCGGGACTTGTGGGGT CCTTCTCCTGTCACTGGTTATCACCAAACGGGGCAGAA AGAAACTCCTGTATATATTCAAACAACCATTTATGAGA CCAGTACAAACTACTCAAGAGGAAGATGGCTGTAGCTG CCGATTTCCAGAAGAAGAAGAAGGAGGATGTGAACTG AGAGTGAAGTTCAGCAGGAGCGCAGACGCCCCCGCGT ACCAGCAGGGCCAGAACCAGCTCTATAACGAGCTCAAT CTAGGACGAAGAGAGGAGTACGATGTTTTGGACAAGA GACGTGGCCGGGACCCTGAGATGGGGGGAAAGCCGAG AAGGAAGAACCCTCAGGAAGGCCTGTACAATGAACTG CAGAAAGATAAGATGGCGGAGGCCTACAGTGAGATTG GGATGAAAGGCGAGCGCCGGAGGGGCAAGGGGCACGA TGGCCTTTACCAGGGTCTCAGTACAGCCACCAAGGACA CCTACGACGCCCTTCACATGCAGGCCCTGCCCCCTCGC | 27 |
| T2A element | TCCGGAGAGGGCAGAGGAAGTCTTCTAACATGCGGTG ACGTGGAGGAGAATCCCGGCCCTAGG | 28 |
| eGFP | GTGAGCAAGGGCGAGGAGCTGTTCACCGGGGTGGTGC CCATCCTGGTCGAGCTGGACGGCGACGTAAACGGCCAC AAGTTCAGCGTGTCCGGCGAGGGCGAGGGCGATGCCA CCTACGGCAAGCTGACCCTGAAGTTCATCTGCACCACC GGCAAGCTGCCCGTGCCCTGGCCCACCCTCGTGACCAC CCTGACCTACGGCGTGCAGTGCTTCAGCCGCTACCCCG ACCACATGAAGCAGCACGACTTCTTCAAGTCCGCCATG CCCGAAGGCTACGTCCAGGAGCGCACCATCTTCTTCAA GGACGACGGCAACTACAAGACCCGCGCCGAGGTGAAG TTCGAGGGCGACACCCTGGTGAACCGCATCGAGCTGAA GGGCATCGACTTCAAGGAGGACGGCAACATCCTGGGG CACAAGCTGGAGTACAACTACAACAGCCACAACGTCTA TATCATGGCCGACAAGCAGAAGAACGGCATCAAGGTG AACTTCAAGATCCGCCACAACATCGAGGACGGCAGCGT GCAGCTCGCCGACCACTACCAGCAGAACACCCCCATCG GCGACGGCCCCGTGCTGCTGCCCGACAACCACTACCTG AGCACCCAGTCCGCCCTGAGCAAAGACCCCAACGAGA AGCGCGATCACATGGTCCTGCTGGAGTTCGTGACCGCC GCCGGGATCACTCTCGGCATGGACGAGCTGTACAAGTG A | 29 |
| VH3VL1-CD28ATD-CD137CSD-CD3zSSD GFP fusion | GAGGTGCAGCTGGTGGAGAGCGGCGGCGGCCTGGTGC AGCCCGGCGGCAGCCTGAGGCTGAGCTGCGCCGCCAG CGGCTTCACCTTCAGCAGGTACTGGATGAACTGGGTGA GGCAGGCCCCCGGCAAGGGCCTGGAGTGGGTGGGCGA GATCACCCCCGACAGCAGCACCATCAACTACGCCCCCA GCCTGAAGGGCAGGTTCACCATCAGCAGGGACAACGC CAAGAACAGCCTGTACCTGCAGATGAACAGCCTGAGG GCCGAGGACACCGCCGTGTACTACTGCGCCAGGCCCTA CGACTACGGCGCCTGGTTCGCCAGCTGGGGCCAGGGCA CCCTGGTGACCGTGAGCAGCGGAGGGGGCGGAAGTGG TGGCGGGGGAAGCGGCGGGGGTGGCAGCGGAGGGGGC GGATCTCAGGCCGTGGTGACCCAGGAGCCCAGCCTGAC CGTGAGCCCCGGCGGCACCGTGACCCTGACCTGCAGGA GCAGCACCGGCGCCGTGACCACCAGCAACTACGCCAA CTGGGTGCAGGAGAAGCCCGACCACCTGTTCACCGGCC TGATCGGCGGCACCAACAAGAGGGCCCCCGGCACCCC CGCCAGGTTCAGCGGCAGCCTGCTGGGCGGCAAGGCC GCCCTGACCCTGAGCGGCGCCCAGCCCGAGGACGAGG CCGAGTACTACTGCGCCCTGTGGTACAGCAACCACTGG GTGTTCGGCGGCGGCACCAAGCTGACCGTCCTAGGAGG | 30 |

TABLE 3-continued

| Exemplary VH3 x VL1 P329G-CAR DNA sequences: | | |
|---|---|---|
| Construct | DNA sequence | SEQ ID NO |
| | GGGCGGATCCTTGAAGCCCACCACGACGCCAGCGCCGC GACCACCAACACCGGCGCCCACCATCGCGTCGCAGCCC CTGTCCCTGCGCCCAGAGGCGTGCCGGCCAGCGGCGGG GGGCGCAGTGCACACGAGGGGGCTGGACTTCGCCTGTG ATATCTACATCTGGGCGCCCCTGGCCGGGACTTGTGGG GTCCTTCTCCTGTCACTGGTTATCACCAAACGGGGCAG AAAGAAACTCCTGTATATATTCAAACAACCATTTATGA GACCAGTACAAACTACTCAAGAGGAAGATGGCTGTAG CTGCCGATTTCCAGAAGAAGAAGAAGGAGGATGTGAA CTGAGAGTGAAGTTCAGCAGGAGCGCAGACGCCCCCG CGTACCAGCAGGGCCAGAACCAGCTCTATAACGAGCTC AATCTAGGACGAAGAGAGGAGTACGATGTTTTGGACA AGAGACGTGGCCGGGACCCTGAGATGGGGGGAAAGCC GAGAAGGAAGAACCCTCAGGAAGGCCTGTACAATGAA CTGCAGAAAGATAAGATGGCGGAGGCCTACAGTGAGA TTGGGATGAAAGGCGAGCGCCGGAGGGGCAAGGGGCA CGATGGCCTTTACCAGGGTCTCAGTACAGCCACCAAGG ACACCTACGACGCCCTTCACATGCAGGCCCTGCCCCCT CGCGAATTCTCCGGAGAGGGCAGAGGAAGTCTTCTAAC ATGCGGTGACGTGGAGGAGAATCCCGGCCCTAGGGTG AGCAAGGGCGAGGAGCTGTTCACCGGGGTGGTGCCCA TCCTGGTCGAGCTGGACGGCGACGTAAACGGCCACAA GTTCAGCGTGTCCGGCGAGGGCGAGGGCGATGCCACCT ACGGCAAGCTGACCCTGAAGTTCATCTGCACCACCGGC AAGCTGCCCGTGCCCTGGCCCACCCTCGTGACCACCCT GACCTACGGCGTGCAGTGCTTCAGCCGCTACCCCGACC ACATGAAGCAGCACGACTTCTTCAAGTCCGCCATGCCC GAAGGCTACGTCCAGGAGCGCACCATCTTCTTCAAGGA CGACGGCAACTACAAGACCCGCGCCGAGGTGAAGTTC GAGGGCGACACCCTGGTGAACCGCATCGAGCTGAAGG GCATCGACTTCAAGGAGGACGGCAACATCCTGGGGCA CAAGCTGGAGTACAACTACAACAGCCACAACGTCTATA TCATGGCCGACAAGCAGAAGAACGGCATCAAGGTGAA CTTCAAGATCCGCCACAACATCGAGGACGGCAGCGTGC AGCTCGCCGACCACTACCAGCAGAACACCCCCATCGGC GACGGCCCCGTGCTGCTGCCCGACAACCACTACCTGAG CACCCAGTCCGCCCTGAGCAAAGACCCCAACGAGAAG CGCGATCACATGGTCCTGCTGGAGTTCGTGACCGCCGC CGGGATCACTCTCGGCATGGACGAGCTGTACAAG | |

TABLE 4

| Exemplary VL1VH3 P329G-CAR amino acid sequences: CDR definition according to Kabat | | |
|---|---|---|
| Construct | Amino acid sequence | SEQ ID NO |
| VH3 CDR H1 | see Table 2 | 1 |
| VH3 CDR H2 | see Table 2 | 2 |
| VH3 CDR H3 | see Table 2 | 3 |
| VL1 CDR L1 | see Table 2 | 4 |
| VL1 CDR L2 | see Table 2 | 5 |
| VL1 CDR L3 | see Table 2 | 6 |
| VL1VH3-CD8ATD-CD137CSD-CD3zSSD fusion | QAVVTQEPSLTVSPGGTVTLTCRSSTGAVTTSNYANWV QEKPDHLFTGLIGGTNKRAPGTPARFSGSLLGGKAALTL SGAQPEDEAEYYCALWYSNHWVFGGGTKLTVLGGGGS GGGGSGGGGSGGGGSEVQLVESGGGLVQPGGSLRLSCA ASGFTFSRYWMNWVRQAPGKGLEWVGEITPDSSTINYA PSLKGRFTISRDNAKNSLYLQMNSLRAEDTAVYYCARP YDYGAWFASWGQGTLVTVSSGGGGSLKPTTTPAPRPPT | 31 |
| VH3 VH | See Table 2 | 8 |
| VL1 VL | See Table 2 | 9 |

TABLE 4-continued

Exemplary VL1VH3 P329G-CAR amino acid sequences: CDR definition according to Kabat

| Construct | Amino acid sequence | SEQ ID NO |
|---|---|---|
| VL1VH3 scFv | MLLLVTSLLLCELPHPAFLLIPAQAVVTQEPSLTVSPGGT VTLTCRSSTGAVTTSNYANWVQEKPDHLFTGLIGGTNK RAPGTPARFSGSLLGGKAALTLSGAQPEDEAEYYCALW YSNHWVFGGGTKLTVLGGGGSGGGGSGGGGSGGGGSE VQLVESGGGLVQPGGSLRLSCAASGFTFSRYWMNWVR QAPGKGLEWVGEITPDSSTINYAPSLKGRFTISRDNAKNS LYLQMNSLRAEDTAVYYCARPYDYGAWFASWGQGTL VTVSS | 32 |
| CD8ATD | see Table 2 | 11 |
| CD137CSD | see Table 2 | 12 |
| CD3zSSD | see Table 2 | 13 |
| CD28ATD-CD137CDS-CD3zSSD | see Table 2 | 14 |
| eGFP | see Table 2 | 15 |
| (G4S)4 linker | see Table 2 | 16 |
| G4S linker | see Table 2 | 17 |
| T2A linker | see Table 2 | 18 |

TABLE 5

Exemplary VL1VH3 P329G-CAR DNA sequences:

| Construct | DNA sequence | SEQ ID NO |
|---|---|---|
| VL1VH3 CD8ATD-CD137CSD-CD3zSSD fusion | CAGGCCGTGGTGACCCAGGAGCCCAGCCTGACCGTGA GCCCCGGCGGCACCGTGACCCTGACCTGCAGGAGCAGC ACCGGCGCCGTGACCACCAGCAACTACGCCAACTGGGT GCAGGAGAAGCCCGACCACCTGTTCACCGGCCTGATCG GCGGCACCAACAAGAGGGCCCCCGGCACCCCCGCCAG GTTCAGCGGCAGCCTGCTGGGCGGCAAGGCCGCCCTGA CCCTGAGCGGCGCCCAGCCCGAGGACGAGGCCGAGTA CTACTGCGCCCTGTGGTACAGCAACCACTGGGTGTTCG GCGGCGGCACCAAGCTGACCGTCCTAGGAGGGGGCGG AAGTGGTGGCGGGGGAAGCGGCGGGGGTGGCAGCGGA GGGGGCGGATCTGAGGTGCAGCTGGTGGAGAGCGGCG GCGGCCTGGTGCAGCCCGGCGGCAGCCTGAGGCTGAG CTGCGCCGCCAGCGGCTTCACCTTCAGCAGGTACTGGA TGAACTGGGTGAGGCAGGCCCCCGGCAAGGGCCTGGA GTGGGTGGGCGAGATCACCCCCGACAGCAGCACCATC AACTACGCCCCCAGCCTGAAGGGCAGGTTCACCATCAG CAGGGACAACGCCAAGAACAGCCTGTACCTGCAGATG AACAGCCTGAGGGCCGAGGACACCGCCGTGTACTACTG CGCCAGGCCCTACGACTACGGCGCCTGGTTCGCCAGCT GGGGCCAGGGCACCCTGGTGACCGTGAGCAGCGGAGG GGGCGGATCCTTGAAGCCCACCACGACGCCAGCGCCGC GACCACCAACACCGGCGCCCACCATCGCGTCGCAGCCC CTGTCCCTGCGCCCAGAGGCGTGCCGGCCAGCGGCGGG GGGCGCAGTGCACACGAGGGGGCTGGACTTCGCCTGTG ATATCTACATCTGGGCGCCCCTGGCCGGGACTTGTGGG GTCCTTCTCCTGTCACTGGTTATCACCAAACGGGGCAG AAAGAAACTCCTGTATATATTCAAACAACCATTTATGA GACCAGTACAAACTACTCAAGAGGAAGATGGCTGTAG CTGCCGATTTCCAGAAGAAGAAGAAGGAGGATGTGAA CTGAGAGTGAAGTTCAGCAGGAGCGCAGACGCCCCCG CGTACCAGCAGGGCCAGAACCAGCTCTATAACGAGCTC AATCTAGGACGAAGAGAGGAGTACGATGTTTTGGACA AGAGACGTGGCCGGGACCCTGAGATGGGGGGAAAGCC GAGAAGGAAGAACCCTCAGGAAGGCCTGTACAATGAA CTGCAGAAAGATAAGATGGCGGAGGCCTACAGTGAGA TTGGGATGAAAGGCGAGCGCCGGAGGGGCAAGGGGCA CGATGGCCTTTACCAGGGTCTCAGTACAGCCACCAAGG | 33 |

TABLE 5-continued

Exemplary VL1VH3 P329G-CAR DNA sequences:

| Construct | DNA sequence | SEQ ID NO |
|---|---|---|
| | ACACCTACGACGCCCTTCACATGCAGGCCCTGCCCCCT CGC | |
| VH3 | See Table 3 | 20 |
| VL1 | See Table 3 | 21 |
| CD8ATD | see Table 3 | 24 |
| CD137CSD | see Table 3 | 25 |
| CD3zSSD | see Table 3 | 26 |
| CD8ATD-CD137CSD-CD3zSSD | see Table 3 | 27 |
| T2A element | see Table 3 | 28 |
| eGFP | see Table 3 | 29 |
| VL1VH3-CD8ATD-CD137CSD-CD3zSSD-eGFP fusion | CAGGCCGTGGTGACCCAGGAGCCCAGCCTGACCGTGA GCCCCGGCGGCACCGTGACCCTGACCTGCAGGAGCAGC ACCGGCGCCGTGACCACCAGCAACTACGCCAACTGGGT GCAGGAGAAGCCCGACCACCTGTTCACCGGCCTGATCG GCGGCACCAACAAGAGGGCCCCCGGCACCCCCGCCAG GTTCAGCGGCAGCCTGCTGGGCGGCAAGGCCGCCCTGA CCCTGAGCGGCGCCCAGCCCGAGGACGAGGCCGAGTA CTACTGCGCCCTGTGGTACAGCAACCACTGGGTGTTCG GCGGCGGCACCAAGCTGACCGTCCTAGGAGGGGGCGG AAGTGGTGGCGGGGGAAGCGGCGGGGGTGGCAGCGGA GGGGGCGGATCTGAGGTGCAGCTGGTGGAGAGCGGCG GCGGCCTGGTGCAGCCCGGCGGCAGCCTGAGGCTGAG CTGCGCCGCCAGCGGCTTCACCTTCAGCAGGTACTGGA TGAACTGGGTGAGGCAGGCCCCCGGCAAGGGCCTGGA GTGGGTGGGCGAGATCACCCCCGACAGCAGCACCATC AACTACGCCCCCAGCCTGAAGGGCAGGTTCACCATCAG CAGGGACAACGCCAAGAACAGCCTGTACCTGCAGATG AACAGCCTGAGGGCCGAGGACACCGCCGTGTACTACTG CGCCAGGCCCTACGACTACGGCGCCTGGTTCGCCAGCT GGGGCCAGGGCACCCTGGTGACCGTGAGCAGCGGAGG GGGCGGATCCTTGAAGCCCACCACGACGCCAGCGCCGC GACCACCAACACCGGCGCCCACCATCGCGTCGCAGCCC CTGTCCCTGCGCCCAGAGGCGTGCCGGCCAGCGGCGGG GGGCGCAGTGCACACGAGGGGGCTGGACTTCGCCTGTG ATATCTACATCTGGGCGCCCCTGGCCGGGACTTGTGGG GTCCTTCTCCTGTCACTGGTTATCACCAAACGGGGCAG AAAGAAACTCCTGTATATATTCAAACAACCATTTATGA GACCAGTACAAACTACTCAAGAGGAAGATGGCTGTAG CTGCCGATTTCCAGAAGAAGAAGAAGGAGGATGTGAA CTGAGAGTGAAGTTCAGCAGGAGCGCAGACGCCCCCG CGTACCAGCAGGGCCAGAACCAGCTCTATAACGAGCTC AATCTAGGACGAAGAGAGGAGTACGATGTTTTGGACA AGAGACGTGGCCGGGACCCTGAGATGGGGGGAAAGCC GAGAAGGAAGAACCCTCAGGAAGGCCTGTACAATGAA CTGCAGAAAGATAAGATGGCGGAGGCCTACAGTGAGA TTGGGATGAAAGGCGAGCGCCGGAGGGGCAAGGGGCA CGATGGCCTTTACCAGGGTCTCAGTACAGCCACCAAGG ACACCTACGACGCCCTTCACATGCAGGCCCTGCCCCCT CGCGAATTCTCCGGAGAGGGCAGAGGAAGTCTTCTAAC ATGCGGTGACGTGGAGGAGAATCCCGGCCCTAGGGTG AGCAAGGGCGAGGAGCTGTTCACCGGGGTGGTGCCCA TCCTGGTCGAGCTGGACGGCGACGTAAACGGCCACAA GTTCAGCGTGTCCGGCGAGGGCGAGGGCGATGCCACCT ACGGCAAGCTGACCCTGAAGTTCATCTGCACCACCGGC AAGCTGCCCGTGCCCTGGCCCACCCTCGTGACCACCCT GACCTACGGCGTGCAGTGCTTCAGCCGCTACCCCGACC ACATGAAGCAGCACGACTTCTTCAAGTCCGCCATGCCC GAAGGCTACGTCCAGGAGCGCACCATCTTCTTCAAGGA CGACGGCAACTACAAGACCCGCGCCGAGGTGAAGTTC GAGGGCGACACCCTGGTGAACCGCATCGAGCTGAAGG GCATCGACTTCAAGGAGGACGGCAACATCCTGGGGCA CAAGCTGGAGTACAACTACAACAGCCACAACGTCTATA TCATGGCCGACAAGCAGAAGAACGGCATCAAGGTGAA CTTCAAGATCCGCCACAACATCGAGGACGGCAGCGTGC | 34 |

TABLE 5-continued

| Exemplary VL1VH3 P329G-CAR DNA sequences: | | |
|---|---|---|
| Construct | DNA sequence | SEQ ID NO |
| | AGCTCGCCGACCACTACCAGCAGAACACCCCCATCGGC GACGGCCCCGTGCTGCTGCCCGACAACCACTACCTGAG CACCCAGTCCGCCCTGAGCAAAGACCCCAACGAGAAG CGCGATCACATGGTCCTGCTGGAGTTCGTGACCGCCGC CGGGATCACTCTCGGCATGGACGAGCTGTACAAG | |

TABLE 6

| exemplary anti-P329G antibodies CDR definition according to Kabat | | |
|---|---|---|
| Anti-P329G (M-1.7.24) huIgG1 | | |
| HCDR1 | RYWMN | 1 |
| HCDR2 | EITPDSSTINYTPSLKD | 35 |
| HCDR3 | PYDYGAWFAS | 3 |
| LCDR1 | RSSTGAVTTSNYAN | 4 |
| LCDR2 | GTNKRAP | 5 |
| LCDR3 | ALWYSNHWV | 6 |
| VH | EVKLLESGGGLVQPGGSLKLSCAASGFDFSRYWMNWVRQ APGKGLEWIGEITPDSSTINYTPSLKDKFIISRDNAKNTL YLQMIKVRSEDTALYYCVRPYDYGAWFASWGQGTLVTVSA | 36 |
| VL | QAVVTQESALTTSPGETVTLTCRSSTGAVTTSNYANWVQE KPDHLFTGLIGGTNKRAPGVPARFSGSLIGDKAALTITGAQ TEDEAIYFCALWYSNHWVFGGGTKLTVL | 37 |
| HC | EVKLLESGGGLVQPGGSLKLSCAASGFDFSRYWMNWVRQAP GKGLEWIGEITPDSSTINYTPSLKDKFIISRDNAKNTLYLQ MIKVRSEDTALYYCVRPYDYGAWFASWGQGTLVTVSAAST KGPSVFPLAPSSKSTSGGTAALGCLVKDYFPEPVTVSWNS GALTSGVHTFPAVLQSSGLYSLSSVVTVPSSSLGTQTYIC NVNHKPSNTKVDKKVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKEYKCK VSNKALPAPIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP | 38 |
| LC | QAVVTQESALTTSPGETVTLTCRSSTGAVTTSNYANWVQE KPDHLFTGLIGGTNKRAPGVPARFSGSLIGDKAALTITGAQ TEDEAIYFCALWYSNHWVFGGGTKLTVLGQPKAAPSVTLF PPSSEELQANKATLVCLISDFYPGAVTVAWKADSSPVKAG VETTTPSKQSNNKYAASSYLSLTPEQWKSHRSYSCQVTHE GSTVEKTVAPTECS | 39 |
| Anti-P329G (VH1VL1) huIgG1 | | |
| HCDR1 | RYWMN | |
| HCDR2 | EITPDSSTINYTPSLKG | 40 |
| HCDR3 | PYDYGAWFAS | 3 |
| LCDR1 | RSSTGAVTTSNYAN | 4 |
| LCDR2 | GTNKRAP | 5 |
| LCDR3 | ALWYSNHWV | 6 |
| VH | EVQLVESGGGLVQPGGSLRLSCAASGFDFSRYWMNWVRQ APGKGLEWVGEITPDSSTINYTPSLKGRFTISRDNAKNSL YLQMNSLRAEDTAVYYCVRPYDYGAWFASWGQGTLVTVSS | 41 |

TABLE 6-continued

| exemplary anti-P329G antibodies CDR definition according to Kabat | | |
|---|---|---|
| VL | QAVVTQEPSLTVSPGGTVTLTCRSSTGAVTTSNYANWVQE KPDHLFTGLIGGTNKRAPGTPARFSGSLLGGKAALTLSGA QPEDEAEYYCALWYSNHWVFGGGTKLTVL | 9 |
| HC | EVQLVESGGGLVQPGGSLRLSCAASGFDFSRYWMNWVRQ APGKGLEWVGEITPDSSTINYTPSLKGRFTISRDNAKNSL YLQMNSLRAEDTAVYYCVRPYDYGAWFASWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 42 |
| LC | QAVVTQEPSLTVSPGGTVTLTCRSSTGAVTTSNYANWVQE KPDHLFTGLIGGTNKRAPGTPARFSGSLLGGKAALTLSGAQ PEDEAEYYCALWYSNHWVFGGGTKLTVLGQPKAAPSVTL FPPSSEELQANKATLVCLISDFYPGAVTVAWKADSSPVKAG VETTTPSKQSNNKYAASSYLSLTPEQWKSHRSYSCQVTHE GSTVEKTVAPTECS | 43 |
| Anti-P329G (VH2VL1) huIgG1 | | |
| HCDR1 | RYWMN | 1 |
| HCDR2 | EITPDSSTINYAPSLKG | 2 |
| HCDR3 | PYDYGAWFAS | 3 |
| LCDR1 | RSSTGAVTTSNYAN | 4 |
| LCDR2 | GTNKRAP | 5 |
| LCDR3 | ALWYSNHWV | 6 |
| VH | EVQLVESGGGLVQPGGSLRLSCAASGFDFSRYWMNWVRQ APGKGLEWVGEITPDSSTINYAPSLKGRFTISRDNAKNSL YLQMNSLRAEDTAVYYCVRPYDYGAWFASWGQGTLVTVSS | 44 |
| VL | QAVVTQEPSLTVSPGGTVTLTCRSSTGAVTTSNYANWVQE KPDHLFTGLIGGTNKRAPGTPARFSGSLLGGKAALTLSGAQ PEDEAEYYCALWYSNHWVFGGGTKLTVL | 9 |
| HC | EVQLVESGGGLVQPGGSLRLSCAASGFDFSRYWMNWVRQ APGKGLEWVGEITPDSSTINYAPSLKGRFTISRDNAKNSL YLQMNSLRAEDTAVYYCVRPYDYGAWFASWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 45 |
| LC | QAVVTQEPSLTVSPGGTVTLTCRSSTGAVTTSNYANWVQE KPDHLFTGLIGGTNKRAPGTPARFSGSLLGGKAALTLSGAQ PEDEAEYYCALWYSNHWVFGGGTKLTVLGQPKAAPSVTL FPPSSEELQANKATLVCLISDFYPGAVTVAWKADSSPVKAG VETTTPSKQSNNKYAASSYLSLTPEQWKSHRSYSCQVTHE GSTVEKTVAPTECS | 43 |
| Anti-P329G (VH3VL1) huIgG1 | | |
| HCDR1 | RYWMN | 1 |
| HCDR2 | EITPDSSTINYAPSLKG | 2 |
| HCDR3 | PYDYGAWFAS | 3 |
| LCDR1 | RSSTGAVTTSNYAN | 4 |

TABLE 6-continued

| exemplary anti-P329G antibodies<br>CDR definition according to Kabat | | |
|---|---|---|
| LCDR2 | GTNKRAP | 5 |
| LCDR3 | ALWYSNHWV | 6 |
| VH | EVQLVESGGGLVQPGGSLRLSCAASGFTFSRYWMNWVRQ<br>APGKGLEWVGEITPDSSTINYAPSLKGRFTISRDNAKNSLYL<br>QMNSLRAEDTAVYYCARPYDYGAWFASWGQGTLVTVSS | 8 |
| VL | QAVVTQEPSLTVSPGGTVTLTCRSSTGAVTTSNYANWVQE<br>KPDHLFTGLIGGTNKRAPGTPARFSGSLLGGKAALTLSGAQ<br>PEDEAEYYCALWYSNHWVFGGGTKLTVL | 9 |
| HC | EVQLVESGGGLVQPGGSLRLSCAASGFTFSRYWMNWVRQ<br>APGKGLEWVGEITPDSSTINYAPSLKGRFTISRDNAKNSLYL<br>QMNSLRAEDTAVYYCARPYDYGAWFASWGQGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEYK<br>CKVSNKALPAPIEKTISKAKGQPREPQVYTLPPSRDELTKN<br>QVSLTCLVKGFYPSDIAVEWESNGQPENNYKTTPPVLDSD<br>GSFFLYSKLTVDKSRWQQGNVFSCSVMHEALHNHYTQKS<br>LSLSP | 46 |
| LC | QAVVTQEPSLTVSPGGTVTLTCRSSTGAVTTSNYANWVQE<br>KPDHLFTGLIGGTNKRAPGTPARFSGSLLGGKAALTLSGAQ<br>PEDEAEYYCALWYSNHWVFGGGTKLTVLGQPKAAPSVTL<br>FPPSSEELQANKATLVCLISDFYPGAVTVAWKADSSPVKAG<br>VETTTPSKQSNNKYAASSYLSLTPEQWKSHRSYSCQVTHE<br>GSTVEKTVAPTECS | 43 |
| Anti-P329G (VH4VL1) huIgG1 | | |
| HCDR1 | RYWMN | 1 |
| HCDR2 | EITPDSSTINYADSVKG | |
| HCDR3 | PYDYGAWFAS | 3 |
| LCDR1 | RSSTGAVTTSNYAN | 4 |
| LCDR2 | GTNKRAP | 5 |
| LCDR3 | ALWYSNHWV | 6 |
| VH | EVQLVESGGGLVQPGGSLRLSCAASGFDFSRYWMNWVRQ<br>APGKGLEWVSEITPDSSTINYADSVKGRFTISRDNAKNSLY<br>LQMNSLRAEDTAVYYCARPYDYGAWFASWGQGTLVTVSS | 48 |
| VL | QAVVTQEPSLTVSPGGTVTLTCRSSTGAVTTSNYANWVQE<br>KPDHLFTGLIGGTNKRAPGTPARFSGSLLGGKAALTLSGAQ<br>PEDEAEYYCALWYSNHWVFGGGTKLTVL | 9 |
| HC | EVQLVESGGGLVQPGGSLRLSCAASGFDFSRYWMNWVRQ<br>APGKGLEWVSEITPDSSTINYADSVKGRFTISRDNAKNSLY<br>LQMNSLRAEDTAVYYCARPYDYGAWFASWGQGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEYK<br>CKVSNKALPAPIEKTISKAKGQPREPQVYTLPPSRDELTKN<br>QVSLTCLVKGFYPSDIAVEWESNGQPENNYKTTPPVLDSD<br>GSFFLYSKLTVDKSRWQQGNVFSCSVMHEALHNHYTQKS<br>LSLSP | 49 |
| LC | QAVVTQEPSLTVSPGGTVTLTCRSSTGAVTTSNYANWVQE<br>KPDHLFTGLIGGTNKRAPGTPARFSGSLLGGKAALTLSGAQ<br>PEDEAEYYCALWYSNHWVFGGGTKLTVLGQPKAAPSVTL<br>FPPSSEELQANKATLVCLISDFYPGAVTVAWKADSSPVKAG<br>VETTTPSKQSNNKYAASSYLSLTPEQWKSHRSYSCQVTHE<br>GSTVEKTVAPTECS | 43 |

TABLE 6-continued

| exemplary anti-P329G antibodies<br>CDR definition according to Kabat | | |
|---|---|---|
| | Anti-P329G (VHIVL2) huIgG1 | |
| HCDR1 | RYWMN | 1 |
| HCDR2 | EITPDSSTINYTPSLKG | 40 |
| HCDR3 | PYDYGAWFAS | 3 |
| LCDR1 | RSSTGAVTTSNYAN | 4 |
| LCDR2 | GTNKRAP | 5 |
| LCDR3 | ALWYSNHWV | 6 |
| VH | EVQLVESGGGLVQPGGSLRLSCAASGFDFSRYWMNWVRQ<br>APGKGLEWVGEITPDSSTINYTPSLKGRFTISRDNAKNSLYL<br>QMNSLRAEDTAVYYCVRPYDYGAWFASWGQGTLVTVSS | 41 |
| VL | QAVVTQEPSLTVSPGGTVTLTCRSSTGAVTTSNYANWFQQ<br>KPGQAFTGLIGGTNKRAPGTPARFSGSLLGGKAALTLSGAQ<br>PEDEAEYYCALWYSNHWVFGGGTKLTVL | 50 |
| HC | EVQLVESGGGLVQPGGSLRLSCAASGFDFSRYWMNWVRQ<br>APGKGLEWVGEITPDSSTINYTPSLKGRFTISRDNAKNSLYL<br>QMNSLRAEDTAVYYCVRPYDYGAWFASWGQGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEYK<br>CKVSNKALPAPIEKTISKAKGQPREPQVYTLPPSRDELTKN<br>QVSLTCLVKGFYPSDIAVEWESNGQPENNYKTTPPVLDSD<br>GSFFLYSKLTVDKSRWQQGNVFSCSVMHEALHNHYTQKS<br>LSLSP | 42 |
| LC | QAVVTQEPSLTVSPGGTVTLTCRSSTGAVTTSNYANWFQQ<br>KPGQAFTGLIGGTNKRAPGTPARFSGSLLGGKAALTLSGAQ<br>PEDEAEYYCALWYSNHWVFGGGTKLTVLGQPKAAPSVTL<br>FPPSSEELQANKATLVCLISDFYPGAVTVAWKADSSPVKAG<br>VETTTPSKQSNNKYAASSYLSLTPEQWKSHRSYSCQVTHE<br>GSTVEKTVAPTECS | 51 |
| | Anti-P329G (VH1VL3) huIgG1 | |
| HCDR1 | RYWMN | 1 |
| HCDR2 | EITPDSSTINYTPSLKG | 40 |
| HCDR3 | PYDYGAWFAS | 3 |
| LCDR1 | GSSTGAVTTSNYAN | 52 |
| LCDR2 | GTNKRAP | 5 |
| LCDR3 | ALWYSNHWV | 6 |
| VH | EVQLVESGGGLVQPGGSLRLSCAASGFDFSRYWMNWVRQ<br>APGKGLEWVGEITPDSSTINYTPSLKGRFTISRDNAKNSLYL<br>QMNSLRAEDTAVYYCVRPYDYGAWFASWGQGTLVTVSS | 41 |
| VL | QAVVTQEPSLTVSPGGTVTLTCGSSTGAVTTSNYANWFQQ<br>KPGQAPRTLIGGTNKRAPGTPARFSGSLLGGKAALTLSGAQ<br>PEDEAEYYCALWYSNHWVFGGGTKLTVL | 53 |
| HC | EVQLVESGGGLVQPGGSLRLSCAASGFDFSRYWMNWVRQ<br>APGKGLEWVGEITPDSSTINYTPSLKGRFTISRDNAKNSLYL<br>QMNSLRAEDTAVYYCVRPYDYGAWFASWGQGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEYK<br>CKVSNKALPAPIEKTISKAKGQPREPQVYTLPPSRDELTKN<br>QVSLTCLVKGFYPSDIAVEWESNGQPENNYKTTPPVLDSD<br>GSFFLYSKLTVDKSRWQQGNVFSCSVMHEALHNHYTQKS<br>LSLSP | 42 |

TABLE 6-continued

| exemplary anti-P329G antibodies<br>CDR definition according to Kabat | | |
|---|---|---|
| LC | QAVVTQEPSLTVSPGGTVTLTCGSSTGAVTTSNYANWFQQ<br>KPGQAPRTLIGGTNKRAPGTPARFSGSLLGGKAALTLSGAQ<br>PEDEAEYYCALWYSNHWVFGGGTKLTVLGQPKAAPSVTL<br>FPPSSEELQANKATLVCLISDFYPGAVTVAWKADSSPVKAG<br>VETTTPSKQSNNKYAASSYLSLTPEQWKSHRSYSCQVTHE<br>GSTVEKTVAPTECS | 54 |

TABLE 7

| P329G IgG1 Fc variant | | |
|---|---|---|
| huIgG1 Fc<br>P329G | EPKSCDKTHTCPPCPAPEAAGGPSVFLFPPK<br>PKDTLMISRTPEVTCVVVDVSHEDPEVKFNW<br>YVDGVEVHNAKTKPREEQYNSTYRVVSVLTV<br>LHQDWLNGKEYKCKVSNKALGAPIEKTISKA<br>KGQPREPQVCTLPPSRDELTKNQVSLSCAVK<br>GFYPSDIAVEWESNGQPENNYKTTPPVLDSD<br>GSFFLVSKLTVDKSRWQQGNVFSCSVMHEAL<br>HNHYTQKSLSLSP | 55 |

TABLE 8

| Construct | Amino acid sequence | SEQ ID NO |
|---|---|---|
| Human CD27 | ATGGCGCGCCCGCATCCGTG<br>GTGGCTGTGCGTGCTGGGCA<br>CCCTGGTGGGCCTGAGCGCG<br>ACCCCGGCGCCGAAAAGCTG<br>CCCGGAACGCCATTATTGGG<br>CGCAGGGCAAACTGTGCTGC<br>CAGATGTGCGAACCGGGCAC<br>CTTTCTGGTGAAAGATTGCG<br>ATCAGCATCGCAAAGCGGCG<br>CAGTGCGATCCGTGCATTCC<br>GGGCGTGAGCTTTAGCCCGG<br>ATCATCATACCCGCCCGCAT<br>TGCGAAAGCTGCCGCCATTG<br>CAACAGCGGCCTGCTGGTGC<br>GCAACTGCACCATTACCGCG<br>AACGCGGAATGCGCGTGCCG<br>CAACGGCTGGCAGTGCCGCG<br>ATAAAGAATGCACCGAATGC<br>GATCCGCTGCCGAACCCGAG<br>CCTGACCGCGCGCAGCAGCC<br>AGGCGCTGAGCCCGCATCCG<br>CAGCCGACCCATCTGCCGTA<br>TGTGAGCGAAATGCTGGAAG<br>CGCGCACCGCGGGCCATATG<br>CAGACCCTGGCGGATTTTCG<br>CCAGCTGCCGGCGCGCACCC<br>TGAGCACCCATTGGCCGCCG<br>CAGCGCAGCCTGTGCAGCAG<br>CGATTTTATTCGCATTCTGG<br>TGATTTTTAGCGGCATGTTT<br>CTGGTGTTTACCCTGGCGGG<br>CGCGCTGTTTCTGCATCAGC<br>GCCGCAAATATCGCAGCAAC<br>AAAGGCGAAAGCCCGGTGGA<br>ACCGGCGGAACCGTGCCATT<br>ATAGCTGCCCGCGCGAAGAA<br>GAAGGCAGCACCATTCCGAT<br>TCAGGAAGATTATCGCAAAC<br>CGGAACCGGCGTGCAGCCCG | 56 |
| Human CD27 | MARPHPWWLCVLGTLVGLSA<br>TPAPKSCPERHYWAQGKLCC<br>QMCEPGTFLVKDCDQHRKAA<br>QCDPCIPGVSFSPDHHTRPH<br>CESCRHCNSGLLVRNCTITA | 57 |

TABLE 8-continued

| Construct | Amino acid sequence | SEQ ID NO |
|---|---|---|
| | NAECACRNGWQCRDKECTEC<br>DPLPNPSLTARSSQALSPHP<br>QPTHLPYVSEMLEARTAGHM<br>QTLADFRQLPARTLSTHWPP<br>QRSLCSSDFIRILVIFSGMF<br>LVFTLAGALFLHQRRKYRSN<br>KGESPVEPAEPCHYSCPREE<br>EGSTIPIQEDYRKPEPACSP | |
| Murine CD27 | ATGGCGTGGCCGCCGCCGTA<br>TTGGCTGTGCATGCTGGGCA<br>CCCTGGTGGGCCTGAGCGCG<br>ACCCTGGCGCCGAACAGCTG<br>CCCGGATAAACATTATTGGA<br>CCGGCGGCGGCCTGTGCTGC<br>CGCATGTGCGAACCGGGCAC<br>CTTTTTTGTGAAAGATTGCG<br>AACAGGATCGCACCGCGGCG<br>CAGTGCGATCCGTGCATTCC<br>GGGCACCAGCTTTAGCCCGG<br>ATTATCATACCCGCCCGCAT<br>TGCGAAAGCTGCCGCCATTG<br>CAACAGCGGCTTTCTGATTC<br>GCAACTGCACCGTGACCGCG<br>AACGCGGAATGCAGCTGCAG<br>CAAAAACTGGCAGTGCCGCG<br>ATCAGGAATGCACCGAATGC<br>GATCCGCCGCTGAACCCGGC<br>GCTGACCCGCCAGCCGAGCG<br>AAACCCCGAGCCCGCAGCCG<br>CCGCCGACCCATCTGCCGCA<br>TGGCACCGAAAAACCGAGCT<br>GGCCGCTGCATCGCCAGCTG<br>CCGAACAGCACCGTGTATAG<br>CCAGCGCAGCAGCCATCGCC<br>CGCTGTGCAGCAGCGATTGC<br>ATTCGCATTTTTGTGACCTT<br>TAGCAGCATGTTTCTGATTT<br>TTGTGCTGGGCGCGATTCTG<br>TTTTTTCATCAGCGCCGCAA<br>CCATGGCCCGAACGAAGATC<br>GCCAGGCGGTGCCGGAAGAA<br>CCGTGCCCGTATAGCTGCCC<br>GCGCGAAGAAGAAGGCAGCG<br>CGATTCCGATTCAGGAAGAT<br>TATCGCAAACCGGAACCGGC<br>GTTTTATCCG | 58 |
| Murine CD27 | MAWPPPYWLCMLGTLVGLSA<br>TLAPNSCPDKHYWTGGGLCC<br>RMCEPGTFFVKDCEQDRTAA<br>QCDPCIPGTSFSPDYHTRPH<br>CESCRHCNSGFLIRNCTVTA<br>NAECSCSKNWQCRDQECTEC<br>DPPLNPALTRQPSETPSPQP<br>PPTHLPHGTEKPSWPLHRQL<br>PNSTVYSQRSSHRPLCSSDC<br>IRIFVTFSSMFLIFVLGAIL<br>FFHQRRNHGPNEDRQAVPEE | 59 |

TABLE 8-continued

| Construct | Amino acid sequence | SEQ ID NO |
|---|---|---|
| | PCPYSCPREEEGSAIPIQEDYRKPEPAFYP | |
| Human CD28 | ATGCTGCGCCTGCTGCTGGCGCTGAACCTGTTTCCGAGCATTCAGGTGACCGGCAACAAAATTCTGGTGAAACAGAGCCCGATGCTGGTGGCGTATGATAACGCGGTGAACCTGAGCTGCAAATATAGCTATAACCTGTTTAGCCGCGAATTTCGCGCGAGCCTGCATAAAGGCCTGGATAGCGCGGTGGAAGTGTGCGTGGTGTATGGCAACTATAGCCAGCAGCTGCAGGTGTATAGCAAAACCGGCTTTAACTGCGATGGCAAACTGGGCAACGAAAGCGTGACCTTTTATCTGCAGAACCTGTATGTGAACCAGACCGATATTTATTTTTGCAAAATTGAAGTGATGTATCCGCCGCCGTATCTGGATAACGAAAAAAGCAACGGCACCATTATTCATGTGAAAGGCAAACATCTGTGCCCGAGCCCGCTGTTTCCGGGCCCGAGCAAACCGTTTTGGGTGCTGGTGGTGGTGGGCGGCGTGCTGGCGTGCTATAGCCTGCTGGTGACCGTGGCGTTTATTATTTTTTGGGTGCGCAGCAAACGCAGCCGCCTGCTGCATAGCGATTATATGAACATGACCCCGCGCCGCCCGGGCCCGACCCGCAAACATTATCAGCCGTATGCGCCGCCGCGCGATTTTGCGGCGTATCGCAGC | 60 |
| Human CD28 | MLRLLLALNLFPSIQVTGNKILVKQSPMLVAYDNAVNLSCKYSYNLFSREFRASLHKGLDSAVEVCVVYGNYSQQLQVYSKTGFNCDGKLGNESVTFYLQNLYVNQTDIYFCKIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRS | 61 |
| Murine CD28 | ATGACCCTGCGCCTGCTGTTTCTGGCGCTGAACTTTTTTAGCGTGCAGGTGACCGAAAACAAAATTCTGGTGAAACAGAGCCCGCTGCTGGTGGTGGATAGCAACGAAGTGAGCCTGAGCTGCCGCTATAGCTATAACCTGCTGGCGAAAGAATTTCGCGCGAGCCTGTATAAAGGCGTGAACAGCGATGTGGAAGTGTGCGTGGGCAACGGCAACTTTACCTATCAGCCGCAGTTTCGCAGCAACGCGGAATTTAACTGCGATGGCGATTTTGATAACGAAACCGTGACCTTTCGCCTGTGGAACCTGCATGTGAACCATACCGATATTTATTTTTGCAAAATTGAATTTATGTATCCGCCGCCGTATCTGGATAACGAACGCAGCAACGGCACCATTATTCATATTAAAGAAAAACATCTGTGCCATACCCAGAGCAGCCCGAAACTGTTTTGGGCGCTGGTGGTGGTGGCGGGCGTGCTGTTTTGCTATGGCCTGCTGGTGACCGTGGCGCTGTGCGTGATTTGGACCAACAGCCGC | 62 |

TABLE 8-continued

| Construct | Amino acid sequence | SEQ ID NO |
|---|---|---|
| | CGCAACCGCCTGCTGCAGAGCGATTATATGAACATGACCCCGCGCCGCCCGGGCCTGACCCGCAAACCGTATCAGCCGTATGCGCCGGCGCGCGATTTTGCGGCGTATCGCCCG | |
| Murine CD28 | MTLRLLFLALNFFSVQVTENKILVKQSPLLVVDSNEVSLSCRYSYNLLAKEFRASLYKGVNSDVEVCVGNGNFTYQPQFRSNAEFNCDGDFDNETVTFRLWNLHVNHTDIYFCKIEFMYPPPYLDNERSNGTIIHIKEKHLCHTQSSPKLFWALVVVAGVLFCYGLLVTVALCVIWTNSRRNRLLQSDYMNMTPRRPGLTRKPYQPYAPARDFAAYRP | 63 |
| Human CD137 | ATGGGAAACAGCTGTTACAACATAGTAGCCACTCTGTTGCTGGTCCTCAACTTTGAGAGGACAAGATCATTGCAGGATCCTTGTAGTAACTGCCCAGCTGGTACATTCTGTGATAATAACAGGAATCAGATTTGCAGTCCCTGTCCTCCAAATAGTTTCTCCAGCGCAGGTGGACAAAGGACCTGTGACATATGCAGGCAGTGTAAAGGTGTTTTCAGGACCAGGAAGGAGTGTTCCTCCACCAGCAATGCAGAGTGTGACTGCACTCCAGGGTTTCACTGCCTGGGGGCAGGATGCAGCATGTGTGAACAGGATTGTAAACAAGGTCAAGAACTGACAAAAAAAGGTTGTAAAGACTGTTGCTTTGGGACATTTAACGATCAGAAACGTGGCATCTGTCGACCCTGGACAAACTGTTCTTTGGATGGAAAGTCTGTGCTTGTGAATGGGACGAAGGAGAGGGACGTGGTCTGTGGACCATCTCCAGCCGACCTCTCTCCGGGAGCATCCTCTGTGACCCCGCCTGCCCCTGCGAGAGAGCCAGGACACTCTCCGCAGATCATCTCCTTCTTTCTTGCGCTGACGTCGACTGCGTTGCTCTTCCTGCTGTTCTTCCTCACGCTCCGTTTCTCTGTTGTTAAACGGGGCAGAAAGAAACTCCTGTATATATTCAAACAACCATTTATGAGACCAGTACAAACTACTCAAGAGGAAGATGGCTGTAGCTGCCGATTTCCAGAAGAAGAAGAAGGAGGATGTGAACTGTGA | 64 |
| Human CD137 | MGNSCYNIVATLLLVLNFERTRSLQDPCSNCPAGTFCDNNRNQICSPCPPNSFSSAGGQRTCDICRQCKGVFRTRKECSSTSNAECDCTPGFHCLGAGCSMCEQDCKQGQELTKKGCKDCCFGTFNDQKRGICRPWTNCSLDGKSVLVNGTKERDVVCGPSPADLSPGASSVTPPAPAREPGHSPQIISFFLALTSTALLFLLFFLTLRFSVVKRGRKKLLYIFKQPFMRPVQTTQEEDGCSCRFPEEEEGGCEL | 65 |
| Murine CD137 | ATGGGCAACAACTGCTATAACGTGGTGGTGATTGTGCTGCTGCTGGTGGGCTGCGAAAAA | 66 |

TABLE 8-continued

| Construct | Amino acid sequence | SEQ ID NO |
|---|---|---|
| | GTGGGCGCGGTGCAGAACAG CTGCGATAACTGCCAGCCGG GCACCTTTTGCCGCAAATAT AACCCGGTGTGCAAAAGCTG CCCGCCGAGCACCTTTAGCA GCATTGGCGGCCAGCCGAAC TGCAACATTTGCCGCGTGTG CGCGGGCTATTTTCGCTTTA AAAAATTTTGCAGCAGCACC CATAACGCGGAATGCGAATG CATTGAAGGCTTTCATTGCC TGGGCCCGCAGTGCACCCGC TGCGAAAAAGATTGCCGCCC GGGCCAGGAACTGACCAAAC AGGGCTGCAAAACCTGCAGC CTGGGCACCTTTAACGATCA GAACGGCACCGGCGTGTGCC GCCCGTGGACCAACTGCAGC CTGGATGGCCGCAGCGTGCT GAAAACCGGCACCACCGAAA AAGATGTGGTGTGCGGCCCG CCGGTGGTGAGCTTTAGCCC GAGCACCACCATTAGCGTGA CCCCGGAAGGCGGCCCGGGC GGCCATAGCCTGCAGGTGCT GACCCTGTTTCTGGCGCTGA CCAGCGCGCTGCTGCTGGCG CTGATTTTTATTACCCTGCT GTTTAGCGTGCTGAAATGGA TTCGCAAAAAATTTCCGCAT ATTTTTAAACAGCCGTTTAA AAAAACCACCGGCGCGGCGC AGGAAGAAGATGCGTGCAGC TGCCGCTGCCCGCAGGAAGA AGAAGGCGGCGGCGGCGGCT ATGAACTG | |
| Murine CD137 | MGNNCYNVVVIVLLLVGCEK VGAVQNSCDNCQPGTFCRKY NPVCKSCPPSTFSSIGGQPN CNICRVCAGYFRFKKFCSST HNAECECIEGFHCLGPQCTR CEKDCRPGQELTKQGCKTCS LGTFNDQNGTGVCRPWTNCS LDGRSVLKTGTTEKDVVCGP PVVSFSPSTTISVTPEGGPG GHSLQVLTLFLALTSALLLA LIFITLLFSVLKWIRKKFPH IFKQPFKKTTGAAQEEDACS CRCPQEEEGGGGGYEL | 67 |
| Human OX40 | ATGTGCGTGGGCGCGCGCCG CCTGGGCCGCGGCCCGTGCG CGGCGCTGCTGCTGCTGGGC CTGGGCCTGAGCACCGTGAC CGGCCTGCATTGCGTGGGCG ATACCTATCCGAGCAACGAT CGCTGCTGCCATGAATGCCG CCCGGGCAACGGCATGGTGA GCCGCTGCAGCCGCAGCCAG AACACCGTGTGCCGCCCGTG CGGCCCGGGCTTTTATAACG ATGTGGTGAGCAGCAAACCG TGCAAACCGTGCACCTGGTG CAACCTGCGCAGCGGCAGCG AACGCAAACAGCTGTGCACC GCGACCCAGGATACCGTGTG CCGCTGCCGCGCGGGCACCC AGCCGCTGGATAGCTATAAA CCGGGCGTGGATTGCGCGCC GTGCCCGCCGGGCCATTTTA GCCCGGGCGATAACCAGGCG TGCAAACCGTGGACCAACTG CACCCTGGCGGGCAAACATA CCCTGCAGCCGGCGAGCAAC AGCAGCGATGCGATTTGCGA | 68 |

TABLE 8-continued

| Construct | Amino acid sequence | SEQ ID NO |
|---|---|---|
| | AGATCGCGATCCGCCGGCGA CCCAGCCGCAGGAAACCCAG GGCCCGCCGGCGCGCCCGAT TACCGTGCAGCCGACCGAAG CGTGGCCGCGCACCAGCCAG GGCCCGAGCACCCGCCCGGT GGAAGTGCCGGGCGGCCGCG CGGTGGCGGCGATTCTGGGC CTGGGCCTGGTGCTGGGCCT GCTGGGCCCGCTGGCGATTC TGCTGGCGCTGTATCTGCTG CGCCGCGATCAGCGCCTGCC GCCGGATGCGCATAAACCGC CGGGCGGCGGCAGCTTTCGC ACCCCGATTCAGGAAGAACA GGCGGATGCGCATAGCACCC TGGCGAAAATT | |
| Human OX40 | MCVGARRLGRGPCAALLLLG LGLSTVTGLHCVGDTYPSND RCCHECRPGNGMVSRCSRSQ NTVCRPCGPGFYNDVVSSKP CKPCTWCNLRSGSERKQLCT ATQDTVCRCRAGTQPLDSYK PGVDCAPCPPGHFSPGDNQA CKPWTNCTLAGKHTLQPASN SSDAICEDRDPPATQPQETQ GPPARPITVQPTEAWPRTSQ GPSTRPVEVPGGRAVAAILG LGLVLGLLGPLAILLALYLL RRDQRLPPDAHKPPGGGSFR TPIQEEQADAHSTLAKI | 69 |
| Murine OX40 | ATGTATGTGTGGGTGCAGCA GCCGACCGCGCTGCTGCTGC TGGCGCTGACCCTGGGCGTG ACCGCGCGCCGCCTGAACTG CGTGAAACATACCTATCCGA GCGGCCATAAATGCTGCCGC GAATGCCAGCCGGGCCATGG CATGGTGAGCCGCTGCGATC ATACCCGCGATACCCTGTGC CATCCGTGCGAAACCGGCTT TTATAACGAAGCGGTGAACT ATGATACCTGCAAACAGTGC ACCCAGTGCAACCATCGCAG CGGCAGCGAACTGAAACAGA ACTGCACCCCGACCCAGGAT ACCGTGTGCCGCTGCCGCCC GGGCACCCAGCCGCGCCAGG ATAGCGGCTATAAACTGGGC GTGGATTGCGTGCCGTGCCC GCCGGGCCATTTTAGCCCGG GCAACAACCAGGCGTGCAAA CCGTGGACCAACTGCACCCT GAGCGGCAAACAGACCCGCC ATCCGGCGAGCGATAGCCTG GATGCGGTGTGCGAAGATCG CAGCCTGCTGGCGACCCTGC TGTGGGAAACCCAGCGCCCG ACCTTTCGCCCGACCACCGT GCAGAGCACCACCGTGTGGC CGCGCACCAGCGAACTGCCG AGCCCGCCGACCCTGGTGAC CCCGGAAGGCCCGGCGTTTG CGGTGCTGCTGGGCCTGGGC CTGGGCCTGCTGGCGCCGCT GACCGTGCTGCTGGCGCTGT ATCTGCTGCGCAAAGCGTGG CGCCTGCCGAACACCCCGAA ACCGTGCTGGGGCAACAGCT TTCGCACCCCGATTCAGGAA GAACATACCGATGCGCATTT TACCCTGGCGAAAATT | 70 |

TABLE 8-continued

| Construct | Amino acid sequence | SEQ ID NO |
|---|---|---|
| Murine OX40 | MYVWVQQPTALLLLALTLGVTARRLNCVKHTYPSGHKCCRECQPGHGMVSRCDHTRDTLCHPCETGFYNEAVNYDTCKQCTQCNHRSGSELKQNCTPTQDTVCRCRPGTQPRQDSGYKLGVDCVPCPPGHFSPGNNQACKPWTNCTLSGKQTRHPASDSLDAVCEDRSLLATLLWETQRPTFRPTTVQSTTVWPRTSELPSPPTLVTPEGPAFAVLLGLGLGLLAPLTVLLALYLLRKAWRLPNTPKPCWGNSFRTPIQEEHTDAHFTLAKI | 71 |
| Human ICOS | ATGAAAAGCGGCCTGTGGTATTTTTTTCTGTTTTGCCTGCGCATTAAAGTGCTGACCGGCGAAATTAACGGCAGCGCGAACTATGAAATGTTTATTTTTCATAACGGCGGCGTGCAGATTCTGTGCAAATATCCGGATATTGTGCAGCAGTTTAAAATGCAGCTGCTGAAAGGCGGCCAGATTCTGTGCGATCTGACCAAAACCAAAGGCAGCGGCAACACCGTGAGCATTAAAAGCCTGAAATTTTGCCATAGCCAGCTGAGCAACAACAGCGTGAGCTTTTTTCTGTATAACCTGGATCATAGCCATGCGAACTATTATTTTTGCAACCTGAGCATTTTTGATCCGCCGCCGTTTAAAGTGACCCTGACCGGCGGCTATCTGCATATTTATGAAAGCCAGCTGTGCTGCCAGCTGAAATTTTGGCTGCCGATTGGCTGCGCGGCGTTTGTGGTGGTGTGCATTCTGGGCTGCATTCTGATTTGCTGGCTGACCAAAAAAAAATATAGCAGCAGCGTGCATGATCCGAACGGCGAATATATGTTTATGCGCGCGGTGAACACCGCGAAAAAAAGCCGCCTGACCGATGTGACCCTG | 72 |
| Human ICOS | MKSGLWYFFLFCLRIKVLTGEINGSANYEMFIFHNGGVQILCKYPDIVQQFKMQLLKGGQILCDLTKTKGSGNTVSIKSLKFCHSQLSNNSVSFFLYNLDHSHANYYFCNLSIFDPPPFKVTLTGGYLHIYESQLCCQLKFWLPIGCAAFVVVCILGCILICWLTKKKYSSSVHDPNGEYMFMRAVNTAKKSRLTDVTL | 73 |
| Murine ICOS | ATGAAACCGTATTTTTGCCGCGTGTTTGTGTTTTGCTTTCTGATTCGCCTGCTGACCGGCGAAATTAACGGCAGCGCGGATCATCGCATGTTTAGCTTTCATAACGGCGGCGTGCAGATTAGCTGCAAATATCCGGAAACCGTGCAGCAGCTGAAAATGCGCCTGTTTCGCGAACGCGAAGTGCTGTGCGAACTGACCAAAACCAAAGGCAGCGGCAACGCGGTGAGCATTAAAAACCCGATGCTGTGCCTGTATCATCTGAGCAACAACAGCGTGAGCTTTTTTCTGAACAACCCGGATAGCAGCCAGGGCAGCTATTATTTTTGCAGCCTGAGCATTTTTGATCCGCCGCCGTTTCAGGAACGCAACCTGAGCGGCGGCTATCTGCATATTTATGAAAGCCAGCTGTGCTGCCAGCTGAAACTGTGGCTGCCGGTGGGCTGCGCGGCGTTTGTGGTGGTGCTGCTGTTTGGCTGCATTCTGATTATTTGGTTTAGCAAAAAAAAATATGGCAGCAGCGTGCATGATCCGAACAGCGAATATATGTTTATGGCGGCGGTGAACACCAACAAAAAAAGCCGCCTGGCGGGCGTGACCAGC | 74 |
| Murine ICOS | MKPYFCRVFVFCFLIRLLTGEINGSADHRMFSFHNGGVQISCKYPETVQQLKMRLFREREVLCELTKTKGSGNAVSIKNPMLCLYHLSNNSVSFFLNNPDSSQGSYYFCSLSIFDPPPFQERNLSGGYLHIYESQLCCQLKLWLPVGCAAFVVVLLFGCILIIWFSKKKYGSSVHDPNSEYMFMAAVNTNKKSRLAGVTS | 75 |
| Human DAP10 | ATGATTCATCTGGGCCATATTCTGTTTCTGCTGCTGCTGCCGGTGGCGGCGGCGCAGACCACCCCGGGCGAACGCAGCAGCCTGCCGGCGTTTTATCCGGGCACCAGCGGCAGCTGCAGCGGCTGCGGCAGCCTGAGCCTGCCGCTGCTGGCGGGCCTGGTGGCGGCGGATGCGGTGGCGAGCCTGCTGATTGTGGGCGCGGTGTTTCTGTGCGCGCGCCCGCGCCGCAGCCCGGCGCAGGAAGATGGCAAAGTGTATATTAACATGCCGGGCCGCGGC | 76 |
| Human DAP10 | MIHLGHILFLLLLPVAAAQTTPGERSSLPAFYPGTSGSCSGCGSLSLPLLAGLVAADAVASLLIVGAVFLCARPRRSPAQEDGKVYINMPGRG | 77 |
| Murine DAP10 | ATGGATCCGCCGGGCTATCTGCTGTTTCTGCTGCTGCTGCCGGTGGCGGCGAGCCAGACCAGCGCGGGCAGCTGCAGCGGCTGCGGCACCCTGAGCCTGCCGCTGCTGGCGGGCCTGGTGGCGGCGGATGCGGTGATGAGCCTGCTGATTGTGGGCGTGGTGTTTGTGTGCATGCGCCCGCATGGCCGCCCGGCGCAGGAAGATGGCCGCGTGTATATTAACATGCCGGGCCGCGGC | 78 |
| Murine DAP10 | MDPPGYLLFLLLLPVAASQTSAGSCSGCGTLSLPLLAGLVAADAVMSLLIVGVVFVCMRPHGRPAQEDGRVYINMPGRG | 79 |
| Human DAP12 | ATGGGGGGACTTGAACCCTGCAGCAGGCTCCTGCTCCTGCCTCTCCTGCTGGCTGTAAGTGGTCTCCGTCCTGTCCAGGCCCAGGCCCAGAGCGATTGCAGTTGCTCTACGGTGAGCCCGGGCGTGCTGGCAGGGATCGTGATGGGAGACCTGGTGCTGACAGTGCTCATTGCCCTGGCCGTGTACTTCCTGGGCCGGCTGGTCCCTCGGGGGCGAGGGGCTGCGGAGGCAGCGACCCGGAAACAGCGTATCACTGAGAC | 80 |

TABLE 8-continued

| Construct | Amino acid sequence | SEQ ID NO |
|---|---|---|
| | CGAGTCGCCTTATCAGGAGC<br>TCCAGGGTCAGAGGTCGGAT<br>GTCTACAGCGACCTCAACAC<br>ACAGAGGCCGTATTACAAAT<br>GA | |
| Human DAP12 | MGGLEPCSRLLLLPLLLAVS<br>GLRPVQAQAQSDCSCSTVSP<br>GVLAGIVMGDLVLTVLIALA<br>VYFLGRLVPRGRGAAEAATR<br>KQRITETESPYQELQGQRSD<br>VYSDLNTQRPYYK | 81 |
| Murine DAP12 | ATGGGGGCTCTGGAGCCCTC<br>CTGGTGCCTTCTGTTCCTTC<br>CTGTCCTCCTGACTGTGGGA<br>GGATTAAGTCCCGTACAGGC<br>CCAGAGTGACACTTTCCCAA<br>GATGCGACTGTTCTTCCGTG<br>AGCCCTGGTGTACTGGCTGG<br>GATTGTTCTGGGTGACTTGG<br>TGTTGACTCTGCTGATTGCC<br>CTGGCTGTGTACTCTCTGGG<br>CCGCCTGGTCTCCCGAGGTC<br>AAGGGACAGCGGAAGGGACC<br>CGGAAACAACACATTGCTGA<br>GACTGAGTCGCCTTATCAGG<br>AGCTTCAGGGTCAGAGACCA<br>GAAGTATACAGTGACCTCAA<br>CACACAGAGGCAATATTACA<br>GATGA | 82 |
| Murine DAP12 | MGALEPSWCLLFLPVLLTVG<br>GLSPVQAQSDTFPRCDCSSV<br>SPGVLAGIVLGDLVLTLLIA<br>LAVYSLGRLVSRGQGTAEGT<br>RKQHIAETESPYQELQGQRP<br>EVYSDLNTQRQYYR | 83 |
| Human CD3z | MKWKALFTAAILQAQLPITE<br>AQSFGLLDPKLCYLLDGILF<br>IYGVILTALFLRVKFSRSAD<br>APAYQQGQNQLYNELNLGRR<br>EEYDVLDKRRGRDPEMGGKP<br>QRRKNPQEGLYNELQKDKMA<br>EAYSEIGMKGERRRGKGHDG<br>LYQGLSTATKDTYDALHMQA<br>LPPR | 84 |
| Human CD3z | ATGAAGTGGAAGGCGCTTTT<br>CACCGCGGCCATCCTGCAGG<br>CACAGTTGCCGATTACAGAG<br>GCACAGAGCTTTGGCCTGCT<br>GGATCCCAAACTCTGCTACC<br>TGCTGGATGGAATCCTCTTC<br>ATCTATGGTGTCATTCTCAC<br>TGCCTTGTTCCTGAGAGTGA<br>AGTTCAGCAGGAGCGCAGAG<br>CCCCCCGCGTACCAGCAGGG<br>CCAGAACCAGCTCTATAACG<br>AGCTCAATCTAGGACGAAGA<br>GAGGAGTACGATGTTTTGGA<br>CAAGAGACGTGGCCGGGACC<br>CTGAGATGGGGGGAAAGCCG<br>AGAAGGAAGAACCCTCAGGA<br>AGGCCTGTACAATGAACTGC<br>AGAAAGATAAGATGGCGGAG<br>GCCTACAGTGAGATTGGGAT<br>GAAAGGCGAGCGCCGGAGGG<br>GCAAGGGGCACGATGGCCTT<br>TACCAGGGTCTCAGTACAGC<br>CACCAAGGACACCTACGACG<br>CCCTTCACATGCAGGCCCTG<br>CCCCCTCGCTAA | 85 |
| Murine CD3z | MKWKVSVLACILHVRFPGAE<br>AQSFGLLDPKLCYLLDGILF<br>IYGVIITALYLRAKFSRSAE<br>TAANLQDPNQLYNELNLGRR<br>EEYDVLEKKRARDPEMGGKQ<br>QRRRNPQEGVYNALQKDKMA<br>EAYSEIGTKGERRRGKGHDG<br>LYQGLSTATKDTYDALHMQT<br>LAPR | 86 |
| Murine CD3z | ATGAAGTGGAAAGTGTCTGT<br>TCTCGCCTGCATCCTCCACG<br>TGCGGTTCCCAGGAGCAGAG<br>GCACAGAGCTTTGGTCTGCT<br>GGATCCCAAACTCTGCTACT<br>TGCTAGATGGAATCCTCTTC<br>ATCTACGGAGTCATCATCAC<br>AGCCCTGTACCTGAGAGCAA<br>AATTCAGCAGGAGTGCAGAG<br>ACTGCTGCCAACCTGCAGGA<br>CCCCAACCAGCTCTACAATG<br>AGCTCAATCTAGGGCGAAGA<br>GAGGAATATGACGTCTTGGA<br>GAAGAAGCGGGCTCGGGATC<br>CAGAGATGGGAGGCAAACAG<br>CAGAGGAGGAGGAACCCCCA<br>GGAAGGCGTATACAATGCAC<br>TGCAGAAAGACAAGATGGCA<br>GAAGCCTACAGTGAGATCGG<br>CACAAAAGGCGAGAGGCGGA<br>GAGGCAAGGGGCACGATGGC<br>CTTTACCAGGGTCTCAGCAC<br>TGCCACCAAGGACACCTATG<br>ATGCCCTGCATATGCAGACC<br>CTGGCCCCTCGCTAA | 87 |
| Human FCGR3A | MWQLLLPTALLLLVSAGMRT<br>EDLPKAVVFLEPQWYRVLEK<br>DSVTLKCQGAYSPEDNSTQW<br>FHNESLISSQASSYFIDAAT<br>VDDSGEYRCQTNLSTLSDPV<br>QLEVHIGWLLLQAPRWVFKE<br>EDPIHLRCHSWKNTALHKVT<br>YLQNGKGRKYFHHNSDFYIP<br>KATLKDSGSYFCRGLFGSKN<br>VSSETVNITITQGLAVSTIS<br>SFFPPGYQVSFCLVMVLLFA<br>VDTGLYFSVKTNIRSSTRDW<br>KDHKFKWRKDPQDK | 88 |
| Human FCGR3A | ATGTGGCAGCTGCTGCTGCC<br>GACCGCGCTGCTGCTGCTGG<br>TGAGCGCGGGCATGCGCACC<br>GAAGATCTGCCGAAAGCGGT<br>GGTGTTTCTGGAACCGCAGT<br>GGTATCGCGTGCTGGAAAAA<br>GATAGCGTGACCCTGAAATG<br>CCAGGGCGCGTATAGCCCGG<br>AAGATAACAGCACCCAGTGG<br>TTTCATAACGAAAGCCTGAT<br>TAGCAGCCAGGCGAGCAGCT<br>ATTTTATTGATGCGGCGACC<br>GTGGATGATAGCGGCGAATA<br>TCGCTGCCAGACCAACCTGA<br>GCACCCTGAGCGATCCGGTG<br>CAGCTGGAAGTGCATATTGG<br>CTGGCTGCTGCTGCAGGCGC<br>CGCGCTGGGTGTTTAAAGAA<br>GAAGATCCGATTCATCTGCG<br>CTGCCATAGCTGGAAAAACA<br>CCGCGCTGCATAAAGTGACC<br>TATCTGCAGAACGGCAAAGG<br>CCGCAAATATTTTCATCATA<br>ACAGCGATTTTTATATTCCG<br>AAAGCGACCCTGAAAGATAG | 89 |

TABLE 8-continued

| Construct | Amino acid sequence | SEQ ID NO |
|---|---|---|
| | CGGCAGCTATTTTTGCCGCG GCCTGTTTGGCAGCAAAAAC GTGAGCAGCGAAACCGTGAA CATTACCATTACCCAGGGCC TGGCGGTGAGCACCATTAGC AGCTTTTTTCCGCCGGGCTA TCAGGTGAGCTTTTGCCTGG TGATGGTGCTGCTGTTTGCG GTGGATACCGGCCTGTATTT TAGCGTGAAAACCAACATTC GCAGCAGCACCCGCGATTGG AAAGATCATAAATTTAAATG GCGCAAAGATCCGCAGGATA AA | |
| Murine FCGR3A | MFQNAHSGSQWLLPPLTILL LFAFADRQSAALPKAVVKLD PPWIQVLKEDMVTLMCEGTH NPGNSSTQWFHNGRSIRSQV QASYTFKATVNDSGEYRCQM EQTRLSDPVDLGVISDWLLL QTPQRVFLEGETITLRCHSW RNKLLNRISFFHNEKSVRYH HYKSNFSIPKANHSHSGDYY CKGSLGSTQHQSKPVTITVQ DPATTSSISLVWYHTAFSLV MCLLFAVDTGLYFYVRRNLQ TPREYWRKSLSIRKHQAPQD K | 90 |
| Murine FCGR3A | ATGTTTCAGAATGCACACTC TGGAAGCCAATGGCTACTTC CACCACTGACAATTCTGCTG CTGTTTGCTTTTGCAGACAG GCAGAGTGCAGCTCTTCCGA AGGCTGTGGTGAAACTGGAC CCCCCATGGATCCAGGTGCT CAAGGAAGACATGGTGACAC TGATGTGCGAAGGGACCCAC AACCCTGGGAACTCTTCTAC CCAGTGGTTCCACAACGGGA GGTCCATCCGGAGCCAGGTC CAAGCCAGTTACACGTTTAA GGCCACAGTCAATGACAGTG GAGAATATCGGTGTCAAATG GAGCAGACCCGCCTCAGCGA CCCTGTAGATCTGGGAGTGA TTTCTGACTGGCTGCTGCTC CAGACCCCTCAGCGGGTGTT TCTGGAAGGGGAAACCATCA CGCTAAGGTGCCATAGCTGG AGGAACAAACTACTGAACAG GATCTCATTCTTCCATAATG AAAAATCCGTGAGGTATCAT CACTACAAAAGTAATTTCTC TATCCCAAAAGCCAACCACA GTCACAGTGGGGACTACTAC TGCAAAGGAAGTCTAGGAAG TACACAGCACCAGTCCAAGC CTGTCACCATCACTGTCCAA GATCCAGCAACTACATCCTC CATCTCTCTAGTCTGGTACC ACACTGCTTTCTCCCTAGTG ATGTGCCTCCTGTTTGCAGT GGACACGGGCCTTTATTTCT ACGTACGGAGAAATCTTCAA ACCCCGAGGGAGTACTGGAG GAAGTCCCTGTCAATCAGAA AGCACCAGGCTCCTCAAGAC AAGTGA | 91 |
| Human NKG2D | MGWIRGRRSRHSWEMSEFHN YNLDLKKSDFSTRWQKQRCP VVKSKCRENASPFFFCCFIA VAMGIRFIIMVAIWSAVFLN SLFNQEVQIPLTESYCGPCP | 92 |

TABLE 8-continued

| Construct | Amino acid sequence | SEQ ID NO |
|---|---|---|
| | KNWICYKNNCYQFFDESKNW YESQASCMSQNASLLKVYSK EDQDLLKLVKSYHWMGLVHI PTNGSWQWEDGSILSPNLLT IIEMQKGDCALYASSFKGYI ENCSTPNTYICMQRTV | |
| Human NKG2D | ATGGGCTGGATTCGCGGCCG CCGCAGCCGCCATAGCTGGG AAATGAGCGAATTTCATAAC TATAACCTGGATCTGAAAAA AAGCGATTTTAGCACCCGCT GGCAGAAACAGCGCTGCCCG GTGGTGAAAAGCAAATGCCG CGAAAACGCGAGCCCGTTTT TTTTTTGCTGCTTTATTGCG GTGGCGATGGGCATTCGCTT TATTATTATGGTGGCGATTT GGAGCGCGGTGTTTCTGAAC AGCCTGTTTAACCAGGAAGT GCAGATTCCGCTGACCGAAA GCTATTGCGGCCCGTGCCCG AAAAACTGGATTTGCTATAA AAACAACTGCTATCAGTTTT TTGATGAAAGCAAAAACTGG TATGAAAGCCAGGCGAGCTG CATGAGCCAGAACGCGAGCC TGCTGAAAGTGTATAGCAAA GAAGATCAGGATCTGCTGAA ACTGGTGAAAAGCTATCATT GGATGGGCCTGGTGCATATT CCGACCAACGGCAGCTGGCA GTGGGAAGATGGCAGCATTC TGAGCCCGAACCTGCTGACC ATTATTGAAATGCAGAAAGG CGATTGCGCGCTGTATGCGA GCAGCTTTAAAGGCTATATT GAAAACTGCAGCACCCCGAA CACCTATATTTGCATGCAGC GCACCGTG | 93 |
| Murine NKG2D | MALIRDRKSHHSEMSKCHNY DLKPAKWDTSQEQQKQRLAL TTSQPGENGIIRGRYPIEKL KISPMFVVRVLAIALAIRFT LNTLMWLAIFKETFQPVLCN KEVPVSSREGYCGPCPNNWI CHRNNCYQFFNEEKTWNQSQ ASCLSQNSSLLKIYSKEEQD FLKLVKSYHWMGLVQIPANG SWQWEDGSSLSYNQLTLVEI PKGSCAVYGSSFKAYTEDCA NLNTYICMKRAV | 94 |
| Murine NKG2D | ATGGCGCTGATTCGCGATCG CAAAAGCCATCATAGCGAAA TGAGCAAATGCCATAACTAT GATCTGAAACCGGCGAAATG GGATACCAGCCAGGAACAGC AGAAACAGCGCCTGGCGCTG ACCACCAGCCAGCCGGGCGA AAACGGCATTATTCGCGGCC GCTATCCGATTGAAAAACTG AAAATTAGCCCGATGTTTGT GGTGCGCGTGCTGGCGATTG CGCTGGCGATTCGCTTTACC CTGAACACCCTGATGTGGCT GGCGATTTTTAAAGAAACCT TTCAGCCGGTGCTGTGCAAC AAAGAAGTGCCGGTGAGCAG CCGCGAAGGCTATTGCGGCC CGTGCCCGAACAACTGGATT TGCCATCGCAACAACTGCTA TCAGTTTTTTAACGAAGAAA AAACCTGGAACCAGAGCCAG GCGAGCTGCCTGAGCCAGAA | 95 |

TABLE 8-continued

| Construct | Amino acid sequence | SEQ ID NO |
|---|---|---|
| | CAGCAGCCTGCTGAAAATTT ATAGCAAAGAAGAACAGGAT TTTCTGAAACTGGTGAAAAG CTATCATTGGATGGGCCTGG TGCAGATTCCGGCGAACGGC AGCTGGCAGTGGGAAGATGG CAGCAGCCTGAGCTATAACC AGCTGACCCTGGTGGAAATT CCGAAAGGCAGCTGCGCGGT GTATGGCAGCAGCTTTAAAG CGTATACCGAAGATTGCGCG AACCTGAACACCTATATTTG CATGAAACGCGCGGTG | |
| CD28 YMNM | YMNM | 96 |
| CD28 PYAP | PYAP | 97 |
| CD28 FMNM | FMNM | 98 |
| CD28 AYAA | AYAA | 99 |
| Signal peptide | ATMGWSCIILFLVATATGVH S | 100 |
| Signal peptide DNA sequence | ATGGGATGGAGCTGTATCAT CCTCTTCTTGGTAGCAACAG CTACCGGTGTGCACTCC | 101 |
| Anti-CD20 (GA101) heavy chain | QVQLVQSGAEVKKPGSSVKV SCKASGYAFSYSWINWVRQA PGQGLEWMGRIFPGDGDTDY NGKFKGRVTITADKSTSTAY MELSSLRSEDTAVYYCARNV FDGYWLVYWGQGTLVTVSSA STKGPSVFPLAPSSKSTSGG TAALGCLVKDYFPEPVTVSW NSGALTSGVHTFPAVLQSSG LYSLSSVVTVPSSSLGTQTY ICNVNHKPSNTKVDKKVEPK SCDKTHTCPPCPAPELLGGP SVFLFPPKPKDTLMISRTPE VTCVVVDVSHEDPEVKFNWY VDGVEVHNAKTKPREEQYNS TYRVVSVLTVLHQDWLNGKE YKCKVSNKALPAPIEKTISK AKGQPREPQVYTLPPSRDEL TKNQVSLTCLVKGFYPSDIA VEWESNGQPENNYKTTPPVL DSDGSFFLYSKLTVDKSRWQ QGNVFSCSVMHEALHNHYTQ KSLSLSPGK | 102 |
| Anti-CD20 (GA101) light chain | DIVMTQTPLSLPVTPGEPAS ISCRSSKSLLHSNGITYLYW YLQKPGQSPQLLIYQMSNLV SGVPDRFSGSGSGTDFTLKI SRVEAEDVGVYYCAQNLELP YTFGGGTKVEIKRTVAAPSV FIFPPSDEQLKSGTASVVCL LNNFYPREAKVQWKVDNALQ SGNSQESVTEQDSKDSTYSL SSTLTLSKADYEKHKVYACE VTHQGLSSPVTKSFNRGEC | 103 |
| Anti-FAP(4B9) PGLALA heavy chain | EVQLLESGGGLVQPGGSLRL SCAASGFTFSSYAMSWVRQA PGKGLEWVSAIIGSGASTYY ADSVKGRFTISRDNSKNTLY LQMNSLRAEDTAVYYCAKGW FGGFNYWGQGTLVTVSSAST | 104 |

TABLE 8-continued

| Construct | Amino acid sequence | SEQ ID NO |
|---|---|---|
| | KGPSVFPLAPSSKSTSGGTA ALGCLVKDYFPEPVTVSWNS GALTSGVHTFPAVLQSSGLY SLSSVVTVPSSSLGTQTYIC NVNHKPSNTKVDKKVEPKSC DKTHTCPPCPAPEAAGGPSV FLFPPKPKDTLMISRTPEVT CVVVDVSHEDPEVKFNWYVD GVEVHNAKTKPREEQYNSTY RVVSVLTVLHQDWLNGKEYK CKVSNKALGAPIEKTISKAK GQPREPQVYTLPPSRDELTK NQVSLTCLVKGFYPSDIAVE WESNGQPENNYKTTPPVLDS DGSFFLYSKLTVDKSRWQQG NVFSCSVMHEALHNHYTQKS LSLSPGK | |
| Anti-FAP(4B9) light chain | EIVLTQSPGTLSLSPGERAT LSCRASQSVTSSYLAWYQQK PGQAPRLLINVGSRRATGIP DRFSGSGSGTDFTLTISRLE PEDFAVYYCQQGIMLPPTFG QGTKVEIKRTVAAPSVFIFP PSDEQLKSGTASVVCLLNNF YPREAKVQWKVDNALQSGNS QESVTEQDSKDSTYSLSSTL TLSKADYEKHKVYACEVTHQ GLSSPVTKSFNRGEC | 105 |
| Anti-CEA (A5B7) PGLALA heavy chain | EVQLVESGGGLVQPGRSLRL SCAASGFTVSSYWMHWVRQA PGKGLEWVGFIRNKANGGTT EYAASVKGRFTISRDDSKNT LYLQMNSLRAEDTAVYYCAR DRGLRFYFDYWGQGTTVTVS SASTKGPSVFPLAPSSKSTS GGTAALGCLVKDYFPEPVTV SWNSGALTSGVHTFPAVLQS SGLYSLSSVVTVPSSSLGTQ TYICNVNHKPSNTKVDKKVE PKSCDKTHTCPPCPAPEAAG GPSVFLFPPKPKDTLMISRT PEVTCVVVDVSHEDPEVKFN WYVDGVEVHNAKTKPREEQY NSTYRVVSVLTVLHQDWLNG KEYKCKVSNKALGAPIEKTI SKAKGQPREPQVYTLPPSRD ELTKNQVSLTCLVKGFYPSD IAVEWESNGQPENNYKTTPP VLDSDGSFFLYSKLTVDKSR WQQGNVFSCSVMHEALHNHY TQKSLSLSPGK | 106 |
| Anti-CEA (A5B7) light chain | QAVLTQPASLSASPGASASL TCTLRRGINVGAYSIYWYQQ KPGSPPQYLLRYKSDSDKQQ GSGVSSRFSASKDASANAGI LLISGLQSEDEADYYCMIWH SGASAVFGGGTKLTVLRTVA APSVFIFPPSDEQLKSGTAS VVCLLNNFYPREAKVQWKVD NALQSGNSQESVTEQDSKDS TYSLSSTLTLSKADYEKHKV YACEVTHQGLSSPVTKSFNR GEC | 107 |
| Anti-CEA (T84.66LC HA) PGLALA heavy chain | QVQLVQSGAEVKKPGSSVKV SCKASGFNIKDTYMHWVRQA PGQGLEWMGRIDPANGNSKY VPKFQGRVTITADTSTSTAY MELSSLRSEDTAVYYCAPFG YYVSDYAMAYWGQGTLVTVS SASTKGPSVFPLAPSSKSTS GGTAALGCLVKDYFPEPVTV SWNSGALTSGVHTFPAVLQS | 108 |

TABLE 8-continued

| Construct | Amino acid sequence | SEQ ID NO |
|---|---|---|
| | SGLYSLSSVVTVPSSSLGTQ<br>TYICNVNHKPSNTKVDKKVE<br>PKSCDKTHTCPPCPAPEAAG<br>GPSVFLFPPKPKDTLMISRT<br>PEVTCVVVDVSHEDPEVKFN<br>WYVDGVEVHNAKTKPREEQY<br>NSTYRVVSVLTVLHQDWLNG<br>KEYKCKVSNKALGAPIEKTI<br>SKAKGQPREPQVYTLPPSRD<br>ELTKNQVSLTCLVKGFYPSD<br>IAVEWESNGQPENNYKTTPP<br>VLDSDGSFFLYSKLTVDKSR<br>WQQGNVFSCSVMHEALHNHY<br>TQKSLSLSPGK | |
| Anti-CEA (T84.66LC HA) light chain | EIVLTQSPATLSLSPGERAT<br>LSCRAGESVDIFGVGFLHWY<br>QQKPGQAPRLLIYRASNRAT<br>GIPARFSGSGSGTDFTLTIS<br>SLEPEDFAVYYCQQTNEDPY<br>TFGQGTKLEIKRTVAAPSVF<br>IFPPSDEQLKSGTASVVCLL<br>NNFYPREAKVQWKVDNALQS<br>GNSQESVTEQDSKDSTYSLS<br>STLTLSKADYEKHKVYACEV<br>THQGLSSPVTKSFNRGEC | 109 |
| Anti-CEA (CH1A1A9 8/992F1) PGLALA heavy chain | QVQLVQSGAEVKKPGASVKV<br>SCKASGYTFTEFGMNWVRQA<br>PGQGLEWMGWINTKTGEATY<br>VEEFKGRVTFTTDTSTSTAY<br>MELRSLRSDDTAVYYCARWD<br>FAYYVEAMDYWGQGTTVTVS<br>SASTKGPSVFPLAPSSKSTS<br>GGTAALGCLVKDYFPEPVTV<br>SWNSGALTSGVHTFPAVLQS<br>SGLYSLSSVVTVPSSSLGTQ<br>TYICNVNHKPSNTKVDKKVE<br>PKSCDKTHTCPPCPAPEAAG<br>GPSVFLFPPKPKDTLMISRT<br>PEVTCVVVDVSHEDPEVKFN<br>WYVDGVEVHNAKTKPREEQY<br>NSTYRVVSVLTVLHQDWLNG<br>KEYKCKVSNKALGAPIEKTI<br>SKAKGQPREPQVCTLPPSRD<br>ELTKNQVSLSCAVKGFYPSD<br>IAVEWESNGQPENNYKTTPP<br>VLDSDGSFFLVSKLTVDKSR<br>WQQGNVFSCSVMHEALHNHY<br>TQKSLSLSPGK | 110 |
| Anti-CEA (CH1A1A9 8/992F1) light chain | DIQMTQSPSSLSASVGDRVT<br>ITCKASAAVGTYVAWYQQKP<br>GKAPKLLIYSASYRKRGVPS<br>RFSGSGSGTDFTLTISSLQP<br>EDFATYYCHQYYTYPLFTFG<br>QGTKLEIKRTVAAPSVFIFP<br>PSDEQLKSGTASVVCLLNNF<br>YPREAKVQWKVDNALQSGNS<br>QESVTEQDSKDSTYSLSSTL<br>TLSKADYEKHKVYACEVTHQ<br>GLSSPVTKSFNRGEC | 111 |
| Anti-CEA (hMN14) PGLALA heavy chain | EVQLVESGGGVVQPGRSLRL<br>SCSASGFDFTTYWMSWVRQA<br>PGKGLEWIGEIHPDSSTINY<br>APSLKDRFTISRDNAKNTLF<br>LQMDSLRPEDTGVYFCASLY<br>FGFPWFAYWGQGTPVTVSSA<br>STKGPSVFPLAPSSKSTSGG<br>TAALGCLVKDYFPEPVTVSW<br>NSGALTSGVHTFPAVLQSSG<br>LYSLSSVVTVPSSSLGTQTY<br>ICNVNHKPSNTKVDKKVEPK<br>SCDKTHTCPPCPAPEAAGGP<br>SVFLFPPKPKDTLMISRTPE | 112 |

TABLE 8-continued

| Construct | Amino acid sequence | SEQ ID NO |
|---|---|---|
| | VTCVVVDVSHEDPEVKFNWY<br>VDGVEVHNAKTKPREEQYNS<br>TYRVVSVLTVLHQDWLNGKE<br>YKCKVSNKALGAPIEKTISK<br>AKGQPREPQVYTLPPSRDEL<br>TKNQVSLTCLVKGFYPSDIA<br>VEWESNGQPENNYKTTPPVL<br>DSDGSFFLYSKLTVDKSRWQ<br>QGNVFSCSVMHEALHNHYTQ<br>KSLSLSPGK | |
| Anti-CEA (hMN14) light chain | DIQLTQSPSSLSASVGDRVT<br>ITCKASQDVGTSVAWYQQKP<br>GKAPKLLIYWTSTRHTGVPS<br>RFSGSGSGTDFTFTISSLQP<br>EDIATYYCQQYSLYRSFGQG<br>TKVEIKRTVAAPSVFIFPPS<br>DEQLKSGTASVVCLLNNFYP<br>REAKVQWKVDNALQSGNSQE<br>SVTEQDSKDSTYSLSSTLTL<br>SKADYEKHKVYACEVTHQGL<br>SSPVTKSFNRGEC | 113 |
| Anti-TNC (2B10) PGLALA heavy chain | QVQLVQSGAEVKKPGSSVKV<br>SCKASGGTFSSYAISWVRQA<br>PGQGLEWMGGIIPIFGTANY<br>AQKFQGRVTITADKSTSTAY<br>MELSSLRSEDTAVYYCARLY<br>GYAYYGAFDYWGQGTTVTVS<br>SASTKGPSVFPLAPSSKSTS<br>GGTAALGCLVKDYFPEPVTV<br>SWNSGALTSGVHTFPAVLQS<br>SGLYSLSSVVTVPSSSLGTQ<br>TYICNVNHKPSNTKVDKKVE<br>PKSCDKTHTCPPCPAPEAAG<br>GPSVFLFPPKPKDTLMISRT<br>PEVTCVVVDVSHEDPEVKFN<br>WYVDGVEVHNAKTKPREEQY<br>NSTYRVVSVLTVLHQDWLNG<br>KEYKCKVSNKALGAPIEKTI<br>SKAKGQPREPQVCTLPPSRD<br>ELTKNQVSLSCAVKGFYPSD<br>IAVEWESNGQPENNYKTTPP<br>VLDSDGSFFLVSKLTVDKSR<br>WQQGNVFSCSVMHEALHNHY<br>TQKSLSLSPGK | 114 |
| Anti-TNC (2B10) light chain | DIQMTQSPSSLSASVGDRVT<br>ITCRASQGIRNDLGWYQQKP<br>GKAPKRLIYAASSLQSGVPS<br>RFSGSGSGTEFTLTISSLQP<br>EDFATYYCLQNGLQPATFGQ<br>GTKVEIKRTVAAPSVFIFPP<br>SDEQLKSGTASVVCLLNNFY<br>PREAKVQWKVDNALQSGNSQ<br>ESVTEQDSKDSTYSLSSTLT<br>LSKADYEKHKVYACEVTHQG<br>LSSPVTKSFNRGEC | 115 |
| Human IgGl Fc | ASTKGPSVFPLAPSSKSTSG<br>GTAALGCLVKDYFPEPVTVS<br>WNSGALTSGVHTFPAVLQSS<br>GLYSLSSVVTVPSSSLGTQT<br>YICNVNHKPSNTKVDKKVEP<br>KSCDKTHTCPPCPAPELLGG<br>PSVFLFPPKPKDTLMISRTP<br>EVTCVVVDVSHEDPEVKFNW<br>YVDGVEVHNAKTKPREEQYN<br>STYRVVSVLTVLHQDWLNGK<br>EYKCKVSNKALPAPIEKTIS<br>KAKGQPREPQVYTLPPSRDE<br>LTKNQVSLTCLVKGFYPSDI<br>AVEWESNGQPENNYKTTPPV<br>LDSDGSFFLYSKLTVDKSRW<br>QQGNVFSCSVMHEALHNHYT<br>QKSLSLSPGK | 116 |

TABLE 8-continued

| Construct | Amino acid sequence | SEQ ID NO |
|---|---|---|
| Human CD8 | MRNQAPGRPKGATFPPRRPT GSRAPPLAPELRAKQRPGER VMALPVTALLLPLALLLHAA RPSQFRVSPLDRTWNLGETV ELKCQVLLSNPTSGCSWLFQ PRGAAASPTFLLYLSQNKPK AAEGLDTQRFSGKRLGDTFV LTLSDFRRENEGYYFCSALS NSIMYFSHFVPVFLPAKPTT TPAPRPPTPAPTIASQPLSL RPEACRPAAGGAVHTRGLDF ACDIYIWAPLAGTCGVLLLS LVITLYCNHRNRRRVCKCPR PVVKSGDKPSLSARYV | 117 |
| Human CD8 | ATGCGCAACCAGGCGCCGGG CCGCCCGAAAGGCGCGACCT TTCCGCCGCGCCGCCCGACC GGCAGCCGCGCGCCGCCGCT GGCGCCGGAACTGCGCGCGA AACAGCGCCCGGGCGAACGC GTGATGGCGCTGCCGGTGAC CGCGCTGCTGCTGCCGCTGG CGCTGCTGCTGCATGCGGCG CGCCCGAGCCAGTTTCGCGT GAGCCCGCTGGATCGCACCT GGAACCTGGGCGAAACCGTG GAACTGAAATGCCAGGTGCT GCTGAGCAACCCGACCAGCG GCTGCAGCTGGCTGTTTCAG CCGCGCGGCGCGGCGGCGAG CCCGACCTTTCTGCTGTATC TGAGCCAGAACAAACCGAAA GCGGCGGAAGGCCTGGATAC CCAGCGCTTTAGCGGCAAAC GCCTGGGCGATACCTTTGTG CTGACCCTGAGCGATTTTCG CCGCGAAAACGAAGGCTATT ATTTTTGCAGCGCGCTGAGC AACAGCATTATGTATTTTAG CCATTTTGTGCCGGTGTTTC TGCCGGCGAAACCGACCACC ACCCCGGCGCCGCGCCCGCC GACCCCGGCGCCGACCATTG CGAGCCAGCCGCTGAGCCTG CGCCCGGAAGCGTGCCGCCC GGCGGCGGGCGGCGCGGTGC ATACCCGCGGCCTGGATTTT GCGTGCGATATTTATATTTG GGCGCCGCTGGCGGGCACCT GCGGCGTGCTGCTGCTGAGC CTGGTGATTACCCTGTATTG CAACCATCGCAACCGCCGCC GCGTGTGCAAATGCCCGCGC CCGGTGGTGAAAAGCGGCGA TAAACCGAGCCTGAGCGCGC GCTATGTG | 118 |
| Murine CD8 | MASPLTRFLSLNLLLMGESI ILGSGEAKPQAPELRIFPKK MDAELGQKVDLVCEVLGSVS QGCSWLFQNSSSKLPQPTFV VYMASSHNKITWDEKLNSSK LFSAVRDTNNKYVLTLNKFS KENEGYYFCSVISNSVMYFS SVVPVLQKVNSTTTKPVLRT PSPVHPTGTSQPQRPEDCRP RGSVKGTGLDFACDIYIWAP LAGICVAPLLSLIITLICYH RSRKRVCKCPRPLVRQEGKP RPSEKIV | 119 |
| Murine CD8 | ATGGCGAGCCCGCTGACCCG CTTTCTGAGCCTGAACCTGC TGCTGATGGGCGAAAGCATT ATTCTGGGCAGCGGCGAAGC GAAACCGCAGGCGCCGGAAC TGCGCATTTTTCCGAAAAAA ATGGATGCGGAACTGGGCCA GAAAGTGGATCTGGTGTGCG AAGTGCTGGGCAGCGTGAGC CAGGGCTGCAGCTGGCTGTT TCAGAACAGCAGCAGCAAAC TGCCGCAGCCGACCTTTGTG GTGTATATGGCGAGCAGCCA TAACAAAATTACCTGGGATG AAAAACTGAACAGCAGCAAA CTGTTTAGCGCGGTGCGCGA TACCAACAACAAATATGTGC TGACCCTGAACAAATTTAGC AAAGAAAACGAAGGCTATTA TTTTTGCAGCGTGATTAGCA ACAGCGTGATGTATTTTAGC AGCGTGGTGCCGGTGCTGCA GAAAGTGAACAGCACCACCA CCAAACCGGTGCTGCGCACC CCGAGCCCGGTGCATCCGAC CGGCACCAGCCAGCCGCAGC GCCCGGAAGATTGCCGCCCG CGCGGCAGCGTGAAAGGCAC CGGCCTGGATTTTGCGTGCG ATATTTATATTTGGGCGCCG CTGGCGGGCATTTGCGTGGC GCCGCTGCTGAGCCTGATTA TTACCCTGATTTGCTATCAT CGCAGCCGCAAACGCGTGTG CAAATGCCCGCGCCCGCTGG TGCGCCAGGAAGGCAAACCG CGCCCGAGCGAAAAAATTGT G | 120 |

TABLE 9

Exemplary VH1VL1 P329G-CAR amino acid sequences: CDR definition according to Kabat

| Construct | Amino acid sequence | SEQ ID NO |
|---|---|---|
| VH1 CDR H1 | see Table 2 | 1 |
| VH1 CDR H2 | see Table 6 | 40 |
| VH1 CDR H3 | see Table 2 | 3 |
| VL1 CDR L1 | see Table 2 | 4 |

TABLE 9-continued

| Exemplary VH1VL1 P329G-CAR amino acid sequences: CDR definition according to Kabat | | |
|---|---|---|
| Construct | Amino acid sequence | SEQ ID NO |
| VL1 CDR L2 | see Table 2 | 5 |
| VL1 CDR L3 | see Table 2 | 6 |
| VH1VL1-CD8ATD-CD137CSD-CD3zSSD fusion | EVQLVESGGGLVQPGGSLRLSCAASGFDFSRYWMNWV RQAPGKGLEWVGEITPDSSTINYTPSLKGRFTISRDNAKN SLYLQMNSLRAEDTAVYYCVRPYDYGAWFASWGQGTL VTVSSGGGGSGGGGSGGGGSGGGGSQAVVTQEPSLTVS PGGTVTLTCRSSTGAVTTSNYANWVQEKPDHLFTGLIGG TNKRAPGTPARFSGSLLGGKAALTLSGAQPEDEAEYYC ALWYSNHWVFGGGTKLTVLGGGGSLKPTTTPAPRPPTP APTIASQPLSLRPEACRPAAGGAVHTRGLDFACDIYIWAP LAGTCGVLLLSLVITKRGRKKLLYIFKQPFMRPVQTTQE EDGCSCRFPEEEEGGCELRVKFSRSADAPAYQQGQNQL YNELNLGRREEYDVLDKRRGRDPEMGGKPRRKNPQEG LYNELQKDKMAEAYSEIGMKGERRRGKGHDGLYQGLS TATKDTYDALHMQALPPR | 121 |
| VH1 VH | see Table 6 | 41 |
| VL1 VL | see Table 2 | 9 |
| VH1VL1 scFv | EVQLVESGGGLVQPGGSLRLSCAASGFDFSRYWMNWV RQAPGKGLEWVGEITPDSSTINYTPSLKGRFTISRDNAKN SLYLQMNSLRAEDTAVYYCVRPYDYGAWFASWGQGTL VTVSSGGGGSGGGGSGGGGSGGGGSQAVVTQEPSLTVS PGGTVTLTCRSSTGAVTTSNYANWVQEKPDHLFTGLIGG TNKRAPGTPARFSGSLLGGKAALTLSGAQPEDEAEYYC ALWYSNHWVFGGGTKLTVL | 122 |
| CD8ATD | see Table 2 | 11 |
| CD137CSD | see Table 2 | 12 |
| CD3zSSD | see Table 2 | 13 |
| CD28ATD- | see Table 2 | 14 |
| CD137CSD-CD3zSSD | | |
| eGFP | see Table 2 | 15 |
| (G4S)4 linker | see Table 2 | 16 |
| G4S linker | see Table 2 | 17 |
| T2A linker | see Table 2 | 18 |
| CD8stalk | see Table 2 | 19 |

TABLE 10

| Exemplary VH2VL1 P329G-CAR amino acid sequences: CDR definition according to Kabat | | |
|---|---|---|
| Construct | Amino acid sequence | SEQ ID NO |
| VH2 CDR H1 | see Table 2 | 1 |
| VH2 CDR H2 | see Table 2 | 2 |
| VH2 CDR H3 | see Table 2 | 3 |
| VL1 CDR L1 | see Table 2 | 4 |
| VL1 CDR L2 | see Table 2 | 5 |
| VL1 CDR L3 | see Table 2 | 6 |

TABLE 10-continued

| Construct | Amino acid sequence | SEQ ID NO |
|---|---|---|
| Exemplary VH2VL1 P329G-CAR amino acid sequences: CDR definition according to Kabat | | |
| VH2VL1-CD8ATD-CD137CSD-CD3zSSD fusion | EVQLVESGGGLVQPGGSLRLSCAASGFDFSRYWMNWVR QAPGKGLEWVGEITPDSSTINYAPSLKGRFTISRDNAK NSLYLQMNSLRAEDTAVYYCVRPYDYGAWFASWGQGTL VTVSSGGGGSGGGGSGGGGSGGGGSQAVVTQEPSLTVS PGGTVTLTCRSSTGAVTTSNYANWVQEKPDHLFTGLIG GTNKRAPGTPARFSGSLLGGKAALTLSGAQPEDEAEYY CALWYSNHWVFGGGTKLTVLGGGGSLKPTTTPAPRPPT PAPTIASQPLSLRPEACRPAAGGAVHTRGLDFACDIYI WAPLAGTCGVLLLSLVITKRGRKKLLYIFKQPFMRPVQ TTQEEDGCSCRFPEEEEGGCELRVKFSRSADAPAYQQG QNQLYNELNLGRREEYDVLDKRRGRDPEMGGKPRRKNP QEGLYNELQKDKMAEAYSEIGMKGERRRGKGHDGLYQG LSTATKDTYDALHMQALPPR | 123 |
| VH2 VH | see Table 6 | 44 |
| VL1 VL | see Table 2 | 9 |
| VH2VL1 scFv | EVQLVESGGGLVQPGGSLRLSCAASGFDFSRYWMNWVR QAPGKGLEWVGEITPDSSTINYAPSLKGRFTISRDNAK NSLYLQMNSLRAEDTAVYYCVRPYDYGAWFASWGQGTL VTVSSGGGGSGGGGSGGGGSGGGGSQAVVTQEPSLTVS PGGTVTLTCRSSTGAVTTSNYANWVQEKPDHLFTGLIG GTNKRAPGTPARFSGSLLGGKAALTLSGAQPEDEAEYY CALWYSNHWVFGGGTKLTVL | 124 |
| CD8ATD | see Table 2 | 11 |
| CD137CSD | see Table 2 | 12 |
| CD3zSSD | see Table 2 | 13 |
| CD28ATD-CD137CSD-CD3zSSD | see Table 2 | 14 |
| eGFP | see Table 2 | 15 |
| (G4S)4 linker | see Table 2 | 16 |
| G4S linker | see Table 2 | 17 |
| T2A linker | see Table 2 | 18 |
| CD8stalk | see Table 2 | 19 |

TABLE 11

| Construct | Amino acid sequence | SEQ ID NO |
|---|---|---|
| Exemplary disulfide stabilized VH3VL1 P329G-CAR amino acid sequences: CDR definition according to Kabat | | |
| VH3 CDR H1 | see Table 2 | 1 |
| VH3 CDR H2 | see Table 2 | 2 |
| VH3 CDR H3 | see Table 2 | 3 |
| VL1 CDR L1 | see Table 2 | 4 |
| VL1 CDR L2 | see Table 2 | 5 |
| VL1 CDR L3 | see Table 2 | 6 |
| VH3VL1(ds)-CD8ATD-CD137CSD-CD3zSSD | EVQLVESGGGLVQPGGSLRLSCAASGFTFSRYWMNWV RQAPGKCLEWVGEITPDSSTINYAPSLKGRFTISRDNAKN SLYLQMNSLRAEDTAVYYCARPYDYGAWFASWGQGTL VTVSSGGGGSGGGGSGGGGSGGGGSQAVVTQEPSLTVS | 125 |

TABLE 11-continued

Exemplary disulfide stabilized VH3VL1 P329G-CAR amino acid sequences: CDR definition according to Kabat

| Construct | Amino acid sequence | SEQ ID NO |
|---|---|---|
| fusion | PGGTVTLTCRSSTGAVTTSNYANWVQEKPDHLFTGLIGG TNKRAPGTPARFSGSLLGGKAALTLSGAQPEDEAEYYC ALWYSNHWVFGCGTKLTVLGGGGSLKPTTTPAPRPPTP APTIASQPLSLRPEACRPAAGGAVHTRGLDFACDIYIWAP LAGTCGVLLLSLVITKRGRKKLLYIFKQPFMRPVQTTQE EDGCSCRFPEEEEGGCELRVKFSRSADAPAYQQGQNQL YNELNLGRREEYDVLDKRRGRDPEMGGKPRRKNPQEG LYNELQKDKMAEAYSEIGMKGERRRGKGHDGLYQGLS TATKDTYDALHMQALPPR | |
| VH3 (ds) VH | EVQLVESGGGLVQPGGSLRLSCAASGFTFSRYWMNWV RQAPGKCLEWVGEITPDSSTINYAPSLKGRFTISRDNAKN SLYLQMNSLRAEDTAVYYCARPYDYGAWFASWGQGTL VTVSS | 126 |
| VL1 (ds) VL | QAVVTQEPSLTVSPGGTVTLTCRSSTGAVTTSNYANWV QEKPDHLFTGLIGGTNKRAPGTPARFSGSLLGGKAALTL SGAQPEDEAEYYCALWYSNHWVFGCGTKLTVL | 127 |
| VH3VL1 (ds) scFv | EVQLVESGGGLVQPGGSLRLSCAASGFTFSRYWMNWV RQAPGKCLEWVGEITPDSSTINYAPSLKGRFTISRDNAKN SLYLQMNSLRAEDTAVYYCARPYDYGAWFASWGQGTL VTVSSGGGGSGGGGSGGGGSGGGGSQAVVTQEPSLTVS PGGTVTLTCRSSTGAVTTSNYANWVQEKPDHLFTGLIGG TNKRAPGTPARFSGSLLGGKAALTLSGAQPEDEAEYYC ALWYSNHWVFGCGTKLTVL | 128 |
| CD8ATD | see Table 2 | 11 |
| CD137CSD | see Table 2 | 12 |
| CD3zSSD | see Table 2 | 13 |
| CD28ATD-CD137CSD-CD3zSSD | see Table 2 | 14 |
| eGFP | see Table 2 | 15 |
| (G4S)4 linker | see Table 2 | 16 |
| G4S linker | see Table 2 | 17 |
| T2A linker | see Table 2 | 18 |
| CD8stalk | see Table 2 | 19 |

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, $5^{th}$ ed., NIH Publication No. 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Production of IgG-Like Proteins in HEK293 EBNA or CHO EBNA Cells

Antibodies and bispecific antibodies were generated by transient transfection of HEK293 EBNA cells or CHO EBNA cells. Cells were centrifuged and, medium was replaced by pre-warmed CD CHO medium (Thermo Fisher, Cat No 10743029). Expression vectors were mixed in CD CHO medium, PEI (Polyethylenimine, Polysciences, Inc, Cat No 23966-1) was added, the solution vortexed and incubated for 10 minutes at room temperature. Afterwards, cells (2 Mio/ml) were mixed with the vector/PEI solution, transferred to a flask and incubated for 3 hours at 37° C. in a shaking incubator with a 5% CO2 atmosphere. After the incubation, Excell medium with supplements (80% of total volume) was added (W. Zhou and A. Kantardjieff, Mammalian Cell Cultures for Biologics Manufacturing, DOI: 10.1007/978-3-642-54050-9; 2014). One day after transfection, supplements (Feed, 12% of total volume) were added. Cell supernatants were harvested after 7 days by centrifugation and subsequent filtration (0.2 μm filter), and proteins were purified from the harvested supernatant by standard methods as indicated below.

Production of IgG-Like Proteins in CHO K1 Cells

Alternatively, the antibodies and bispecific antibodies described herein were prepared by Evitria using their proprietary vector system with conventional (non-PCR based) cloning techniques and using suspension-adapted CHO K1 cells (originally received from ATCC and adapted to serum-free growth in suspension culture at Evitria). For the production, Evitria used its proprietary, animal-component free and serum-free media (eviGrow and eviMake2) and its proprietary transfection reagent (eviFect). Supernatant was harvested by centrifugation and subsequent filtration (0.2 μm filter) and, proteins were purified from the harvested supernatant by standard methods.

Purification of IgG-Like Proteins

Proteins were purified from filtered cell culture supernatants referring to standard protocols. In brief, Fc containing proteins were purified from cell culture supernatants by Protein A-affinity chromatography (equilibration buffer: 20 mM sodium citrate, 20 mM sodium phosphate, pH 7.5; elution buffer: 20 mM sodium citrate, pH 3.0). Elution was achieved at pH 3.0 followed by immediate pH neutralization of the sample. The protein was concentrated by centrifugation (Millipore Amicon® ULTRA-15 (Art.Nr.: UFC903096), and aggregated protein was separated from monomeric protein by size exclusion chromatography in 20 mM histidine, 140 mM sodium chloride, pH 6.0.

Analytics of IgG-Like Proteins

The concentrations of purified proteins were determined by measuring the absorption at 280 nm using the mass extinction coefficient calculated on the basis of the amino acid sequence according to Pace, et al., Protein Science, 1995, 4, 2411-1423. Purity and molecular weight of the proteins were analyzed by CE-SDS in the presence and absence of a reducing agent using a LabChip® GXII or LabChip® GX Touch™ (Perkin Elmer) (Perkin Elmer). Determination of the aggregate content was performed by HPLC chromatography at 25° C. using analytical size-exclusion column (TSKgel® G3000SWXL or UP-SW3000) equilibrated in running buffer (200 mM KH2PO4, 250 mM KCl pH 6.2, 0.02% NaN3).

Preparation of Lentivirus Supernatants and Transduction of Jurkat-NFAT Cells

Lipofectamine LTX™-based transfection was performed using ~80% confluent Hek293T cells (ATCC CRL3216) and CAR encoding transfer vectors as well as packaging vectors pCAG-VSVG and psPAX2 at a 2:2:1 molar ratio (Giry-Laterriere M, et al Methods Mol Biol. 2011; 737:183-209, Myburgh R, et al Mol Ther Nucleic Acids. 2014). After 66 h, the supernatant was collected, centrifuged for 5 min at 350×g and filtrated through a 0.45-μm polyethersulfon filter to harvest and purify the virus particles. Virus particles were either used directly or concentrated (Lenti-X™ Concentrator, Takara) and used for spinfection of Jurkat NFAT T cells (GloResponse™ Jurkat NFAT-RE-luc2P, Promega #CS176501 at 900×g for 2 h and 31° C.

Jurkat NFAT Activation Assay

The Jurkat NFAT activation assay measures T cell activation of a human acute lymphatic leukemia reporter cell line (GloResponse™ Jurkat NFAT-RE-luc2P, Promega #CS176501). This immortalized T cell line is genetically engineered to stably express a luciferase reporter driven by an NFAT-response element (NFAT-RE). Further, the cell line expresses a chimeric antigen receptor (CAR) construct possessing a CD3z signaling domain. Binding of the CAR to an immobilized adapter molecule (e.g. a tumor antigen bound adapter molecule) leads to CAR crosslinking resulting in T cell activation and in the expression of luciferase. After addition of a substrate the cellular changes of the NFAT activity can be measured as relative light units (Darowski et al. Protein Engineering, Design and Selection, Volume 32, Issue 5, May 2019, Pages 207-218, https://doi.org/10.1093/protein/gzz027). In general, the assay was performed in a 384 plate (Falcon #353963 white, clear bottom). Target cells (CAR-Jurkat-NFAT cells) and effector cells were seeded in a 1:5 ratio (2000 target cells and 10 000 effector cells) in 10 μl each, in RPMI-1640+10% FCS+1% GlutaMAX™ (growth medium) in triplicates. Further, a serial dilution of the antibody of interest was prepared in growth medium to obtain a final concentrations ranging from 67 nM to 0.000067 nM in the assay plate with a final volume of 30 μl per well in total. The 384 well plate was centrifuged for 1 min at 300 g and RT and incubated at 37° C. and 5% $CO_2$ in a humidity atmosphere. After 7 h incubation 20% of the final volume of ONE-Glo™ Luciferase Assay (E6120, Promega) was added, and plates were centrifuged for 1 min at 350×g. Afterwards, the relative luminescence units (RLU) per s/well were measured immediately using a Tecan microplate reader. Concentration-response curves were fitted and $EC_{50}$ values were calculated using GraphPadPrism version 7. As p value the New England Journal of Medicine style was used as listed in GraphPadPrism 7. Meaning *=P≤0, 033; =P≤0,002; *=P≤0.001.

Example 1

Generation and Characterization of Humanized Anti-P329G Antibodies

Parental and humanized anti-P329G antibodies were produced in HEK cells and purified by ProteinA affinity chromatography and size exclusion chromatography. All antibodies were purified in good quality (Table 2).

TABLE 2

Biochemical analysis of anti-P329G antibodies. Monomer content determined by analytical size exclusion chromatography. Purity determined by non-reducing SDS capillary electrophoresis.

| Molecule | Monomer [%] | Purity [%] |
|---|---|---|
| Anti-P329G (M-1.7.24) huIgG1 | 100 | 85 |
| Anti-P329G (VH1VL1) huIgG1 | 100 | 97 |

TABLE 2-continued

Biochemical analysis of anti-P329G antibodies. Monomer content determined by analytical size exclusion chromatography. Purity determined by non-reducing SDS capillary electrophoresis.

| Molecule | Monomer [%] | Purity [%] |
|---|---|---|
| Anti-P329G (VH2VL1) huIgG1 | 100 | 87 |
| Anti-P329G (VH3VL1) huIgG1 | 100 | 97 |

Binding of Parental and Six Humanization Variants of Anti-P329G Binder M-1.7.24 to Human Fc (P329G)

Instrumentation: Biacore™ T200

Chip: CM5 (#772)

Fc1 to 4: anti-human Fab specific (GE Healthcare 28-9583-25)

Capture: 50 nM IgGs for 60 s

Analyte: human Fc (P329G) (P1AD9000-004)

Running buffer: HBS-EP

T°: 25° C.

Dilution: 2-fold dilution in HBS-EP from 0.59 to 37.5 nM

Flow: 30 μl/min

Association: 240 sec

Dissociation: 800 sec

Regeneration: 10 mM glycine pH 2.1 for 2×60 sec

SPR experiments were performed on a Biacore™ T200 with HBS-EP+ as running buffer (0.01 M HEPES pH 7.4, 0.15 M NaCl, 0.005% Surfactant P20 (BR-1006-69, GE Healthcare)). Anti-human Fab specific antibodies (GE Healthcare 28-9583-25) were directly immobilized by amine coupling on a CM5 chip (GE Healthcare). The IgGs were captured for 60 s at 50 nM. A two-fold dilution series of the human Fc (P329G) was passed over the ligand at 30 μl/min for 240 sec to record the association phase. The dissociation phase was monitored for 800 s and triggered by switching from the sample solution to HBS-EP+. The chip surface was regenerated after every cycle using two injections of 10 mM glycine pH 2.1 for 60 sec. Bulk refractive index differences were corrected for by subtracting the response obtained on the reference flow cell 1. The affinity constants were derived from the kinetic rate constants by fitting to a 1:1 Langmuir binding using the Biaeval software (GE Healthcare). The measure was performed in triplicate with independent dilution series.

Following samples were analyzed for binding to human Fc (P329G) (Table 3).

TABLE 3

Description of the samples analyzed for binding to human Fc (P329G).

| Binder | TAPIR ID | Format |
|---|---|---|
| Anti-P329G (M-1.7.24) (parental) | P1AE9963 | IgG, supernatant/purified |
| Anti-P329G (VH3VL1) | P1AE9957 | IgG, supernatant/purified |
| Anti-P329G (VH1VL1) | P1AE9955 | IgG, supernatant/purified |
| Anti-P329G (VH2VL1) | P1AE9956 | IgG, supernatant/purified |
| Anti-P329G (VH4VL1) | P1AE9958 | IgG, supernatant |
| Anti-P329G (VH1VL2) | P1AE9959 | IgG, supernatant |
| Anti-P329G (VH1VL3) | P1AE9960 | IgG, supernatant |
| human Fc (P329G) | P1AD9000-004 | Antigen used as analyte |

Human Fc (P329G) was prepared by plasmin digestion of a human IgG1 followed by affinity purification by ProteinA and size exclusion chromatography.

Binding of Parental and Six Humanization Variants of Anti-P329G Binder M-1.7.24 to Human Fc (P329G)

The dissociation phase was fitted to a single curve to help characterize the off-rate. The ratio between binding to capture response level was calculated. (Table 4).

TABLE 4

Binding assessment of six humanization variants for binding to human Fc (P329G).

| Binder | TAPIR ID | kd (1/s) | Ratio binding/capture | Binding |
|---|---|---|---|---|
| Anti-P329G (M-1.7.24) (parental) | P1AE9963-001 | 5.73E−03 | 20 | parental |
| Anti-P329G (VH3VL1) | P1AE9957-001 | 5.49E−03 | 20 | as parental |
| Anti-P329G (VH1VL1) | P1AE9955-001 | 3.88E−03 | 20 | as parental |
| Anti-P329G (VH2VL1) | P1AE9956-001 | 2.79E−03 | 23 | as parental |
| Anti-P329G (VH4VL1) | P1AE9958-001 | 1.11E−02 | 19 | reduced |
| Anti-P329G (VH1VL2) | P1AE9959-001 | 7.86E−03 | 10 | reduced |
| Anti-P329G (VH1VL3) | P1AE9960-001 | 1.29E−01 | 3 | reduced |

Affinity of Parental and Three Humanization Variants of Anti-P329G Binder M-1.7.24 to Human Fc (P329G)

Three humanization variants with binding pattern similar to parental were assessed in more details. The kinetic constants for a 1:1 Langmuir binding are summarized in Table 5.

TABLE 5

Kinetic constants (1:1 Langmuir binding). Average and standard deviation (in parenthesis) of independent triplicate (independent dilutions series within the same run).

| Binder | TAPIR ID | ka (1/Ms) | kd (1/s) | KD (M) | Rmax (RU) |
|---|---|---|---|---|---|
| Anti-P329G (M-1.7.24) (parental) | P1AE9963-003 | 5.03E+05 (4.75E+04) | 1.58E−03 (3.8E−05) | 3.17E−09 (3.7E−10) | 44 (2) |
| Anti-P329G (VH3VL1) | P1AE9957-003 | 2.74E+05 (5.51E+03) | 1.44E−03 (7.51E−05) | 5.27E−09 (3.3E−10) | 55 (3) |
| Anti-P329G (VH1VL1) | P1AE9955-003 | 2.83E+05 (7.94E+03) | 1.20E−03 (4.73E−05) | 4.24E−09 (2.5E−10) | 48 (2) |
| Anti-P329G (VH2VL1) | P1AE9956-003 | 2.53E+05 (3.79E+03) | 1.22E−03 (3.61E−05) | 4.81E−09 (2.1E−10) | 54 (5) |

Conclusion

Six humanization variants were generated. Three of them (VH4VL1, VH1VL2, VH1VL3) showed decreased binding to human Fc (P329G) compared to parental M-1.7.24. The other three humanization variants (VH1VL1, VH2VL1, VH3VL1) have a binding kinetic very similar to the parental binder and did not lose affinity through humanization.

Example 2

Preparation of Humanized Anti-P329G Antigen Binding Receptors

To assess the functionality of the humanized P329G variants the different variable domains of heavy (VH) and light chain (VL) DNA sequences encoding a binder specific for the P329G Fc mutation were cloned as single chain variable Fragment (scFv) binding moieties and employed as antigen binding domain in a second generation chimeric antigen receptor (CAR).

The different humanized variants of the P329G binder comprise an Ig heavy chain variable main domain (VL) and an Ig light chain variable domain (VL). VH and VL are connected via (G4S)4 linker. The scFv antigen binding domain was fused to the anchoring transmembrane domain (ATD) CD8a (Uniprot P01732[183-203]), which is fused to an intracellular co-stimulatory signalling domain (CSD) CD137 (Uniprot Q07011AA 214-255), which in turn is fused to a stimulatory signalling domain (SSD) CD3ζ (Uniprot P20963 AA 52-164). The scFv of the anti-P329G CAR was constructed in two different orientations VH×VL (FIG. 1 A) or VL×VH (FIG. 1B). A graphical representation of an exemplary expression construct (including the GFP reporter) for the VHVL configuration is shown in FIG. 1C and for the VLVH configuration in FIG. 1D.

Example 3

Expression of Anti-P329G Antigen Binding Receptors in Jurkat-NFAT Cells

The different humanized anti-P329G antigen binding receptors were virally transduced into Jurkat (GloResponse™ Jurkat NFAT-RE-luc2P, Promega #CS176501) cells.

The anti-P329G antigen binding receptor expression was assessed via flow cytometry. Jurkat cells employing different humanized anti-P329G antigen binding receptors were harvested, washed with PBS and seeded at 50.000 cells per well in a 96 well flat bottom plate. After staining for 45 min in the dark and the fridge (4-8° C.) with different concentrations (500 nM-0 nM serial dilution of 1:5) of antibody comprising the P329G mutation in the Fc domain, samples were washed three times with FACS-buffer (PBS containing 2% FBS, 10% 0.5 M EDTA, pH 8 and 0.5 g/L NaN3). Samples were then stained with 2.5 μg/mL polyclonal anti-human IgG Fcγ fragment-specific and PE-conjugated AffiniPure® $F(ab')_2$ goat fragment antibody for 30 min in the dark in the fridge analyzed with flow cytometry (LSRFortessa™ BD). Additionally, the anti-P329G antigen binding receptors comprised an intracellular GFP reporter (see FIG. 1C).

Compared to the humanized versions (VH1VL1, VH2VL1 and VH3VL1) of the P329G binder the original non-humanized binder shows weak CAR-labeling on the cell surface (FIG. 2A), although the GFP expression is comparable. Interestingly, the VL1VH1 construct (see FIG. 1D) shows a high GFP expression but also weak CAR-labeling on the cell surface, indicating that this is a non-favorable confirmation of the binder.

Overall, unexpectedly, the VH3VL1 version shows the highest GFP expression and CAR surface expression. Furthermore, all tested constructs in the VHVL confirmation (VH1VL1, VH2VL1 and VH3VL1) show enhanced GFP signal upon transduction into Jurkat T cells compared to the original non-humanized P329G antigen binding receptor and, interestingly, the construct in the VLVH confirmation (VL1VH3).

In conclusion, the VHVL confirmation seems to favor expression levels of the antigen binding receptors as well as correct targeting to the cell surface.

To further, characterise the selectivity, specificity and safety of the humanised anti-P329G antigen binding receptors different tests were conducted.

Example 4

Specific T Cell Activation in the Presence of Targeting Antibody Comprising the P329G Mutation in the Fc Domain To exclude unspecific binding of the different humanised anti-P329G-scFv variants, Jurkat NFAT cells expressing the antigen binding receptors comprising these variants were evaluated towards their activation in the presence of CD20-positive WSUDLCL2 target cells and anti-CD20 (GA101) antibodies with different Fc variants (Fc wild type, Fc P329G mutation, LALA mutation, D246A mutation or combinations thereof). The CAR-Jurkat NFAT activation assay was performed as described above and the anti-CD20 (GA101) wild type IgG1 (FIG. 3 A), anti-CD20 (GA101) P329G LALA IgG1 (FIG. 3 B), anti-CD20 (GA101) LALA IgG1 (FIG. 3 D), anti-CD20 (GA101) D246A P329G IgG1 (FIG. 3 F) or a non-specific DP-47 P329G LALA IgG1 (FIG. 3 E) were used to evaluate the potential of unspecific binding. No unspecific anti-P329G CAR activation could be detected for anti-CD20 (GA101) wild type IgG1 (FIG. 3 A), anti-CD20 (GA101) LALA IgG1 (FIG. 3 D) or the non-specific DP-47 P329G LALA IgG1 (FIG. 3 E).

Specific anti-P329G CAR activation could be detected in the presence of anti-CD20 (GA101) P329G LALA IgG1 (FIG. 3 B) and anti-CD20 (GA101) D246A P329G IgG1 (FIG. 3 F). The assessed $EC_{50}$ was comparable between all humanised anti-P329G variants and did not differ from the $EC_{50}$ of the original binder.

Interestingly, the antigen binding receptors comprising scFv binders in the VHVL conformation lead to stronger activation of the Jurkat NFAT T cells compared to the original non-humanized binder and the humanized binder in the VLVH conformation. The higher plateau (see for example FIG. 3F) could be due to the improved expression levels and/or improved transport to the cell surface of the antigen binding receptors resulting in a stronger activation. Furthermore, the conformation could have an impact on binding to the P329G mutation.

To investigate the risk of potential antigen binding domain clustering, resulting in tonic signalling or unspecific activation of the T cells, the Jurkat NFAT activation assay was performed as described above whereas the initial antibody concentration used was elevated and the serial dilution was started with 100 nM of GA101 P329G LALA IgG1 and further no target cells were seeded.

As depicted in FIG. 3 C, no activation was detectable for all tested humanised P329G variants, indicating detectable receptor clustering or unspecific activation in the absence of target cells.

Example 5

Sensitivity of Different Humanized P329G Antigen Binding Receptor Variants Assessed by T Cell Activation on Target Cells Expressing Different Levels of Antigen To further, characterise the sensitivity and selectivity of the humanised anti-P329G antigen binding receptors the Jurkat NFAT activation assay was performed as described above.

The Jurkat NFAT reporter cells expressing the different humanised anti-P329G-scFv variant antigen binding receptors were evaluated towards their ability to discriminate between high (HeLa-FolR1), medium (Skov3) and low (HT29) FolR1-positive target cells. Different variants of the anti-P329G binder were used as scFv antigen recognition scaffold in the Jurkat-Reporter cell line in combination with antibodies that poses high (16D5) (FIGS. 4 A, 4D, 4G), medium (16D5 W96Y) (FIGS. 4 B, 4E, 4H) or low (16D5 G49S/K53A) (FIGS. 4 C, 4F, 4I) affinities towards FolR1. High expressing target cells HeLa-FolR1, combined with high anti-FolR1 16D5 (FIG. 4 A), medium anti-FolR1 16D5 W96Y (FIG. 4 B) and low affinity Adapter-IgG anti-FolR1 G49S K53A (FIG. 4 C) showed a dose dependent activation. Medium expressing target cells Skov3, combined with high anti-FolR1 16D5 (FIG. 4 D), medium anti-FolR1 16D5 W96Y (FIG. 4 E) and low affinity adaptor-IgG anti-FolR1 G49S K53A (FIG. 4 F) showed a dose dependent activation. For low expressing target cells HT29, combined with the different affinity binder anti-FolR1 16D5 (FIG. 4 G), anti-FolR1 16D5 W96Y (FIG. 4 H) or low affinity Adaptor-IgG anti-FolR1 G49S K53A (FIG. 4I), no signal could be detected. Further, interestingly, the antigen binding receptors in the VHVL format result with higher activation of the Jurkat NFAT T cells compared to the original non-humanized binder and the humanized binder in the VLVH format. The humanised variant VH3VL1 scFv binder results with the highest signal intensity of all constructs (FIGS. 4 A-4F).

Further, the Jurkat NFAT activation assay was performed on HeLa (FolR1+ and HER2+) cells used in combination with either anti-FolR1 16D5 P329G LALA IgG1 (FIG. 5) or anti-HER2 P329G LALA IgG1 (FIG. 6). Both confirm the finding that the VHVL orientation is superior compared to the VLVH orientation. The humanised variant VH3VL1 leads to the strongest activation of the Jurkat NFAT T cells.

Example 6

Expression of Further Anti-P329G Antigen Binding Receptors in Jurkat-NFAT Cells

A disulfide humanized anti-P329G antigen binding receptor was virally transduced into Jurkat (GloResponse™ Jurkat NFAT-RE-luc2P, Promega #CS176501) cells. The anti-P329G antigen binding receptor expression was assessed via flow cytometry. Jurkat cells employing the disulfide stabilized humanized anti-P329G antigen binding receptor were harvested, washed with PBS and seeded at 50.000 cells per well in a 96 well flat bottom plate. After staining for 45 min in the dark and the fridge (4-8° C.) with different concentrations (600 nM-0 nM serial dilution of 1:10) of antibody comprising the P329G mutation in the Fc domain, samples were washed three times with FACS-buffer (PBS containing 2% FBS, 10% 0.5 M EDTA, pH 8 and 0.5 g/L NaN3). Samples were then stained with 2.5 μg/mL polyclonal anti-human IgG Fey fragment-specific and PE-conjugated AffiniPure® $F(ab')_2$ goat fragment antibody for 30 min in the dark in the fridge and analysed with flow cytometry (LSRFortessa™ BD). Additionally, the anti-P329G antigen binding receptors comprised an intracellular GFP reporter (see FIG. 1C). The CAR-expression was normalized to the GFP signal.

Compared to the humanized versions VH3VL1 and the VL1VH3 the disulfide stabilised P329G binder shows comparable CAR-labelling on the cell surface (FIG. 7).

SEQUENCE LISTING

```
Sequence total quantity: 128
SEQ ID NO: 1            moltype = AA  length = 5
FEATURE                 Location/Qualifiers
REGION                  1..5
                        note = Synthetic construct
source                  1..5
                        mol_type = protein
                        organism = synthetic construct
SEQUENCE: 1
RYWMN                                                                5

SEQ ID NO: 2            moltype = AA  length = 17
FEATURE                 Location/Qualifiers
REGION                  1..17
                        note = Synthetic construct
source                  1..17
                        mol_type = protein
                        organism = synthetic construct
SEQUENCE: 2
EITPDSSTIN YAPSLKG                                                   17

SEQ ID NO: 3            moltype = AA  length = 10
FEATURE                 Location/Qualifiers
REGION                  1..10
                        note = Synthetic construct
source                  1..10
                        mol_type = protein
```

```
                        organism = synthetic construct
SEQUENCE: 3
PYDYGAWFAS                                                    10

SEQ ID NO: 4            moltype = AA  length = 14
FEATURE                 Location/Qualifiers
REGION                  1..14
                        note = Synthetic construct
source                  1..14
                        mol_type = protein
                        organism = synthetic construct
SEQUENCE: 4
RSSTGAVTTS NYAN                                               14

SEQ ID NO: 5            moltype = AA  length = 7
FEATURE                 Location/Qualifiers
REGION                  1..7
                        note = Synthetic construct
source                  1..7
                        mol_type = protein
                        organism = synthetic construct
SEQUENCE: 5
GTNKRAP                                                       7

SEQ ID NO: 6            moltype = AA  length = 9
FEATURE                 Location/Qualifiers
REGION                  1..9
                        note = Synthetic construct
source                  1..9
                        mol_type = protein
                        organism = synthetic construct
SEQUENCE: 6
ALWYSNHWV                                                     9

SEQ ID NO: 7            moltype = AA  length = 476
FEATURE                 Location/Qualifiers
REGION                  1..476
                        note = Synthetic construct
source                  1..476
                        mol_type = protein
                        organism = synthetic construct
SEQUENCE: 7
EVQLVESGGG LVQPGGSLRL SCAASGFTFS RYWMNWVRQA PGKGLEWVGE ITPDSSTINY  60
APSLKGRFTI SRDNAKNSLY LQMNSLRAED TAVYYCARPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
GGTKLTVLGG GGSLKPTTTP APRPPTPAPT IASQPLSLRP EACRPAAGGA VHTRGLDFAC  300
DIYIWAPLAG TCGVLLLSLV ITKRGRKKLL YIFKQPFMRP VQTTQEEDGC SCRFPEEEEG  360
GCELRVKFSR SADAPAYQQG QNQLYNELNL GRREEYDVLD KRRGRDPEMG GKPRRKNPQE  420
GLYNELQKDK MAEAYSEIGM KGERRRGKGH DGLYQGLSTA TKDTYDALHM QALPPR      476

SEQ ID NO: 8            moltype = AA  length = 119
FEATURE                 Location/Qualifiers
REGION                  1..119
                        note = Synthetic construct
source                  1..119
                        mol_type = protein
                        organism = synthetic construct
SEQUENCE: 8
EVQLVESGGG LVQPGGSLRL SCAASGFTFS RYWMNWVRQA PGKGLEWVGE ITPDSSTINY  60
APSLKGRFTI SRDNAKNSLY LQMNSLRAED TAVYYCARPY DYGAWFASWG QGTLVTVSS   119

SEQ ID NO: 9            moltype = AA  length = 109
FEATURE                 Location/Qualifiers
REGION                  1..109
                        note = Synthetic construct
source                  1..109
                        mol_type = protein
                        organism = synthetic construct
SEQUENCE: 9
QAVVTQEPSL TVSPGGTVTL TCRSSTGAVT TSNYANWVQE KPDHLFTGLI GGTNKRAPGT  60
PARFSGSLLG GKAALTLSGA QPEDEAEYYC ALWYSNHWVF GGGTKLTVL             109

SEQ ID NO: 10           moltype = AA  length = 248
FEATURE                 Location/Qualifiers
REGION                  1..248
                        note = Synthetic construct
source                  1..248
                        mol_type = protein
```

```
                         organism = synthetic construct
SEQUENCE: 10
EVQLVESGGG LVQPGGSLRL SCAASGFTFS RYWMNWVRQA PGKGLEWVGE ITPDSSTINY  60
APSLKGRFTI SRDNAKNSLY LQMNSLRAED TAVYYCARPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
GGTKLTVL                                                          248

SEQ ID NO: 11            moltype = AA  length = 21
FEATURE                  Location/Qualifiers
REGION                   1..21
                         note = Synthetic construct
source                   1..21
                         mol_type = protein
                         organism = synthetic construct
SEQUENCE: 11
IYIWAPLAGT CGVLLLSLVI T                                          21

SEQ ID NO: 12            moltype = AA  length = 42
FEATURE                  Location/Qualifiers
REGION                   1..42
                         note = Synthetic construct
source                   1..42
                         mol_type = protein
                         organism = synthetic construct
SEQUENCE: 12
KRGRKKLLYI FKQPFMRPVQ TTQEEDGCSC RFPEEEEGGC EL                   42

SEQ ID NO: 13            moltype = AA  length = 112
FEATURE                  Location/Qualifiers
REGION                   1..112
                         note = Synthetic construct
source                   1..112
                         mol_type = protein
                         organism = synthetic construct
SEQUENCE: 13
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112

SEQ ID NO: 14            moltype = AA  length = 222
FEATURE                  Location/Qualifiers
REGION                   1..222
                         note = Synthetic construct
source                   1..222
                         mol_type = protein
                         organism = synthetic construct
SEQUENCE: 14
KPTTTPAPRP PTPAPTIASQ PLSLRPEACR PAAGGAVHTR GLDFACDIYI WAPLAGTCGV  60
LLLSLVITKR GRKKLLYIFK QPFMRPVQTT QEEDGCSCRF PEEEEGGCEL RVKFSRSADA  120
PAYQQGQNQL YNELNLGRRE EYDVLDKRRG RDPEMGGKPR RKNPQEGLYN ELQKDKMAEA  180
YSEIGMKGER RRGKGHDGLY QGLSTATKDT YDALHMQALP PR                    222

SEQ ID NO: 15            moltype = AA  length = 238
FEATURE                  Location/Qualifiers
REGION                   1..238
                         note = Synthetic construct
source                   1..238
                         mol_type = protein
                         organism = synthetic construct
SEQUENCE: 15
VSKGEELFTG VVPILVELDG DVNGHKFSVS GEGEGDATYG KLTLKFICTT GKLPVPWPTL  60
VTTLTYGVQC FSRYPDHMKQ HDFFKSAMPE GYVQERTIFF KDDGNYKTRA EVKFEGDTLV  120
NRIELKGIDF KEDGNILGHK LEYNYNSHNV YIMADKQKNG IKVNFKIRHN IEDGSVQLAD  180
HYQQNTPIGD GPVLLPDNHY LSTQSALSKD PNEKRDHMVL LEFVTAAGIT LGMDELYK    238

SEQ ID NO: 16            moltype = AA  length = 20
FEATURE                  Location/Qualifiers
REGION                   1..20
                         note = Synthetic construct
source                   1..20
                         mol_type = protein
                         organism = synthetic construct
SEQUENCE: 16
GGGGSGGGGS GGGGSGGGGS                                            20

SEQ ID NO: 17            moltype = AA  length = 5
FEATURE                  Location/Qualifiers
REGION                   1..5
                         note = Synthetic construct
```

```
source                  1..5
                        mol_type = protein
                        organism = synthetic construct
SEQUENCE: 17
GGGGS                                                                     5

SEQ ID NO: 18           moltype = AA  length = 19
FEATURE                 Location/Qualifiers
REGION                  1..19
                        note = Synthetic construct
source                  1..19
                        mol_type = protein
                        organism = synthetic construct
SEQUENCE: 18
GEGRGSLLTC GDVEENPGP                                                      19

SEQ ID NO: 19           moltype = AA  length = 47
FEATURE                 Location/Qualifiers
REGION                  1..47
                        note = Synthetic construct
source                  1..47
                        mol_type = protein
                        organism = synthetic construct
SEQUENCE: 19
KPTTTPAPRP PTPAPTIASQ PLSLRPEACR PAAGGAVHTR GLDFACD                       47

SEQ ID NO: 20           moltype = AA  length = 1428
FEATURE                 Location/Qualifiers
REGION                  1..1428
                        note = Synthetic construct
source                  1..1428
                        mol_type = protein
                        organism = synthetic construct
SEQUENCE: 20
GAGGTGCAGC TGGTGGAGAG CGGCGGCGGC CTGGTGCAGC CCGGCGGCAG CCTGAGGCTG  60
AGCTGCGCCG CCAGCGGCTT CACCTTCAGC AGGTACTGGA TGAACTGGGT GAGGCAGGCC  120
CCCGGCAAGG GCCTGGAGTG GGTGGGCGAG ATCACCCCCG ACAGCAGCAC CATCAACTAC  180
GCCCCCAGCC TGAAGGGCAG GTTCACCATC AGCAGGGACA ACGCCAAGAA CAGCCTGTAC  240
CTGCAGATGA ACAGCCTGAG GGCCGAGGAC ACCGCCGTGT ACTACTGCGC CAGGCCCTAC  300
GACTACGGCG CCTGGTTCGC CAGCTGGGGC CAGGGCACCC TGGTGACCGT GAGCAGCGGA  360
GGGGGCGGAA GTGGTGGCGG GGGAAGCGGC GGGGGTGGCA GCGGAGGGGG CGGATCTCAG  420
GCCGTGGTGA CCCAGGAGCC CAGCCTGACC GTGAGCCCCG GCGGCACCGT GACCCTGACC  480
TGCAGGAGCA GCACCGGCGC CGTGACCACC AGCAACTACG CCAACTGGGT GCAGGAGAAG  540
CCCGACCACC TGTTCACCGG CCTGATCGGC GGCACCAACA AGAGGGCCCC CGGCACCCCC  600
GCCAGGTTCA GCGGCAGCCT GCTGGGCGGC AAGGCCGCCC TGACCCTGAG CGGCGCCCAG  660
CCCGAGGACG AGGCCGAGTA CTACTGCGCC CTGTGGTACA GCAACCACTG GGTGTTCGGC  720
GGCGGCACCA AGCTGACCGT CCTAGGAGGG GGCGGATCCT TGAAGCCCAC CACGACGCCA  780
GCGCCGCGAC CACCAACACC GGCGCCCACC ATCGCGTCGC AGCCCCTGTC CCTGCGCCCA  840
GAGGCGTGCC GGCCAGCGGC GGGGGGCGCA GTGCACACGA GGGGGCTGGA CTTCGCCTGT  900
GATATCTACA TCTGGGCGCC CCTGGCCGGG ACTTGTGGGG TCCTTCTCCT GTCACTGGTT  960
ATCACCAAAC GGGGCAGAAA GAAACTCCTG TATATATTCA AACAACCATT TATGAGACCA  1020
GTACAAACTA CTCAAGAGGA AGATGGCTGT AGCTGCCGAT TTCCAGAAGA AGAAGAAGGA  1080
GGATGTGAAC TGAGAGTGAA GTTCAGCAGG AGCGCAGACG CCCCCGCGTA CCAGCAGGGC  1140
CAGAACCAGC TCTATAACGA GCTCAATCTA GGACGAAGAG AGGAGTACGA TGTTTTGGAC  1200
AAGAGACGTG GCCGGGACCC TGAGATGGGG GGAAAGCCGA GAAGGAAGAA CCCTCAGGAA  1260
GGCCTGTACA ATGAACTGCA GAAAGATAAG ATGGCGGAGG CCTACAGTGA GATTGGGATG  1320
AAAGGCGAGC GCCGGAGGGG CAAGGGGCAC GATGGCCTTT ACCAGGGTCT CAGTACAGCC  1380
ACCAAGGACA CCTACGACGC CCTTCACATG CAGGCCCTGC CCCCTCGC              1428

SEQ ID NO: 21           moltype = AA  length = 357
FEATURE                 Location/Qualifiers
REGION                  1..357
                        note = Synthetic construct
source                  1..357
                        mol_type = protein
                        organism = synthetic construct
SEQUENCE: 21
GAGGTGCAGC TGGTGGAGAG CGGCGGCGGC CTGGTGCAGC CCGGCGGCAG CCTGAGGCTG  60
AGCTGCGCCG CCAGCGGCTT CACCTTCAGC AGGTACTGGA TGAACTGGGT GAGGCAGGCC  120
CCCGGCAAGG GCCTGGAGTG GGTGGGCGAG ATCACCCCCG ACAGCAGCAC CATCAACTAC  180
GCCCCCAGCC TGAAGGGCAG GTTCACCATC AGCAGGGACA ACGCCAAGAA CAGCCTGTAC  240
CTGCAGATGA ACAGCCTGAG GGCCGAGGAC ACCGCCGTGT ACTACTGCGC CAGGCCCTAC  300
GACTACGGCG CCTGGTTCGC CAGCTGGGGC CAGGGCACCC TGGTGACCGT GAGCAGC     357

SEQ ID NO: 22           moltype = AA  length = 327
FEATURE                 Location/Qualifiers
REGION                  1..327
                        note = Synthetic construct
source                  1..327
```

```
                        mol_type = protein
                        organism = synthetic construct
SEQUENCE: 22
CAGGCCGTGG TGACCCAGGA GCCCAGCCTG ACCGTGAGCC CCGGCGGCAC CGTGACCCTG  60
ACCTGCAGGA GCAGCACCGG CGCCGTGACC ACCAGCAACT ACGCCAACTG GGTGCAGGAG  120
AAGCCCGACC ACCTGTTCAC CGGCCTGATC GGCGGCACCA ACAAGAGGGC CCCCGGCACC  180
CCCGCCAGGT TCAGCGGCAG CCTGCTGGGC GGCAAGGCCG CCCTGACCCT GAGCGGCGCC  240
CAGCCCGAGG ACGAGGCCGA GTACTACTGC GCCCTGTGGT ACAGCAACCA CTGGGTGTTC  300
GGCGGCGGCA CCAAGCTGAC CGTCCTA                                      327

SEQ ID NO: 23           moltype = AA  length = 744
FEATURE                 Location/Qualifiers
REGION                  1..744
                        note = Synthetic construct
source                  1..744
                        mol_type = protein
                        organism = synthetic construct
SEQUENCE: 23
GAGGTGCAGC TGGTGGAGAG CGGCGGCGGC CTGGTGCAGC CCGGCGGCAG CCTGAGGCTG  60
AGCTGCGCCG CCAGCGGCTT CACCTTCAGC AGGTACTGGA TGAACTGGGT GAGGCAGGCC  120
CCCGGCAAGG GCCTGGAGTG GGTGGGCGAG ATCACCCCCG ACAGCAGCAC CATCAACTAC  180
GCCCCCAGCC TGAAGGGCAG GTTCACCATC AGCAGGGACA ACGCCAAGAA CAGCCTGTAC  240
CTGCAGATGA ACAGCCTGAG GGCCGAGGAC ACCGCCGTGT ACTACTGCGC CAGGCCCTAC  300
GACTACGGCG CCTGGTTCGC CAGCTGGGGC CAGGGCACCC TGGTGACCGT GAGCAGCGGA  360
GGGGGCGGAA GTGGTGGCGG GGGAAGCGGC GGGGGTGGCA GCGGAGGGGG CGGATCTCAG  420
GCCGTGGTGA CCCAGGAGCC CAGCCTGACC GTGAGCCCCG GCGGCACCGT GACCCTGACC  480
TGCAGGAGCA GCACCGGCGC CGTGACCACC AGCAACTACG CCAACTGGGT GCAGGAGAAG  540
CCCGACCACC TGTTCACCGG CCTGATCGGC GGCACCAACA AGAGGGCCCC CGGCACCCCC  600
GCCAGGTTCA GCGGCAGCCT GCTGGGCGGC AAGGCCGCCC TGACCCTGAG CGGCGCCCAG  660
CCCGAGGACG AGGCCGAGTA CTACTGCGCC CTGTGGTACA GCAACCACTG GGTGTTCGGC  720
GGCGGCACCA AGCTGACCGT CCTA                                         744

SEQ ID NO: 24           moltype = AA  length = 63
FEATURE                 Location/Qualifiers
REGION                  1..63
                        note = Synthetic construct
source                  1..63
                        mol_type = protein
                        organism = synthetic construct
SEQUENCE: 24
ATCTACATCT GGGCGCCCCT GGCCGGGACT TGTGGGGTCC TTCTCCTGTC ACTGGTTATC  60
ACC                                                                63

SEQ ID NO: 25           moltype = AA  length = 126
FEATURE                 Location/Qualifiers
REGION                  1..126
                        note = Synthetic construct
source                  1..126
                        mol_type = protein
                        organism = synthetic construct
SEQUENCE: 25
AAACGGGGCA GAAAGAAACT CCTGTATATA TTCAAACAAC CATTTATGAG ACCAGTACAA  60
ACTACTCAAG AGGAAGATGG CTGTAGCTGC CGATTTCCAG AAGAAGAAGA AGGAGGATGT  120
GAACTG                                                             126

SEQ ID NO: 26           moltype = AA  length = 336
FEATURE                 Location/Qualifiers
REGION                  1..336
                        note = Synthetic construct
source                  1..336
                        mol_type = protein
                        organism = synthetic construct
SEQUENCE: 26
AGAGTGAAGT TCAGCAGGAG CGCAGACGCC CCCGCGTACC AGCAGGGCCA GAACCAGCTC  60
TATAACGAGC TCAATCTAGG ACGAAGAGAG GAGTACGATG TTTTGGACAA GAGACGTGGC  120
CGGGACCCTG AGATGGGGGG AAAGCCGAGA AGGAAGAACC CTCAGGAAGG CCTGTACAAT  180
GAACTGCAGA AAGATAAGAT GGCGGAGGCC TACAGTGAGA TTGGGATGAA AGGCGAGCGC  240
CGGAGGGGCA AGGGGCACGA TGGCCTTTAC CAGGGTCTCA GTACAGCCAC CAAGGACACC  300
TACGACGCCC TTCACATGCA GGCCCTGCCC CCTCGC                             336

SEQ ID NO: 27           moltype = AA  length = 525
FEATURE                 Location/Qualifiers
REGION                  1..525
                        note = Synthetic construct
source                  1..525
                        mol_type = protein
                        organism = synthetic construct
SEQUENCE: 27
ATCTACATCT GGGCGCCCCT GGCCGGGACT TGTGGGGTCC TTCTCCTGTC ACTGGTTATC  60
```

```
ACCAAACGGG GCAGAAAGAA ACTCCTGTAT ATATTCAAAC AACCATTTAT GAGACCAGTA  120
CAAACTACTC AAGAGGAAGA TGGCTGTAGC TGCCGATTTC CAGAAGAAGA AGAAGGAGGA  180
TGTGAACTGA GAGTGAAGTT CAGCAGGAGC GCAGACGCCC CCGCGTACCA GCAGGGCCAG  240
AACCAGCTCT ATAACGAGCT CAATCTAGGA CGAAGAGAGG AGTACGATGT TTTGGACAAG  300
AGACGTGGCC GGGACCCTGA GATGGGGGGA AAGCCGAGAA GGAAGAACCC TCAGGAAGGC  360
CTGTACAATG AACTGCAGAA AGATAAGATG GCGGAGGCCT ACAGTGAGAT TGGGATGAAA  420
GGCGAGCGCC GGAGGGGCAA GGGGCACGAT GGCCTTTACC AGGGTCTCAG TACAGCCACC  480
AAGGACACCT ACGACGCCCT TCACATGCAG GCCCTGCCCC CTCGC                  525

SEQ ID NO: 28          moltype = AA  length = 63
FEATURE                Location/Qualifiers
REGION                 1..63
                       note = Synthetic construct
source                 1..63
                       mol_type = protein
                       organism = synthetic construct
SEQUENCE: 28
TCCGGAGAGG GCAGAGGAAG TCTTCTAACA TGCGGTGACG TGGAGGAGAA TCCCGGCCCT  60
AGG                                                                63

SEQ ID NO: 29          moltype = AA  length = 717
FEATURE                Location/Qualifiers
REGION                 1..717
                       note = Synthetic construct
source                 1..717
                       mol_type = protein
                       organism = synthetic construct
SEQUENCE: 29
GTGAGCAAGG GCGAGGAGCT GTTCACCGGG GTGGTGCCCA TCCTGGTCGA GCTGGACGGC  60
GACGTAAACG GCCACAAGTT CAGCGTGTCC GGCGAGGGCG AGGGCGATGC CACCTACGGC  120
AAGCTGACCC TGAAGTTCAT CTGCACCACC GGCAAGCTGC CCGTGCCCTG GCCCACCCTC  180
GTGACCACCC TGACCTACGG CGTGCAGTGC TTCAGCCGCT ACCCCGACCA CATGAAGCAG  240
CACGACTTCT TCAAGTCCGC CATGCCCGAA GGCTACGTCC AGGAGCGCAC CATCTTCTTC  300
AAGGACGACG GCAACTACAA GACCCGCGCC GAGGTGAAGT TCGAGGGCGA CACCCTGGTG  360
AACCGCATCG AGCTGAAGGG CATCGACTTC AAGGAGGACG GCAACATCCT GGGGCACAAG  420
CTGGAGTACA ACTACAACAG CCACAACGTC TATATCATGG CCGACAAGCA GAAGAACGGC  480
ATCAAGGTGA ACTTCAAGAT CCGCCACAAC ATCGAGGACG GCAGCGTGCA GCTCGCCGAC  540
CACTACCAGC AGAACACCCC CATCGGCGAC GGCCCCGTGC TGCTGCCCGA CAACCACTAC  600
CTGAGCACCC AGTCCGCCCT GAGCAAAGAC CCCAACGAGA AGCGCGATCA CATGGTCCTG  660
CTGGAGTTCG TGACCGCCGC CGGGATCACT CTCGGCATGG ACGAGCTGTA CAAGTGA     717

SEQ ID NO: 30          moltype = AA  length = 2211
FEATURE                Location/Qualifiers
REGION                 1..2211
                       note = Synthetic construct
source                 1..2211
                       mol_type = protein
                       organism = synthetic construct
SEQUENCE: 30
GAGGTGCAGC TGGTGGAGAG CGGCGGCGGC CTGGTGCAGC CCGGCGGCAG CCTGAGGCTG  60
AGCTGCGCCG CCAGCGGCTT CACCTTCAGC AGGTACTGGA TGAACTGGGT GAGGCAGGCC  120
CCCGGCAAGG GCCTGGAGTG GGTGGGCGAG ATCACCCCCG ACAGCAGCAC CATCAACTAC  180
GCCCCCAGCC TGAAGGGCAG GTTCACCATC AGCAGGGACA ACGCCAAGAA CAGCCTGTAC  240
CTGCAGATGA ACAGCCTGAG GGCCGAGGAC ACCGCCGTGT ACTACTGCGC CAGGCCCTAC  300
GACTACGGCG CCTGGTTCGC CAGCTGGGGC CAGGGCACCC TGGTGACCGT GAGCAGCGGA  360
GGGGGCGGAA GTGGTGGCGG GGGAAGCGGC GGGGGTGGCA GCGGAGGGGG CGGATCTCAG  420
GCCGTGGTGA CCCAGGAGCC CAGCCTGACC GTGAGCCCCG GCGGCACCGT GACCCTGACC  480
TGCAGGAGCA GCACCGGCGC CGTGACCACC AGCAACTACG CCAACTGGGT GCAGGAGAAG  540
CCCGACCACC TGTTCACCGG CCTGATCGGC GGCACCAACA AGAGGGCCCC CGGCACCCCC  600
GCCAGGTTCA GCGGCAGCCT GCTGGGCGGC AAGGCCGCCC TGACCCTGAG CGGCGCCCAG  660
CCCGAGGACG AGGCCGAGTA CTACTGCGCC CTGTGGTACA GCAACCACTG GGTGTTCGGC  720
GGCGGCACCA AGCTGACCGT CCTAGGAGGG GGCGGATCCT TGAAGCCCAC CACGACGCCA  780
GCGCCGCGAC CACCAACACC GGCGCCCACC ATCGCGTCGC AGCCCCTGTC CCTGCGCCCA  840
GAGGCGTGCC GGCCAGCGGC GGGGGGCGCA GTGCACACGA GGGGGCTGGA CTTCGCCTGT  900
GATATCTACA TCTGGGCGCC CCTGGCCGGG ACTTGTGGGG TCCTTCTCCT GTCACTGGTT  960
ATCACCAAAC GGGGCAGAAA GAAACTCCTG TATATATTCA AACAACCATT TATGAGACCA  1020
GTACAAACTA CTCAAGAGGA AGATGGCTGT AGCTGCCGAT TTCCAGAAGA AGAAGAAGGA  1080
GGATGTGAAC TGAGAGTGAA GTTCAGCAGG AGCGCAGACG CCCCCGCGTA CCAGCAGGGC  1140
CAGAACCAGC TCTATAACGA GCTCAATCTA GGACGAAGAG AGGAGTACGA TGTTTTGGAC  1200
AAGAGACGTG GCCGGGACCC TGAGATGGGG GGAAAGCCGA GAAGGAAGAA CCCTCAGGAA  1260
GGCCTGTACA ATGAACTGCA GAAAGATAAG ATGGCGGAGG CCTACAGTGA GATTGGGATG  1320
AAAGGCGAGC GCCGGAGGGG CAAGGGGCAC GATGGCCTTT ACCAGGGTCT CAGTACAGCC  1380
ACCAAGGACA CCTACGACGC CCTTCACATG CAGGCCCTGC CCCCTCGCGA ATTCTCCGGA  1440
GAGGGCAGAG GAAGTCTTCT AACATGCGGT GACGTGGAGG AGAATCCCGG CCCTAGGGTG  1500
AGCAAGGGCG AGGAGCTGTT CACCGGGGTG GTGCCCATCC TGGTCGAGCT GGACGGCGAC  1560
GTAAACGGCC ACAAGTTCAG CGTGTCCGGC GAGGGCGAGG GCGATGCCAC CTACGGCAAG  1620
CTGACCCTGA AGTTCATCTG CACCACCGGC AAGCTGCCCG TGCCCTGGCC CACCCTCGTG  1680
ACCACCCTGA CCTACGGCGT GCAGTGCTTC AGCCGCTACC CCGACCACAT GAAGCAGCAC  1740
GACTTCTTCA AGTCCGCCAT GCCCGAAGGC TACGTCCAGG AGCGCACCAT CTTCTTCAAG  1800
```

-continued

```
GACGACGGCA ACTACAAGAC CCGCGCCGAG GTGAAGTTCG AGGGCGACAC CCTGGTGAAC  1860
CGCATCGAGC TGAAGGGCAT CGACTTCAAG GAGGACGGCA ACATCCTGGG GCACAAGCTG  1920
GAGTACAACT ACAACAGCCA CAACGTCTAT ATCATGGCCG ACAAGCAGAA GAACGGCATC  1980
AAGGTGAACT TCAAGATCCG CCACAACATC GAGGACGGCA GCGTGCAGCT CGCCGACCAC  2040
TACCAGCAGA ACACCCCCAT CGGCGACGGC CCCGTGCTGC TGCCCGACAA CCACTACCTG  2100
AGCACCCAGT CCGCCCTGAG CAAAGACCCC AACGAGAAGC GCGATCACAT GGTCCTGCTG  2160
GAGTTCGTGA CCGCCGCCGG GATCACTCTC GGCATGGACG AGCTGTACAA G           2211

SEQ ID NO: 31          moltype = AA  length = 266
FEATURE                Location/Qualifiers
REGION                 1..266
                       note = Synthetic construct
source                 1..266
                       mol_type = protein
                       organism = synthetic construct
SEQUENCE: 31
QAVVTQEPSL TVSPGGTVTL TCRSSTGAVT TSNYANWVQE KPDHLFTGLI GGTNKRAPGT  60
PARFSGSLLG GKAALTLSGA QPEDEAEYYC ALWYSNHWVF GGGTKLTVLG GGGSGGGGSG  120
GGGSGGGGSE VQLVESGGGL VQPGGSLRLS CAASGFTFSR YWMNWVRQAP GKGLEWVGEI  180
TPDSSTINYA PSLKGRFTIS RDNAKNSLYL QMNSLRAEDT AVYYCARPYD YGAWFASWGQ  240
GTLVTVSSGG GGSLKPTTTP APRPPT                                      266

SEQ ID NO: 32          moltype = AA  length = 271
FEATURE                Location/Qualifiers
REGION                 1..271
                       note = Synthetic construct
source                 1..271
                       mol_type = protein
                       organism = synthetic construct
SEQUENCE: 32
MLLLVTSLLL CELPHPAFLL IPAQAVVTQE PSLTVSPGGT VTLTCRSSTG AVTTSNYANW  60
VQEKPDHLFT GLIGGTNKRA PGTPARFSGS LLGGKAALTL SGAQPEDEAE YYCALWYSNH  120
WVFGGGTKLT VLGGGGSGGG GSGGGGSGGG GSEVQLVESG GGLVQPGGSL RLSCAASGFT  180
FSRYWMNWVR QAPGKGLEWV GEITPDSSTI NYAPSLKGRF TISRDNAKNS LYLQMNSLRA  240
EDTAVYYCAR PYDYGAWFAS WGQGTLVTVS S                                271

SEQ ID NO: 33          moltype = AA  length = 1428
FEATURE                Location/Qualifiers
REGION                 1..1428
                       note = Synthetic construct
source                 1..1428
                       mol_type = protein
                       organism = synthetic construct
SEQUENCE: 33
CAGGCCGTGG TGACCCAGGA GCCCAGCCTG ACCGTGAGCC CCGGCGGCAC CGTGACCCTG  60
ACCTGCAGGA GCAGCACCGG CGCCGTGACC ACCAGCAACT ACGCCAACTG GGTGCAGGAG  120
AAGCCCGACC ACCTGTTCAC CGGCCTGATC GGCGGCACCA ACAAGAGGGC CCCCGGCACC  180
CCCGCCAGGT TCAGCGGCAG CCTGCTGGGC GGCAAGGCCG CCCTGACCCT GAGCGGCGCC  240
CAGCCCGAGG ACGAGGCCGA GTACTACTGC GCCCTGTGGT ACAGCAACCA CTGGGTGTTC  300
GGCGGCGGCA CCAAGCTGAC CGTCCTAGGA GGGGGCGGAA GTGGTGGCGG GGGAAGCGGC  360
GGGGGTGGCA GCGGAGGGGG CGGATCTGAG GTGCAGCTGG TGGAGAGCGG CGGCGGCCTG  420
GTGCAGCCCG GCGGCAGCCT GAGGCTGAGC TGCGCCGCCA GCGGCTTCAC CTTCAGCAGG  480
TACTGGATGA ACTGGGTGAG GCAGGCCCCC GGCAAGGGCC TGGAGTGGGT GGGCGAGATC  540
ACCCCCGACA GCAGCACCAT CAACTACGCC CCCAGCCTGA AGGGCAGGTT CACCATCAGC  600
AGGGACAACG CCAAGAACAG CCTGTACCTG CAGATGAACA GCCTGAGGGC CGAGGACACC  660
GCCGTGTACT ACTGCGCCAG GCCCTACGAC TACGGCGCCT GGTTCGCCAG CTGGGGCCAG  720
GGCACCCTGG TGACCGTGAG CAGCGGAGGG GGCGGATCCT TGAAGCCCAC CACGACGCCA  780
GCGCCGCGAC CACCAACACC GGCGCCCACC ATCGCGTCGC AGCCCCTGTC CCTGCGCCCA  840
GAGGCGTGCC GGCCAGCGGC GGGGGGCGCA GTGCACACGA GGGGGCTGGA CTTCGCCTGT  900
GATATCTACA TCTGGGCGCC CCTGGCCGGG ACTTGTGGGG TCCTTCTCCT GTCACTGGTT  960
ATCACCAAAC GGGGCAGAAA GAAACTCCTG TATATATTCA AACAACCATT TATGAGACCA  1020
GTACAAACTA CTCAAGAGGA AGATGGCTGT AGCTGCCGAT TTCCAGAAGA AGAAGAAGGA  1080
GGATGTGAAC TGAGAGTGAA GTTCAGCAGG AGCGCAGACG CCCCCGCGTA CCAGCAGGGC  1140
CAGAACCAGC TCTATAACGA GCTCAATCTA GGACGAAGAG AGGAGTACGA TGTTTTGGAC  1200
AAGAGACGTG GCCGGGACCC TGAGATGGGG GGAAAGCCGA GAAGGAAGAA CCCTCAGGAA  1260
GGCCTGTACA ATGAACTGCA GAAAGATAAG ATGGCGGAGG CCTACAGTGA GATTGGGATG  1320
AAAGGCGAGC GCCGGAGGGG CAAGGGGCAC GATGGCCTTT ACCAGGGTCT CAGTACAGCC  1380
ACCAAGGACA CCTACGACGC CCTTCACATG CAGGCCCTGC CCCCTCGC              1428

SEQ ID NO: 34          moltype = AA  length = 2211
FEATURE                Location/Qualifiers
REGION                 1..2211
                       note = Synthetic construct
source                 1..2211
                       mol_type = protein
                       organism = synthetic construct
SEQUENCE: 34
CAGGCCGTGG TGACCCAGGA GCCCAGCCTG ACCGTGAGCC CCGGCGGCAC CGTGACCCTG  60
ACCTGCAGGA GCAGCACCGG CGCCGTGACC ACCAGCAACT ACGCCAACTG GGTGCAGGAG  120
```

-continued

```
AAGCCCGACC ACCTGTTCAC CGGCCTGATC GGCGGCACCA ACAAGAGGGC CCCCGGCACC  180
CCCGCCAGGT TCAGCGGCAG CCTGCTGGGC GGCAAGGCCG CCCTGACCCT GAGCGGCGCC  240
CAGCCCGAGG ACGAGGCCGA GTACTACTGC GCCCTGTGGT ACAGCAACCA CTGGGTGTTC  300
GGCGGCGGCA CCAAGCTGAC CGTCCTAGGA GGGGGCGGAA GTGGTGGCGG GGGAAGCGGC  360
GGGGGTGGCA GCGGAGGGGG CGGATCTGAG GTGCAGCTGG TGGAGAGCGG CGGCGGCCTG  420
GTGCAGCCCG GCGGCAGCCT GAGGCTGAGC TGCGCCGCCA GCGGCTTCAC CTTCAGCAGG  480
TACTGGATGA ACTGGGTGAG GCAGGCCCCC GGCAAGGGCC TGGAGTGGGT GGGCGAGATC  540
ACCCCCGACA GCAGCACCAT CAACTACGCC CCCAGCCTGA AGGGCAGGTT CACCATCAGC  600
AGGGACAACG CCAAGAACAG CCTGTACCTG CAGATGAACA GCCTGAGGGC CGAGGACACC  660
GCCGTGTACT ACTGCGCCAG GCCCTACGAC TACGGCGCCT GGTTCGCCAG CTGGGGCCAG  720
GGCACCCTGG TGACCGTGAG CAGCGGAGGG GGCGGATCCT TGAAGCCCAC CACGACGCCA  780
GCGCCGCGAC CACCAACACC GGCGCCCACC ATCGCGTCGC AGCCCCTGTC CCTGCGCCCA  840
GAGGCGTGCC GGCCAGCGGC GGGGGGCGCA GTGCACACGA GGGGGCTGGA CTTCGCCTGT  900
GATATCTACA TCTGGGCGCC CCTGGCCGGG ACTTGTGGGG TCCTTCTCCT GTCACTGGTT  960
ATCACCAAAC GGGGCAGAAA GAAACTCCTG TATATATTCA AACAACCATT TATGAGACCA  1020
GTACAAACTA CTCAAGAGGA AGATGGCTGT AGCTGCCGAT TTCCAGAAGA AGAAGAAGGA  1080
GGATGTGAAC TGAGAGTGAA GTTCAGCAGG AGCGCAGACG CCCCCGCGTA CCAGCAGGGC  1140
CAGAACCAGC TCTATAACGA GCTCAATCTA GGACGAAGAG AGGAGTACGA TGTTTTGGAC  1200
AAGAGACGTG GCCGGGACCC TGAGATGGGG GGAAAGCCGA GAAGGAAGAA CCCTCAGGAA  1260
GGCCTGTACA ATGAACTGCA GAAAGATAAG ATGGCGGAGG CCTACAGTGA GATTGGGATG  1320
AAAGGCGAGC GCCGGAGGGG CAAGGGGCAC GATGGCCTTT ACCAGGGTCT CAGTACAGCC  1380
ACCAAGGACA CCTACGACGC CCTTCACATG CAGGCCCTGC CCCCTCGCGA ATTCTCCGGA  1440
GAGGGCAGAG GAAGTCTTCT AACATGCGGT GACGTGGAGG AGAATCCCGG CCCTAGGGTG  1500
AGCAAGGGCG AGGAGCTGTT CACCGGGGTG GTGCCCATCC TGGTCGAGCT GGACGGCGAC  1560
GTAAACGGCC ACAAGTTCAG CGTGTCCGGC GAGGGCGAGG GCGATGCCAC CTACGGCAAG  1620
CTGACCCTGA AGTTCATCTG CACCACCGGC AAGCTGCCCG TGCCCTGGCC CACCCTCGTG  1680
ACCACCCTGA CCTACGGCGT GCAGTGCTTC AGCCGCTACC CCGACCACAT GAAGCAGCAC  1740
GACTTCTTCA AGTCCGCCAT GCCCGAAGGC TACGTCCAGG AGCGCACCAT CTTCTTCAAG  1800
GACGACGGCA ACTACAAGAC CCGCGCCGAG GTGAAGTTCG AGGGCGACAC CCTGGTGAAC  1860
CGCATCGAGC TGAAGGGCAT CGACTTCAAG GAGGACGGCA ACATCCTGGG GCACAAGCTG  1920
GAGTACAACT ACAACAGCCA CAACGTCTAT ATCATGGCCG ACAAGCAGAA GAACGGCATC  1980
AAGGTGAACT TCAAGATCCG CCACAACATC GAGGACGGCA GCGTGCAGCT CGCCGACCAC  2040
TACCAGCAGA ACACCCCCAT CGGCGACGGC CCCGTGCTGC TGCCCGACAA CCACTACCTG  2100
AGCACCCAGT CCGCCCTGAG CAAAGACCCC AACGAGAAGC GCGATCACAT GGTCCTGCTG  2160
GAGTTCGTGA CCGCCGCCGG GATCACTCTC GGCATGGACG AGCTGTACAA G           2211

SEQ ID NO: 35          moltype = AA  length = 17
FEATURE                Location/Qualifiers
REGION                 1..17
                       note = Synthetic construct
source                 1..17
                       mol_type = protein
                       organism = synthetic construct
SEQUENCE: 35
EITPDSSTIN YTPSLKD                                                 17

SEQ ID NO: 36          moltype = AA  length = 119
FEATURE                Location/Qualifiers
REGION                 1..119
                       note = Synthetic construct
source                 1..119
                       mol_type = protein
                       organism = synthetic construct
SEQUENCE: 36
EVKLLESGGG LVQPGGSLKL SCAASGFDFS RYWMNWVRQA PGKGLEWIGE ITPDSSTINY  60
TPSLKDKFII SRDNAKNTLY LQMIKVRSED TALYYCVRPY DYGAWFASWG QGTLVTVSA   119

SEQ ID NO: 37          moltype = AA  length = 109
FEATURE                Location/Qualifiers
REGION                 1..109
                       note = Synthetic construct
source                 1..109
                       mol_type = protein
                       organism = synthetic construct
SEQUENCE: 37
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNHWVF GGGTKLTVL             109

SEQ ID NO: 38          moltype = AA  length = 447
FEATURE                Location/Qualifiers
REGION                 1..447
                       note = Synthetic construct
source                 1..447
                       mol_type = protein
                       organism = synthetic construct
SEQUENCE: 38
EVKLLESGGG LVQPGGSLKL SCAASGFDFS RYWMNWVRQA PGKGLEWIGE ITPDSSTINY  60
TPSLKDKFII SRDNAKNTLY LQMIKVRSED TALYYCVRPY DYGAWFASWG QGTLVTVSAA  120
STKGPSVFPL APSSKSTSGG TAALGCLVKD YFPEPVTVSW NSGALTSGVH TFPAVLQSSG  180
```

```
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                     447

SEQ ID NO: 39          moltype = AA  length = 215
FEATURE                Location/Qualifiers
REGION                 1..215
                       note = Synthetic construct
source                 1..215
                       mol_type = protein
                       organism = synthetic construct
SEQUENCE: 39
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNHWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                            215

SEQ ID NO: 40          moltype = AA  length = 17
FEATURE                Location/Qualifiers
REGION                 1..17
                       note = Synthetic construct
source                 1..17
                       mol_type = protein
                       organism = synthetic construct
SEQUENCE: 40
EITPDSSTIN YTPSLKG                                                17

SEQ ID NO: 41          moltype = AA  length = 119
FEATURE                Location/Qualifiers
REGION                 1..119
                       note = Synthetic construct
source                 1..119
                       mol_type = protein
                       organism = synthetic construct
SEQUENCE: 41
EVQLVESGGG LVQPGGSLRL SCAASGFDFS RYWMNWVRQA PGKGLEWVGE ITPDSSTINY  60
TPSLKGRFTI SRDNAKNSLY LQMNSLRAED TAVYYCVRPY DYGAWFASWG QGTLVTVSS   119

SEQ ID NO: 42          moltype = AA  length = 447
FEATURE                Location/Qualifiers
REGION                 1..447
                       note = Synthetic construct
source                 1..447
                       mol_type = protein
                       organism = synthetic construct
SEQUENCE: 42
EVQLVESGGG LVQPGGSLRL SCAASGFDFS RYWMNWVRQA PGKGLEWVGE ITPDSSTINY  60
TPSLKGRFTI SRDNAKNSLY LQMNSLRAED TAVYYCVRPY DYGAWFASWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                     447

SEQ ID NO: 43          moltype = AA  length = 215
FEATURE                Location/Qualifiers
REGION                 1..215
                       note = Synthetic construct
source                 1..215
                       mol_type = protein
                       organism = synthetic construct
SEQUENCE: 43
QAVVTQEPSL TVSPGGTVTL TCRSSTGAVT TSNYANWVQE KPDHLFTGLI GGTNKRAPGT  60
PARFSGSLLG GKAALTLSGA QPEDEAEYYC ALWYSNHWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                            215

SEQ ID NO: 44          moltype = AA  length = 119
FEATURE                Location/Qualifiers
REGION                 1..119
                       note = Synthetic construct
source                 1..119
                       mol_type = protein
                       organism = synthetic construct
SEQUENCE: 44
EVQLVESGGG LVQPGGSLRL SCAASGFDFS RYWMNWVRQA PGKGLEWVGE ITPDSSTINY  60
```

```
APSLKGRFTI SRDNAKNSLY LQMNSLRAED TAVYYCVRPY DYGAWFASWG QGTLVTVSS   119

SEQ ID NO: 45          moltype = AA  length = 447
FEATURE                Location/Qualifiers
REGION                 1..447
                       note = Synthetic construct
source                 1..447
                       mol_type = protein
                       organism = synthetic construct
SEQUENCE: 45
EVQLVESGGG LVQPGGSLRL SCAASGFDFS RYWMNWVRQA PGKGLEWVGE ITPDSSTINY  60
APSLKGRFTI SRDNAKNSLY LQMNSLRAED TAVYYCVRPY DYGAWFASWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                      447

SEQ ID NO: 46          moltype = AA  length = 447
FEATURE                Location/Qualifiers
REGION                 1..447
                       note = Synthetic construct
source                 1..447
                       mol_type = protein
                       organism = synthetic construct
SEQUENCE: 46
EVQLVESGGG LVQPGGSLRL SCAASGFTFS RYWMNWVRQA PGKGLEWVGE ITPDSSTINY  60
APSLKGRFTI SRDNAKNSLY LQMNSLRAED TAVYYCARPY DYGAWFASWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                      447

SEQ ID NO: 47          moltype = AA  length = 17
FEATURE                Location/Qualifiers
REGION                 1..17
                       note = Synthetic construct
source                 1..17
                       mol_type = protein
                       organism = synthetic construct
SEQUENCE: 47
EITPDSSTIN YADSVKG                                                 17

SEQ ID NO: 48          moltype = AA  length = 119
FEATURE                Location/Qualifiers
REGION                 1..119
                       note = Synthetic construct
source                 1..119
                       mol_type = protein
                       organism = synthetic construct
SEQUENCE: 48
EVQLVESGGG LVQPGGSLRL SCAASGFDFS RYWMNWVRQA PGKGLEWVSE ITPDSSTINY  60
ADSVKGRFTI SRDNAKNSLY LQMNSLRAED TAVYYCARPY DYGAWFASWG QGTLVTVSS   119

SEQ ID NO: 49          moltype = AA  length = 447
FEATURE                Location/Qualifiers
REGION                 1..447
                       note = Synthetic construct
source                 1..447
                       mol_type = protein
                       organism = synthetic construct
SEQUENCE: 49
EVQLVESGGG LVQPGGSLRL SCAASGFDFS RYWMNWVRQA PGKGLEWVSE ITPDSSTINY  60
ADSVKGRFTI SRDNAKNSLY LQMNSLRAED TAVYYCARPY DYGAWFASWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                      447

SEQ ID NO: 50          moltype = AA  length = 109
FEATURE                Location/Qualifiers
REGION                 1..109
                       note = Synthetic construct
source                 1..109
```

```
                        mol_type = protein
                        organism = synthetic construct
SEQUENCE: 50
QAVVTQEPSL TVSPGGTVTL TCRSSTGAVT TSNYANWFQQ KPGQAFTGLI GGTNKRAPGT  60
PARFSGSLLG GKAALTLSGA QPEDEAEYYC ALWYSNHWVF GGGTKLTVL              109

SEQ ID NO: 51           moltype = AA  length = 215
FEATURE                 Location/Qualifiers
REGION                  1..215
                        note = Synthetic construct
source                  1..215
                        mol_type = protein
                        organism = synthetic construct
SEQUENCE: 51
QAVVTQEPSL TVSPGGTVTL TCRSSTGAVT TSNYANWFQQ KPGQAFTGLI GGTNKRAPGT  60
PARFSGSLLG GKAALTLSGA QPEDEAEYYC ALWYSNHWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215

SEQ ID NO: 52           moltype = AA  length = 14
FEATURE                 Location/Qualifiers
REGION                  1..14
                        note = Synthetic construct
source                  1..14
                        mol_type = protein
                        organism = synthetic construct
SEQUENCE: 52
GSSTGAVTTS NYAN                                                    14

SEQ ID NO: 53           moltype = AA  length = 109
FEATURE                 Location/Qualifiers
REGION                  1..109
                        note = Synthetic construct
source                  1..109
                        mol_type = protein
                        organism = synthetic construct
SEQUENCE: 53
QAVVTQEPSL TVSPGGTVTL TCGSSTGAVT TSNYANWFQQ KPGQAPRTLI GGTNKRAPGT  60
PARFSGSLLG GKAALTLSGA QPEDEAEYYC ALWYSNHWVF GGGTKLTVL              109

SEQ ID NO: 54           moltype = AA  length = 215
FEATURE                 Location/Qualifiers
REGION                  1..215
                        note = Synthetic construct
source                  1..215
                        mol_type = protein
                        organism = synthetic construct
SEQUENCE: 54
QAVVTQEPSL TVSPGGTVTL TCGSSTGAVT TSNYANWFQQ KPGQAPRTLI GGTNKRAPGT  60
PARFSGSLLG GKAALTLSGA QPEDEAEYYC ALWYSNHWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215

SEQ ID NO: 55           moltype = AA  length = 230
FEATURE                 Location/Qualifiers
REGION                  1..230
                        note = Synthetic construct
source                  1..230
                        mol_type = protein
                        organism = synthetic construct
SEQUENCE: 55
EPKSCDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALGAPIEKT  120
ISKAKGQPRE PQVCTLPPSR DELTKNQVSL SCAVKGFYPS DIAVEWESNG QPENNYKTTP  180
PVLDSDGSFF LVSKLTVDKS RWQQGNVFSC SVMHEALHNH YTQKSLSLSP             230

SEQ ID NO: 56           moltype = AA  length = 780
FEATURE                 Location/Qualifiers
source                  1..780
                        mol_type = protein
                        organism = Homo sapiens
SEQUENCE: 56
ATGGCGCGCC CGCATCCGTG GTGGCTGTGC GTGCTGGGCA CCCTGGTGGG CCTGAGCGCG  60
ACCCCGGCGC CGAAAAGCTG CCCGGAACGC CATTATTGGG CGCAGGGCAA ACTGTGCTGC  120
CAGATGTGCG AACCGGGCAC CTTTCTGGTG AAAGATTGCG ATCAGCATCG CAAAGCGGCG  180
CAGTGCGATC CGTGCATTCC GGGCGTGAGC TTTAGCCCGG ATCATCATAC CCGCCCGCAT  240
TGCGAAAGCT GCCGCCATTG CAACAGCGGC CTGCTGGTGC GCAACTGCAC CATTACCGCG  300
AACGCGGAAT GCGCGTGCCG CAACGGCTGG CAGTGCCGCG ATAAAGAATG CACCGAATGC  360
GATCCGCTGC CGAACCCGAG CCTGACCGCG CGCAGCAGCC AGGCGCTGAG CCCGCATCCG  420
```

```
CAGCCGACCC ATCTGCCGTA TGTGAGCGAA ATGCTGGAAG CGCGCACCGC GGGCCATATG  480
CAGACCCTGG CGGATTTTCG CCAGCTGCCG GCGCGCACCC TGAGCACCCA TTGGCCGCCG  540
CAGCGCAGCC TGTGCAGCAG CGATTTTATT CGCATTCTGG TGATTTTTAG CGGCATGTTT  600
CTGGTGTTTA CCCTGGCGGG CGCGCTGTTT CTGCATCAGC GCCGCAAATA TCGCAGCAAC  660
AAAGGCGAAA GCCCGGTGGA ACCGGCGGAA CCGTGCCATT ATAGCTGCCC GCGCGAAGAA  720
GAAGGCAGCA CCATTCCGAT TCAGGAAGAT TATCGCAAAC CGGAACCGGC GTGCAGCCCG  780

SEQ ID NO: 57          moltype = AA  length = 260
FEATURE                Location/Qualifiers
source                 1..260
                       mol_type = protein
                       organism = Homo sapiens
SEQUENCE: 57
MARPHPWWLC VLGTLVGLSA TPAPKSCPER HYWAQGKLCC QMCEPGTFLV KDCDQHRKAA  60
QCDPCIPGVS FSPDHHTRPH CESCRHCNSG LLVRNCTITA NAECACRNGW QCRDKECTEC  120
DPLPNPSLTA RSSQALSPHP QPTHLPYVSE MLEARTAGHM QTLADFRQLP ARTLSTHWPP  180
QRSLCSSDFI RILVIFSGMF LVFTLAGALF LHQRRKYRSN KGESPVEPAE PCHYSCPREE  240
EGSTIPIQED YRKPEPACSP                                            260

SEQ ID NO: 58          moltype = AA  length = 750
FEATURE                Location/Qualifiers
source                 1..750
                       mol_type = protein
                       organism = Mus musculus
SEQUENCE: 58
ATGGCGTGGC CGCCGCCGTA TTGGCTGTGC ATGCTGGGCA CCCTGGTGGG CCTGAGCGCG  60
ACCCTGGCGC CGAACAGCTG CCCGGATAAA CATTATTGGA CCGGCGGCGG CCTGTGCTGC  120
CGCATGTGCG AACCGGGCAC CTTTTTTGTG AAAGATTGCG AACAGGATCG CACCGCGGCG  180
CAGTGCGATC CGTGCATTCC GGGCACCAGC TTTAGCCCGG ATTATCATAC CCGCCCGCAT  240
TGCGAAAGCT GCCGCCATTG CAACAGCGGC TTTCTGATTC GCAACTGCAC CGTGACCGCG  300
AACGCGGAAT GCAGCTGCAG CAAAAACTGG CAGTGCCGCG ATCAGGAATG CACCGAATGC  360
GATCCGCCGC TGAACCCGGC GCTGACCCGC CAGCCGAGCG AAACCCCGAG CCCGCAGCCG  420
CCGCCGACCC ATCTGCCGCA TGGCACCGAA AAACCGAGCT GGCCGCTGCA TCGCCAGCTG  480
CCGAACAGCA CCGTGTATAG CCAGCGCAGC AGCCATCGCC CGCTGTGCAG CAGCGATTGC  540
ATTCGCATTT TTGTGACCTT TAGCAGCATG TTTCTGATTT TTGTGCTGGG CGCGATTCTG  600
TTTTTTCATC AGCGCCGCAA CCATGGCCCG AACGAAGATC GCCAGGCGGT GCCGGAAGAA  660
CCGTGCCCGT ATAGCTGCCC GCGCGAAGAA GAAGGCAGCG CGATTCCGAT TCAGGAAGAT  720
TATCGCAAAC CGGAACCGGC GTTTTATCCG                                 750

SEQ ID NO: 59          moltype = AA  length = 250
FEATURE                Location/Qualifiers
source                 1..250
                       mol_type = protein
                       organism = Mus musculus
SEQUENCE: 59
MAWPPPYWLC MLGTLVGLSA TLAPNSCPDK HYWTGGGLCC RMCEPGTFFV KDCEQDRTAA  60
QCDPCIPGTS FSPDYHTRPH CESCRHCNSG FLIRNCTVTA NAECSCSKNW QCRDQECTEC  120
DPPLNPALTR QPSETPSPQP PPTHLPHGTE KPSWPLHRQL PNSTVYSQRS SHRPLCSSDC  180
IRIFVTFSSM FLIFVLGAIL FFHQRRNHGP NEDRQAVPEE PCPYSCPREE EGSAIPIQED  240
YRKPEPAFYP                                                       250

SEQ ID NO: 60          moltype = AA  length = 660
FEATURE                Location/Qualifiers
source                 1..660
                       mol_type = protein
                       organism = Homo sapiens
SEQUENCE: 60
ATGCTGCGCC TGCTGCTGGC GCTGAACCTG TTTCCGAGCA TTCAGGTGAC CGGCAACAAA  60
ATTCTGGTGA AACAGAGCCC GATGCTGGTG GCGTATGATA ACGCGGTGAA CCTGAGCTGC  120
AAATATAGCT ATAACCTGTT TAGCCGCGAA TTTCGCGCGA GCCTGCATAA AGGCCTGGAT  180
AGCGCGGTGG AAGTGTGCGT GGTGTATGGC AACTATAGCC AGCAGCTGCA GGTGTATAGC  240
AAAACCGGCT TTAACTGCGA TGGCAAACTG GGCAACGAAA GCGTGACCTT TTATCTGCAG  300
AACCTGTATG TGAACCAGAC CGATATTTAT TTTTGCAAAA TTGAAGTGAT GTATCCGCCG  360
CCGTATCTGG ATAACGAAAA AAGCAACGGC ACCATTATTC ATGTGAAAGG CAAACATCTG  420
TGCCCGAGCC CGCTGTTTCC GGGCCCGAGC AAACCGTTTT GGGTGCTGGT GGTGGTGGGC  480
GGCGTGCTGG CGTGCTATAG CCTGCTGGTG ACCGTGGCGT TTATTATTTT TTGGGTGCGC  540
AGCAAACGCA GCCGCCTGCT GCATAGCGAT TATATGAACA TGACCCCGCG CCGCCCGGGC  600
CCGACCCGCA AACATTATCA GCCGTATGCG CCGCCGCGCG ATTTTGCGGC GTATCGCAGC  660

SEQ ID NO: 61          moltype = AA  length = 220
FEATURE                Location/Qualifiers
source                 1..220
                       mol_type = protein
                       organism = Homo sapiens
SEQUENCE: 61
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                      220
```

```
SEQ ID NO: 62          moltype = AA  length = 654
FEATURE                Location/Qualifiers
source                 1..654
                       mol_type = protein
                       organism = Mus musculus
SEQUENCE: 62
ATGACCCTGC GCCTGCTGTT TCTGGCGCTG AACTTTTTTA GCGTGCAGGT GACCGAAAAC  60
AAAATTCTGG TGAAACAGAG CCCGCTGCTG GTGGTGGATA GCAACGAAGT GAGCCTGAGC  120
TGCCGCTATA GCTATAACCT GCTGGCGAAA GAATTTCGCG CGAGCCTGTA TAAAGGCGTG  180
AACAGCGATG TGGAAGTGTG CGTGGGCAAC GGCAACTTTA CCTATCAGCC GCAGTTTCGC  240
AGCAACGCGG AATTTAACTG CGATGGCGAT TTTGATAACG AAACCGTGAC CTTTCGCCTG  300
TGGAACCTGC ATGTGAACCA TACCGATATT TATTTTTGCA AAATTGAATT TATGTATCCG  360
CCGCCGTATC TGGATAACGA ACGCAGCAAC GGCACCATTA TTCATATTAA AGAAAAACAT  420
CTGTGCCATA CCCAGAGCAG CCCGAAACTG TTTTGGGCGC TGGTGGTGGT GGCGGGCGTG  480
CTGTTTTGCT ATGGCCTGCT GGTGACCGTG GCGCTGTGCG TGATTTGGAC CAACAGCCGC  540
CGCAACCGCC TGCTGCAGAG CGATTATATG AACATGACCC CGCGCCGCCC GGGCCTGACC  600
CGCAAACCGT ATCAGCCGTA TGCGCCGGCG CGCGATTTTG CGGCGTATCG CCCG        654

SEQ ID NO: 63          moltype = AA  length = 218
FEATURE                Location/Qualifiers
source                 1..218
                       mol_type = protein
                       organism = Mus musculus
SEQUENCE: 63
MTLRLLFLAL NFFSVQVTEN KILVKQSPLL VVDSNEVSLS CRYSYNLLAK EFRASLYKGV  60
NSDVEVCVGN GNFTYQPQFR SNAEFNCDGD FDNETVTFRL WNLHVNHTDI YFCKIEFMYP  120
PPYLDNERSN GTIIHIKEKH LCHTQSSPKL FWALVVVAGV LFCYGLLVTV ALCVIWTNSR  180
RNRLLQSDYM NMTPRRPGLT RKPYQPYAPA RDFAAYRP                         218

SEQ ID NO: 64          moltype = AA  length = 768
FEATURE                Location/Qualifiers
source                 1..768
                       mol_type = protein
                       organism = Homo sapiens
SEQUENCE: 64
ATGGGAAACA GCTGTTACAA CATAGTAGCC ACTCTGTTGC TGGTCCTCAA CTTTGAGAGG  60
ACAAGATCAT TGCAGGATCC TTGTAGTAAC TGCCCAGCTG GTACATTCTG TGATAATAAC  120
AGGAATCAGA TTTGCAGTCC CTGTCCTCCA AATAGTTTCT CCAGCGCAGG TGGACAAAGG  180
ACCTGTGACA TATGCAGGCA GTGTAAAGGT GTTTTCAGGA CCAGGAAGGA GTGTTCCTCC  240
ACCAGCAATG CAGAGTGTGA CTGCACTCCA GGGTTTCACT GCCTGGGGGC AGGATGCAGC  300
ATGTGTGAAC AGGATTGTAA ACAAGGTCAA GAACTGACAA AAAAAGGTTG TAAAGACTGT  360
TGCTTTGGGA CATTTAACGA TCAGAAACGT GGCATCTGTC GACCCTGGAC AAACTGTTCT  420
TTGGATGGAA AGTCTGTGCT TGTGAATGGG ACGAAGGAGA GGGACGTGGT CTGTGGACCA  480
TCTCCAGCCG ACCTCTCTCC GGGAGCATCC TCTGTGACCC CGCCTGCCCC TGCGAGAGAG  540
CCAGGACACT CTCCGCAGAT CATCTCCTTC TTTCTTGCGC TGACGTCGAC TGCGTTGCTC  600
TTCCTGCTGT TCTTCCTCAC GCTCCGTTTC TCTGTTGTTA AACGGGGCAG AAAGAAACTC  660
CTGTATATAT TCAAACAACC ATTTATGAGA CCAGTACAAA CTACTCAAGA GGAAGATGGC  720
TGTAGCTGCC GATTTCCAGA AGAAGAAGAA GGAGGATGTG AACTGTGA               768

SEQ ID NO: 65          moltype = AA  length = 255
FEATURE                Location/Qualifiers
source                 1..255
                       mol_type = protein
                       organism = Homo sapiens
SEQUENCE: 65
MGNSCYNIVA TLLLVLNFER TRSLQDPCSN CPAGTFCDNN RNQICSPCPP NSFSSAGGQR  60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                  255

SEQ ID NO: 66          moltype = AA  length = 768
FEATURE                Location/Qualifiers
source                 1..768
                       mol_type = protein
                       organism = Mus musculus
SEQUENCE: 66
ATGGGCAACA ACTGCTATAA CGTGGTGGTG ATTGTGCTGC TGCTGGTGGG CTGCGAAAAA  60
GTGGGCGCGG TGCAGAACAG CTGCGATAAC TGCCAGCCGG GCACCTTTTG CCGCAAATAT  120
AACCCGGTGT GCAAAAGCTG CCCGCCGAGC ACCTTTAGCA GCATTGGCGG CCAGCCGAAC  180
TGCAACATTT GCCGCGTGTG CGCGGGCTAT TTTCGCTTTA AAAAATTTTG CAGCAGCACC  240
CATAACGCGG AATGCGAATG CATTGAAGGC TTTCATTGCC TGGGCCCGCA GTGCACCCGC  300
TGCGAAAAAG ATTGCCGCCC GGGCCAGGAA CTGACCAAAC AGGGCTGCAA AACCTGCAGC  360
CTGGGCACCT TTAACGATCA GAACGGCACC GGCGTGTGCC GCCCGTGGAC CAACTGCAGC  420
CTGGATGGCC GCAGCGTGCT GAAAACCGGC ACCACCGAAA AAGATGTGGT GTGCGGCCCG  480
CCGGTGGTGA GCTTTAGCCC GAGCACCACC ATTAGCGTGA CCCCGGAAGG CGGCCCGGGC  540
GGCCATAGCC TGCAGGTGCT GACCCTGTTT CTGGCGCTGA CCAGCGCGCT GCTGCTGGCG  600
CTGATTTTTA TTACCCTGCT GTTTAGCGTG CTGAAATGGA TTCGCAAAAA ATTTCCGCAT  660
```

```
ATTTTTAAAC AGCCGTTTAA AAAAACCACC GGCGCGGCGC AGGAAGAAGA TGCGTGCAGC  720
TGCCGCTGCC CGCAGGAAGA AGAAGGCGGC GGCGGCGGCT ATGAACTG              768

SEQ ID NO: 67          moltype = AA  length = 256
FEATURE                Location/Qualifiers
source                 1..256
                       mol_type = protein
                       organism = Mus musculus
SEQUENCE: 67
MGNNCYNVVV IVLLLVGCEK VGAVQNSCDN CQPGTFCRKY NPVCKSCPPS TFSSIGGQPN  60
CNICRVCAGY FRFKKFCSST HNAECECIEG FHCLGPQCTR CEKDCRPGQE LTKQGCKTCS  120
LGTFNDQNGT GVCRPWTNCS LDGRSVLKTG TTEKDVVCGP PVVSFSPSTT ISVTPEGGPG  180
GHSLQVLTLF LALTSALLLA LIFITLLFSV LKWIRKKFPH IFKQPFKKTT GAAQEEDACS  240
CRCPQEEEGG GGGYEL                                                256

SEQ ID NO: 68          moltype = AA  length = 831
FEATURE                Location/Qualifiers
source                 1..831
                       mol_type = protein
                       organism = Homo sapiens
SEQUENCE: 68
ATGTGCGTGG GCGCGCGCCG CCTGGGCCGC GGCCCGTGCG CGGCGCTGCT GCTGCTGGGC  60
CTGGGCCTGA GCACCGTGAC CGGCCTGCAT TGCGTGGGCG ATACCTATCC GAGCAACGAT  120
CGCTGCTGCC ATGAATGCCG CCCGGGCAAC GGCATGGTGA GCCGCTGCAG CCGCAGCCAG  180
AACACCGTGT GCCGCCCGTG CGGCCCGGGC TTTTATAACG ATGTGGTGAG CAGCAAACCG  240
TGCAAACCGT GCACCTGGTG CAACCTGCGC AGCGGCAGCG AACGCAAACA GCTGTGCACC  300
GCGACCCAGG ATACCGTGTG CCGCTGCCGC GCGGGCACCC AGCCGCTGGA TAGCTATAAA  360
CCGGGCGTGG ATTGCGCGCC GTGCCCGCCG GGCCATTTTA GCCCGGGCGA TAACCAGGCG  420
TGCAAACCGT GGACCAACTG CACCCTGGCG GGCAAACATA CCCTGCAGCC GGCGAGCAAC  480
AGCAGCGATG CGATTTGCGA AGATCGCGAT CCGCCGGCGA CCCAGCCGCA GGAAACCCAG  540
GGCCCGCCGG CGCGCCCGAT TACCGTGCAG CCGACCGAAG CGTGGCCGCG CACCAGCCAG  600
GGCCCGAGCA CCCGCCCGGT GGAAGTGCCG GGCGGCCGCG CGGTGGCGGC GATTCTGGGC  660
CTGGGCCTGG TGCTGGGCCT GCTGGGCCCG CTGGCGATTC TGCTGGCGCT GTATCTGCTG  720
CGCCGCGATC AGCGCCTGCC GCCGGATGCG CATAAACCGC CGGGCGGCGG CAGCTTTCGC  780
ACCCCGATTC AGGAAGAACA GGCGGATGCG CATAGCACCC TGGCGAAAAT T          831

SEQ ID NO: 69          moltype = AA  length = 277
FEATURE                Location/Qualifiers
source                 1..277
                       mol_type = protein
                       organism = Homo sapiens
SEQUENCE: 69
MCVGARRLGR GPCAALLLLG LGLSTVTGLH CVGDTYPSND RCCHECRPGN GMVSRCSRSQ  60
NTVCRPCGPG FYNDVVSSKP CKPCTWCNLR SGSERKQLCT ATQDTVCRCR AGTQPLDSYK  120
PGVDCAPCPP GHFSPGDNQA CKPWTNCTLA GKHTLQPASN SSDAICEDRD PPATQPQETQ  180
GPPARPITVQ PTEAWPRTSQ GPSTRPVEVP GGRAVAAILG LGLVLGLLGP LAILLALYLL  240
RRDQRLPPDA HKPPGGGSFR TPIQEEQADA HSTLAKI                         277

SEQ ID NO: 70          moltype = AA  length = 816
FEATURE                Location/Qualifiers
source                 1..816
                       mol_type = protein
                       organism = Mus musculus
SEQUENCE: 70
ATGTATGTGT GGGTGCAGCA GCCGACCGCG CTGCTGCTGC TGGCGCTGAC CCTGGGCGTG  60
ACCGCGCGCC GCCTGAACTG CGTGAAACAT ACCTATCCGA GCGGCCATAA ATGCTGCCGC  120
GAATGCCAGC CGGGCCATGG CATGGTGAGC CGCTGCGATC ATACCCGCGA TACCCTGTGC  180
CATCCGTGCG AAACCGGCTT TTATAACGAA GCGGTGAACT ATGATACCTG CAAACAGTGC  240
ACCCAGTGCA ACCATCGCAG CGGCAGCGAA CTGAAACAGA ACTGCACCCC GACCCAGGAT  300
ACCGTGTGCC GCTGCCGCCC GGGCACCCAG CCGCGCCAGG ATAGCGGCTA TAAACTGGGC  360
GTGGATTGCG TGCCGTGCCC GCCGGGCCAT TTTAGCCCGG GCAACAACCA GGCGTGCAAA  420
CCGTGGACCA ACTGCACCCT GAGCGGCAAA CAGACCCGCC ATCCGGCGAG CGATAGCCTG  480
GATGCGGTGT GCGAAGATCG CAGCCTGCTG GCGACCCTGC TGTGGGAAAC CCAGCGCCCG  540
ACCTTTCGCC CGACCACCGT GCAGAGCACC ACCGTGTGGC CGCGCACCAG CGAACTGCCG  600
AGCCCGCCGA CCCTGGTGAC CCCGGAAGGC CCGGCGTTTG CGGTGCTGCT GGGCCTGGGC  660
CTGGGCCTGC TGGCGCCGCT GACCGTGCTG CTGGCGCTGT ATCTGCTGCG CAAAGCGTGG  720
CGCCTGCCGA ACACCCCGAA ACCGTGCTGG GGCAACAGCT TTCGCACCCC GATTCAGGAA  780
GAACATACCG ATGCGCATTT TACCCTGGCG AAAATT                           816

SEQ ID NO: 71          moltype = AA  length = 272
FEATURE                Location/Qualifiers
source                 1..272
                       mol_type = protein
                       organism = Mus musculus
SEQUENCE: 71
MYVWVQQPTA LLLLALTLGV TARRLNCVKH TYPSGHKCCR ECQPGHGMVS RCDHTRDTLC  60
HPCETGFYNE AVNYDTCKQC TQCNHRSGSE LKQNCTPTQD TVCRCRPGTQ PRQDSGYKLG  120
VDCVPCPPGH FSPGNNQACK PWTNCTLSGK QTRHPASDSL DAVCEDRSLL ATLLWETQRP  180
TFRPTTVQST TVWPRTSELP SPPTLVTPEG PAFAVLLGLG LGLLAPLTVL LALYLLRKAW  240
```

```
RLPNTPKPCW GNSFRTPIQE EHTDAHFTLA KI                            272

SEQ ID NO: 72          moltype = AA  length = 597
FEATURE                Location/Qualifiers
source                 1..597
                       mol_type = protein
                       organism = Homo sapiens
SEQUENCE: 72
ATGAAAAGCG GCCTGTGGTA TTTTTTTCTG TTTTGCCTGC GCATTAAAGT GCTGACCGGC  60
GAAATTAACG GCAGCGCGAA CTATGAAATG TTTATTTTTC ATAACGGCGG CGTGCAGATT  120
CTGTGCAAAT ATCCGGATAT TGTGCAGCAG TTTAAAATGC AGCTGCTGAA AGGCGGCCAG  180
ATTCTGTGCG ATCTGACCAA AACCAAAGGC AGCGGCAACA CCGTGAGCAT TAAAAGCCTG  240
AAATTTTGCC ATAGCCAGCT GAGCAACAAC AGCGTGAGCT TTTTTCTGTA TAACCTGGAT  300
CATAGCCATG CGAACTATTA TTTTTGCAAC CTGAGCATTT TTGATCCGCC GCCGTTTAAA  360
GTGACCCTGA CCGGCGGCTA TCTGCATATT TATGAAAGCC AGCTGTGCTG CCAGCTGAAA  420
TTTTGGCTGC CGATTGGCTG CGCGGCGTTT GTGGTGGTGT GCATTCTGGG CTGCATTCTG  480
ATTTGCTGGC TGACCAAAAA AAAATATAGC AGCAGCGTGC ATGATCCGAA CGGCGAATAT  540
ATGTTTATGC GCGCGGTGAA CACCGCGAAA AAAAGCCGCC TGACCGATGT GACCCTG     597

SEQ ID NO: 73          moltype = AA  length = 199
FEATURE                Location/Qualifiers
source                 1..199
                       mol_type = protein
                       organism = Homo sapiens
SEQUENCE: 73
MKSGLWYFFL FCLRIKVLTG EINGSANYEM FIFHNGGVQI LCKYPDIVQQ FKMQLLKGGQ  60
ILCDLTKTKG SGNTVSIKSL KFCHSQLSNN SVSFFLYNLD HSHANYYFCN LSIFDPPPFK  120
VTLTGGYLHI YESQLCCQLK FWLPIGCAAF VVVCILGCIL ICWLTKKKYS SSVHDPNGEY  180
MFMRAVNTAK KSRLTDVTL                                           199

SEQ ID NO: 74          moltype = AA  length = 600
FEATURE                Location/Qualifiers
source                 1..600
                       mol_type = protein
                       organism = Mus musculus
SEQUENCE: 74
ATGAAACCGT ATTTTTGCCG CGTGTTTGTG TTTTGCTTTC TGATTCGCCT GCTGACCGGC  60
GAAATTAACG GCAGCGCGGA TCATCGCATG TTTAGCTTTC ATAACGGCGG CGTGCAGATT  120
AGCTGCAAAT ATCCGGAAAC CGTGCAGCAG CTGAAAATGC GCCTGTTTCG CGAACGCGAA  180
GTGCTGTGCG AACTGACCAA AACCAAAGGC AGCGGCAACG CGGTGAGCAT TAAAAACCCG  240
ATGCTGTGCC TGTATCATCT GAGCAACAAC AGCGTGAGCT TTTTTCTGAA CAACCCGGAT  300
AGCAGCCAGG GCAGCTATTA TTTTTGCAGC CTGAGCATTT TTGATCCGCC GCCGTTTCAG  360
GAACGCAACC TGAGCGGCGG CTATCTGCAT ATTTATGAAA GCCAGCTGTG CTGCCAGCTG  420
AAACTGTGGC TGCCGGTGGG CTGCGCGGCG TTTGTGGTGG TGCTGCTGTT TGGCTGCATT  480
CTGATTATTT GGTTTAGCAA AAAAAAATAT GGCAGCAGCG TGCATGATCC GAACAGCGAA  540
TATATGTTTA TGGCGGCGGT GAACACCAAC AAAAAAAGCC GCCTGGCGGG CGTGACCAGC  600

SEQ ID NO: 75          moltype = AA  length = 200
FEATURE                Location/Qualifiers
source                 1..200
                       mol_type = protein
                       organism = Mus musculus
SEQUENCE: 75
MKPYFCRVFV FCFLIRLLTG EINGSADHRM FSFHNGGVQI SCKYPETVQQ LKMRLFRERE  60
VLCELTKTKG SGNAVSIKNP MLCLYHLSNN SVSFFLNNPD SSQGSYYFCS LSIFDPPPFQ  120
ERNLSGGYLH IYESQLCCQL KLWLPVGCAA FVVVLLFGCI LIIWFSKKKY GSSVHDPNSE  180
YMFMAAVNTN KKSRLAGVTS                                          200

SEQ ID NO: 76          moltype = AA  length = 279
FEATURE                Location/Qualifiers
source                 1..279
                       mol_type = protein
                       organism = Homo sapiens
SEQUENCE: 76
ATGATTCATC TGGGCCATAT TCTGTTTCTG CTGCTGCTGC CGGTGGCGGC GGCGCAGACC  60
ACCCCGGGCG AACGCAGCAG CCTGCCGGCG TTTTATCCGG GCACCAGCGG CAGCTGCAGC  120
GGCTGCGGCA GCCTGAGCCT GCCGCTGCTG GCGGGCCTGG TGGCGGCGGA TGCGGTGGCG  180
AGCCTGCTGA TTGTGGGCGC GGTGTTTCTG TGCGCGCGCC CGCGCCGCAG CCCGGCGCAG  240
GAAGATGGCA AAGTGTATAT TAACATGCCG GGCCGCGGC                     279

SEQ ID NO: 77          moltype = AA  length = 93
FEATURE                Location/Qualifiers
source                 1..93
                       mol_type = protein
                       organism = Homo sapiens
SEQUENCE: 77
MIHLGHILFL LLLPVAAAQT TPGERSSLPA FYPGTSGSCS GCGSLSLPLL AGLVAADAVA  60
SLLIVGAVFL CARPRRSPAQ EDGKVYINMP GRG                           93
```

```
SEQ ID NO: 78          moltype = AA  length = 237
FEATURE                Location/Qualifiers
source                 1..237
                       mol_type = protein
                       organism = Mus musculus
SEQUENCE: 78
ATGGATCCGC CGGGCTATCT GCTGTTTCTG CTGCTGCTGC CGGTGGCGGC GAGCCAGACC  60
AGCGCGGGCA GCTGCAGCGG CTGCGGCACC CTGAGCCTGC CGCTGCTGGC GGGCCTGGTG  120
GCGGCGGATG CGGTGATGAG CCTGCTGATT GTGGGCGTGG TGTTTGTGTG CATGCGCCCG  180
CATGGCCGCC CGGCGCAGGA AGATGGCCGC GTGTATATTA ACATGCCGGG CCGCGGC     237

SEQ ID NO: 79          moltype = AA  length = 79
FEATURE                Location/Qualifiers
source                 1..79
                       mol_type = protein
                       organism = Mus musculus
SEQUENCE: 79
MDPPGYLLFL LLLPVAASQT SAGSCSGCGT LSLPLLAGLV AADAVMSLLI VGVVFVCMRP  60
HGRPAQEDGR VYINMPGRG                                               79

SEQ ID NO: 80          moltype = AA  length = 342
FEATURE                Location/Qualifiers
source                 1..342
                       mol_type = protein
                       organism = Homo sapiens
SEQUENCE: 80
ATGGGGGGAC TTGAACCCTG CAGCAGGCTC CTGCTCCTGC CTCTCCTGCT GGCTGTAAGT  60
GGTCTCCGTC CTGTCCAGGC CCAGGCCCAG AGCGATTGCA GTTGCTCTAC GGTGAGCCCG  120
GGCGTGCTGG CAGGGATCGT GATGGGAGAC CTGGTGCTGA CAGTGCTCAT TGCCCTGGCC  180
GTGTACTTCC TGGGCCGGCT GGTCCCTCGG GGGCGAGGGG CTGCGGAGGC AGCGACCCGG  240
AAACAGCGTA TCACTGAGAC CGAGTCGCCT TATCAGGAGC TCCAGGGTCA GAGGTCGGAT  300
GTCTACAGCG ACCTCAACAC ACAGAGGCCG TATTACAAAT GA                     342

SEQ ID NO: 81          moltype = AA  length = 113
FEATURE                Location/Qualifiers
source                 1..113
                       mol_type = protein
                       organism = Homo sapiens
SEQUENCE: 81
MGGLEPCSRL LLLPLLLAVS GLRPVQAQAQ SDCSCSTVSP GVLAGIVMGD LVLTVLIALA  60
VYFLGRLVPR GRGAAEAATR KQRITETESP YQELQGQRSD VYSDLNTQRP YYK         113

SEQ ID NO: 82          moltype = AA  length = 345
FEATURE                Location/Qualifiers
source                 1..345
                       mol_type = protein
                       organism = Mus musculus
SEQUENCE: 82
ATGGGGGCTC TGGAGCCCTC CTGGTGCCTT CTGTTCCTTC CTGTCCTCCT GACTGTGGGA  60
GGATTAAGTC CCGTACAGGC CCAGAGTGAC ACTTTCCCAA GATGCGACTG TTCTTCCGTG  120
AGCCCTGGTG TACTGGCTGG GATTGTTCTG GGTGACTTGG TGTTGACTCT GCTGATTGCC  180
CTGGCTGTGT ACTCTCTGGG CCGCCTGGTC TCCCGAGGTC AAGGGACAGC GGAAGGGACC  240
CGGAAACAAC ACATTGCTGA GACTGAGTCG CCTTATCAGG AGCTTCAGGG TCAGAGACCA  300
GAAGTATACA GTGACCTCAA CACACAGAGG CAATATTACA GATGA                  345

SEQ ID NO: 83          moltype = AA  length = 114
FEATURE                Location/Qualifiers
source                 1..114
                       mol_type = protein
                       organism = Mus musculus
SEQUENCE: 83
MGALEPSWCL LFLPVLLTVG GLSPVQAQSD TFPRCDCSSV SPGVLAGIVL GDLVLTLLIA  60
LAVYSLGRLV SRGQGTAEGT RKQHIAETES PYQELQGQRP EVYSDLNTQR QYYR        114

SEQ ID NO: 84          moltype = AA  length = 164
FEATURE                Location/Qualifiers
source                 1..164
                       mol_type = protein
                       organism = Homo sapiens
SEQUENCE: 84
MKWKALFTAA ILQAQLPITE AQSFGLLDPK LCYLLDGILF IYGVILTALF LRVKFSRSAD  60
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                   164

SEQ ID NO: 85          moltype = AA  length = 492
FEATURE                Location/Qualifiers
source                 1..492
                       mol_type = protein
                       organism = Homo sapiens
```

```
SEQUENCE: 85
ATGAAGTGGA AGGCGCTTTT CACCGCGGCC ATCCTGCAGG CACAGTTGCC GATTACAGAG  60
GCACAGAGCT TTGGCCTGCT GGATCCCAAA CTCTGCTACC TGCTGGATGG AATCCTCTTC  120
ATCTATGGTG TCATTCTCAC TGCCTTGTTC CTGAGAGTGA AGTTCAGCAG GAGCGCAGAG  180
CCCCCCGCGT ACCAGCAGGG CCAGAACCAG CTCTATAACG AGCTCAATCT AGGACGAAGA  240
GAGGAGTACG ATGTTTTGGA CAAGAGACGT GGCCGGGACC CTGAGATGGG GGGAAAGCCG  300
AGAAGGAAGA ACCCTCAGGA AGGCCTGTAC AATGAACTGC AGAAAGATAA GATGGCGGAG  360
GCCTACAGTG AGATTGGGAT GAAAGGCGAG CGCCGGAGGG GCAAGGGGCA CGATGGCCTT  420
TACCAGGGTC TCAGTACAGC CACCAAGGAC ACCTACGACG CCCTTCACAT GCAGGCCCTG  480
CCCCCTCGCT AA                                                    492

SEQ ID NO: 86          moltype = AA  length = 164
FEATURE                Location/Qualifiers
source                 1..164
                       mol_type = protein
                       organism = Mus musculus
SEQUENCE: 86
MKWKVSVLAC ILHVRFPGAE AQSFGLLDPK LCYLLDGILF IYGVIITALY LRAKFSRSAE  60
TAANLQDPNQ LYNELNLGRR EEYDVLEKKR ARDPEMGGKQ QRRRNPQEGV YNALQKDKMA  120
EAYSEIGTKG ERRRGKGHDG LYQGLSTATK DTYDALHMQT LAPR                 164

SEQ ID NO: 87          moltype = AA  length = 495
FEATURE                Location/Qualifiers
source                 1..495
                       mol_type = protein
                       organism = Mus musculus
SEQUENCE: 87
ATGAAGTGGA AAGTGTCTGT TCTCGCCTGC ATCCTCCACG TGCGGTTCCC AGGAGCAGAG  60
GCACAGAGCT TTGGTCTGCT GGATCCCAAA CTCTGCTACT TGCTAGATGG AATCCTCTTC  120
ATCTACGGAG TCATCATCAC AGCCCTGTAC CTGAGAGCAA AATTCAGCAG GAGTGCAGAG  180
ACTGCTGCCA ACCTGCAGGA CCCCAACCAG CTCTACAATG AGCTCAATCT AGGGCGAAGA  240
GAGGAATATG ACGTCTTGGA GAAGAAGCGG GCTCGGGATC CAGAGATGGG AGGCAAACAG  300
CAGAGGAGGA GGAACCCCCA GGAAGGCGTA TACAATGCAC TGCAGAAAGA CAAGATGGCA  360
GAAGCCTACA GTGAGATCGG CACAAAAGGC GAGAGGCGGA GAGGCAAGGG GCACGATGGC  420
CTTTACCAGG GTCTCAGCAC TGCCACCAAG GACACCTATG ATGCCCTGCA TATGCAGACC  480
CTGGCCCCTC GCTAA                                                 495

SEQ ID NO: 88          moltype = AA  length = 254
FEATURE                Location/Qualifiers
source                 1..254
                       mol_type = protein
                       organism = Homo sapiens
SEQUENCE: 88
MWQLLLPTAL LLLVSAGMRT EDLPKAVVFL EPQWYRVLEK DSVTLKCQGA YSPEDNSTQW  60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLFGSKN  180
VSSETVNITI TQGLAVSTIS SFFPPGYQVS FCLVMVLLFA VDTGLYFSVK TNIRSSTRDW  240
KDHKFKWRKD PQDK                                                  254

SEQ ID NO: 89          moltype = AA  length = 762
FEATURE                Location/Qualifiers
source                 1..762
                       mol_type = protein
                       organism = Homo sapiens
SEQUENCE: 89
ATGTGGCAGC TGCTGCTGCC GACCGCGCTG CTGCTGCTGG TGAGCGCGGG CATGCGCACC  60
GAAGATCTGC CGAAAGCGGT GGTGTTTCTG GAACCGCAGT GGTATCGCGT GCTGGAAAAA  120
GATAGCGTGA CCCTGAAATG CCAGGGCGCG TATAGCCCGG AAGATAACAG CACCCAGTGG  180
TTTCATAACG AAAGCCTGAT TAGCAGCCAG GCGAGCAGCT ATTTTATTGA TGCGGCGACC  240
GTGGATGATA GCGGCGAATA TCGCTGCCAG ACCAACCTGA GCACCCTGAG CGATCCGGTG  300
CAGCTGGAAG TGCATATTGG CTGGCTGCTG CTGCAGGCGC CGCGCTGGGT GTTTAAAGAA  360
GAAGATCCGA TTCATCTGCG CTGCCATAGC TGGAAAAACA CCGCGCTGCA TAAAGTGACC  420
TATCTGCAGA ACGGCAAAGG CCGCAAATAT TTTCATCATA ACAGCGATTT TTATATTCCG  480
AAAGCGACCC TGAAAGATAG CGGCAGCTAT TTTTGCCGCG GCCTGTTTGG CAGCAAAAAC  540
GTGAGCAGCG AAACCGTGAA CATTACCATT ACCCAGGGCC TGGCGGTGAG CACCATTAGC  600
AGCTTTTTTC CGCCGGGCTA TCAGGTGAGC TTTTGCCTGG TGATGGTGCT GCTGTTTGCG  660
GTGGATACCG GCCTGTATTT TAGCGTGAAA ACCAACATTC GCAGCAGCAC CCGCGATTGG  720
AAAGATCATA AATTTAAATG GCGCAAAGAT CCGCAGGATA AA                   762

SEQ ID NO: 90          moltype = AA  length = 261
FEATURE                Location/Qualifiers
source                 1..261
                       mol_type = protein
                       organism = Mus musculus
SEQUENCE: 90
MFQNAHSGSQ WLLPPLTILL LFAFADRQSA ALPKAVVKLD PPWIQVLKED MVTLMCEGTH  60
NPGNSSTQWF HNGRSIRSQV QASYTFKATV NDSGEYRCQM EQTRLSDPVD LGVISDWLLL  120
QTPQRVFLEG ETITLRCHSW RNKLLNRISF FHNEKSVRYH HYKSNFSIPK ANHSHSGDYY  180
CKGSLGSTQH QSKPVTITVQ DPATTSSISL VWYHTAFSLV MCLLFAVDTG LYFYVRRNLQ  240
```

```
TPREYWRKSL SIRKHQAPQD K                                      261

SEQ ID NO: 91          moltype = AA  length = 786
FEATURE                Location/Qualifiers
source                 1..786
                       mol_type = protein
                       organism = Mus musculus
SEQUENCE: 91
ATGTTTCAGA ATGCACACTC TGGAAGCCAA TGGCTACTTC CACCACTGAC AATTCTGCTG  60
CTGTTTGCTT TTGCAGACAG GCAGAGTGCA GCTCTTCCGA AGGCTGTGGT GAAACTGGAC  120
CCCCCATGGA TCCAGGTGCT CAAGGAAGAC ATGGTGACAC TGATGTGCGA AGGGACCCAC  180
AACCCTGGGA ACTCTTCTAC CCAGTGGTTC CACAACGGGA GGTCCATCCG GAGCCAGGTC  240
CAAGCCAGTT ACACGTTTAA GGCCACAGTC AATGACAGTG GAGAATATCG GTGTCAAATG  300
GAGCAGACCC GCCTCAGCGA CCCTGTAGAT CTGGGAGTGA TTTCTGACTG GCTGCTGCTC  360
CAGACCCCTC AGCGGGTGTT TCTGGAAGGG GAAACCATCA CGCTAAGGTG CCATAGCTGG  420
AGGAACAAAC TACTGAACAG GATCTCATTC TTCCATAATG AAAAATCCGT GAGGTATCAT  480
CACTACAAAA GTAATTTCTC TATCCCAAAA GCCAACCACA GTCACAGTGG GGACTACTAC  540
TGCAAAGGAA GTCTAGGAAG TACACAGCAC CAGTCCAAGC CTGTCACCAT CACTGTCCAA  600
GATCCAGCAA CTACATCCTC CATCTCTCTA GTCTGGTACC ACACTGCTTT CTCCCTAGTG  660
ATGTGCCTCC TGTTTGCAGT GGACACGGGC CTTTATTTCT ACGTACGGAG AAATCTTCAA  720
ACCCCGAGGG AGTACTGGAG GAAGTCCCTG TCAATCAGAA AGCACCAGGC TCCTCAAGAC  780
AAGTGA                                                       786

SEQ ID NO: 92          moltype = AA  length = 216
FEATURE                Location/Qualifiers
source                 1..216
                       mol_type = protein
                       organism = Homo sapiens
SEQUENCE: 92
MGWIRGRRSR HSWEMSEFHN YNLDLKKSDF STRWQKQRCP VVKSKCRENA SPFFFCCFIA  60
VAMGIRFIIM VAIWSAVFLN SLFNQEVQIP LTESYCGPCP KNWICYKNNC YQFFDESKNW  120
YESQASCMSQ NASLLKVYSK EDQDLLKLVK SYHWMGLVHI PTNGSWQWED GSILSPNLLT  180
IIEMQKGDCA LYASSFKGYI ENCSTPNTYI CMQRTV                      216

SEQ ID NO: 93          moltype = AA  length = 648
FEATURE                Location/Qualifiers
source                 1..648
                       mol_type = protein
                       organism = Homo sapiens
SEQUENCE: 93
ATGGGCTGGA TTCGCGGCCG CCGCAGCCGC CATAGCTGGG AAATGAGCGA ATTTCATAAC  60
TATAACCTGG ATCTGAAAAA AAGCGATTTT AGCACCCGCT GGCAGAAACA GCGCTGCCCG  120
GTGGTGAAAA GCAAATGCCG CGAAAACGCG AGCCCGTTTT TTTTTTGCTG CTTTATTGCG  180
GTGGCGATGG GCATTCGCTT TATTATTATG GTGGCGATTT GGAGCGCGGT GTTTCTGAAC  240
AGCCTGTTTA ACCAGGAAGT GCAGATTCCG CTGACCGAAA GCTATTGCGG CCCGTGCCCG  300
AAAAACTGGA TTTGCTATAA AAACAACTGC TATCAGTTTT TTGATGAAAG CAAAAACTGG  360
TATGAAAGCC AGGCGAGCTG CATGAGCCAG AACGCGAGCC TGCTGAAAGT GTATAGCAAA  420
GAAGATCAGG ATCTGCTGAA ACTGGTGAAA AGCTATCATT GGATGGGCCT GGTGCATATT  480
CCGACCAACG GCAGCTGGCA GTGGGAAGAT GGCAGCATTC TGAGCCCGAA CCTGCTGACC  540
ATTATTGAAA TGCAGAAAGG CGATTGCGCG CTGTATGCGA GCAGCTTTAA AGGCTATATT  600
GAAAACTGCA GCACCCCGAA CACCTATATT TGCATGCAGC GCACCGTG         648

SEQ ID NO: 94          moltype = AA  length = 232
FEATURE                Location/Qualifiers
source                 1..232
                       mol_type = protein
                       organism = Mus musculus
SEQUENCE: 94
MALIRDRKSH HSEMSKCHNY DLKPAKWDTS QEQQKQRLAL TTSQPGENGI IRGRYPIEKL  60
KISPMFVVRV LAIALAIRFT LNTLMWLAIF KETFQPVLCN KEVPVSSREG YCGPCPNNWI  120
CHRNNCYQFF NEEKTWNQSQ ASCLSQNSSL LKIYSKEEQD FLKLVKSYHW MGLVQIPANG  180
SWQWEDGSSL SYNQLTLVEI PKGSCAVYGS SFKAYTEDCA NLNTYICMKR AV    232

SEQ ID NO: 95          moltype = AA  length = 696
FEATURE                Location/Qualifiers
source                 1..696
                       mol_type = protein
                       organism = Mus musculus
SEQUENCE: 95
ATGGCGCTGA TTCGCGATCG CAAAAGCCAT CATAGCGAAA TGAGCAAATG CCATAACTAT  60
GATCTGAAAC CGGCGAAATG GGATACCAGC CAGGAACAGC AGAAACAGCG CCTGGCGCTG  120
ACCACCAGCC AGCCGGGCGA AAACGGCATT ATTCGCGGCC GCTATCCGAT TGAAAAACTG  180
AAAATTAGCC CGATGTTTGT GGTGCGCGTG CTGGCGATTG CGCTGGCGAT TCGCTTTACC  240
CTGAACACCC TGATGTGGCT GGCGATTTTT AAAGAAACCT TTCAGCCGGT GCTGTGCAAC  300
AAAGAAGTGC CGGTGAGCAG CCGCGAAGGC TATTGCGGCC CGTGCCCGAA CAACTGGATT  360
TGCCATCGCA ACAACTGCTA TCAGTTTTTT AACGAAGAAA AAACCTGGAA CCAGAGCCAG  420
GCGAGCTGCC TGAGCCAGAA CAGCAGCCTG CTGAAAATTT ATAGCAAAGA AGAACAGGAT  480
TTTCTGAAAC TGGTGAAAAG CTATCATTGG ATGGGCCTGG TGCAGATTCC GGCGAACGGC  540
AGCTGGCAGT GGGAAGATGG CAGCAGCCTG AGCTATAACC AGCTGACCCT GGTGGAAATT  600
```

```
CCGAAAGGCA GCTGCGCGGT GTATGGCAGC AGCTTTAAAG CGTATACCGA AGATTGCGCG  660
AACCTGAACA CCTATATTTG CATGAAACGC GCGGTG                            696

SEQ ID NO: 96          moltype = AA  length = 4
FEATURE                Location/Qualifiers
REGION                 1..4
                       note = Synthetic construct
source                 1..4
                       mol_type = protein
                       organism = synthetic construct
SEQUENCE: 96
YMNM                                                               4

SEQ ID NO: 97          moltype = AA  length = 4
FEATURE                Location/Qualifiers
REGION                 1..4
                       note = Synthetic construct
source                 1..4
                       mol_type = protein
                       organism = synthetic construct
SEQUENCE: 97
PYAP                                                               4

SEQ ID NO: 98          moltype = AA  length = 4
FEATURE                Location/Qualifiers
REGION                 1..4
                       note = Synthetic construct
source                 1..4
                       mol_type = protein
                       organism = synthetic construct
SEQUENCE: 98
FMNM                                                               4

SEQ ID NO: 99          moltype = AA  length = 4
FEATURE                Location/Qualifiers
REGION                 1..4
                       note = Synthetic construct
source                 1..4
                       mol_type = protein
                       organism = synthetic construct
SEQUENCE: 99
AYAA                                                               4

SEQ ID NO: 100         moltype = AA  length = 21
FEATURE                Location/Qualifiers
REGION                 1..21
                       note = Synthetic construct
source                 1..21
                       mol_type = protein
                       organism = synthetic construct
SEQUENCE: 100
ATMGWSCIIL FLVATATGVH S                                            21

SEQ ID NO: 101         moltype = AA  length = 57
FEATURE                Location/Qualifiers
REGION                 1..57
                       note = Synthetic construct
source                 1..57
                       mol_type = protein
                       organism = synthetic construct
SEQUENCE: 101
ATGGGATGGA GCTGTATCAT CCTCTTCTTG GTAGCAACAG CTACCGGTGT GCACTCC     57

SEQ ID NO: 102         moltype = AA  length = 449
FEATURE                Location/Qualifiers
REGION                 1..449
                       note = Synthetic construct
source                 1..449
                       mol_type = protein
                       organism = synthetic construct
SEQUENCE: 102
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449
```

```
SEQ ID NO: 103         moltype = AA  length = 219
FEATURE                Location/Qualifiers
REGION                 1..219
                       note = Synthetic construct
source                 1..219
                       mol_type = protein
                       organism = synthetic construct
SEQUENCE: 103
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 104         moltype = AA  length = 447
FEATURE                Location/Qualifiers
REGION                 1..447
                       note = Synthetic construct
source                 1..447
                       mol_type = protein
                       organism = synthetic construct
SEQUENCE: 104
EVQLLESGGG LVQPGGSLRL SCAASGFTFS SYAMSWVRQA PGKGLEWVSA IIGSGASTYY  60
ADSVKGRFTI SRDNSKNTLY LQMNSLRAED TAVYYCAKGW FGGFNYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 105         moltype = AA  length = 215
FEATURE                Location/Qualifiers
REGION                 1..215
                       note = Synthetic construct
source                 1..215
                       mol_type = protein
                       organism = synthetic construct
SEQUENCE: 105
EIVLTQSPGT LSLSPGERAT LSCRASQSVT SSYLAWYQQK PGQAPRLLIN VGSRRATGIP  60
DRFSGSGSGT DFTLTISRLE PEDFAVYYCQ QGIMLPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 106         moltype = AA  length = 451
FEATURE                Location/Qualifiers
REGION                 1..451
                       note = Synthetic construct
source                 1..451
                       mol_type = protein
                       organism = synthetic construct
SEQUENCE: 106
EVQLVESGGG LVQPGRSLRL SCAASGFTVS SYWMHWVRQA PGKGLEWVGF IRNKANGGTT  60
EYAASVKGRF TISRDDSKNT LYLQMNSLRA EDTAVYYCAR DRGLRFYFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 107         moltype = AA  length = 223
FEATURE                Location/Qualifiers
REGION                 1..223
                       note = Synthetic construct
source                 1..223
                       mol_type = protein
                       organism = synthetic construct
SEQUENCE: 107
QAVLTQPASL SASPGASASL TCTLRRGINV GAYSIYWYQQ KPGSPPQYLL RYKSDSDKQQ  60
GSGVSSRFSA SKDASANAGI LLISGLQSED EADYYCMIWH SGASAVFGGG TKLTVLRTVA  120
APSVFIFPPS DEQLKSGTAS VVCLLNNFYP REAKVQWKVD NALQSGNSQE SVTEQDSKDS  180
TYSLSSTLTL SKADYEKHKV YACEVTHQGL SSPVTKSFNR GEC                   223

SEQ ID NO: 108         moltype = AA  length = 451
FEATURE                Location/Qualifiers
REGION                 1..451
                       note = Synthetic construct
source                 1..451
```

```
                        mol_type = protein
                        organism = synthetic construct
SEQUENCE: 108
QVQLVQSGAE VKKPGSSVKV SCKASGFNIK DTYMHWVRQA PGQGLEWMGR IDPANGNSKY  60
VPKFQGRVTI TADTSTSTAY MELSSLRSED TAVYYCAPFG YYVSDYAMAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 109          moltype = AA  length = 218
FEATURE                 Location/Qualifiers
REGION                  1..218
                        note = Synthetic construct
source                  1..218
                        mol_type = protein
                        organism = synthetic construct
SEQUENCE: 109
EIVLTQSPAT LSLSPGERAT LSCRAGESVD IFGVGFLHWY QQKPGQAPRL LIYRASNRAT  60
GIPARFSGSG SGTDFTLTIS SLEPEDFAVY YCQQTNEDPY TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 110          moltype = AA  length = 451
FEATURE                 Location/Qualifiers
REGION                  1..451
                        note = Synthetic construct
source                  1..451
                        mol_type = protein
                        organism = synthetic construct
SEQUENCE: 110
QVQLVQSGAE VKKPGASVKV SCKASGYTFT EFGMNWVRQA PGQGLEWMGW INTKTGEATY  60
VEEFKGRVTF TTDTSTSTAY MELRSLRSDD TAVYYCARWD FAYYVEAMDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNHY TQKSLSLSPG K                                 451

SEQ ID NO: 111          moltype = AA  length = 215
FEATURE                 Location/Qualifiers
REGION                  1..215
                        note = Synthetic construct
source                  1..215
                        mol_type = protein
                        organism = synthetic construct
SEQUENCE: 111
DIQMTQSPSS LSASVGDRVT ITCKASAAVG TYVAWYQQKP GKAPKLLIYS ASYRKRGVPS  60
RFSGSGSGTD FTLTISSLQP EDFATYYCHQ YYTYPLFTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 112          moltype = AA  length = 449
FEATURE                 Location/Qualifiers
REGION                  1..449
                        note = Synthetic construct
source                  1..449
                        mol_type = protein
                        organism = synthetic construct
SEQUENCE: 112
EVQLVESGGG VVQPGRSLRL SCSASGFDFT TYWMSWVRQA PGKGLEWIGE IHPDSSTINY  60
APSLKDRFTI SRDNAKNTLF LQMDSLRPED TGVYFCASLY FGFPWFAYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL GAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 113          moltype = AA  length = 213
FEATURE                 Location/Qualifiers
REGION                  1..213
                        note = Synthetic construct
source                  1..213
                        mol_type = protein
                        organism = synthetic construct
```

```
SEQUENCE: 113
DIQLTQSPSS LSASVGDRVT ITCKASQDVG TSVAWYQQKP GKAPKLLIYW TSTRHTGVPS  60
RFSGSGSGTD FTFTISSLQP EDIATYYCQQ YSLYRSFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 114         moltype = AA  length = 451
FEATURE                Location/Qualifiers
REGION                 1..451
                       note = Synthetic construct
source                 1..451
                       mol_type = protein
                       organism = synthetic construct
SEQUENCE: 114
QVQLVQSGAE VKKPGSSVKV SCKASGGTFS SYAISWVRQA PGQGLEWMGG IIPIFGTANY  60
AQKFQGRVTI TADKSTSTAY MELSSLRSED TAVYYCARLY GYAYYGAFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNHY TQKSLSLSPG K                                451

SEQ ID NO: 115         moltype = AA  length = 214
FEATURE                Location/Qualifiers
REGION                 1..214
                       note = Synthetic construct
source                 1..214
                       mol_type = protein
                       organism = synthetic construct
SEQUENCE: 115
DIQMTQSPSS LSASVGDRVT ITCRASQGIR NDLGWYQQKP GKAPKRLIYA ASSLQSGVPS  60
RFSGSGSGTE FTLTISSLQP EDFATYYCLQ NGLQPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 116         moltype = AA  length = 330
FEATURE                Location/Qualifiers
REGION                 1..330
                       note = Synthetic construct
source                 1..330
                       mol_type = protein
                       organism = synthetic construct
SEQUENCE: 116
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 117         moltype = AA  length = 276
FEATURE                Location/Qualifiers
source                 1..276
                       mol_type = protein
                       organism = Homo sapiens
SEQUENCE: 117
MRNQAPGRPK GATFPPRRPT GSRAPPLAPE LRAKQRPGER VMALPVTALL LPLALLLHAA  60
RPSQFRVSPL DRTWNLGETV ELKCQVLLSN PTSGCSWLFQ PRGAAASPTF LLYLSQNKPK  120
AAEGLDTQRF SGKRLGDTFV LTLSDFRREN EGYYFCSALS NSIMYFSHFV PVFLPAKPTT  180
TPAPRPPTPA PTIASQPLSL RPEACRPAAG GAVHTRGLDF ACDIYIWAPL AGTCGVLLLS  240
LVITLYCNHR NRRRVCKCPR PVVKSGDKPS LSARYV                            276

SEQ ID NO: 118         moltype = AA  length = 828
FEATURE                Location/Qualifiers
source                 1..828
                       mol_type = protein
                       organism = Homo sapiens
SEQUENCE: 118
ATGCGCAACC AGGCGCCGGG CCGCCCGAAA GGCGCGACCT TTCCGCCGCG CCGCCCGACC  60
GGCAGCCGCG CGCCGCCGCT GGCGCCGGAA CTGCGCGCGA AACAGCGCCC GGGCGAACGC  120
GTGATGGCGC TGCCGGTGAC CGCGCTGCTG CTGCCGCTGG CGCTGCTGCT GCATGCGGCG  180
CGCCCGAGCC AGTTTCGCGT GAGCCCGCTG GATCGCACCT GGAACCTGGG CGAAACCGTG  240
GAACTGAAAT GCCAGGTGCT GCTGAGCAAC CCGACCAGCG GCTGCAGCTG GCTGTTTCAG  300
CCGCGCGGCG CGGCGGCGAG CCCGACCTTT CTGCTGTATC TGAGCCAGAA CAAACCGAAA  360
GCGGCGGAAG GCCTGGATAC CCAGCGCTTT AGCGGCAAAC GCCTGGGCGA TACCTTTGTG  420
CTGACCCTGA GCGATTTTCG CCGCGAAAAC GAAGGCTATT ATTTTTGCAG CGCGCTGAGC  480
AACAGCATTA TGTATTTTAG CCATTTTGTG CCGGTGTTTC TGCCGGCGAA ACCGACCACC  540
ACCCCGGCGC CGCGCCCGCC GACCCCGGCG CCGACCATTG CGAGCCAGCC GCTGAGCCTG  600
```

```
CGCCCGGAAG CGTGCCGCCC GGCGGCGGGC GGCGCGGTGC ATACCCGCGG CCTGGATTTT  660
GCGTGCGATA TTTATATTTG GGCGCCGCTG GCGGGCACCT GCGGCGTGCT GCTGCTGAGC  720
CTGGTGATTA CCCTGTATTG CAACCATCGC AACCGCCGCC GCGTGTGCAA ATGCCCGCGC  780
CCGGTGGTGA AAAGCGGCGA TAAACCGAGC CTGAGCGCGC GCTATGTG               828

SEQ ID NO: 119          moltype = AA  length = 247
FEATURE                 Location/Qualifiers
source                  1..247
                        mol_type = protein
                        organism = Mus musculus
SEQUENCE: 119
MASPLTRFLS LNLLLMGESI ILGSGEAKPQ APELRIFPKK MDAELGQKVD LVCEVLGSVS  60
QGCSWLFQNS SSKLPQPTFV VYMASSHNKI TWDEKLNSSK LFSAVRDTNN KYVLTLNKFS  120
KENEGYYFCS VISNSVMYFS SVVPVLQKVN STTTKPVLRT PSPVHPTGTS QPQRPEDCRP  180
RGSVKGTGLD FACDIYIWAP LAGICVAPLL SLIITLICYH RSRKRVCKCP RPLVRQEGKP  240
RPSEKIV                                                            247

SEQ ID NO: 120          moltype = AA  length = 741
FEATURE                 Location/Qualifiers
source                  1..741
                        mol_type = protein
                        organism = Mus musculus
SEQUENCE: 120
ATGGCGAGCC CGCTGACCCG CTTTCTGAGC CTGAACCTGC TGCTGATGGG CGAAAGCATT  60
ATTCTGGGCA GCGGCGAAGC GAAACCGCAG GCGCCGGAAC TGCGCATTTT TCCGAAAAAA  120
ATGGATGCGG AACTGGGCCA GAAAGTGGAT CTGGTGTGCG AAGTGCTGGG CAGCGTGAGC  180
CAGGGCTGCA GCTGGCTGTT TCAGAACAGC AGCAGCAAAC TGCCGCAGCC GACCTTTGTG  240
GTGTATATGG CGAGCAGCCA TAACAAAATT ACCTGGGATG AAAAACTGAA CAGCAGCAAA  300
CTGTTTAGCG CGGTGCGCGA TACCAACAAC AAATATGTGC TGACCCTGAA CAAATTTAGC  360
AAAGAAAACG AAGGCTATTA TTTTTGCAGC GTGATTAGCA ACAGCGTGAT GTATTTTAGC  420
AGCGTGGTGC CGGTGCTGCA GAAAGTGAAC AGCACCACCA CCAAACCGGT GCTGCGCACC  480
CCGAGCCCGG TGCATCCGAC CGGCACCAGC CAGCCGCAGC GCCCGGAAGA TTGCCGCCCG  540
CGCGGCAGCG TGAAAGGCAC CGGCCTGGAT TTTGCGTGCG ATATTTATAT TTGGGCGCCG  600
CTGGCGGGCA TTTGCGTGGC GCCGCTGCTG AGCCTGATTA TTACCCTGAT TTGCTATCAT  660
CGCAGCCGCA AACGCGTGTG CAAATGCCCG CGCCCGCTGG TGCGCCAGGA AGGCAAACCG  720
CGCCCGAGCG AAAAAATTGT G                                            741

SEQ ID NO: 121          moltype = AA  length = 476
FEATURE                 Location/Qualifiers
REGION                  1..476
                        note = Synthetic construct
source                  1..476
                        mol_type = protein
                        organism = synthetic construct
SEQUENCE: 121
EVQLVESGGG LVQPGGSLRL SCAASGFDFS RYWMNWVRQA PGKGLEWVGE ITPDSSTINY  60
TPSLKGRFTI SRDNAKNSLY LQMNSLRAED TAVYYCVRPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
GGTKLTVLGG GGSLKPTTTP APRPPTPAPT IASQPLSLRP EACRPAAGGA VHTRGLDFAC  300
DIYIWAPLAG TCGVLLLSLV ITKRGRKKLL YIFKQPFMRP VQTTQEEDGC SCRFPEEEEG  360
GCELRVKFSR SADAPAYQQG QNQLYNELNL GRREEYDVLD KRRGRDPEMG GKPRRKNPQE  420
GLYNELQKDK MAEAYSEIGM KGERRRGKGH DGLYQGLSTA TKDTYDALHM QALPPR      476

SEQ ID NO: 122          moltype = AA  length = 248
FEATURE                 Location/Qualifiers
REGION                  1..248
                        note = Synthetic construct
source                  1..248
                        mol_type = protein
                        organism = synthetic construct
SEQUENCE: 122
EVQLVESGGG LVQPGGSLRL SCAASGFDFS RYWMNWVRQA PGKGLEWVGE ITPDSSTINY  60
TPSLKGRFTI SRDNAKNSLY LQMNSLRAED TAVYYCVRPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
GGTKLTVL                                                           248

SEQ ID NO: 123          moltype = AA  length = 476
FEATURE                 Location/Qualifiers
REGION                  1..476
                        note = Synthetic construct
source                  1..476
                        mol_type = protein
                        organism = synthetic construct
SEQUENCE: 123
EVQLVESGGG LVQPGGSLRL SCAASGFDFS RYWMNWVRQA PGKGLEWVGE ITPDSSTINY  60
APSLKGRFTI SRDNAKNSLY LQMNSLRAED TAVYYCVRPY DYGAWFASWG QGTLVTVSSG  120
GGGSGGGGSG GGGSGGGGSQ AVVTQEPSLT VSPGGTVTLT CRSSTGAVTT SNYANWVQEK  180
```

-continued

```
PDHLFTGLIG GTNKRAPGTP ARFSGSLLGG KAALTLSGAQ PEDEAEYYCA LWYSNHWVFG  240
GGTKLTVLGG GGSLKPTTTP APRPPTPAPT IASQPLSLRP EACRPAAGGA VHTRGLDFAC  300
DIYIWAPLAG TCGVLLLSLV ITKRGRKKLL YIFKQPFMRP VQTTQEEDGC SCRFPEEEEG  360
GCELRVKFSR SADAPAYQQG QNQLYNELNL GRREEYDVLD KRRGRDPEMG GKPRRKNPQE  420
GLYNELQKDK MAEAYSEIGM KGERRRGKGH DGLYQGLSTA TKDTYDALHM QALPPR      476

SEQ ID NO: 124          moltype = AA  length = 248
FEATURE                 Location/Qualifiers
REGION                  1..248
                        note = Synthetic construct
source                  1..248
                        mol_type = protein
                        organism = synthetic construct
SEQUENCE: 124
EVQLVESGGG LVQPGGSLRL SCAASGFDFS RYWMNWVRQA PGKGLEWVGE ITPDSSTINY  60
APSLKGRFTI SRDNAKNSLY LQMNSLRAED TAVYYCVRPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
GGTKLTVL                                                          248

SEQ ID NO: 125          moltype = AA  length = 476
FEATURE                 Location/Qualifiers
REGION                  1..476
                        note = Synthetic construct
source                  1..476
                        mol_type = protein
                        organism = synthetic construct
SEQUENCE: 125
EVQLVESGGG LVQPGGSLRL SCAASGFTFS RYWMNWVRQA PGKCLEWVGE ITPDSSTINY  60
APSLKGRFTI SRDNAKNSLY LQMNSLRAED TAVYYCARPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
CGTKLTVLGG GGSLKPTTTP APRPPTPAPT IASQPLSLRP EACRPAAGGA VHTRGLDFAC  300
DIYIWAPLAG TCGVLLLSLV ITKRGRKKLL YIFKQPFMRP VQTTQEEDGC SCRFPEEEEG  360
GCELRVKFSR SADAPAYQQG QNQLYNELNL GRREEYDVLD KRRGRDPEMG GKPRRKNPQE  420
GLYNELQKDK MAEAYSEIGM KGERRRGKGH DGLYQGLSTA TKDTYDALHM QALPPR      476

SEQ ID NO: 126          moltype = AA  length = 119
FEATURE                 Location/Qualifiers
REGION                  1..119
                        note = Synthetic construct
source                  1..119
                        mol_type = protein
                        organism = synthetic construct
SEQUENCE: 126
EVQLVESGGG LVQPGGSLRL SCAASGFTFS RYWMNWVRQA PGKCLEWVGE ITPDSSTINY  60
APSLKGRFTI SRDNAKNSLY LQMNSLRAED TAVYYCARPY DYGAWFASWG QGTLVTVSS   119

SEQ ID NO: 127          moltype = AA  length = 109
FEATURE                 Location/Qualifiers
REGION                  1..109
                        note = Synthetic construct
source                  1..109
                        mol_type = protein
                        organism = synthetic construct
SEQUENCE: 127
QAVVTQEPSL TVSPGGTVTL TCRSSTGAVT TSNYANWVQE KPDHLFTGLI GGTNKRAPGT  60
PARFSGSLLG GKAALTLSGA QPEDEAEYYC ALWYSNHWVF GCGTKLTVL             109

SEQ ID NO: 128          moltype = AA  length = 248
FEATURE                 Location/Qualifiers
REGION                  1..248
                        note = Synthetic construct
source                  1..248
                        mol_type = protein
                        organism = synthetic construct
SEQUENCE: 128
EVQLVESGGG LVQPGGSLRL SCAASGFTFS RYWMNWVRQA PGKCLEWVGE ITPDSSTINY  60
APSLKGRFTI SRDNAKNSLY LQMNSLRAED TAVYYCARPY DYGAWFASWG QGTLVTVSSG  120
GGGSGGGGSG GGGSGGGGSQ AVVTQEPSLT VSPGGTVTLT CRSSTGAVTT SNYANWVQEK  180
PDHLFTGLIG GTNKRAPGTP ARFSGSLLGG KAALTLSGAQ PEDEAEYYCA LWYSNHWVFG  240
CGTKLTVL                                                          248
```

The invention claimed is:

1. An antigen binding receptor comprising an anchoring transmembrane domain and an extracellular domain, wherein the extracellular domain comprises an antigen binding moiety comprising (i) a heavy chain variable domain (VH) comprising the heavy chain complementary determining region (HCDR) 1 of SEQ ID NO:1, the HCDR 2 of SEQ ID NO:2 or SEQ ID NO:40, and the HCDR 3 of SEQ ID NO:3, and (ii) a light chain variable domain (VL) comprising the light chain complementarity determining region (LCDR) 1 of SEQ ID NO:4, the LCDR 2 of SEQ ID NO:5 and the LCDR 3 of SEQ ID NO:6, wherein the antigen binding moiety specifically binds to a mutated Fc domain comprising the amino acid mutation P329G according to EU numbering.

2. The antigen binding receptor of claim 1, wherein the VH domain comprises an amino acid sequence that is at least 95% identical to an amino acid sequence selected from the group consisting of SEQ ID NO:8, SEQ ID NO:41, SEQ ID NO.44 and SEQ ID NO:126.

3. The antigen binding receptor of claim 1 or 2, wherein the VL domain comprises an amino acid sequence that is at least 95% identical to the amino acid sequence of SEQ ID NO:9 or SEQ ID NO:127.

4. The antigen binding receptor of claim 1 or 2, wherein the anchoring transmembrane domain is a transmembrane domain selected from the group consisting of the CD8, the CD4, the CD3z, the FCGR3A, the NKG2D, the CD27, the CD28, the CD137, the OX40, the ICOS, the DAP10 or the DAP12 transmembrane domain or a fragment thereof, in particular wherein the anchoring transmembrane domain is the CD8 transmembrane domain or a fragment thereof.

5. The antigen binding receptor of claim 1 or 2, further comprising at least one stimulatory signaling domain and/or at least one co-stimulatory signaling domain.

6. The antigen binding receptor of claim 1 or 2, wherein the at least one stimulatory signaling domain is individually selected from the group consisting of the intracellular domain of CD3z, of FCGR3A and of NKG2D, or fragments thereof that retains stimulatory signaling activity, in particular wherein the at least one stimulatory signaling domain is the CD3z intracellular domain or a fragment thereof that retains CD3z stimulatory signaling activity.

7. The antigen binding receptor of claim 1 or 2, wherein the at least one co-stimulatory signaling domain is individually selected from the group consisting of the intracellular domain of CD27, of CD28, of CD137, of OX40, of ICOS, of DAP10 and of DAP12, or fragments thereof that retain co-stimulatory signaling activity.

8. The antigen binding receptor of claim 1 or 2, comprising at least one CD28 costimulatory domain or a fragment thereof that retains CD28 co-stimulatory activity, and/or at least one CD137 costimulatory domain or a fragment thereof that retains CD137 co-stimulatory activity.

9. The antigen binding receptor of claim 1 or 2, wherein the antigen binding receptor comprises a stimulatory signaling domain comprising the intracellular domain of CD3z, or a fragment thereof that retains CD3z stimulatory signaling activity, and wherein the antigen binding receptor comprises a co-stimulatory signaling domain comprising the intracellular domain of CD28, or a fragment thereof that retains CD28 co-stimulatory signaling activity.

10. The antigen binding receptor of claim 1 or 2, wherein the antigen binding receptor comprises one stimulatory signaling domain comprising the intracellular domain of CD3z, or a fragment thereof that retains CD3z stimulatory signaling activity, and wherein the antigen binding receptor comprises one co-stimulatory signaling domain comprising the intracellular domain of CD137, or a fragment thereof that retains CD137 co-stimulatory signaling activity.

11. The antigen binding receptor of claim 1 or 2, wherein the antigen binding moiety is connected at the C-terminus to the N-terminus of the anchoring transmembrane domain, optionally through a peptide linker.

12. The antigen binding receptor of claim 1 or 2, wherein the light chain variable domain (VL) of the antigen binding moiety is connected at the C-terminus to the N-terminus of the anchoring transmembrane domain, optionally through a peptide linker, and/or wherein the heavy chain variable domain (VH) is connected at the C-terminus to the N-terminus of the light chain variable domain (VL), optionally through a peptide linker.

* * * * *